(12) United States Patent
Yoshida et al.

(10) Patent No.: US 8,530,138 B2
(45) Date of Patent: *Sep. 10, 2013

(54) SALT AND PHOTORESIST COMPOSITION COMPRISING THE SAME

(75) Inventors: Isao Yoshida, Osaka (JP); Koji Ichikawa, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 78 days.

This patent is subject to a terminal disclaimer.

(21) Appl. No.: 13/216,776

(22) Filed: Aug. 24, 2011

(65) Prior Publication Data

US 2012/0052440 A1    Mar. 1, 2012

(30) Foreign Application Priority Data

Aug. 27, 2010   (JP) ................................ 2010-190566

(51) Int. Cl.
| | | |
|---|---|---|
| *G03F 7/00* | (2006.01) | |
| *G03F 7/028* | (2006.01) | |
| *C07D 343/00* | (2006.01) | |
| *C07D 411/00* | (2006.01) | |
| *C07C 309/00* | (2006.01) | |

(52) U.S. Cl.
USPC ............ 430/270.1; 430/913; 549/16; 562/41; 562/42

(58) Field of Classification Search
USPC .................. 430/270.1, 913; 549/16; 562/41, 562/42
See application file for complete search history.

(56) References Cited

U.S. PATENT DOCUMENTS

| 5,914,219 | A | 6/1999 | Funhoff et al. | |
|---|---|---|---|---|
| 7,304,175 | B2 | 12/2007 | Harada et al. | |
| 7,439,006 | B2 | 10/2008 | Yoshida et al. | |
| 8,252,505 | B2 * | 8/2012 | Kawaue et al. | 430/270.1 |
| 8,288,077 | B2 * | 10/2012 | Ichikawa et al. | 430/270.1 |
| 8,318,403 | B2 * | 11/2012 | Ichikawa et al. | 430/270.1 |
| 2006/0194982 | A1 | 8/2006 | Harada et al. | |
| 2007/0027336 | A1 | 2/2007 | Yoshida et al. | |
| 2007/0078269 | A1 | 4/2007 | Harada et al. | |
| 2007/0122750 | A1 | 5/2007 | Yamaguchi et al. | |
| 2008/0076063 | A1 | 3/2008 | Yoshida et al. | |
| 2008/0081925 | A1 | 4/2008 | Sakamoto et al. | |
| 2009/0208871 | A1 | 8/2009 | Kawaue et al. | |
| 2010/0304293 | A1 * | 12/2010 | Ichikawa et al. | 430/270.1 |
| 2010/0316951 | A1 * | 12/2010 | Ichikawa et al. | 430/270.1 |
| 2011/0117493 | A1 * | 5/2011 | Ichikawa et al. | 430/270.1 |
| 2011/0117494 | A1 * | 5/2011 | Ichikawa et al. | 430/270.1 |
| 2011/0117495 | A1 * | 5/2011 | Ichikawa et al. | 430/270.1 |
| 2011/0171576 | A1 * | 7/2011 | Yamaguchi et al. | 430/270.1 |
| 2011/0318688 | A1 * | 12/2011 | Hiraoka et al. | 430/270.1 |

FOREIGN PATENT DOCUMENTS

JP    2012-6907 A    1/2012

* cited by examiner

*Primary Examiner* — Amanda C. Walke
(74) *Attorney, Agent, or Firm* — Birch, Stewart, Kolasch & Birch, LLP

(57) ABSTRACT

The present invention provides a salt represented by the formula (I):

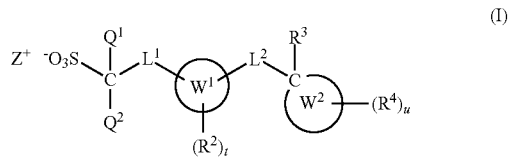

wherein $Q^1$ and $Q^2$ independently each represent a fluorine atom or a C1-C6 perfluoroalkyl group, $L^1$ and $L^2$ independently each represent a C1-C17 divalent saturated hydrocarbon group in which one or more —$CH_2$— can be replaced by —O— or —CO—, ring $W^1$ and ring $W^2$ independently each represent a C3-C36 aliphatic ring, $R^2$ is independently in each occurrence a C1-C6 alkyl group, $R^4$ is independently in each occurrence a C1-C6 alkyl group, $R^3$ represents a C1-C12 hydrocarbon group, t represents an integer of 0 to 2, u represents an integer of 0 to 2, and $Z^+$ represents an organic counter ion.

8 Claims, No Drawings

SALT AND PHOTORESIST COMPOSITION COMPRISING THE SAME

This nonprovisional application claims priority under 35 U.S.C. §119(a) on Patent Application No. 2010-190556 filed in JAPAN on Aug. 27, 2010, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

US 2008/0076063 A1 discloses a salt represented by the following formula:

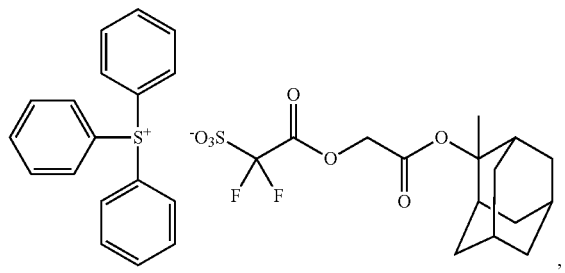

and a photoresist composition containing the same as an acid generator.

SUMMARY OF THE INVENTION

The present invention is to provide a salt for suitable for an acid generator and a photoresist composition comprising the same.

The present invention relates to the followings:
<1> A salt represented by the formula (I):

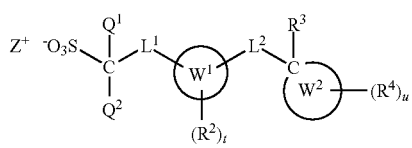

wherein $Q^1$ and $Q^2$ independently each represent a fluorine atom or a C1-C6 perfluoroalkyl group, $L^1$ and $L^2$ independently each represent a C1-C17 divalent saturated hydrocarbon group in which one or more —$CH_2$— can be replaced by —O— or —CO—, ring $W^1$ and ring $W^2$ independently each represent a C3-C36 aliphatic ring, $R^2$ is independently in each occurrence a C1-C6 alkyl group, $R^4$ is independently in each occurrence a C1-C6 alkyl group, $R^3$ represents a C1-C12 hydrocarbon group, t represents an integer of 0 to 2, u represents an integer of 0 to 2, and $Z^+$ represents an organic counter ion;
<2> The salt according to <1>, wherein $L^1$ is *—CO—O— in which * represents a binding position to —C($Q^1$)($Q^2$)-;
<3> The salt according to <1> or <2>, wherein $L^2$ is *—CO—O—$CH_2$—CO—O— or *—O—$CH_2$—CO—O— in which * represents a binding position to ring $W^1$;
<4> The salt according to <1>, <2> or <3>, wherein $Z^+$ is an arylsulfonium cation;
<5> An acid generator comprising the salt according to any one of <1> to <4>;
<6> A photoresist composition comprising the acid generator according to <5> and a resin having an acid-labile group, being insoluble or poorly soluble in an aqueous alkali solution but becoming soluble in an aqueous alkali solution by the action of an acid;
<7> The photoresist composition according to <6>, which further comprises a basic compound;
<8> A process for producing a photoresist pattern comprising the following steps (1) to (5):
  (1) a step of applying the photoresist composition according to <6> or <7> on a substrate,
  (2) a step of forming a photoresist film by conducting drying,
  (3) a step of exposing the photoresist film to radiation,
  (4) a step of baking the exposed photoresist film, and
  (5) a step of developing the baked photoresist film with an alkaline developer, thereby forming a photoresist pattern.

DESCRIPTION OF PREFERRED EMBODIMENTS

First, the salt represented by the formula (I) will be illustrated.

The salt of the present invention is represented by the formula (I):

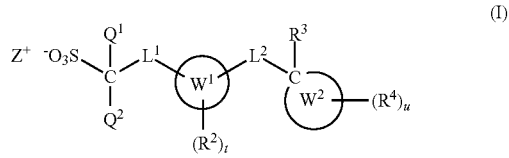

wherein $Q^1$ and $Q^2$ independently each represent a fluorine atom or a C1-C6 perfluoroalkyl group, $L^1$ and $L^2$ independently each represent a C1-C17 divalent saturated hydrocarbon group in which one or more —$CH_2$— can be replaced by —O— or —CO—, ring $W^1$ and ring $W^2$ independently each represent a C3-C36 aliphatic ring, $R^2$ is independently in each occurrence a C1-C6 alkyl group, $R^4$ is independently in each occurrence a C1-C6 alkyl group, $R^3$ represents a C1-C12 hydrocarbon group, t represents an integer of 0 to 2, u represents an integer of 0 to 2, and $Z^+$ represents an organic counter ion (hereinafter, simply referred to as SALT (I)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. It is preferred that $Q^1$ and $Q^2$ independently each represent a fluorine atom or a trifluoromethyl group, and it is more preferred that $Q^1$ and $Q^2$ are fluorine atoms.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a puropane-1,1-diyl group and a propane-2,2-diyl group; a C2-C17 branched alkanediyl group such as a 1-methyl-1,3-propylene group, a 2-methyl-1,3-propylene group, a 2-methyl-1,2-propylene group, a 1-methyl-1,4-butylene group, and a 2-methyl-1,4-butylene group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

When $L^1$ represents a C1-C17 divalent saturated hydrocarbon group in which one or more —$CH_2$— are replaced by —O— or —CO—, examples thereof include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, CO—O-$L^{b10}$-O-$L^{b9}$-CO—O— and *—O-$L^{b12}$-CO—O-$L^{11}$, wherein $L^{b2}$ represents a single bond or a C1-C15 saturated hydrocarbon group, $L^{b3}$ represents a single bond or a C1-C12 saturated hydrocarbon group, $L^{b4}$ represents C1-C13 saturated hydrocarbon group, with the proviso that total carbon number of $L^{b3}$ and $L^{b4}$ is 1 to 13, $L^{b5}$ represents a C1-C15 saturated hydrocarbon group, $L^{b6}$ represents a C1-C15 saturated hydrocarbon group, $L^{b7}$ represents a C1-C15 saturated hydrocarbon group, with the proviso that total carbon number of $L^{b6}$ and $L^{b7}$ is 1 to 16, $L^{b8}$ represents a C1-C14 saturated hydrocarbon group, $L^{b9}$ represents a C1-C11 saturated hydrocarbon group, $L^{b10}$ represents a C1-C11 saturated hydrocarbon group, with the proviso that total carbon number of $L^{b9}$ and $L^{b10}$ is 1 to 12, $L^{b11}$ represents a single bond or a C1-C13 saturated hydrocarbon group, $L^{b12}$ represents a C1-C14 saturated hydrocarbon group, with the proviso that total carbon number of $L^{b11}$ and $L^{b12}$ is 1 to 14 and * represents a binding position to —$C(Q^1)(Q^2)$ $L^1$ is preferably*—CO—O-$L^{b2}$-, and $L^1$ is more preferably *—CO—O-$L^{b2}$- in which $L^{b2}$ is a single bond or —CH—.

When $L^2$ represents a C1-C17 divalent saturated hydrocarbon group in which one or more —$CH_2$— are replaced by —O— or —CO—, examples thereof include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, *—CO—O-$L^{b10}$-O-$L^{b9}$-CO—O— and *—O-$L^{b12}$-CO—O-$L^{b11}$-, wherein $L^{b2}$, $L^{b3}$, $L^{b4}$, $L^{b5}$, $L^{b6}$, $L^{b7}$, $L^{b8}$, $L^{b9}$, $L^{b10}$, $L^{b11}$ and $L^{b12}$ are the same as defined above, and * represents a binding position to —$W^1$—. $L^2$ is preferably *—CO—O-$L^{b4}$-CO—O-$L^{b3}$- or *—O-$L^{b12}$-CO—O-$L^{b11}$-, and $L^2$ is more preferably *—CO—O-$L^{b4}$-CO—O-$L^{b3}$- in which $L^{b3}$ is a single bond and $L^{b4}$ is —$CH_2$—, or *—O-$L^{b12}$-CO—O-$L^{b11}$- in which $L^{b11}$ is a single bond and $L^{b12}$ is —$CH_2$—.

Examples of *—CO—O-$L^{b2}$- include *—CO—O— and *—CO—O—$CH_2$. Examples of *—CO—O-$L^{b4}$-CO—O-$L^{b3}$- include *—CO—O—$CH_2$—CO—O—, *—CO—O—$(CH_2)_2$—CO—O—, *—CO—O—$(CH_2)_3$—CO—O—, *—CO—O—$(CH_2)_4$—CO—O—, *—CO—O—$(CH_2)_6$—CO—O—, *—CO—O—$(CH_2)_8$—CO—O—, *—CO—O—$CH_2$—CH($CH_3$)—CO—O—, *—CO—O—$CH_2$—C($CH_3$)$_2$—CO—O—, *—CO—O—$CH_2$—CO—O—$CH_2$—, *—CO—O—$CH_2$—CO—O—$(CH_2)_2$—, and the following:

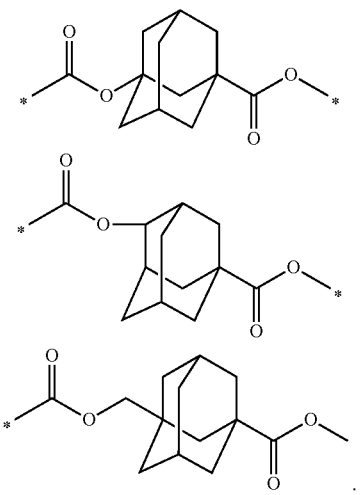

Examples of *-$L^{b5}$-O—CO— include *—$CH_2$—O—CO—, *—$(CH_2)_2$—O—CO—, *—$(CH_2)_3$—O—CO—, *—$(CH_2)_4$—O—CO—, *—$(CH_2)_6$—O—CO— and *—$(CH_2)_8$—O—CO—.

Examples of *-$L^{b7}$-O-$L^{b6}$- include *—$CH_2$—O—$CH_2$—.

Examples of *—CO—O-$L^{b8}$-O— include *—CO—O—$CH_2$—O—, *—CO—O—$(CH_2)_2$—O—, *—CO—O—$(CH_2)_3$—O—, *—CO—O—$(CH_2)_4$—O— and *—CO—O—$(CH_2)_6$—O—.

Examples of *—CO—O-$L^{b10}$-O-$L^{b9}$-CO—O— include the following.

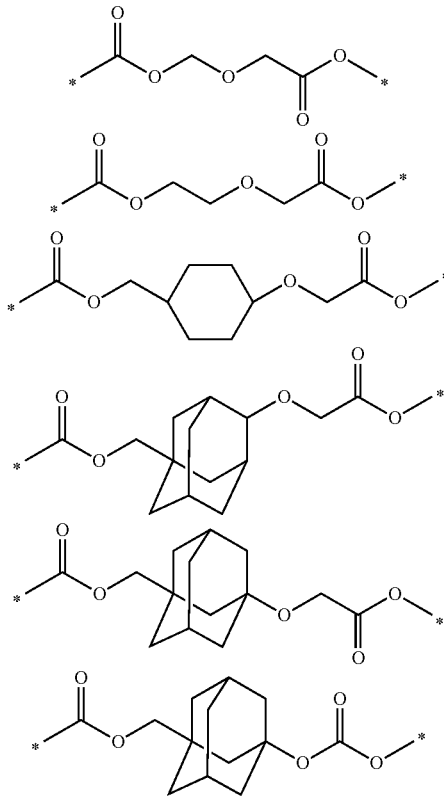

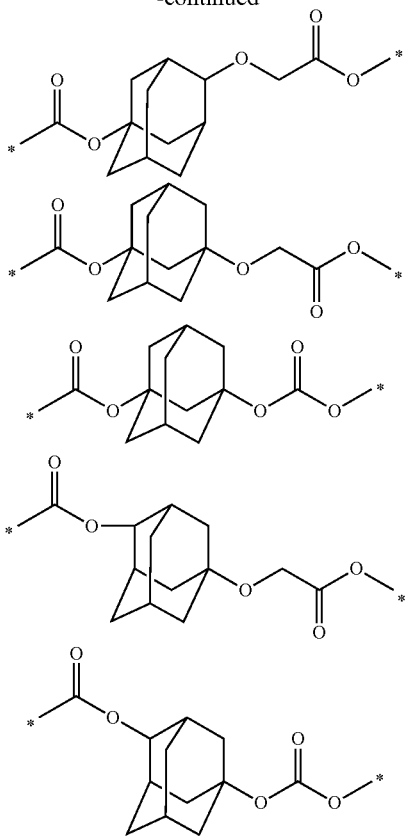

Examples of *—O—L$^{b12}$—CO—O—L$^{b11}$- include *—O—CH$_2$—CO—O—, *—O—(CH$_2$)$_2$—CO—O—, *—O—(CH$_2$)$_3$—CO—O—, *—O—(CH$_2$)$_4$—CO—O—, *—O—(CH$_2$)$_6$—CO—O—, *—O—(CH$_2$)$_8$—CO—O—, *—O—CH$_2$—CH(CH$_3$)—CO—O—, and *—O—CH$_2$—C(CH$_3$)$_2$—CO—O—.

The C3-C36 aliphatic ring represented by ring W$^1$ or ring W$^2$ has no unsaturated bond. Examples of the aliphatic ring include a cyclohexane ring and an adamantane ring, and an adamantane ring is preferable.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group. Examples of the C1-C12 hydrocarbon group include a linear alkyl group, a branched chain alkyl group, and a monocyclic or polycyclic alicyclic hydrocarbon group, and specific examples thereof include a methyl group, an ethyl group, an isopropyl group and a cyclohexyl group.

Examples of the group represented by the following formula (I-A):

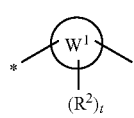

(I-A)

wherein ring W$^1$, R$^2$ and t are the same as defined above, and * represents a binding position to L$^1$, include the following.

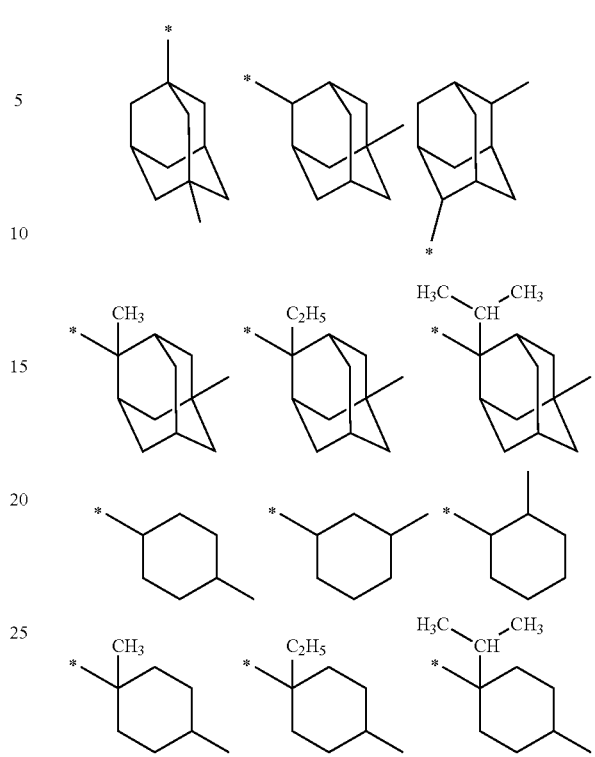

Examples of the group represented by the following formula (I-B):

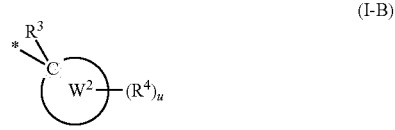

(I-B)

wherein ring W$^2$, R$^3$, R$^4$ and u are the same as defined above, and * represents a binding position to L$^2$, include the following.

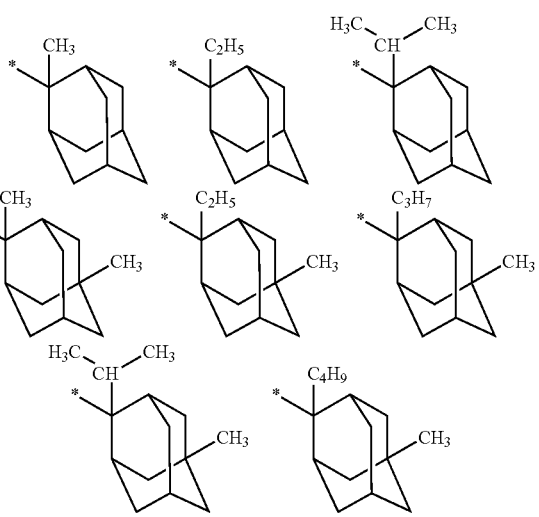

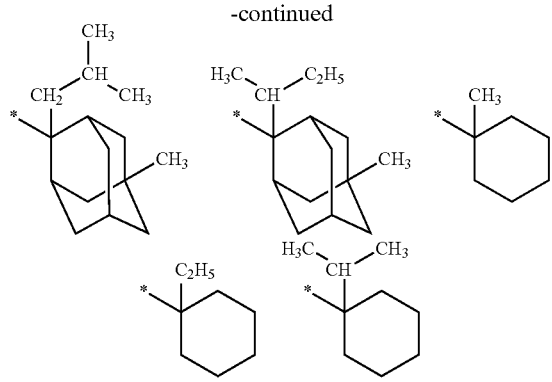
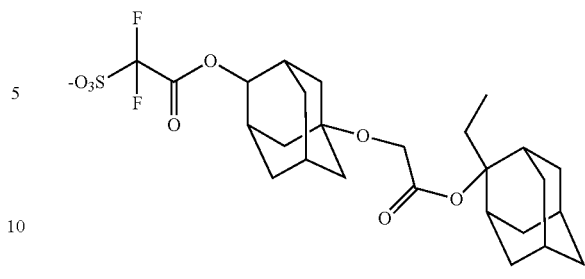
Examples of the anion part of SALT (I) include the following.
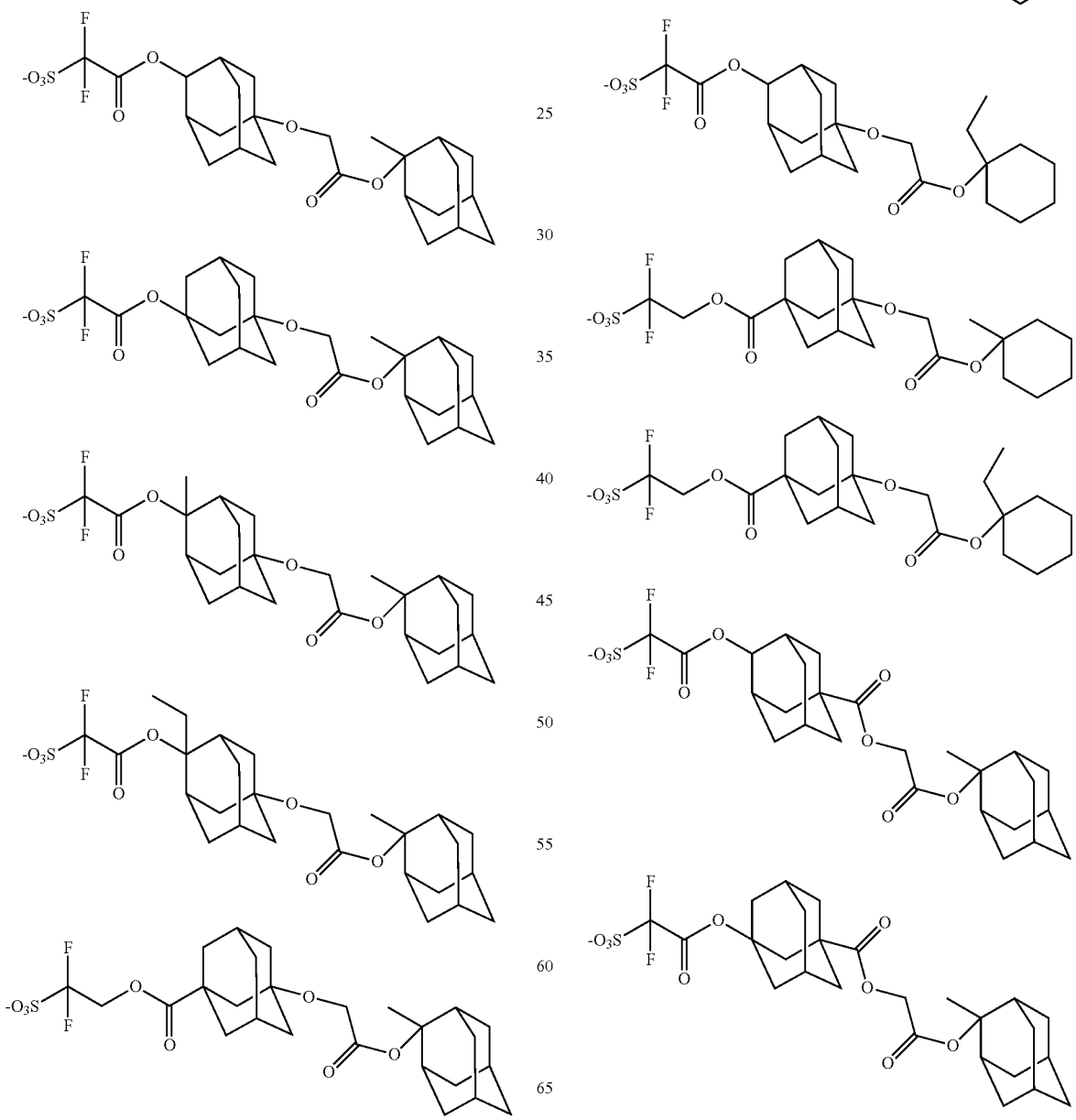

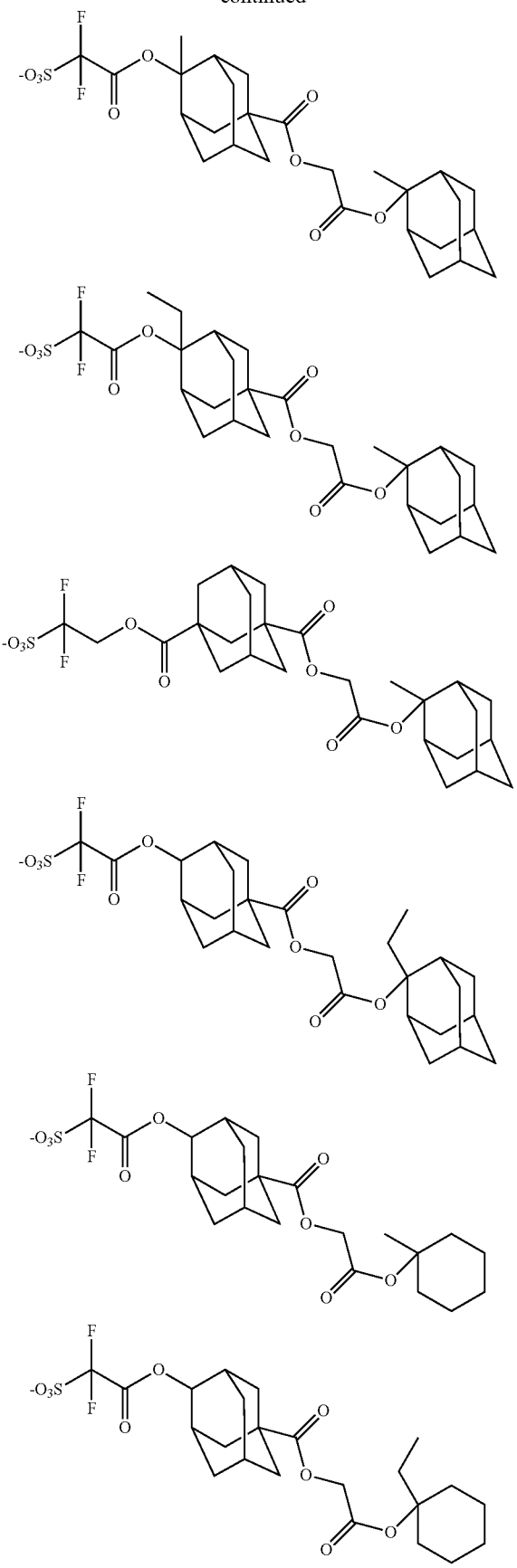

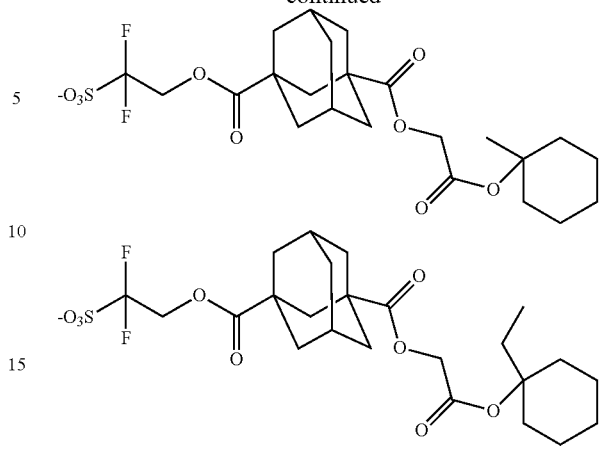

Examples of the organic counter ion represented by $Z^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the organic counter ion represented by $Z^+$ include the organic cations represented by the formulae (b2-1) to (b2-4):

(b2-1)

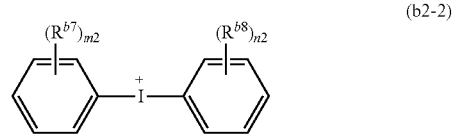

(b2-2)

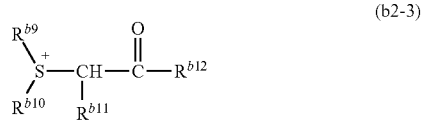

(b2-3)

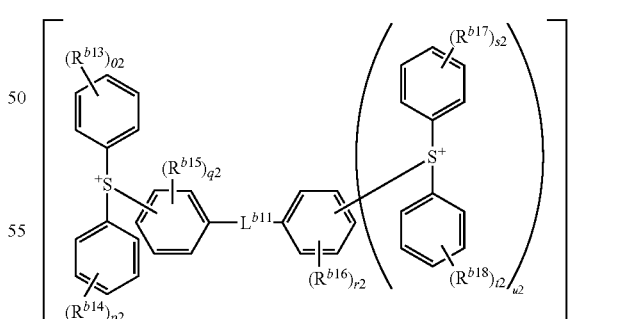

(b2-4)

wherein $R^{b4}$, $R^{b5}$ and $R^{b6}$ independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C18 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 saturated cyclic hydrocarbon group and a C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ independently represent a C1-C18 aliphatic hydrocarbon group or a C3-C18 saturated cyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C1-C18 aliphatic hydrocarbon group, a C3-C18 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Preferable examples of the aliphatic hydrocarbon group represented by $R^{b4}$ to $R^{b6}$ include an alkyl group such as a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group.

Preferable examples of the saturated cyclic hydrocarbon group represented by $R^{b4}$ to $R^{b6}$ include a cyclopentyl group, a cyclohexyl group, an adamantyl group and an isobornyl group, and more preferable examples thereof include a cyclopentyl group and a cyclohexyl group.

Preferable examples of the aromatic group include represented by by $R^{b4}$ to $R^{b6}$ a phenyl group, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the halogen atom include a fluorine atom, a chlorine atom, a bromine atom and an iodine atom. Examples of the C2-C4 acyl group include an acetyl group, a propyonyl group and a butyryl group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms.

Preferable examples of the aliphatic hydrocarbon group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group represented by $R^{b9}$ to $R^{b11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group represented by $R^{b11}$ to $R^{b12}$ include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group.

Examples of the C3-C12 divalent acyclic hydrocarbon group formed by bonding $R^{b9}$ and $R^{b10}$ include a trimethylene group, a tetramethylene group and a pentamethylene group. Examples of the divalent ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

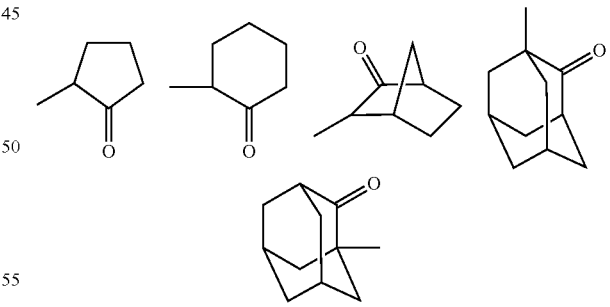

A C1-C5 divalent acyclic hydrocarbon group is preferable.

Examples of the C2-C13 acyloxy group include an acetyloxy group, a propyonyloxy group, a butyryloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

Among the above-mentioned cations, preferred is the cation represented by the formula (b2-1), and more preferred is the cation represented by the formula (b2-1-1). A triphenyl-sulfonium cation and a trytolysulfonium cation are especially preferable.

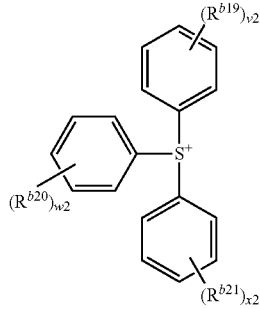

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, a C3-C18 saturated cyclic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and $R^{b19}$ and $R^{b20}$, and $R^{b19}$ and $R^{b21}$ or $R^{b20}$ and $R^{b21}$ can be bonded each other to form a single bond, —O— or a C1-C4 aliphatic divalent hydrocarbon group which forms a sulfur containing ring together with $S^+$ and v2, w2 and x2 independently each represent an integer of 0 to 5.

The aliphatic hydrocarbon group has preferably 1 to 12 carbon atoms, and the saturated cyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

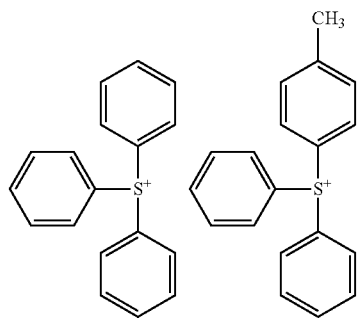

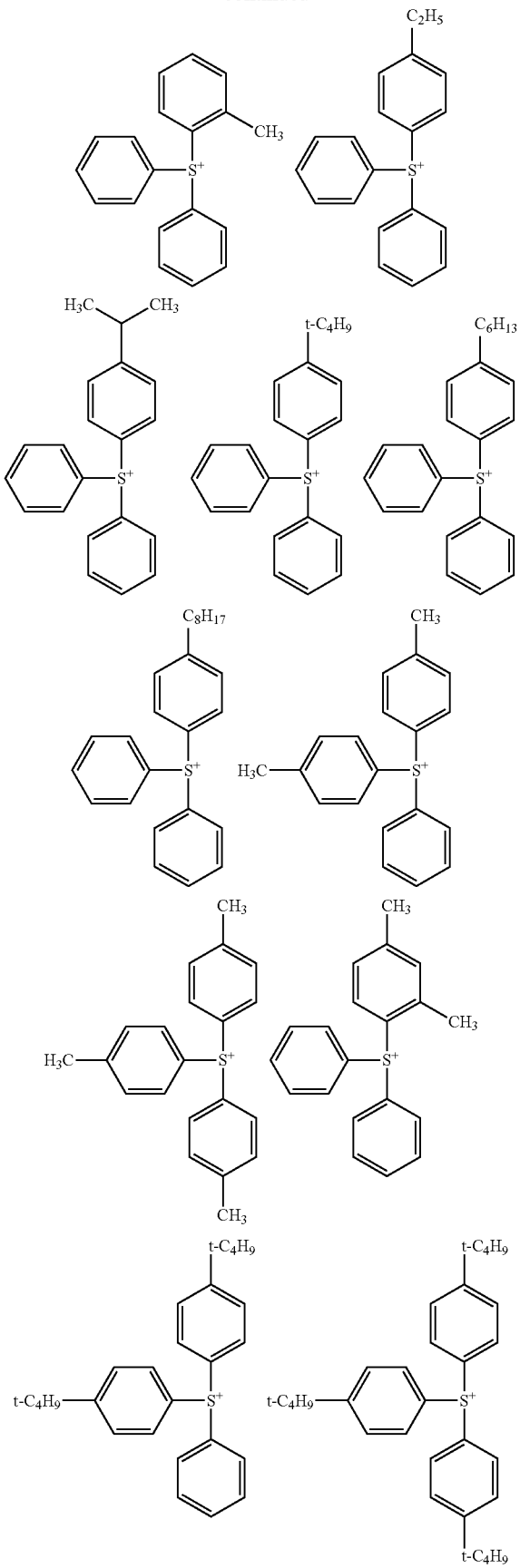

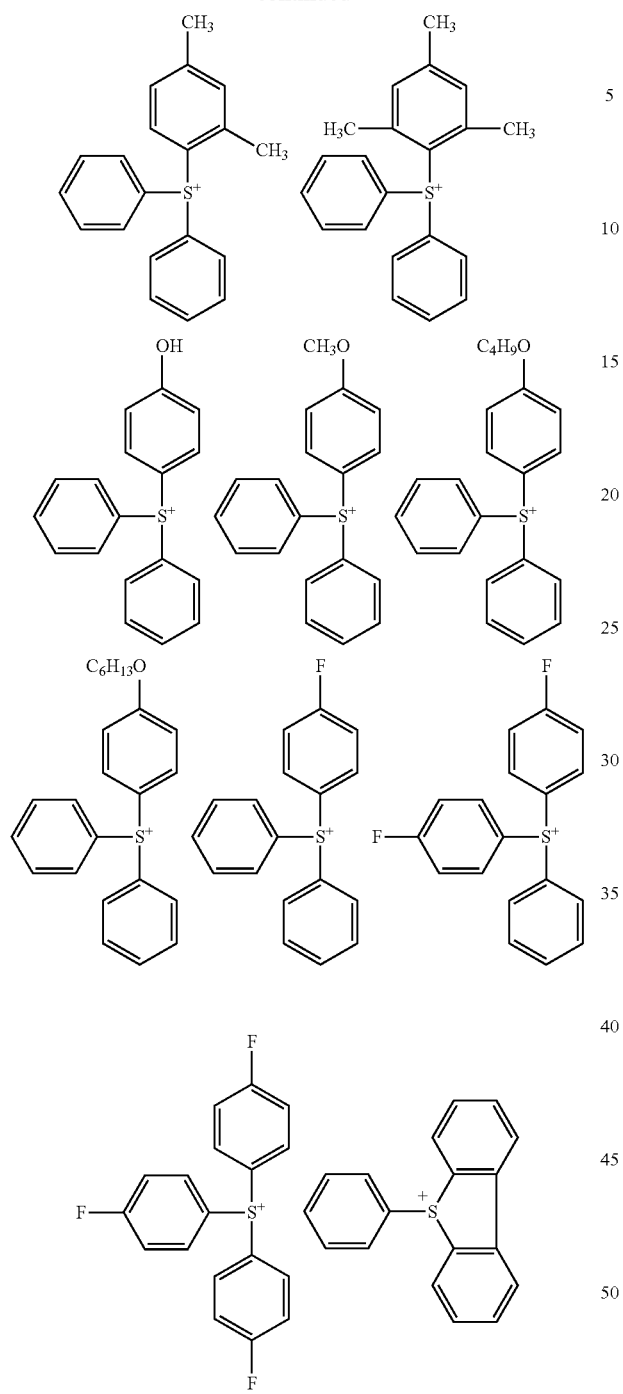
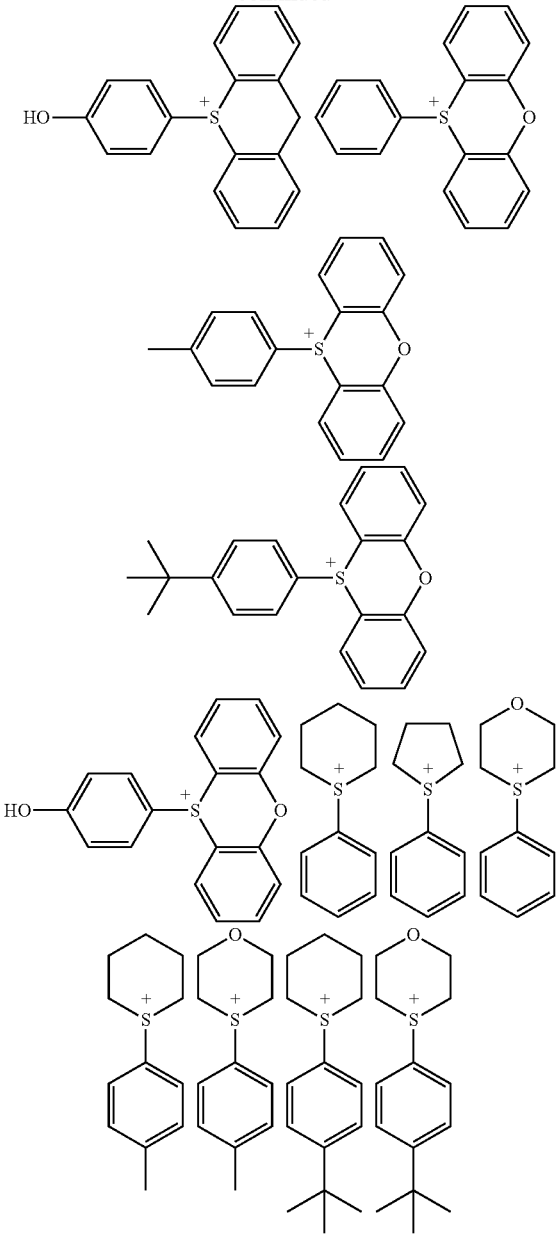
Examples of the cation represented by the formula (b2-2) include the followings.
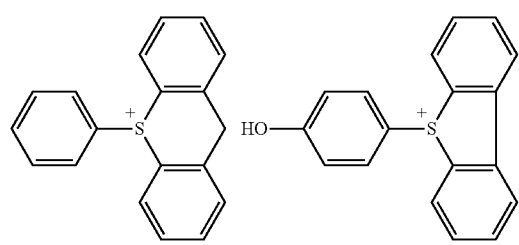
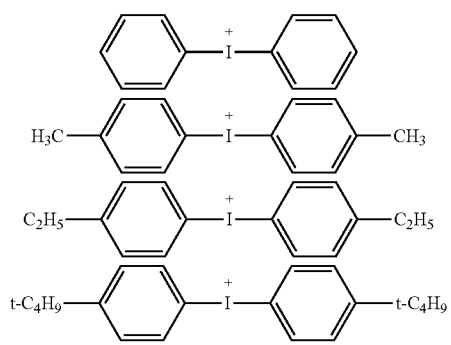

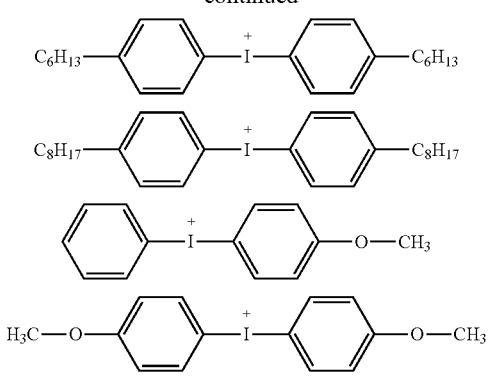
Examples of the cation represented by the formula (b2-3) include the followings.
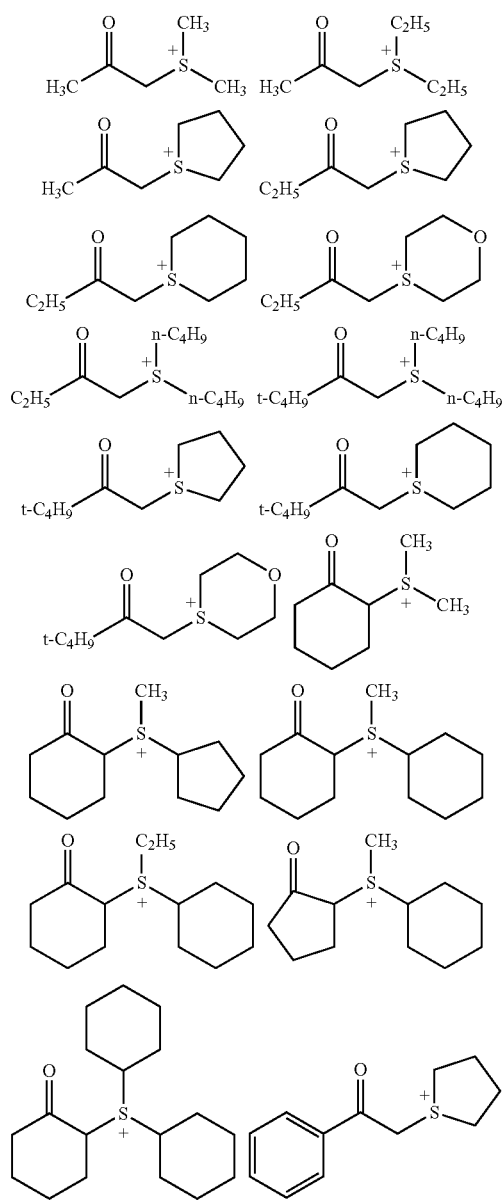
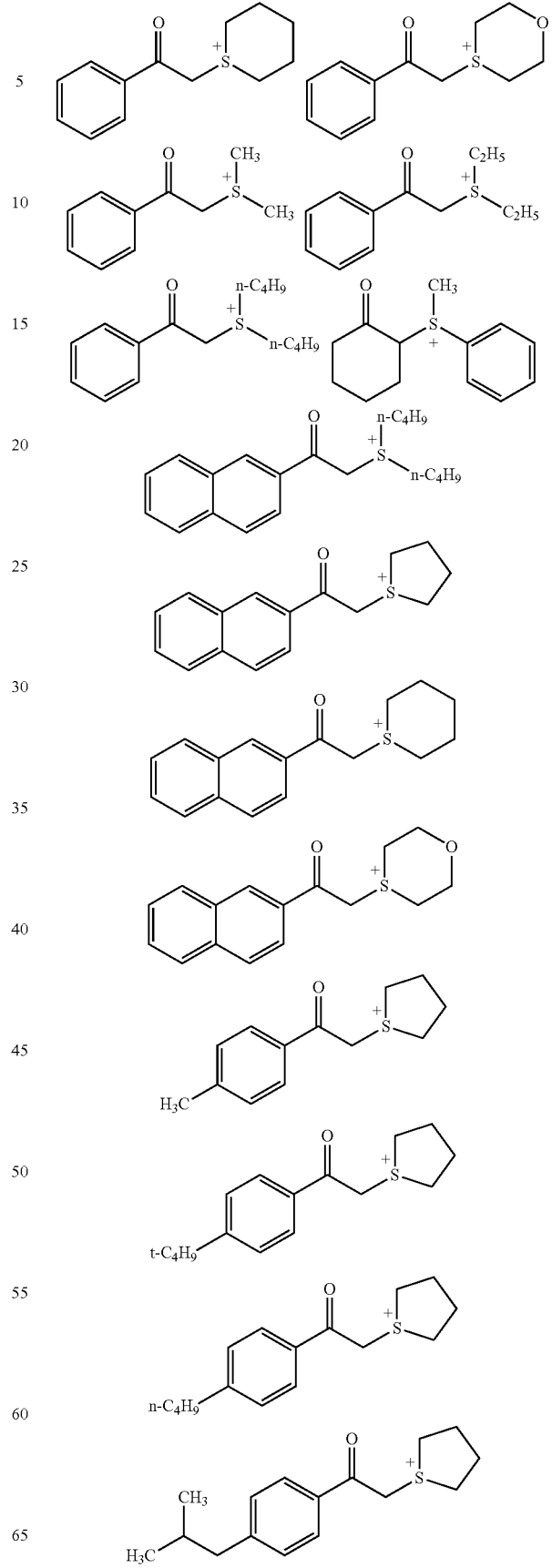

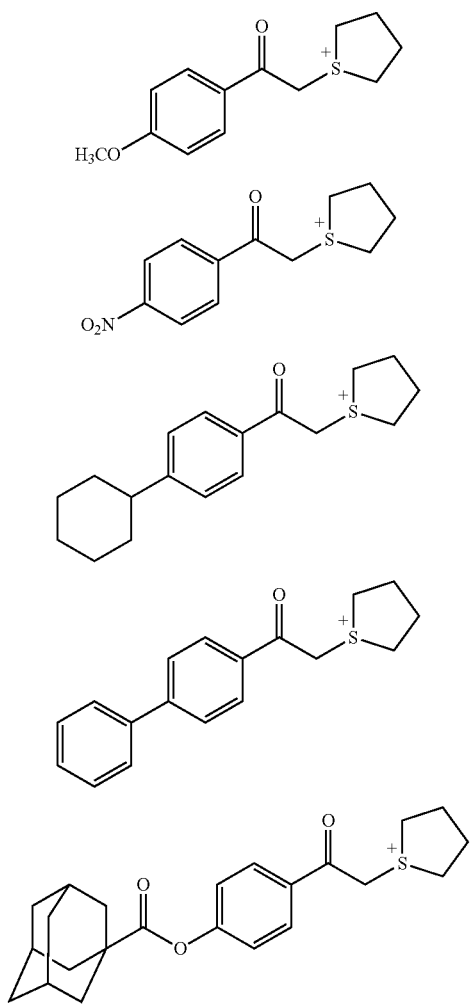
Examples of the cation represented by the formula (b2-4) include the followings.
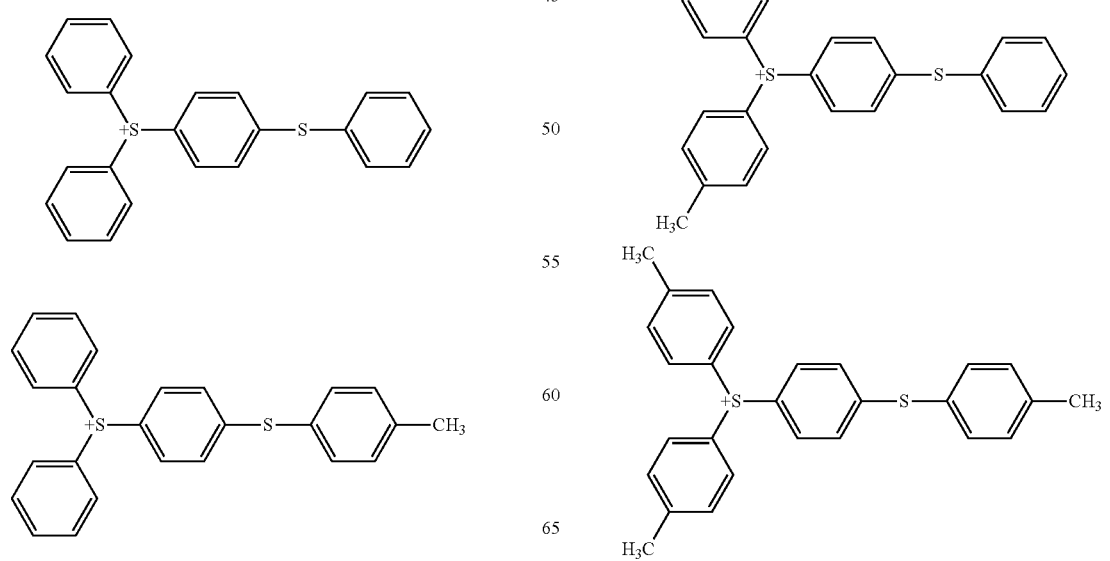

-continued
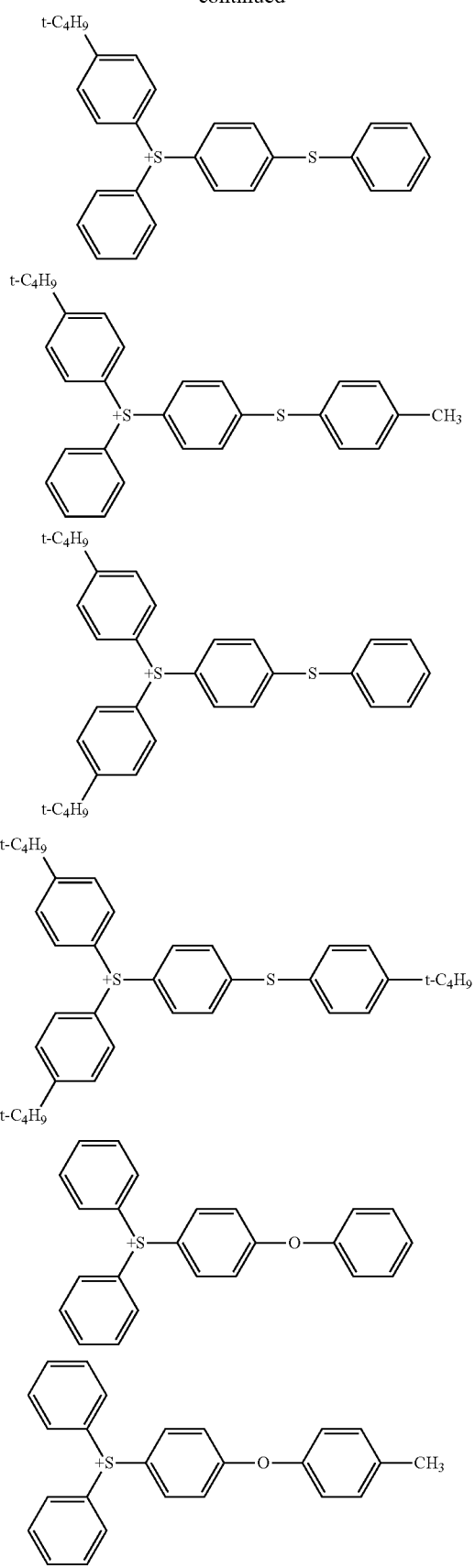
-continued
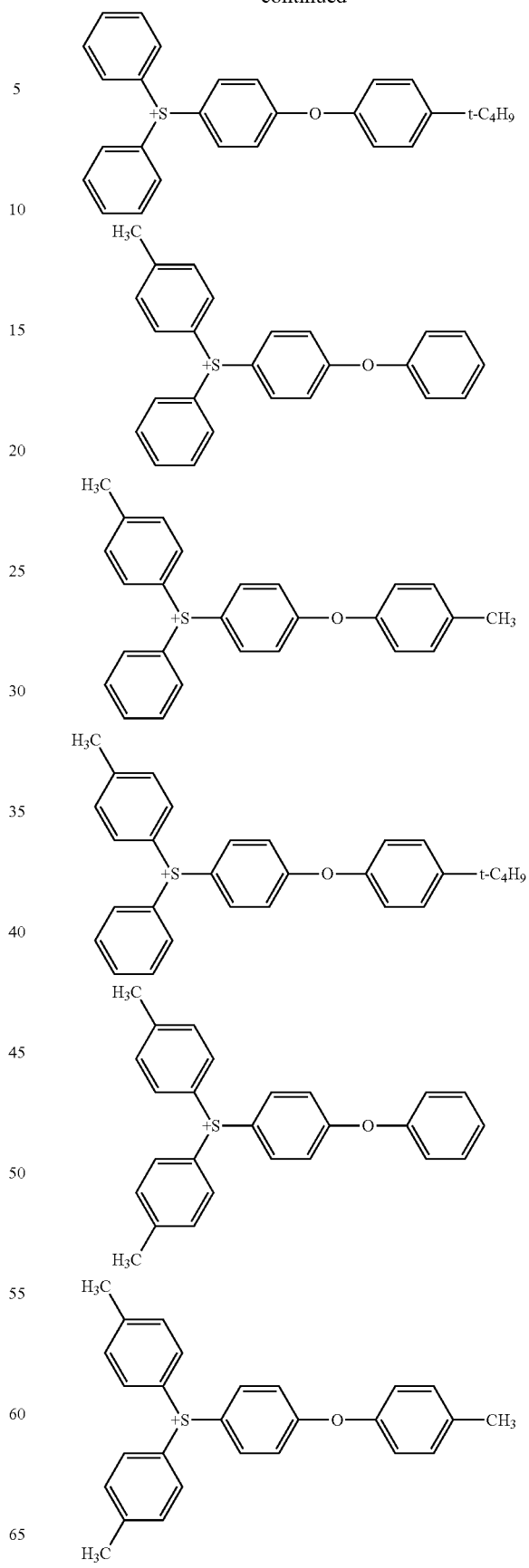

-continued
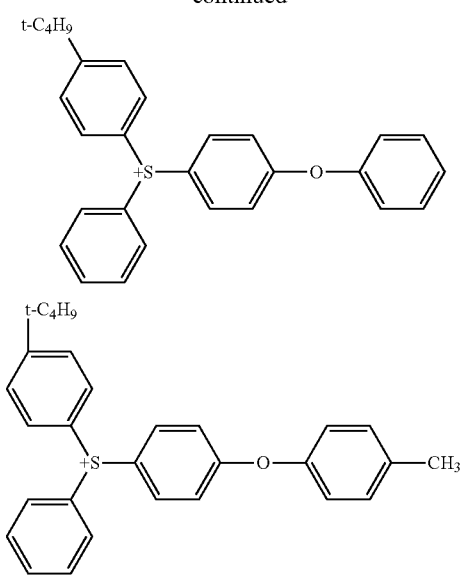
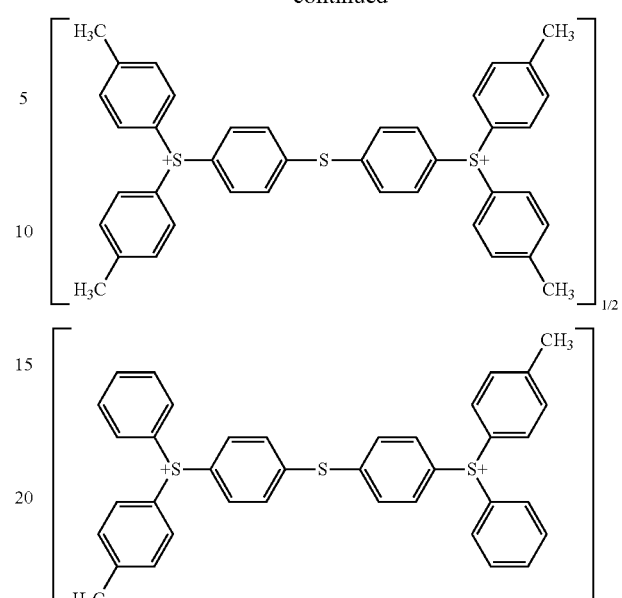
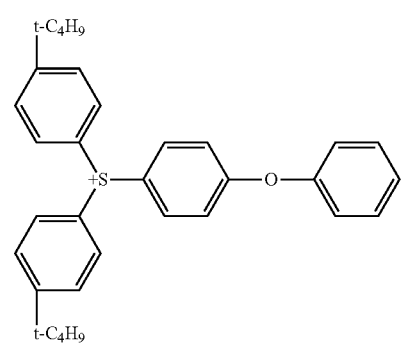
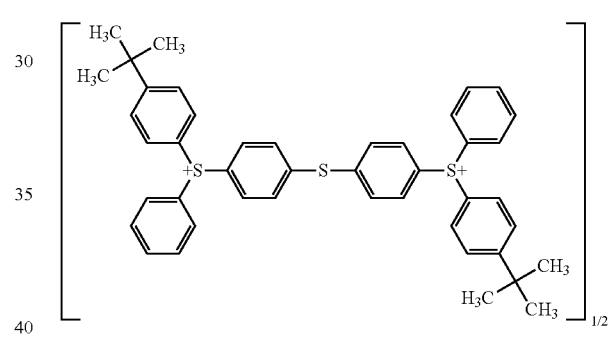
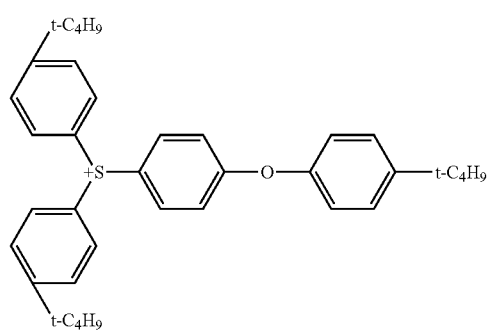
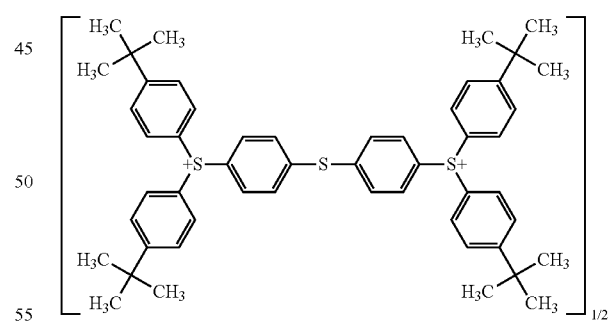
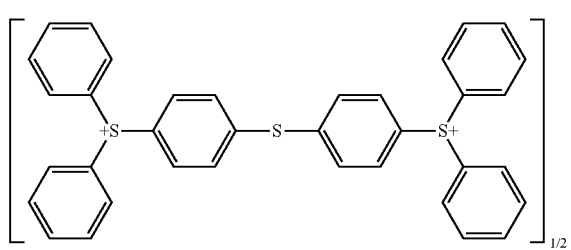
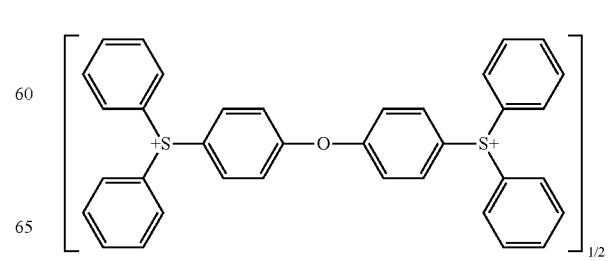

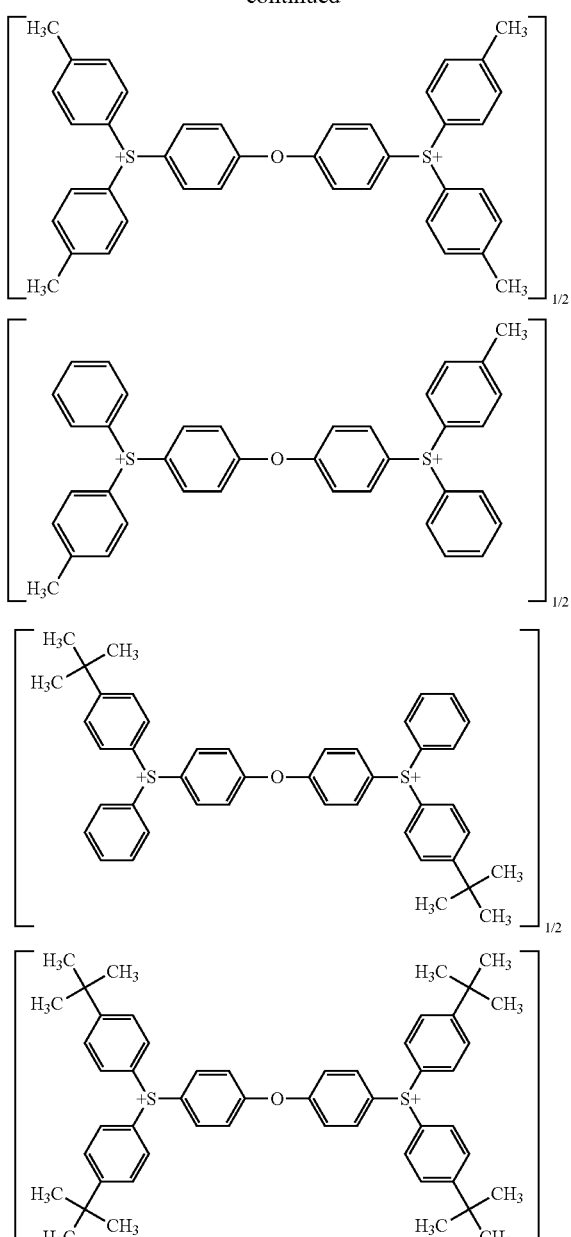
Examples of SALT (I) include a salt wherein the anion is any one of the above-mentioned anions and the cation is any one of organic cations. Preferable examples of SALT (I) include the following.
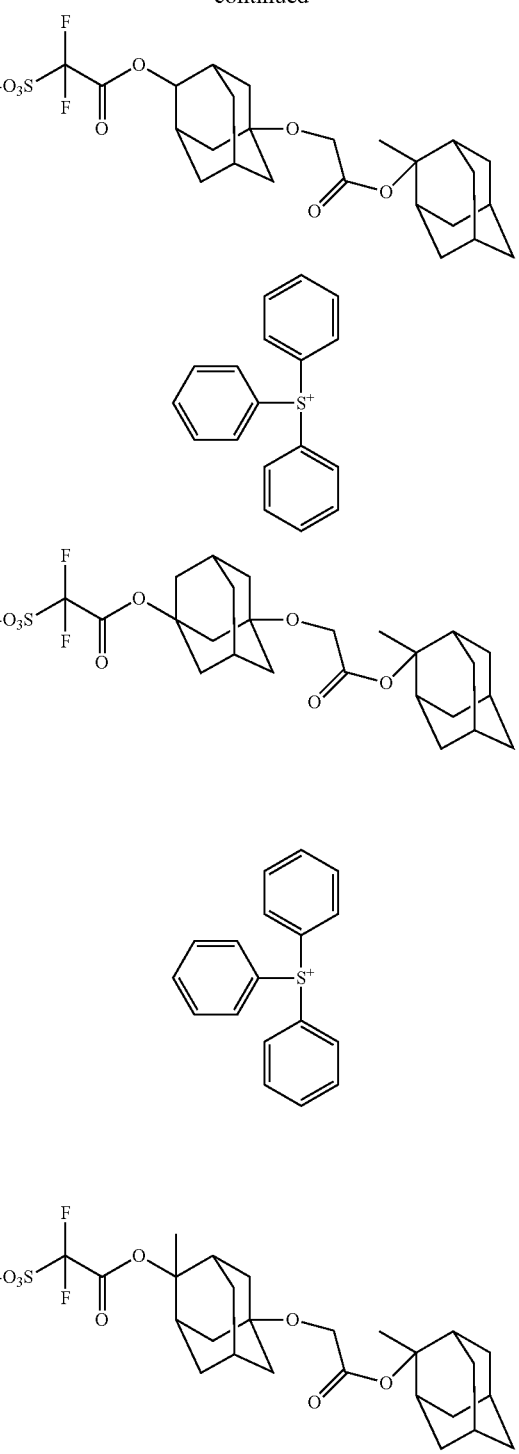

27
-continued
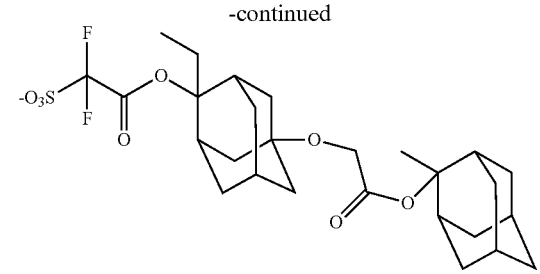
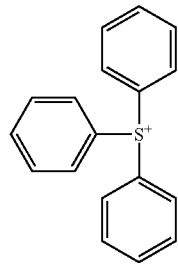
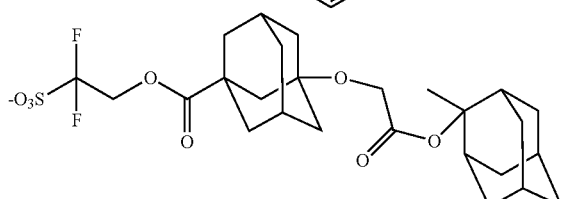
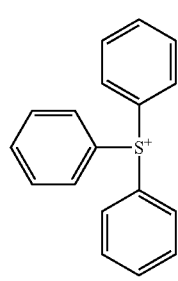
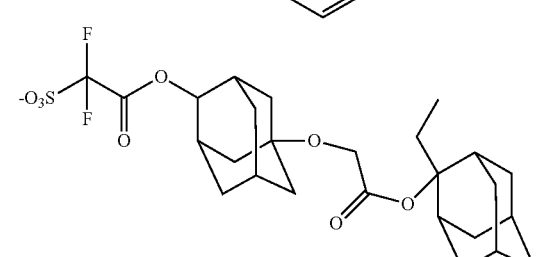
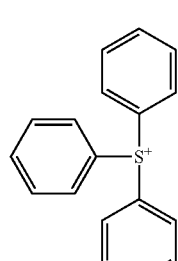
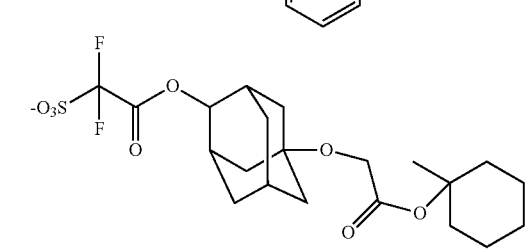
28
-continued
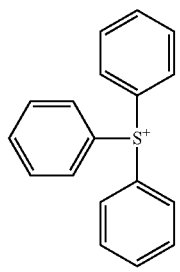
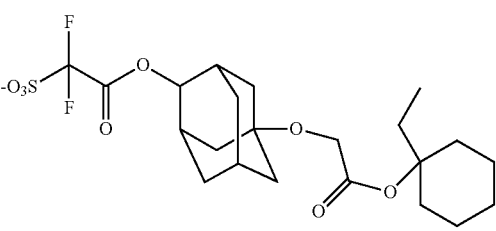
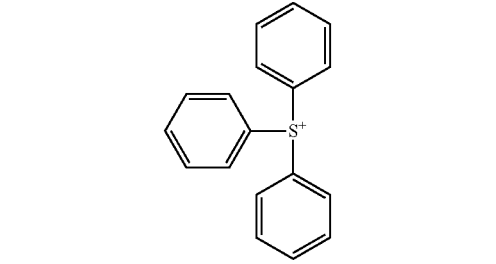
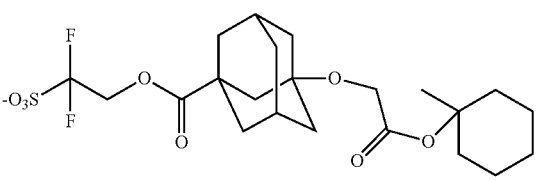
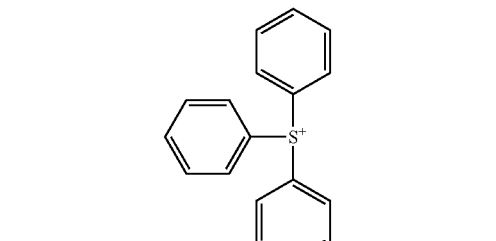
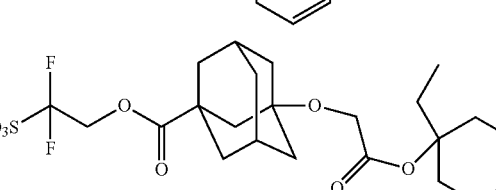
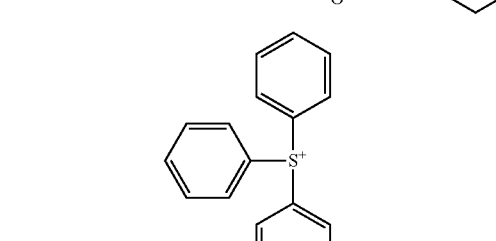
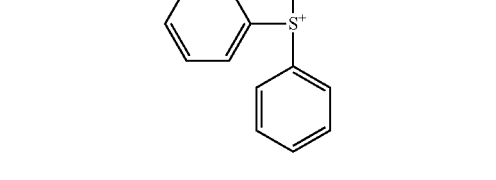

29
-continued
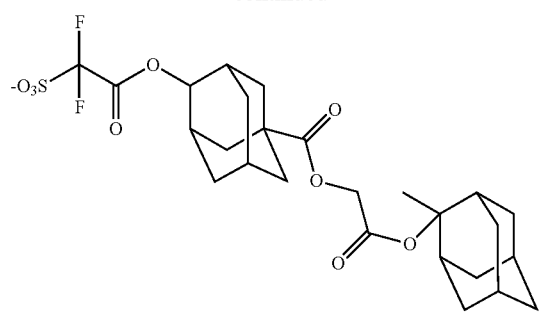
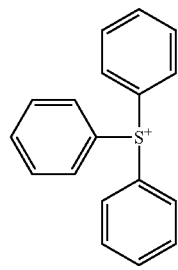
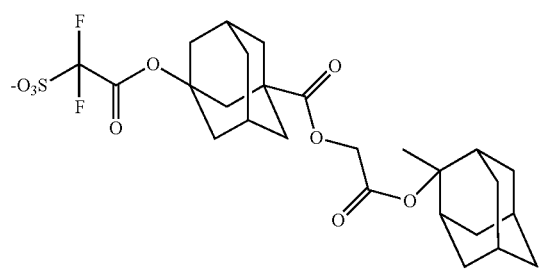
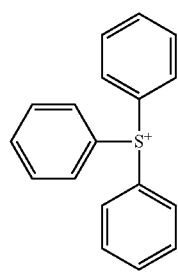
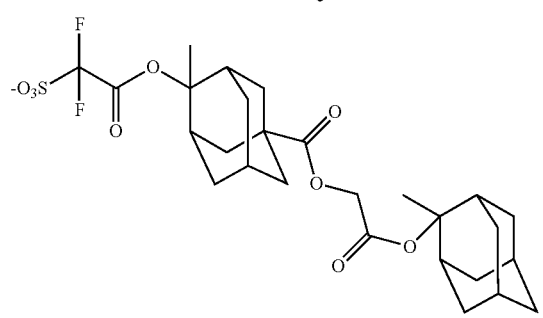
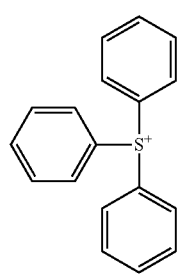
30
-continued
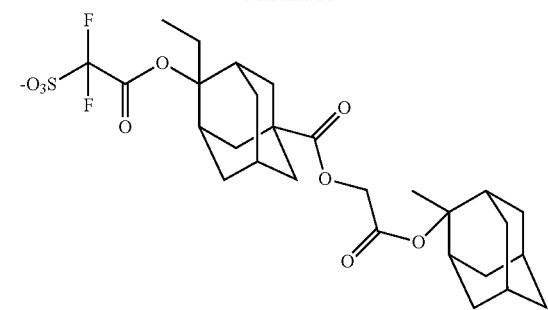
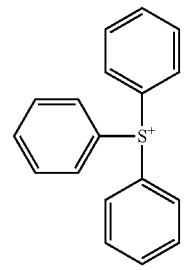
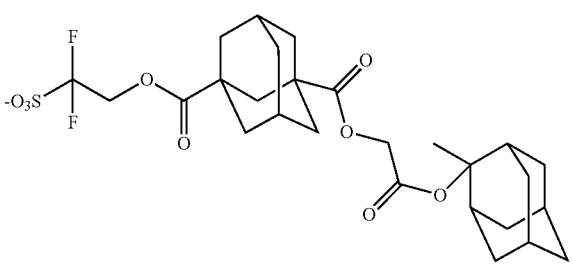
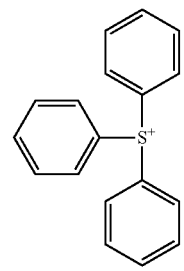
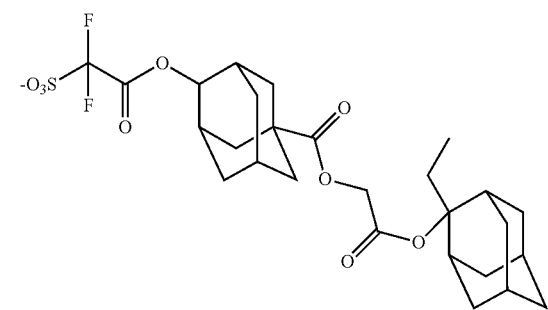
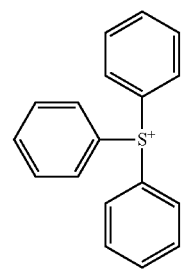

31
-continued
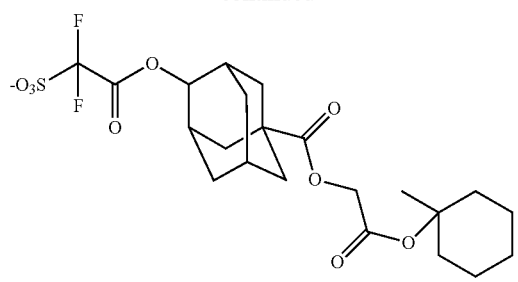
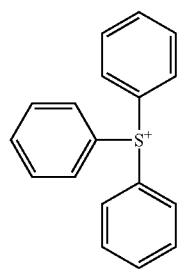
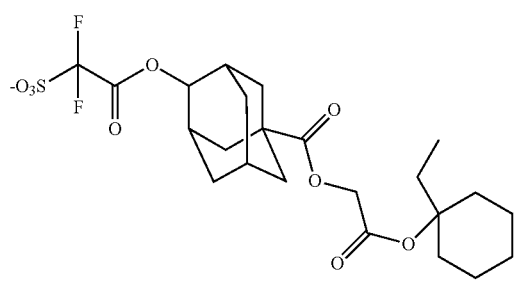
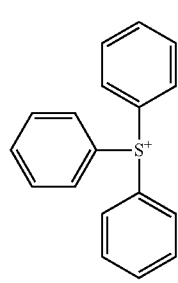
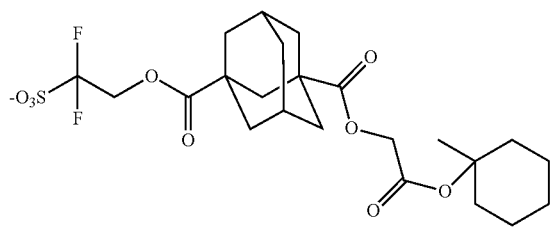
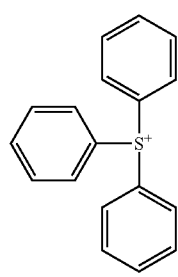
32
-continued
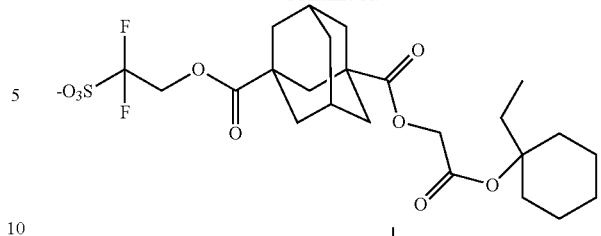
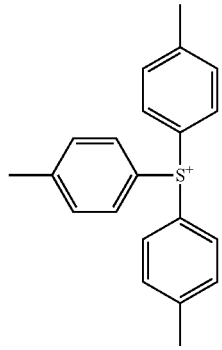
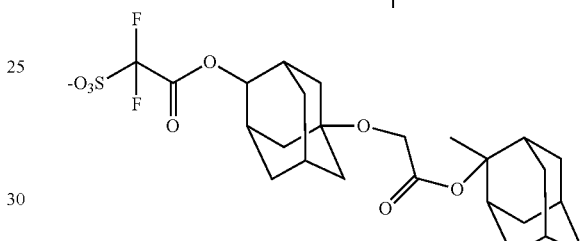
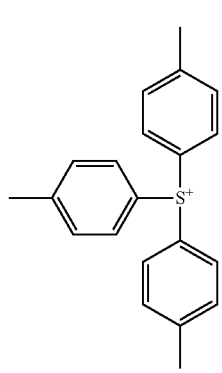
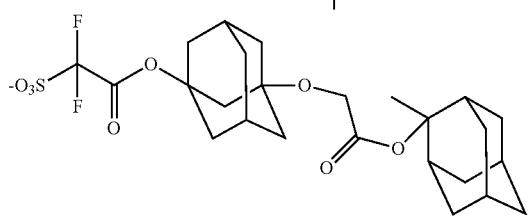
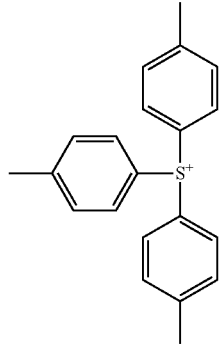

33
-continued
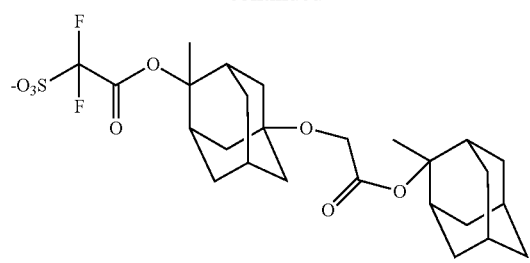
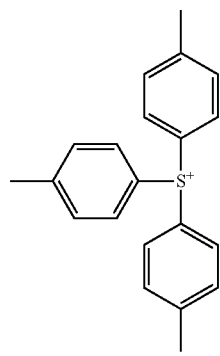
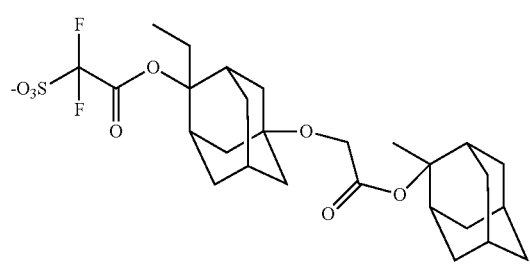
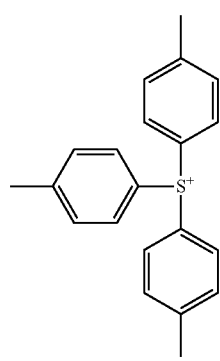
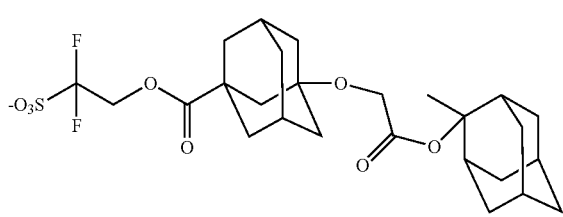
34
-continued
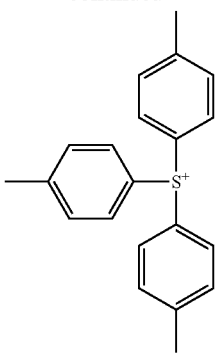
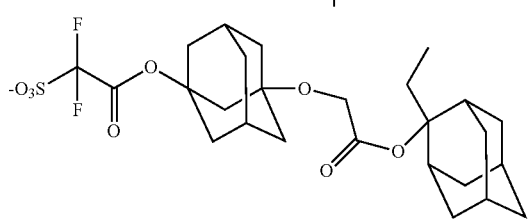
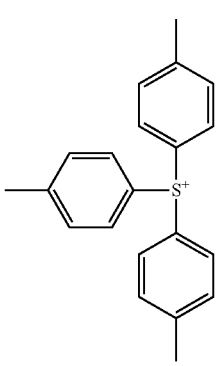
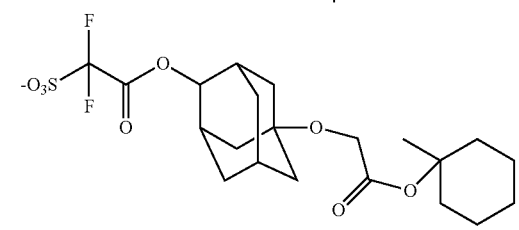
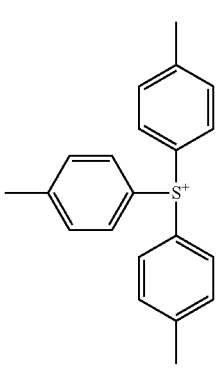
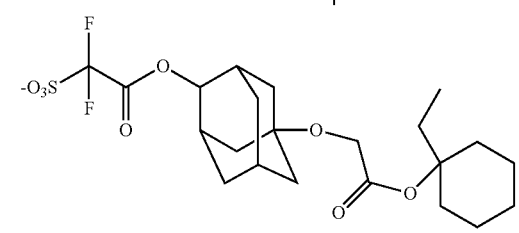

35
-continued
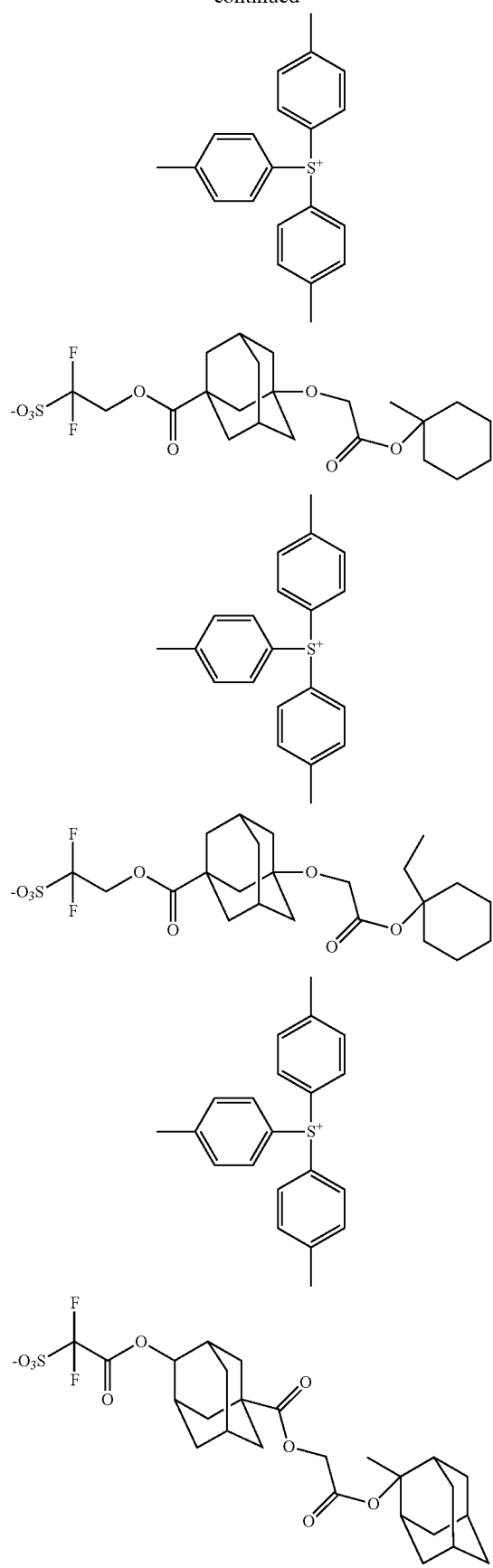
36
-continued
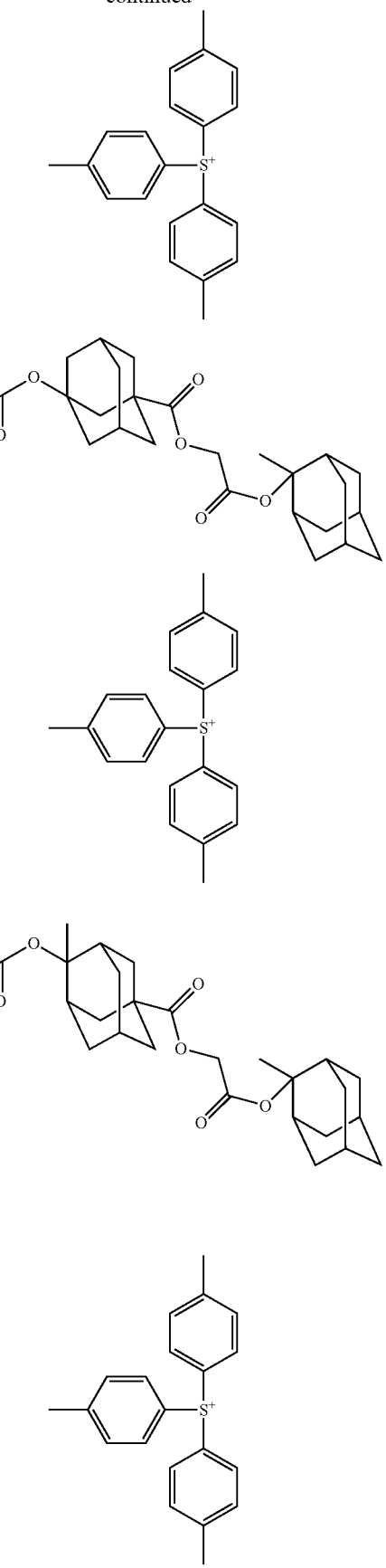

37
-continued
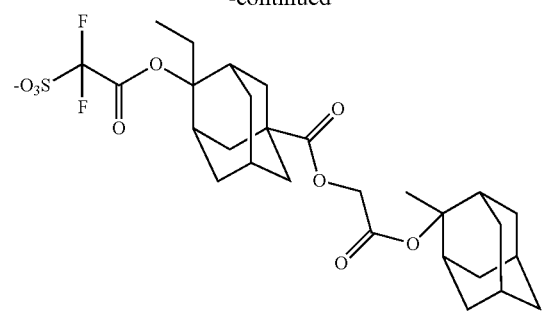
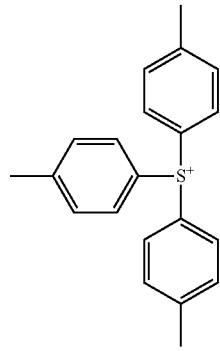
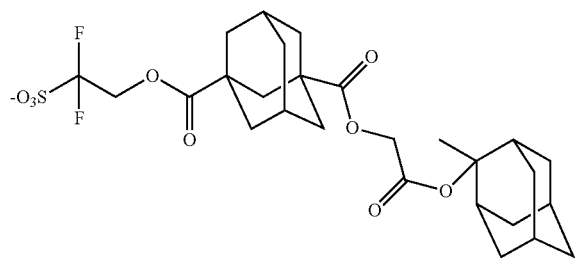
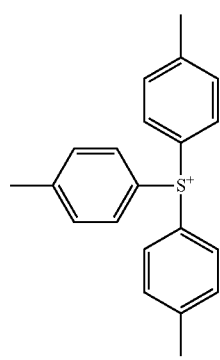
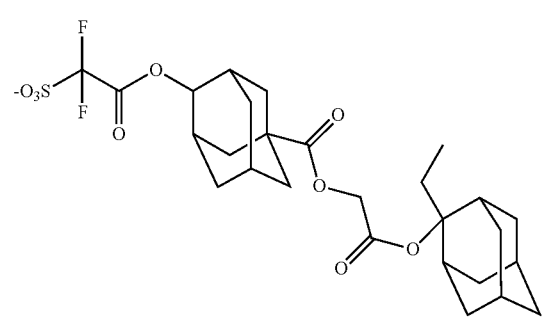
38
-continued
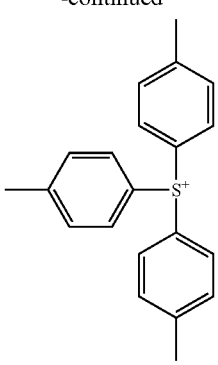
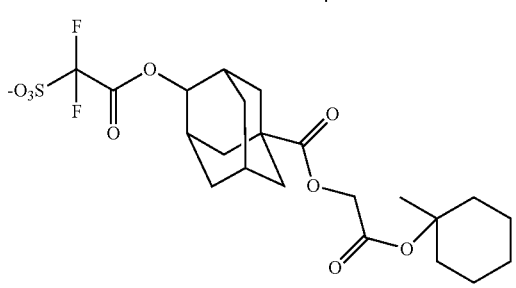
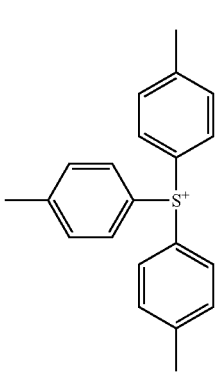
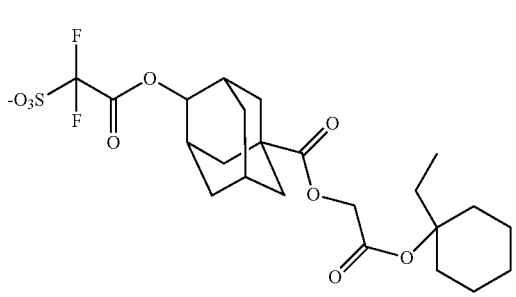
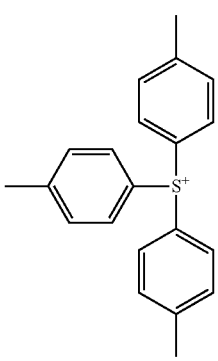

-continued
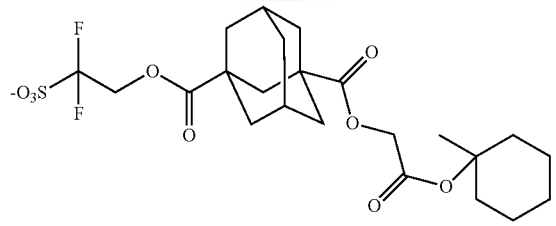
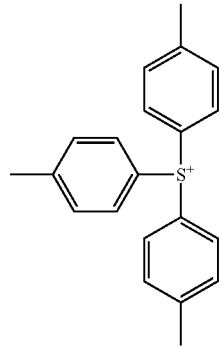
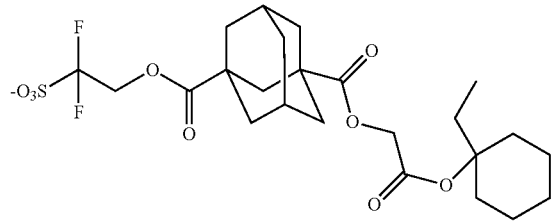
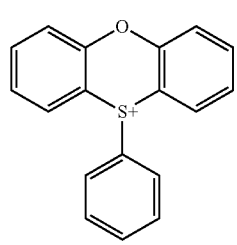
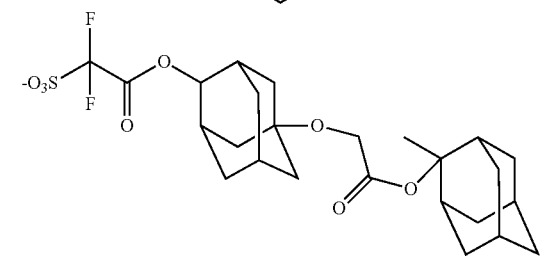
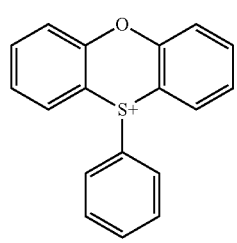
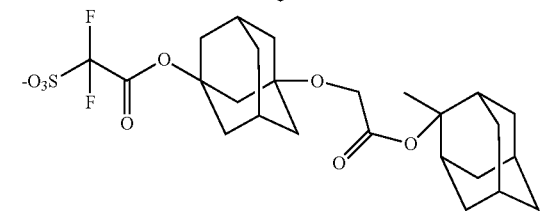
-continued
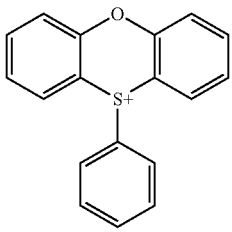
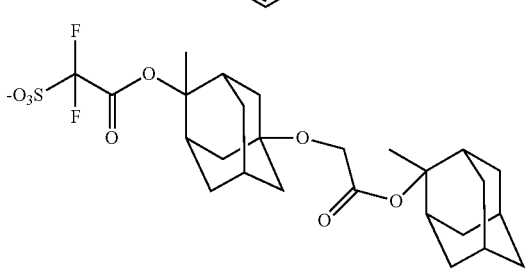
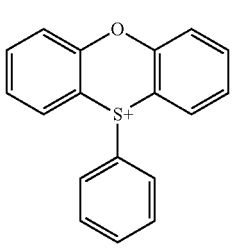
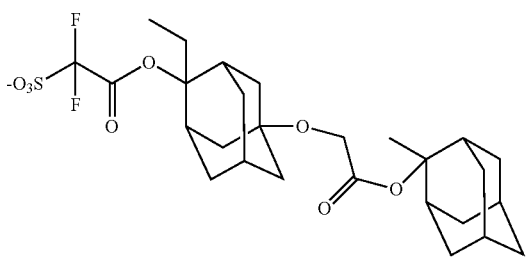
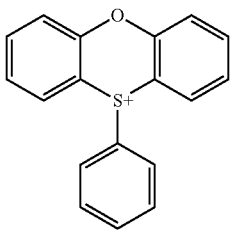
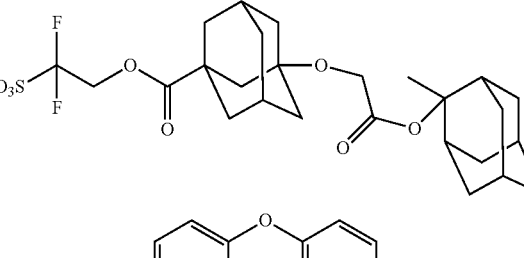
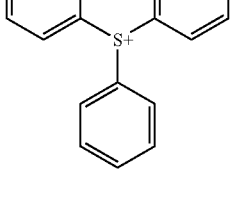

41
-continued
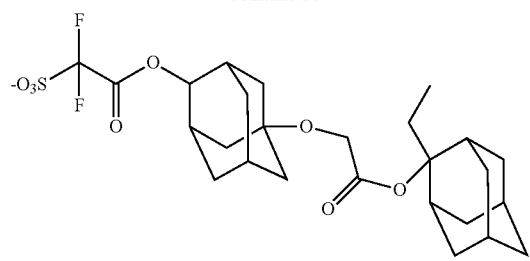
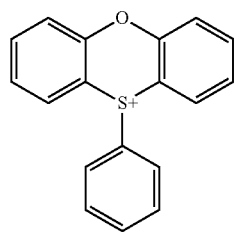
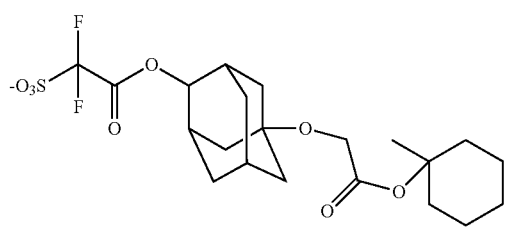
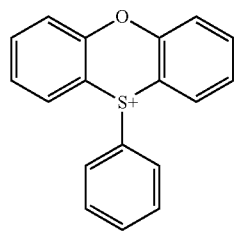
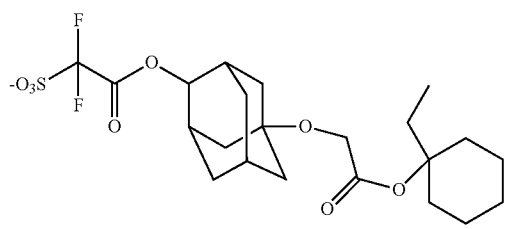
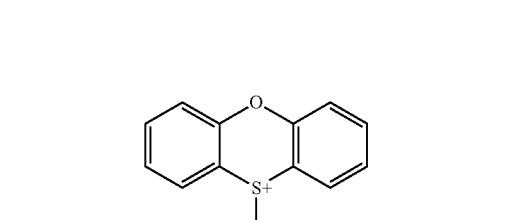
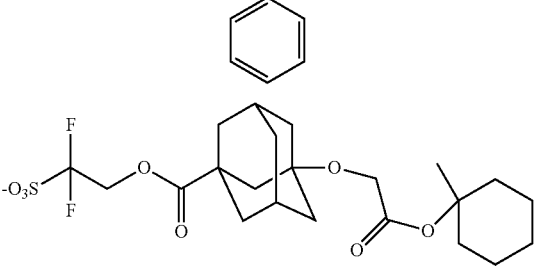
42
-continued
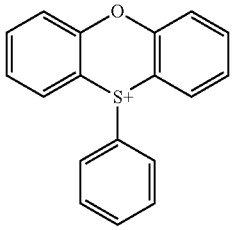
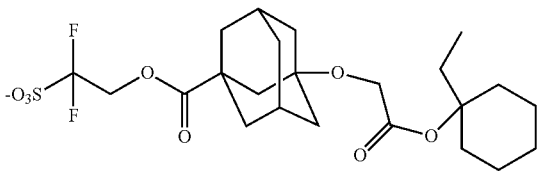
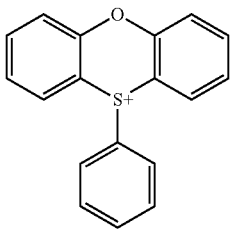
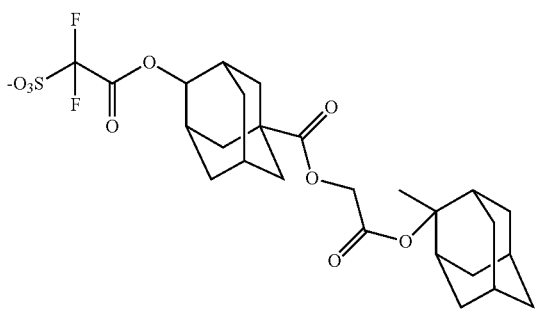
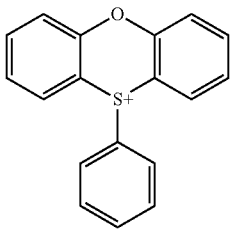
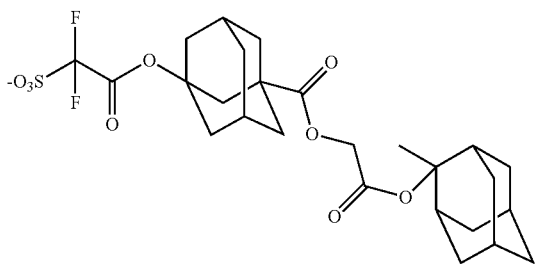
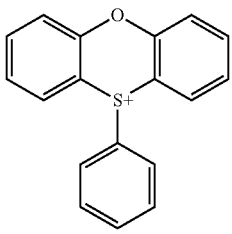

43
-continued
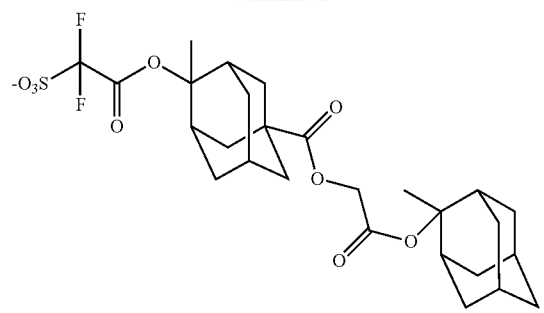
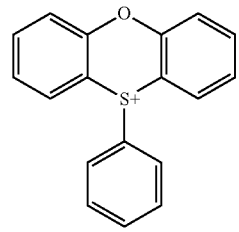
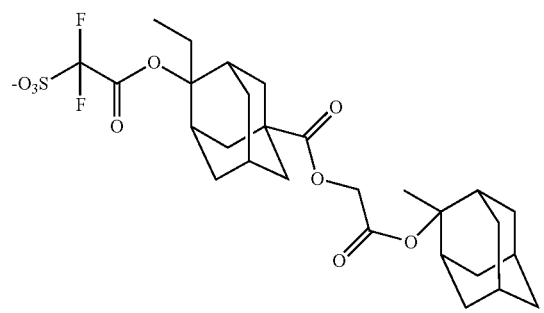
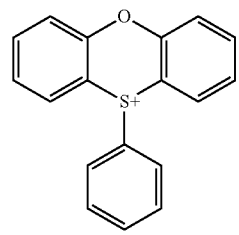
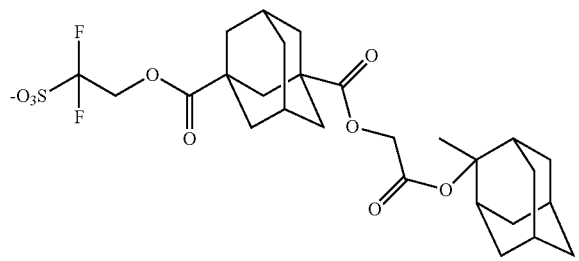
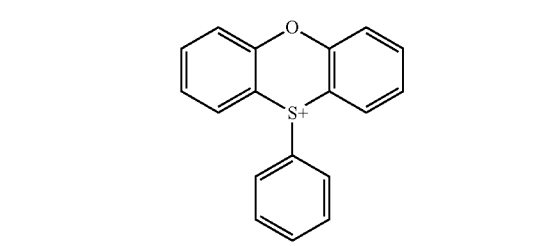
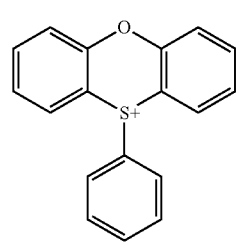
44
-continued
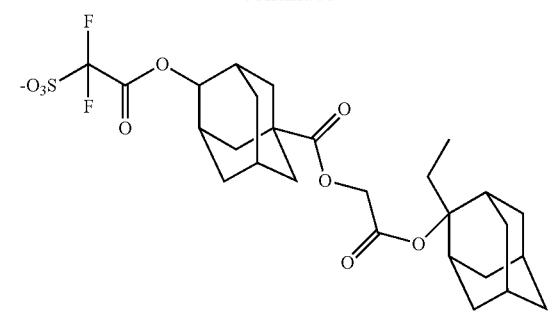
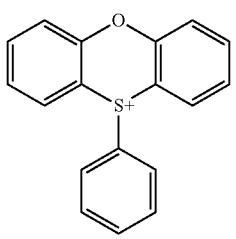
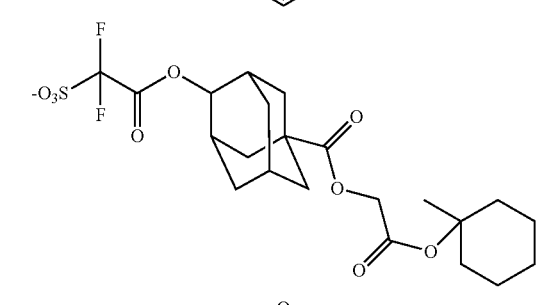
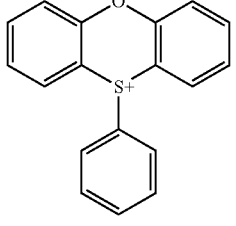
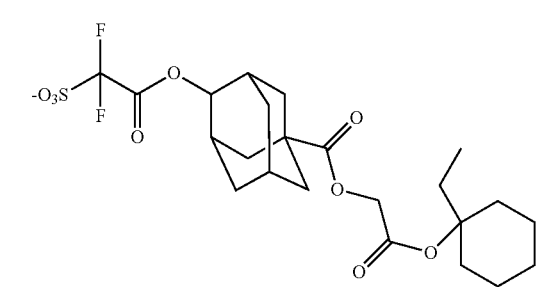
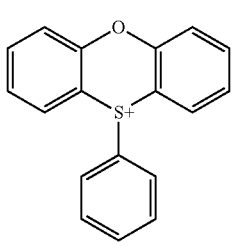

45
-continued
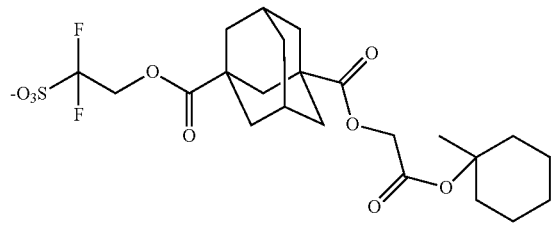
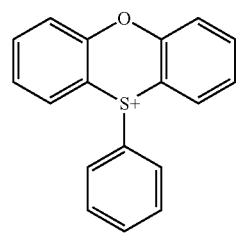
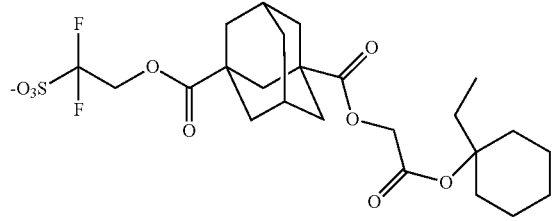
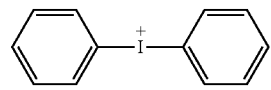
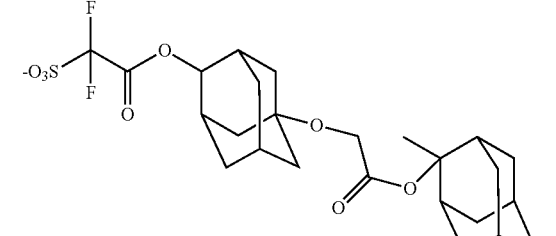
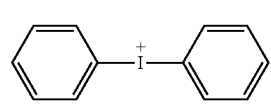
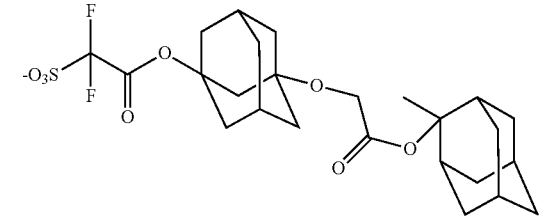
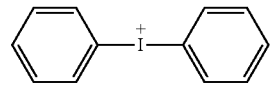
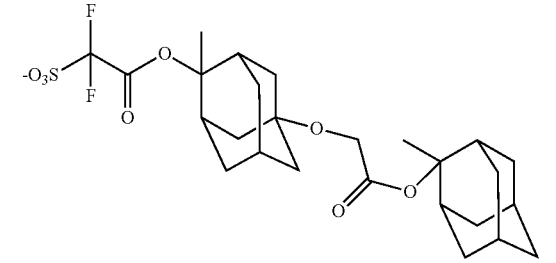
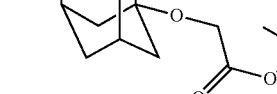
46
-continued
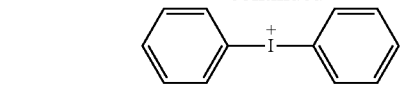
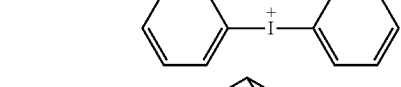
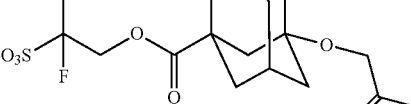
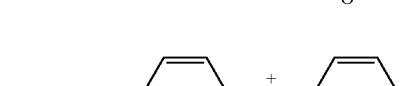
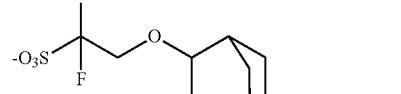
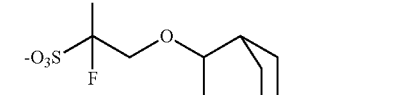

47
-continued
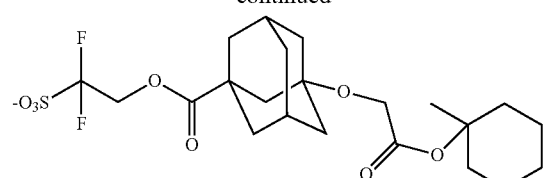
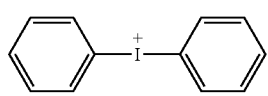
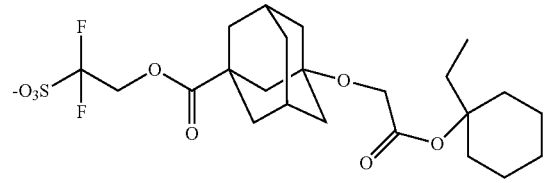
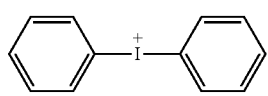
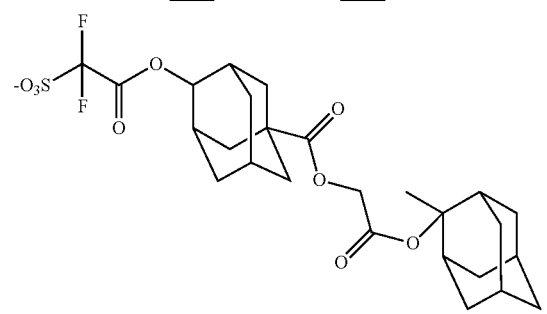
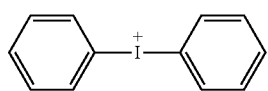
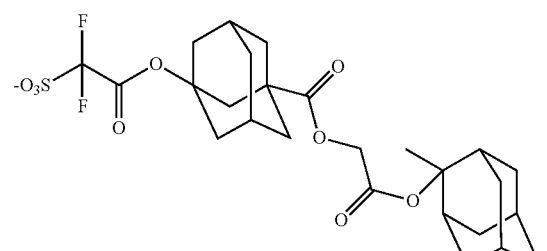
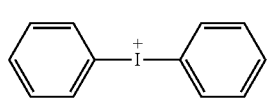
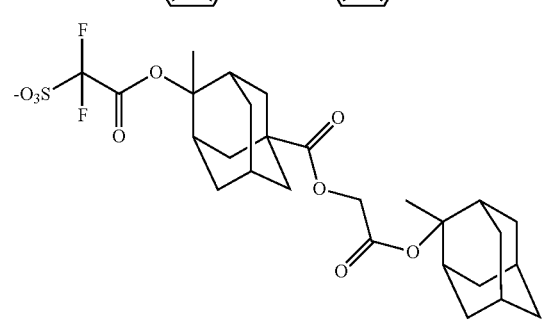
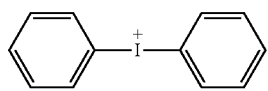
48
-continued
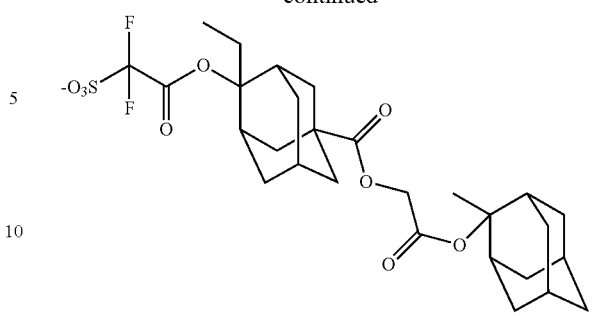
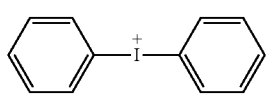
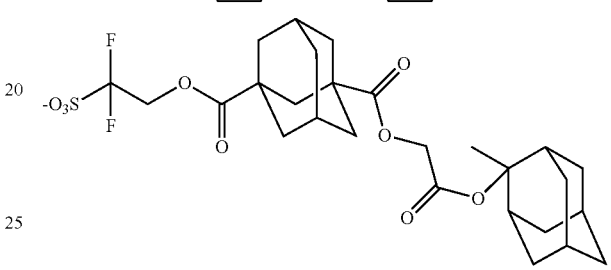
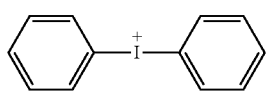
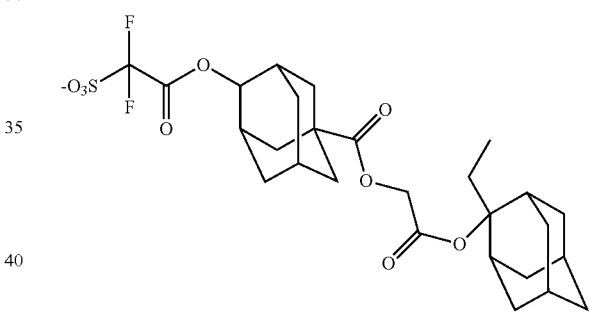
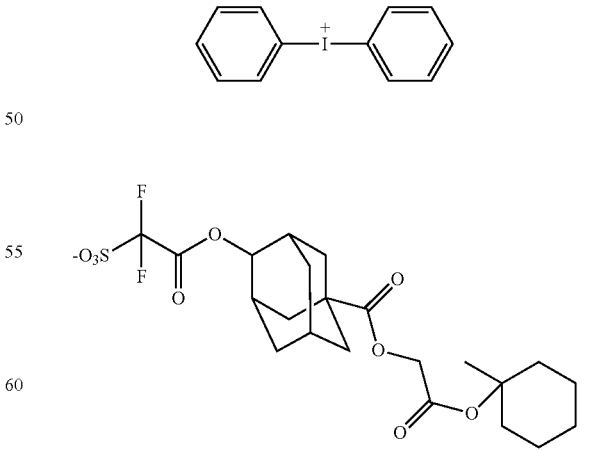
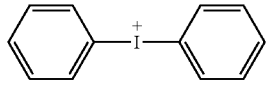

49
-continued
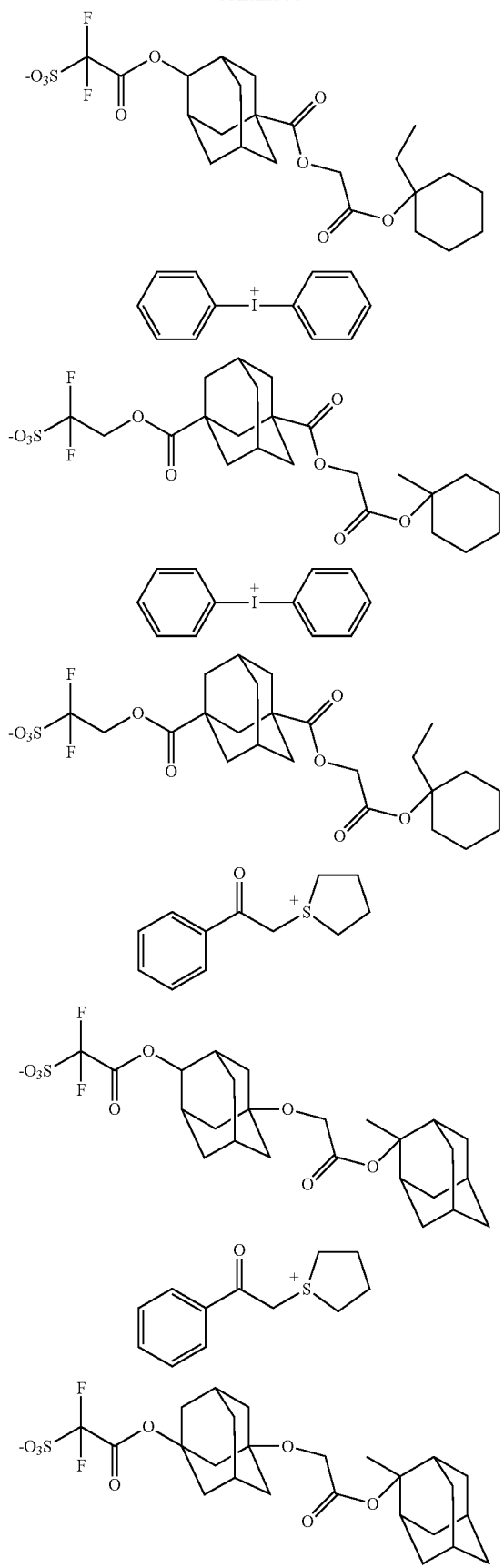
50
-continued
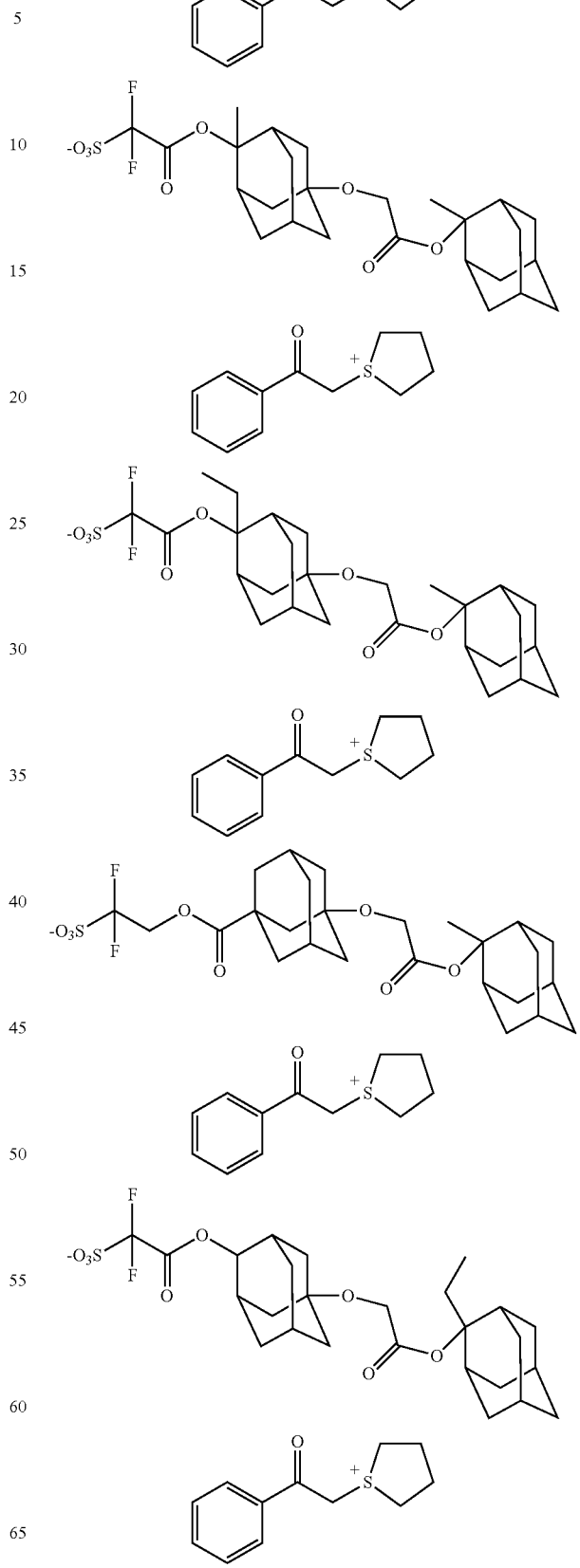

51
-continued
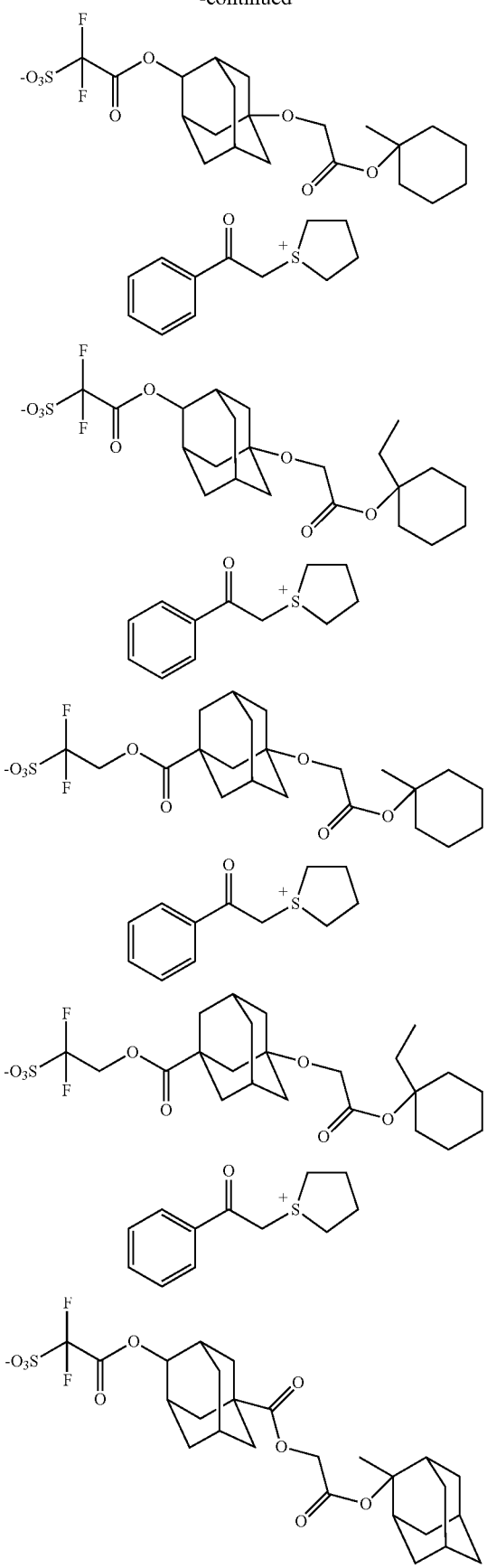
52
-continued
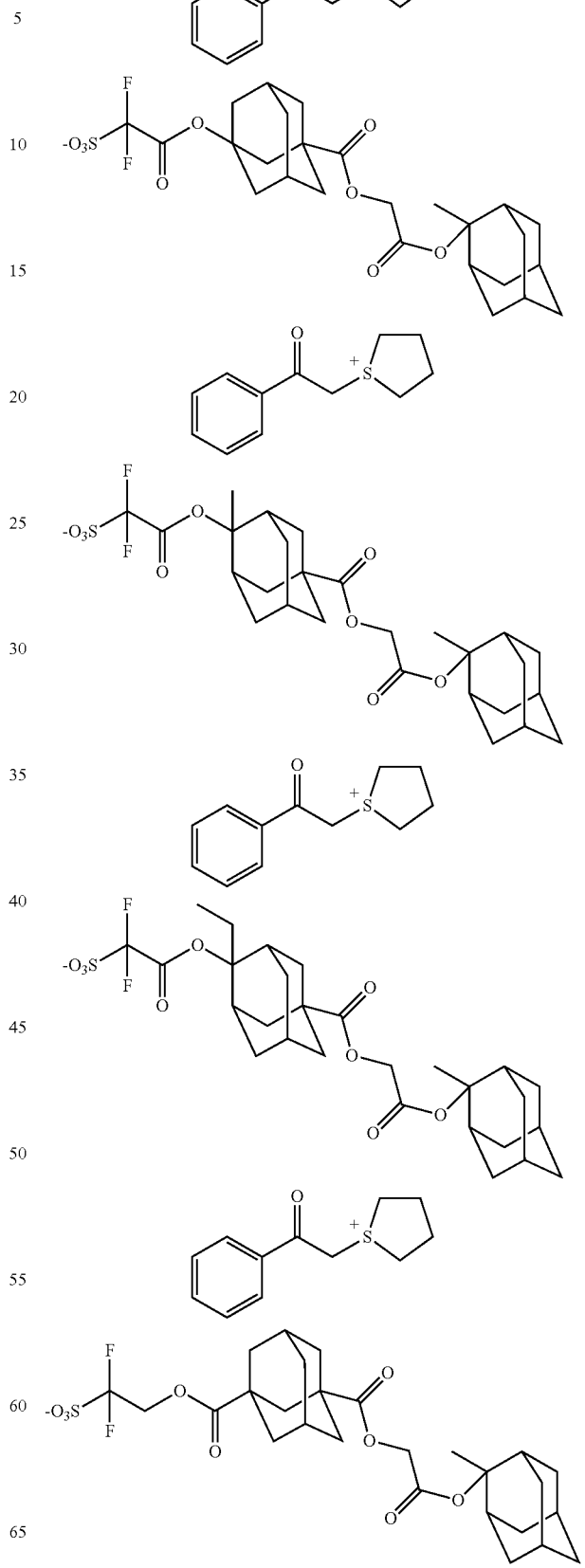

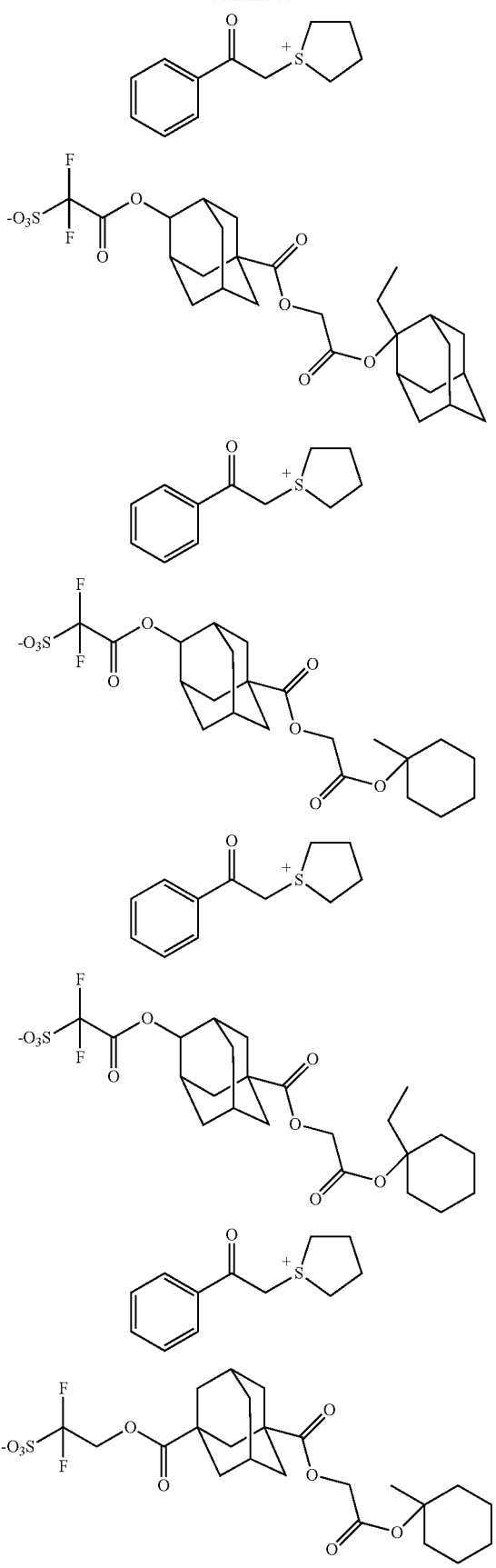

The process for producing SALT (I) will be illustrated.

For example, a salt represented by the formula (b1):

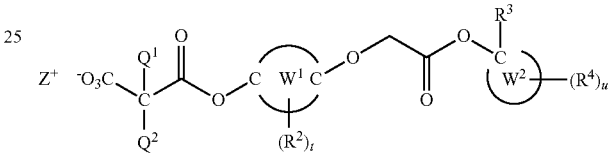

wherein $Q^1$, $Q^2$, $R^2$, $R^3$, $R^4$, ring $W^1$, ring $W^2$, $Z^+$, t and u are the same as defined above, can be produced by the following process.

The compound represented by the formula (b1-c) can be produced by reacting a compound represented by the formula (b1-a) with a compound represented by the formula (b1-b) in a solvent such as tetrahydrofuran in the presence of a basic catalyst such as pyridine.

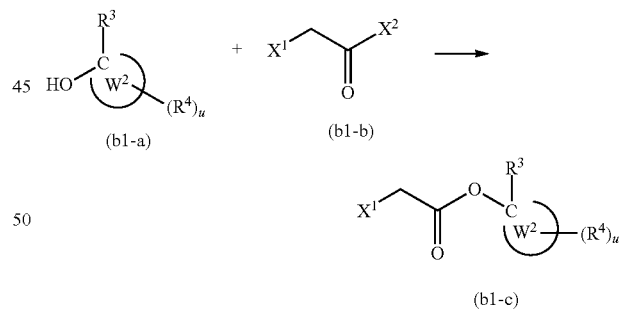

wherein $R^3$, $R^4$, ring $W^2$, and u are the same as defined above, and $X^1$ and $X^2$ independently each represent a halogen atom.

Examples of the halogen atom include a fluorine atom, a chlorine atom, a bromine atom and an iodine atom. It is preferred that $X^1$ and $X^2$ are the same halogen atoms and it is more preferred that $X^1$ and $X^2$ are chlorine atoms.

The compound represented by the formula (b1-e) can be produced by reacting a compound represented by the formula (b1-c) with a compound represented by the formula (b1-d) in a solvent such as N,N-dimethylformamide in the presence of a catalyst such as potassium carbonate and potassium iodide.

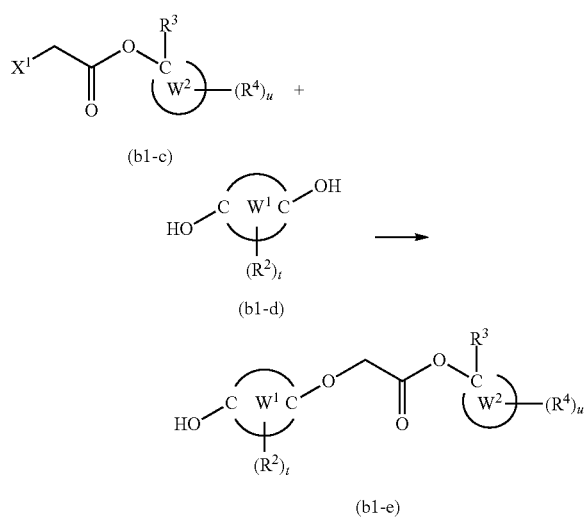

(b1-c)

(b1-d)

(b1-e)

wherein $X^1$, $R^3$, $R^4$, ring $W^2$, $R^2$, ring $W^1$, t and u are the same as defined above.

The salt represented by the formula (b1) can be produced by reacting the compound represented by the formula (b1-e) with a salt represented by the formula (b1-f) in a solvent such as N,N-dimethylformamide in the presence of a catalyst such as lithium amide. The salt represented by the formula (b1-f) can be produced, for example, according to the method described in JP 2008-13551 A.

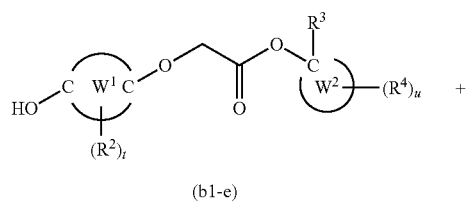

(b1-e)

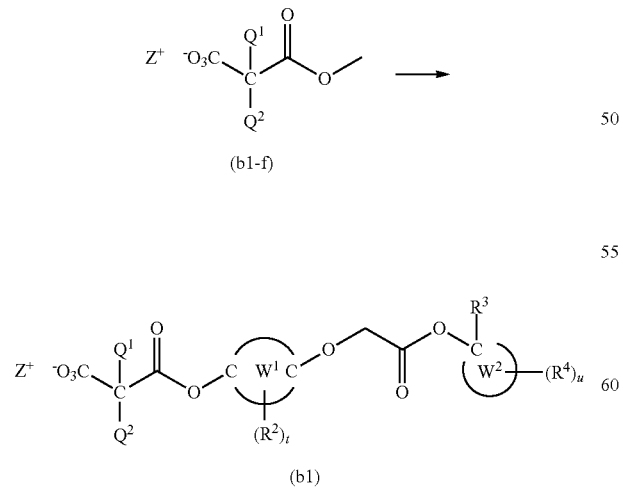

(b1-f)

(b1)

wherein $Q^1$, $Q^2$, $R^2$, $R^3$, $R^4$, ring $W^1$, ring $W^2$, $Z^+$, t and u are the same as defined above.

For example, a salt represented by the formula (b2):

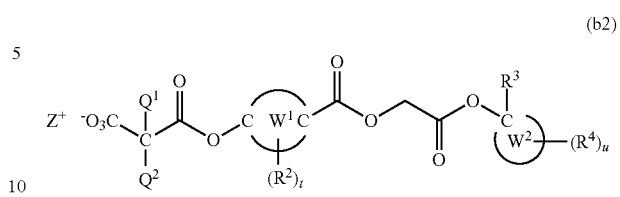

(b2)

wherein $Q^1$, $Q^2$, $R^2$, $R^3$, $R^4$, ring $W^1$, ring $W^2$, $Z^+$, t and u are the same as defined above, can be produced by the following process.

The compound represented by the formula (b2-c) can be produced by reacting a compound represented by the formula (b2-a) with a compound represented by the formula (b2-b) in a solvent such as tetrahydrofuran in the presence of a basic catalyst such as pyridine.

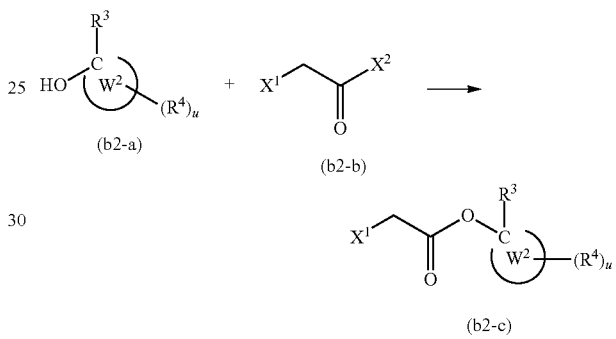

(b2-a)  (b2-b)

(b2-c)

wherein $R^3$, $R^4$, ring $W^2$, u, $X^1$ and $X^2$ are the same as defined above.

The compound represented by the formula (b2-e) can be produced by reacting a compound represented by the formula (b2-c) with a compound represented by the formula (b2-d) in a solvent such as N,N-dimethylformamide in the presence of a catalyst such as potassium carbonate and potassium iodide.

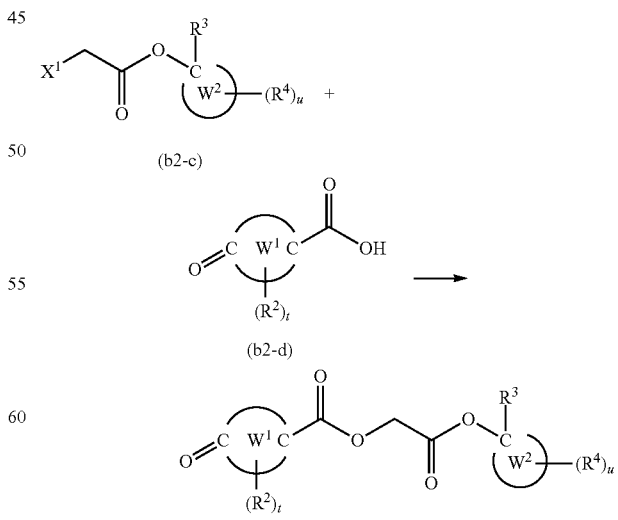

(b2-c)

(b2-d)

(b2-e)

wherein $X^1$, $R^3$, $R^4$, ring $W^2$, $R^2$, ring $W^1$, t and u are the same as defined above.

The compound represented by the formula (b2-f) can be produced by reducing the compound represented by the formula (b2-e) with a reducing agent such as sodium borohydride in a solvent such as acetonitrile.

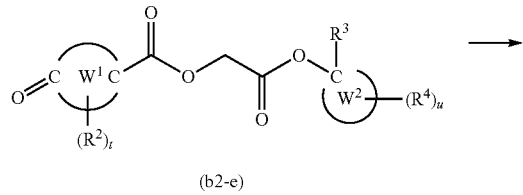

(b2-e)

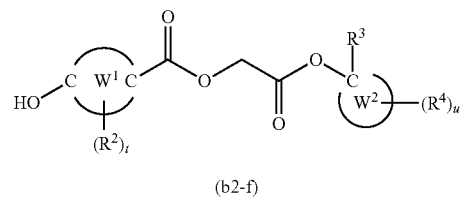

(b2-f)

wherein $R^3$, $R^4$, ring $W^2$, $R^2$, ring $W^1$, t and u are the same as defined above.

The salt represented by the formula (b2-i) can be produced by reacting a salt represented by the formula (b2-g) with a compound represented by the formula (b2-h). The salt represented by the formula (b2-g) can be produced, for example, according to the method described in JP 2008-13551 A.

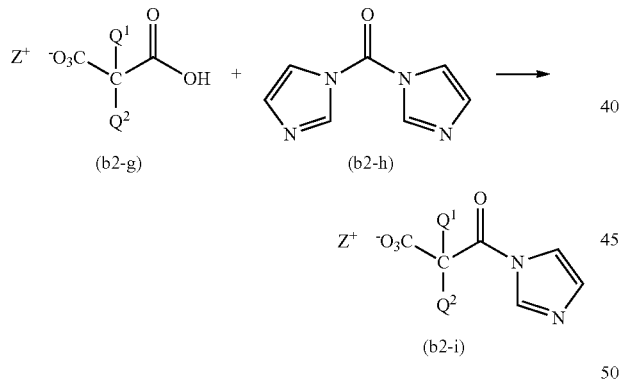

(b2-g)        (b2-h)

wherein $Q^1$, $Q^2$ and $Z^+$ are the same as defined above.

The salt represented by the formula (b2) can be produced by reacting the compound represented by the formula (b2-f) with the salt represented by the formula (b2-i) in a solvent such as acetonitrile.

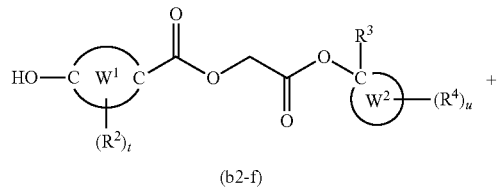

(b2-f)

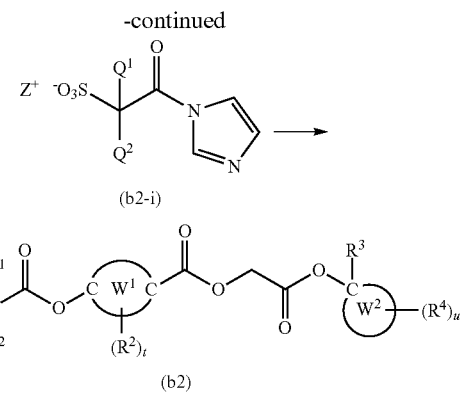

wherein $Q^1$, $Q^2$, $R^2$, $R^3$, $R^4$, $W^1$, $W^2$, $Z^+$, t and u are the same as defined above.

Next, the acid generator of the present invention will be illustrated.

The acid generator of the present invention comprises SALT (I). The acid generator of the present invention can contain two or more kinds of SALT (I). The acid generator of the present invention may consist of SALT (I). The acid generator of the present invention can contain one or more known acid generators other than SALT (I) in addition to SALT (I). The acid generator of the present invention contains SALT (I) in an effective amount.

Preferable examples of the acid generator other than SALT (I) include salts represented by the formulae (B1-1) to (B1-17), the salt containing a triphenylsulfonium cation or a tritolylsulfonium cation is more preferable, and the salts represented by the formulae (B1-1), (B1-2), (B1-3), (B1-6), (B1-11), (B1-12), (B1-13) and (B1-14) are especially preferable.

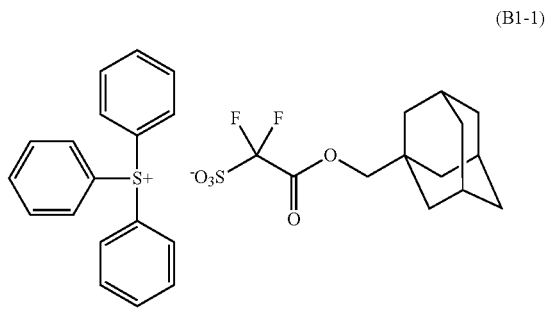

(B1-1)

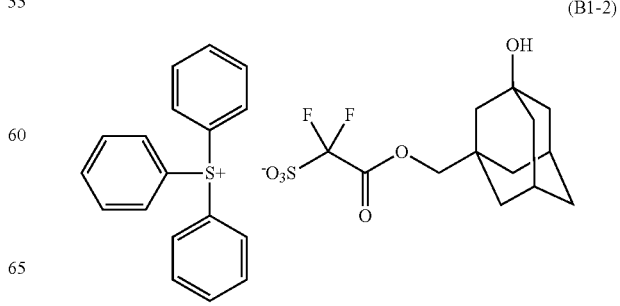

(B1-2)

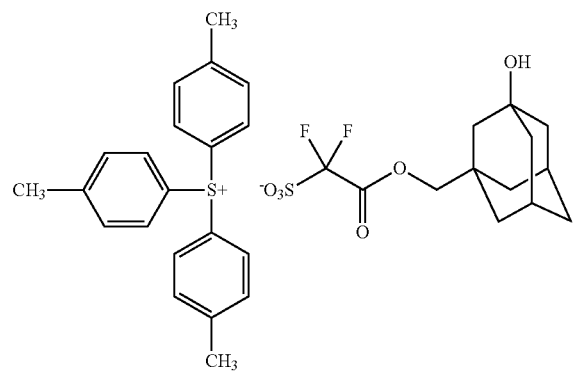
(B1-3)
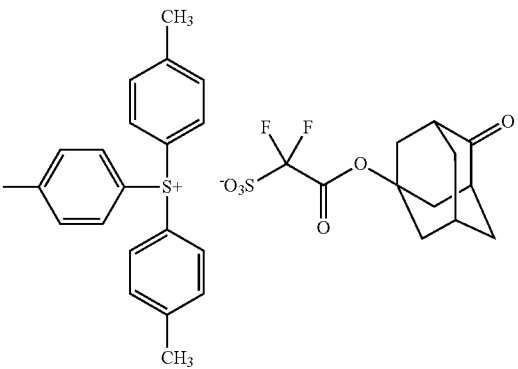
(B1-7)
(B1-4)
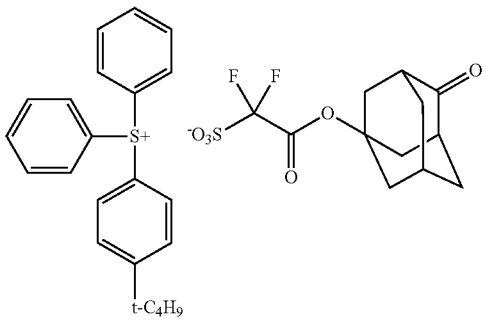
(B1-8)
(B1-5)
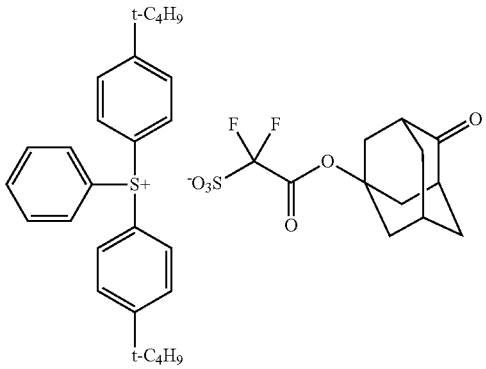
(B1-9)
(B1-6)
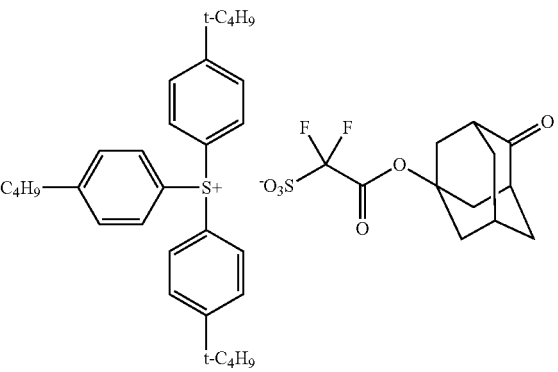
(B1-10)

-continued

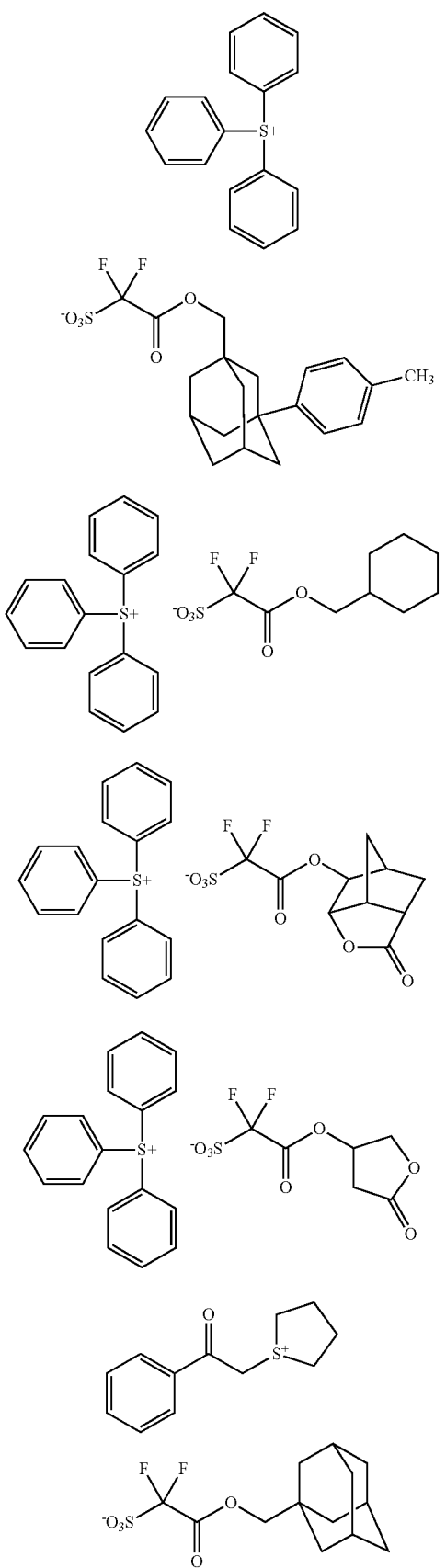

(B1-11)
(B1-12)
(B1-13)
(B1-14)
(B1-15)

-continued

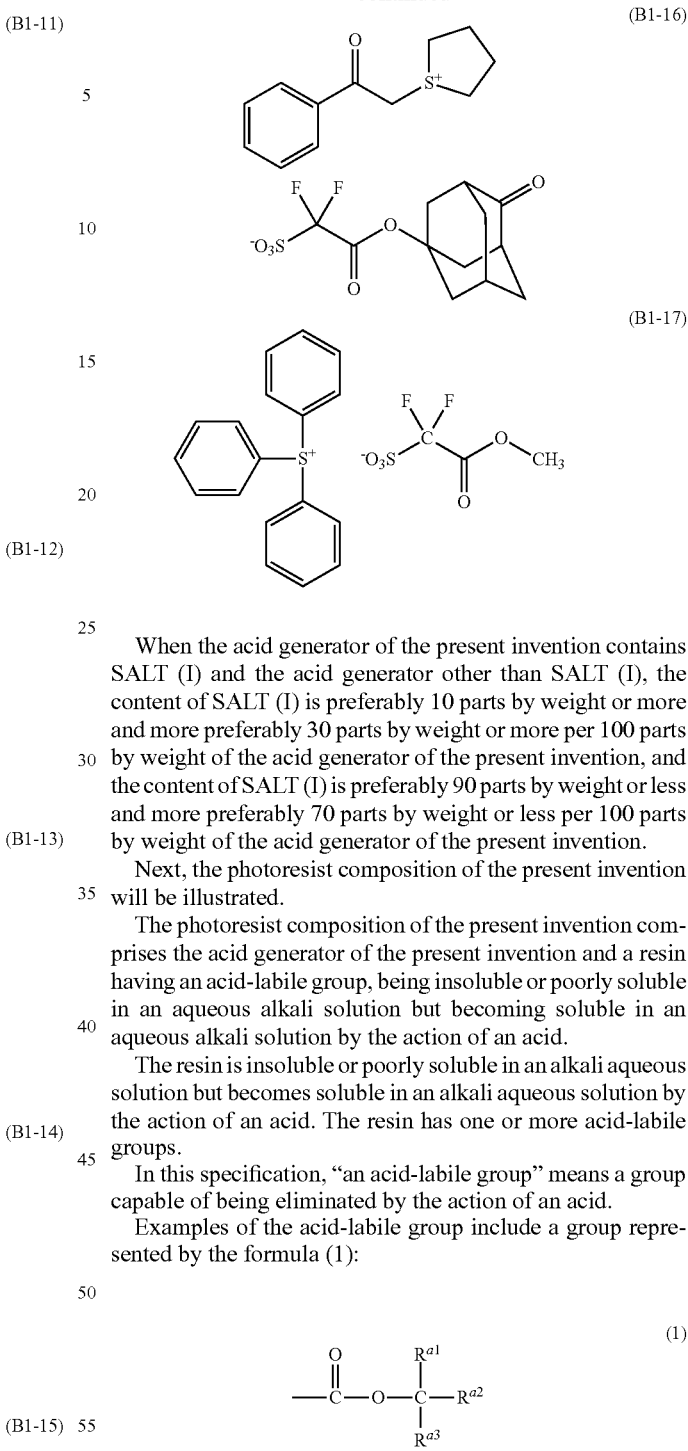

(B1-16)
(B1-17)

When the acid generator of the present invention contains SALT (I) and the acid generator other than SALT (I), the content of SALT (I) is preferably 10 parts by weight or more and more preferably 30 parts by weight or more per 100 parts by weight of the acid generator of the present invention, and the content of SALT (I) is preferably 90 parts by weight or less and more preferably 70 parts by weight or less per 100 parts by weight of the acid generator of the present invention.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid.

The resin is insoluble or poorly soluble in an alkali aqueous solution but becomes soluble in an alkali aqueous solution by the action of an acid. The resin has one or more acid-labile groups.

In this specification, "an acid-labile group" means a group capable of being eliminated by the action of an acid.

Examples of the acid-labile group include a group represented by the formula (1):

$$\begin{matrix} & & & R^{a1} \\ & \text{O} & & | \\ -\text{C}-\text{O}-\text{C}-R^{a2} \\ & & & | \\ & & & R^{a3} \end{matrix} \quad (1)$$

wherein $R^{a1}$, $R^{a2}$ and $R^{a3}$ independently each represent a C1-C8 aliphatic hydrocarbon group or a C3-C20 alicyclic hydrocarbon group, and $R^{a1}$ and $R^{a2}$ can be bonded each other to form a C3-C20 ring together with a carbon atom to which $R^{a1}$ and $R^{a2}$ are bonded, and one or more —CH$_2$— in the aliphatic hydrocarbon group, the alicyclic hydrocarbon group and the ring can be replaced by —O—, —S— or —CO—.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

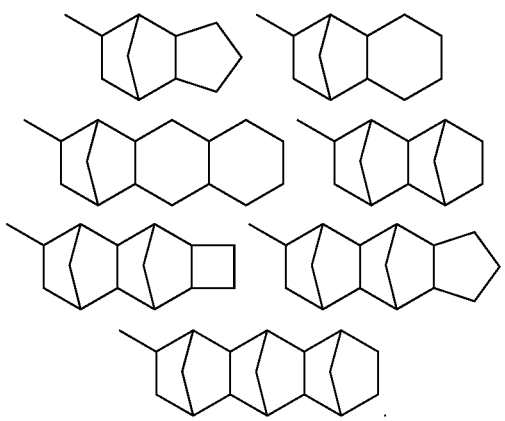

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

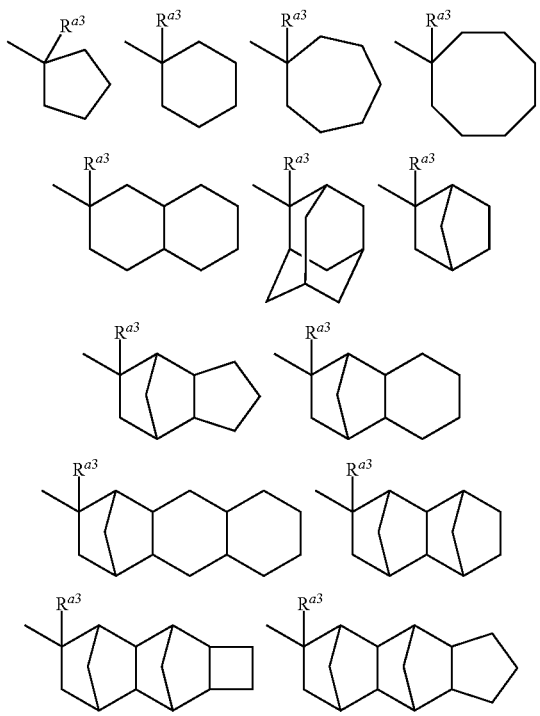

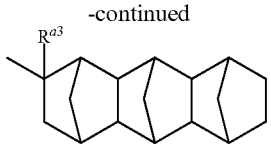

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

Examples of the acid-labile group include a group represented by the formula (20):

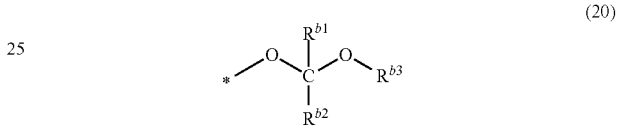

(20)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C3-C20 ring together with the carbon atom and the oxygen atom to which they are bonded, and one or more —CH$_2$— in the hydrocarbon group and the ring can be replaced by —O—, —S— or —CO—.

The group represented by the formula (20) has an acetal structure.

Examples of the hydrocarbon group include an aliphatic hydrocarbon group, an alicyclic hydrocarbon group and an aromatic hydrocarbon group. Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (20) include the following.

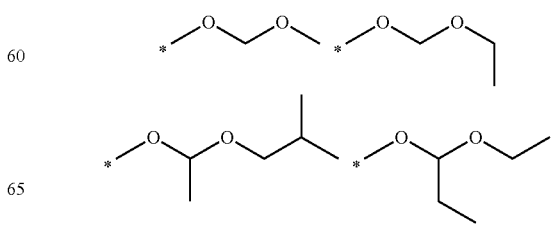

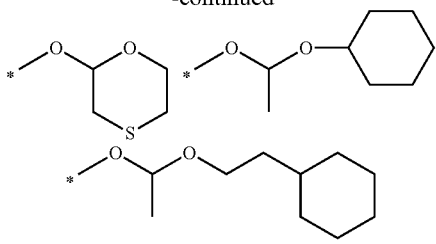
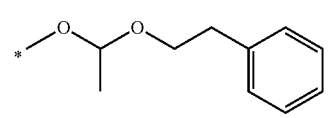
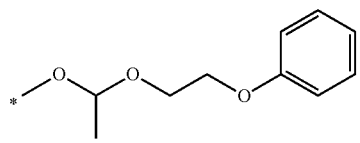
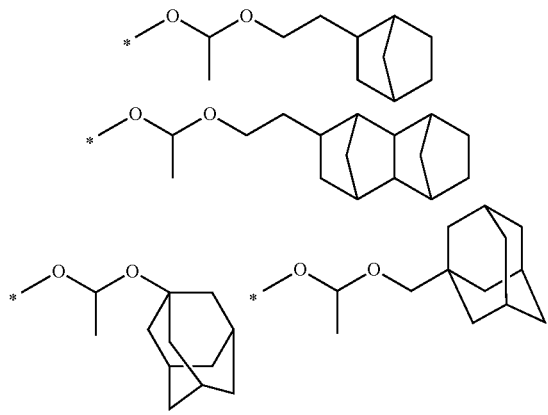

The compound having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (10) or (20) in its side chain and a carbon-carbon double bond is preferable, and an acrylate monomer having the group represented by the formula (10) in its side chain or a methacryalte monomer having the group represented by the formula (10) in its side chain is more preferable.

An acrylate monomer having the group represented by the formula (10) in which $R^{a1}$ and $R^{a2}$ are bonded each other to form a C5-C20 alicycle together with the carbon atom to which they are bonded In its side chain or a methacryalte monomer having the group represented by the formula (10) in which $R^{a1}$ and $R^{a2}$ are bonded each other to form a C5-C20 alicycle together with the carbon atom to which they are bonded in its side chain is especially preferable.

Preferable examples of the compound having an acid-labile group include monomers represented by the formulae (a1-1) and (a1-2):

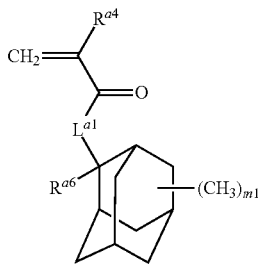

(a1-1)

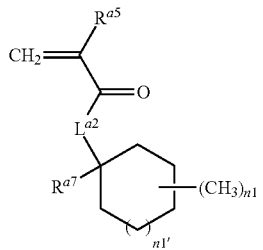

(a1-2)

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 alicyclic hydrocarbon group, $L^{a1}$ and $L^{a2}$ each independently represents *—O— or *—O—$(CH_2)_{k1}$—O— in which * represents a binding position to —CO—, and k1 represents an integer of 1 to 7, and m1 represents an integer of 0 to 14, n1 represents an integer of 0 to 10, and n1' represents 0 or 1.

The aliphatic hydrocarbon group preferably has 1 to 6 carbon atoms, and the alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

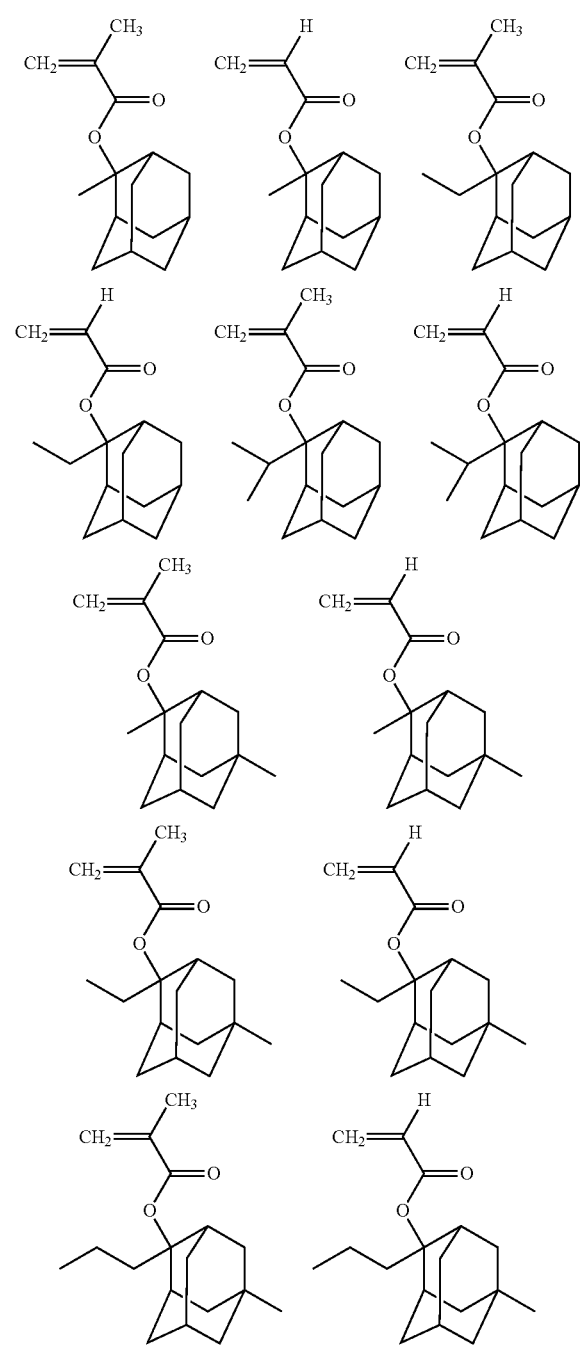

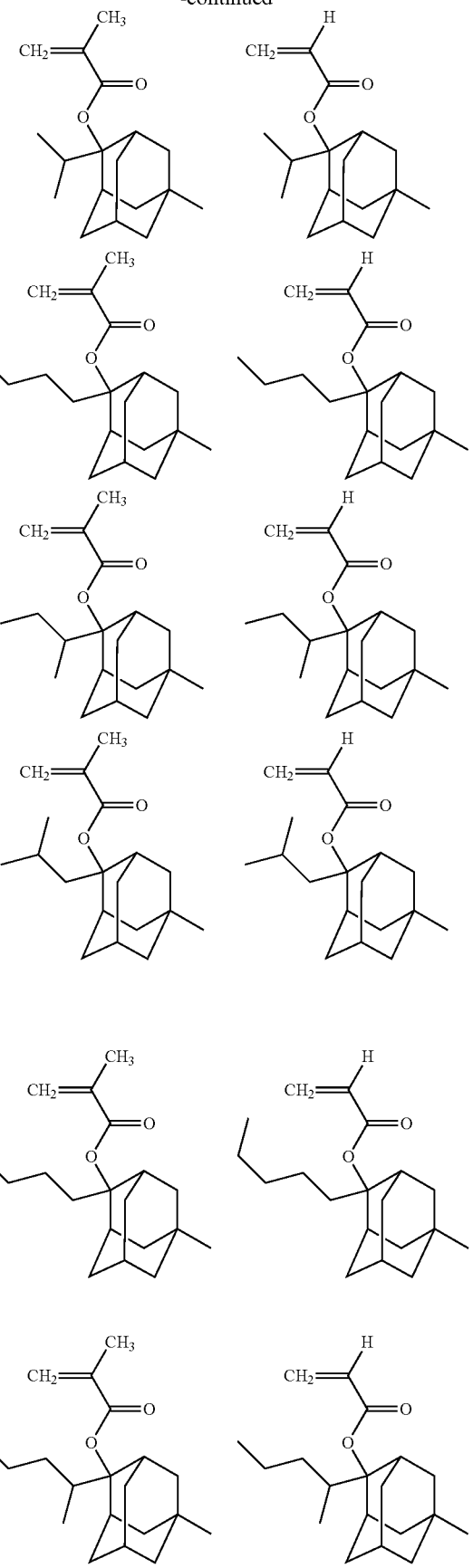

69
-continued
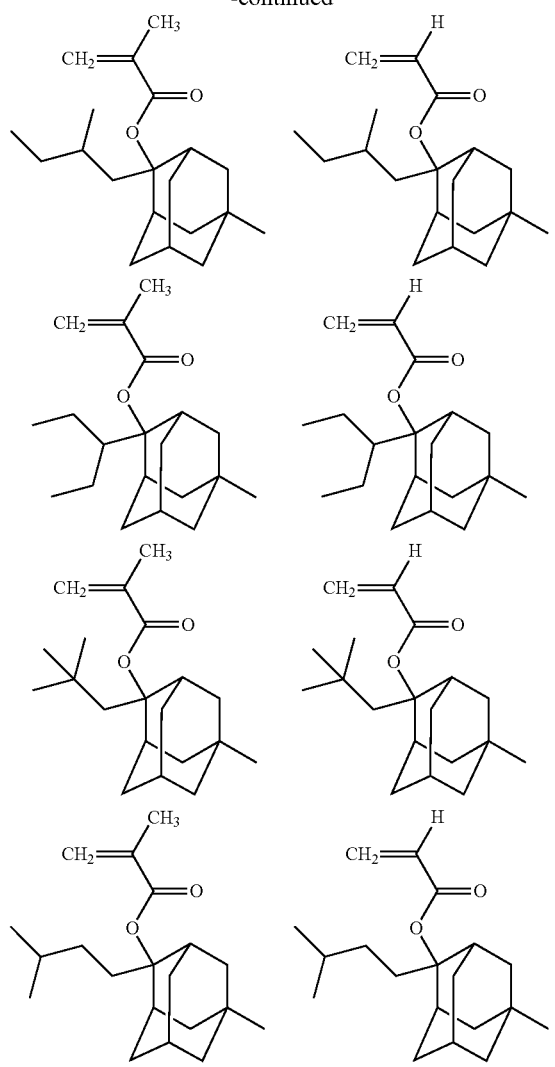
70
-continued
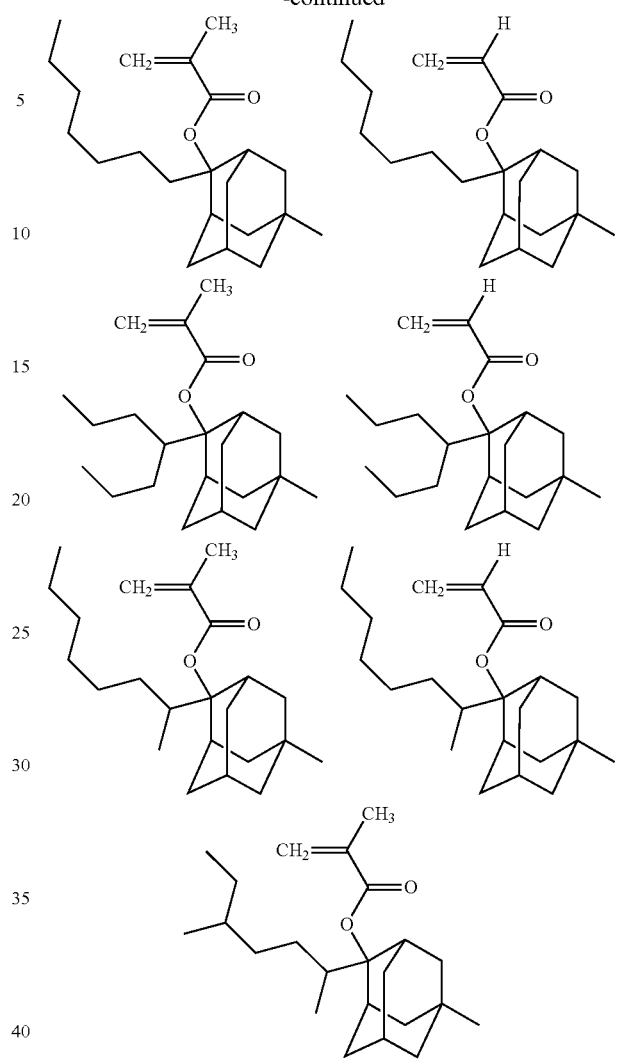
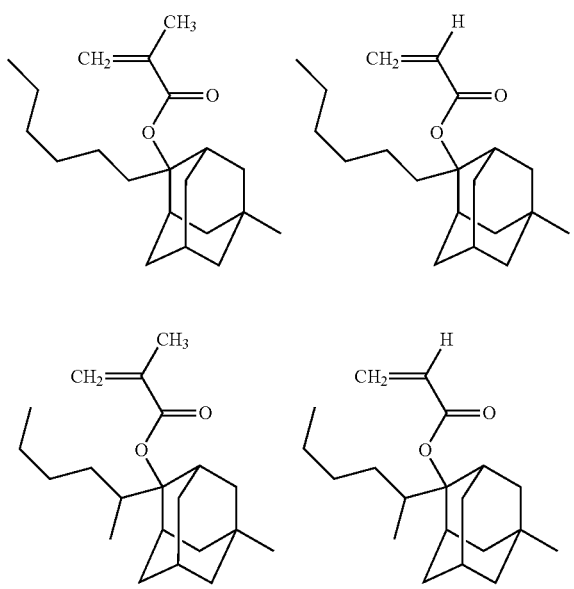
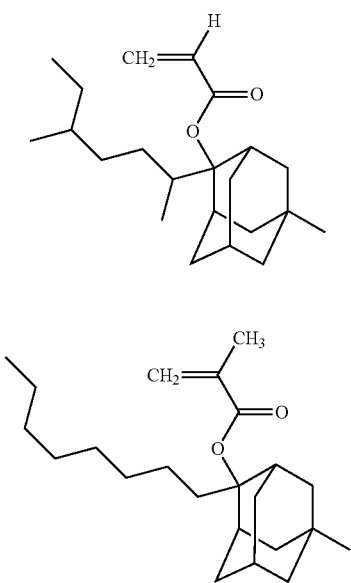

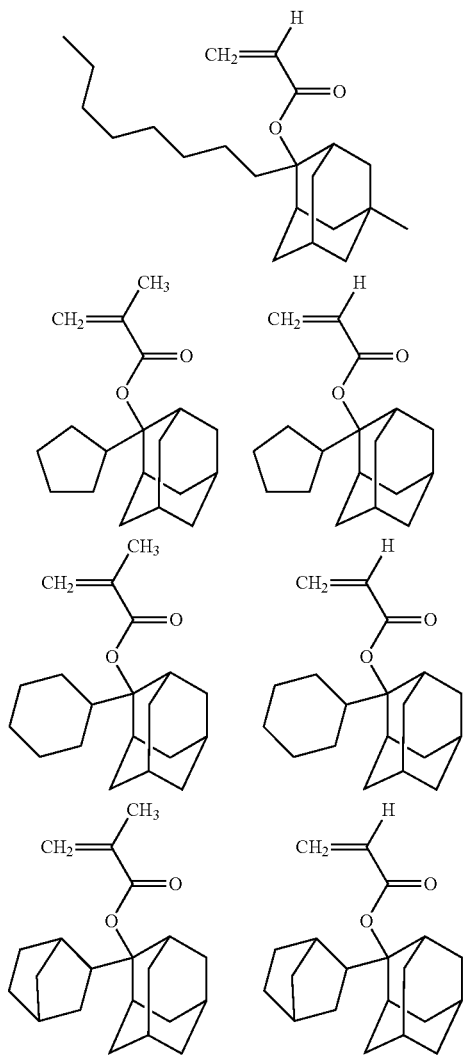
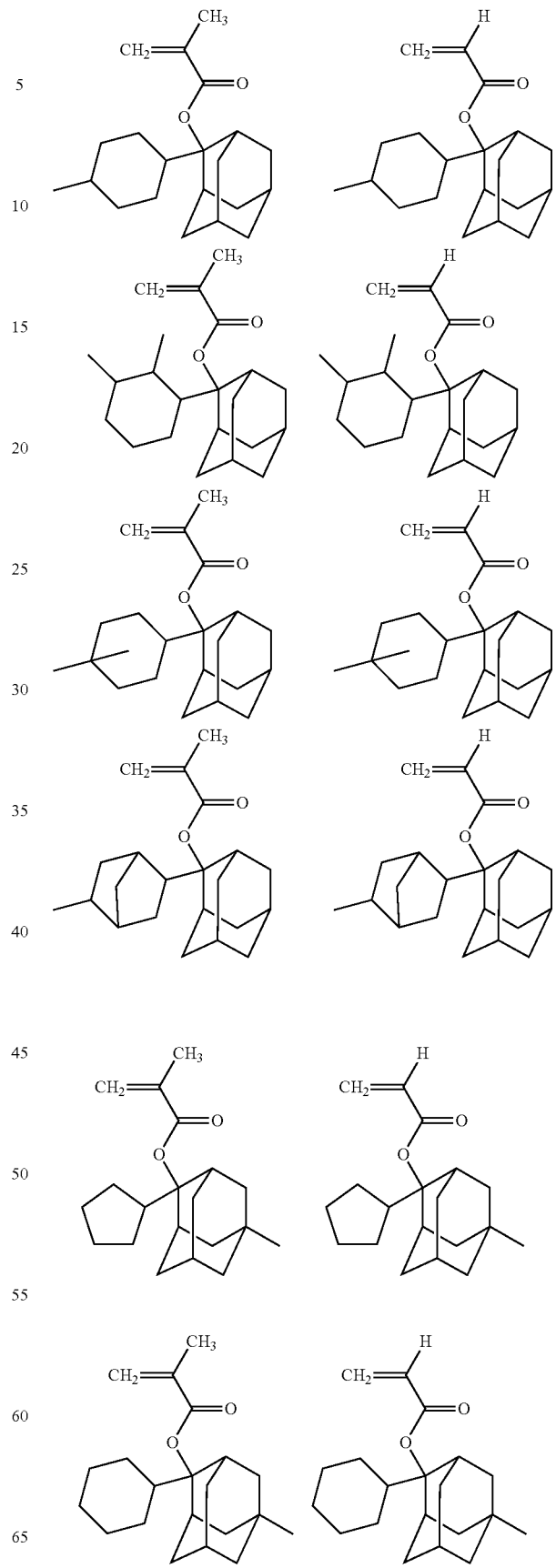

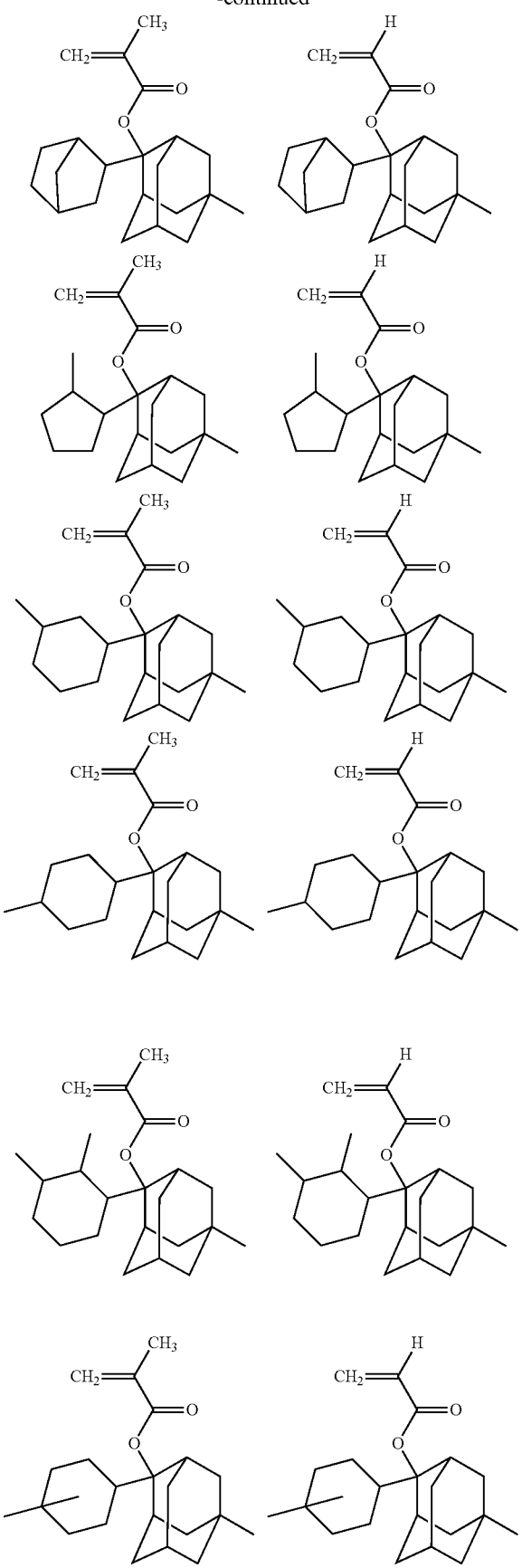
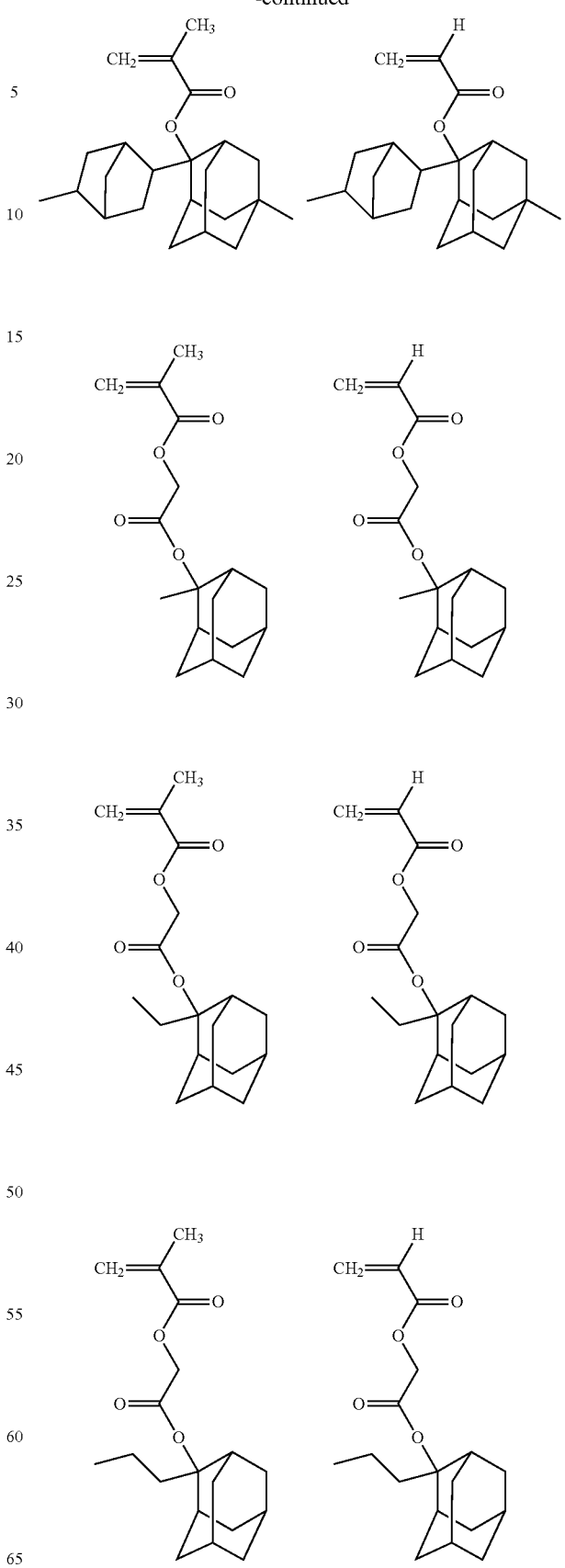

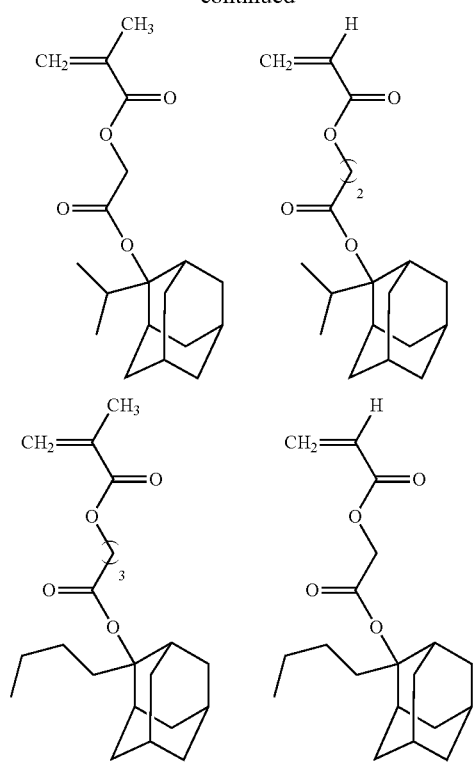
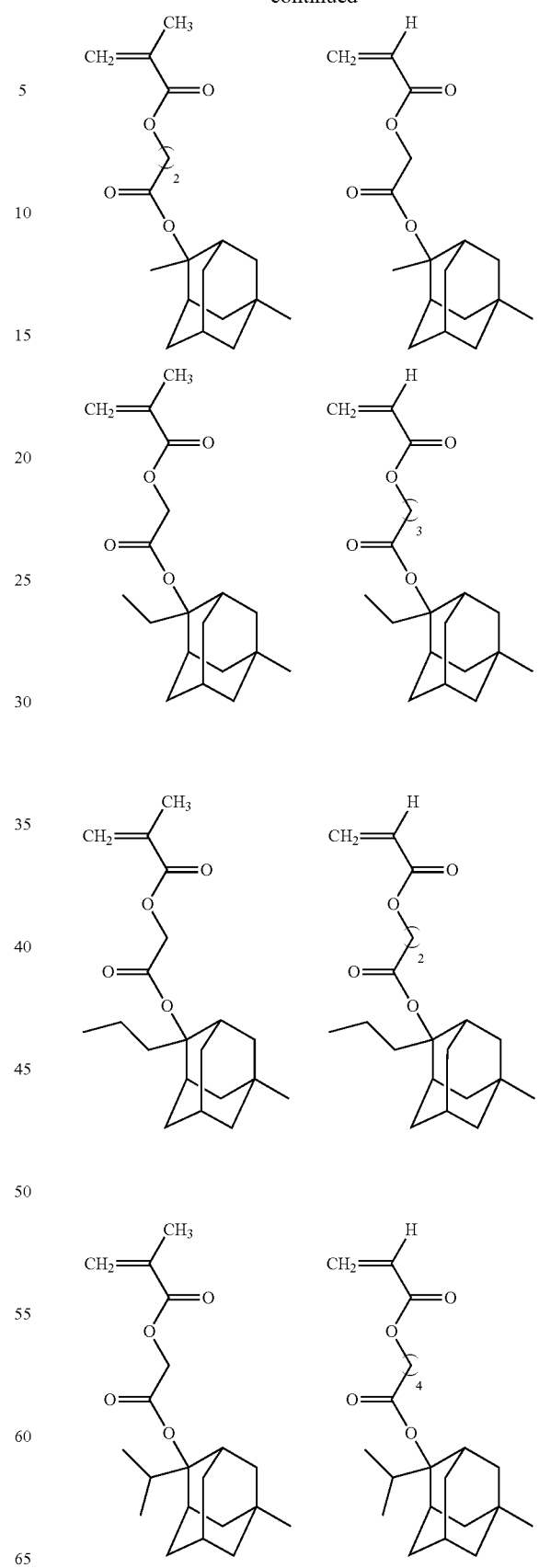

77
-continued
78
-continued
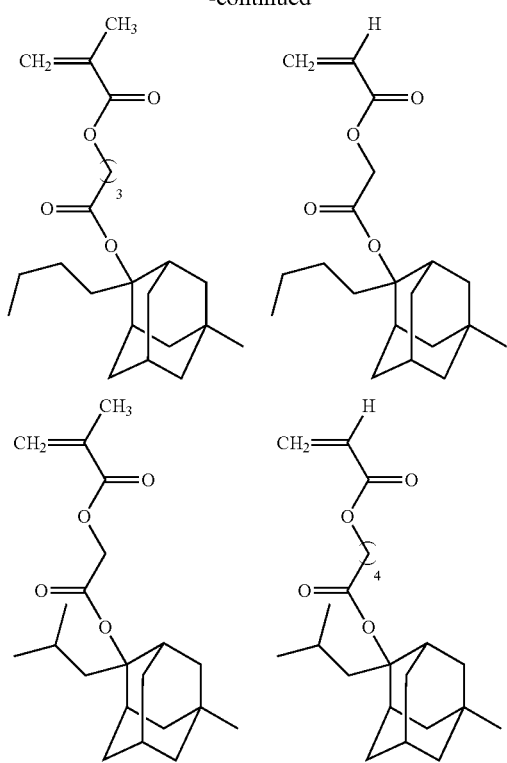
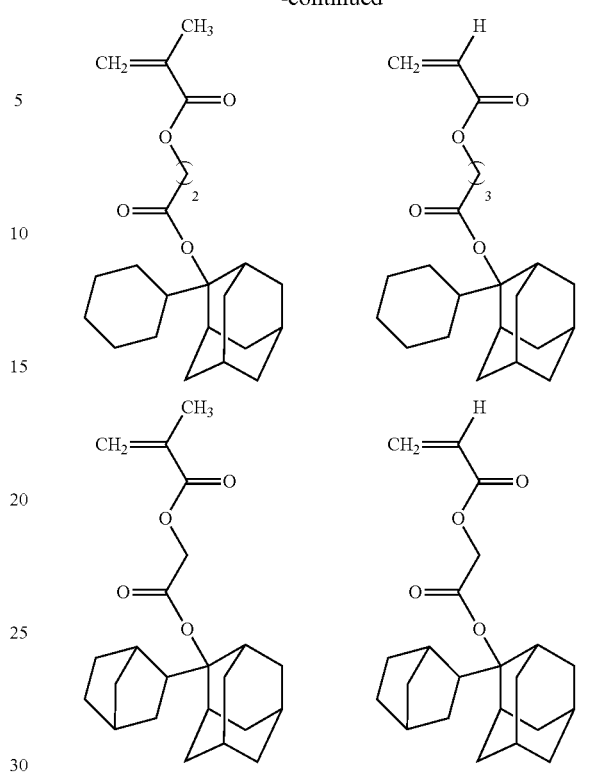
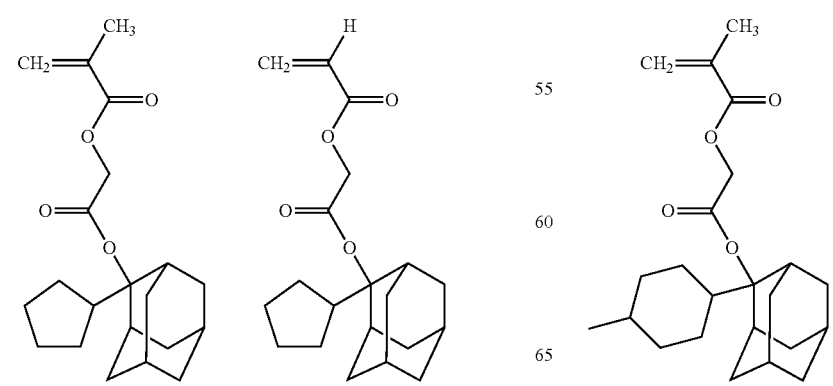

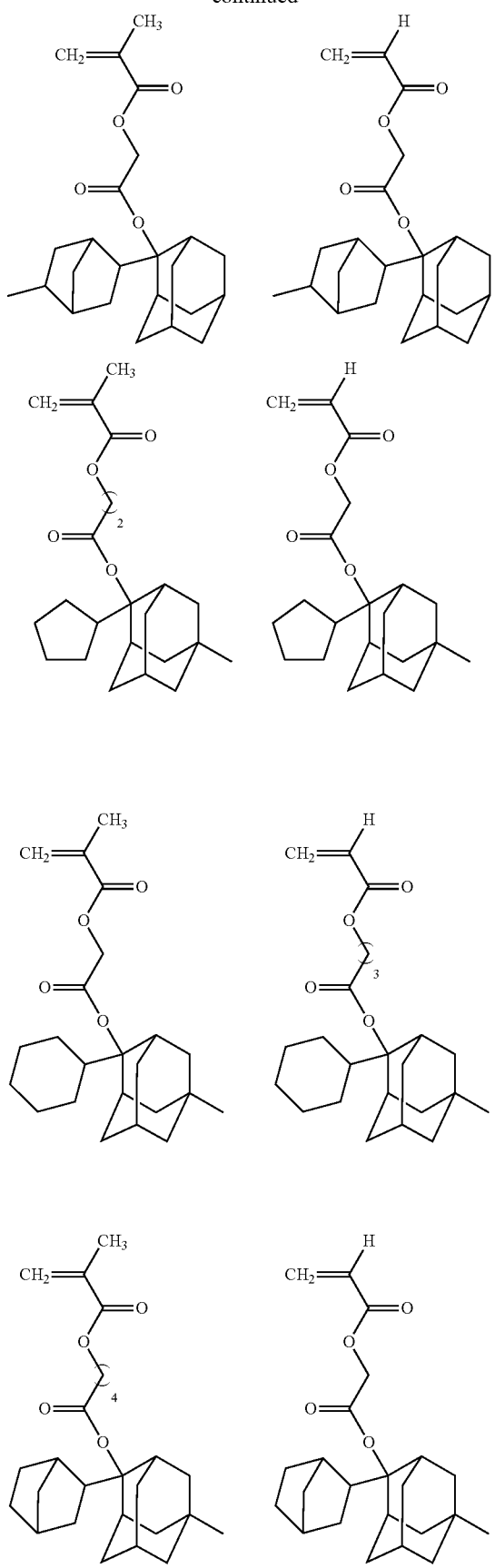
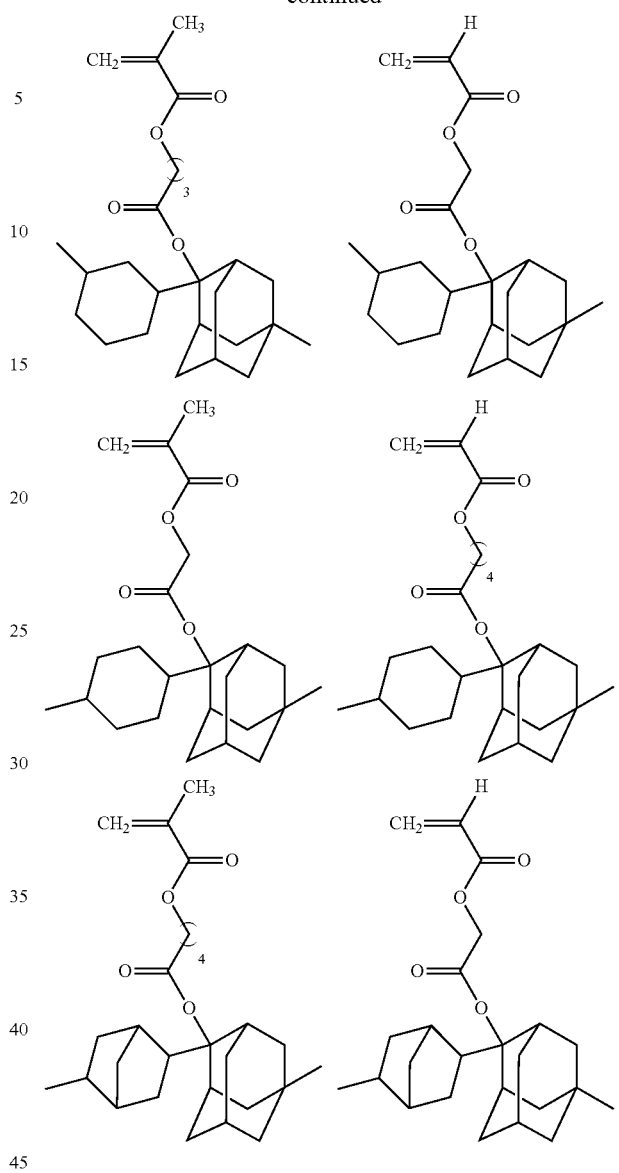

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

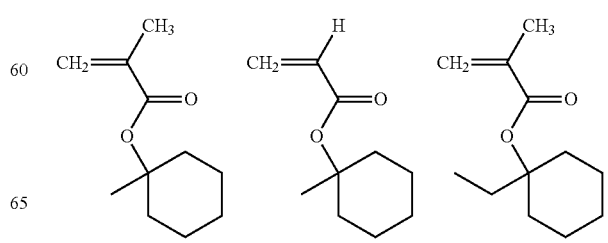

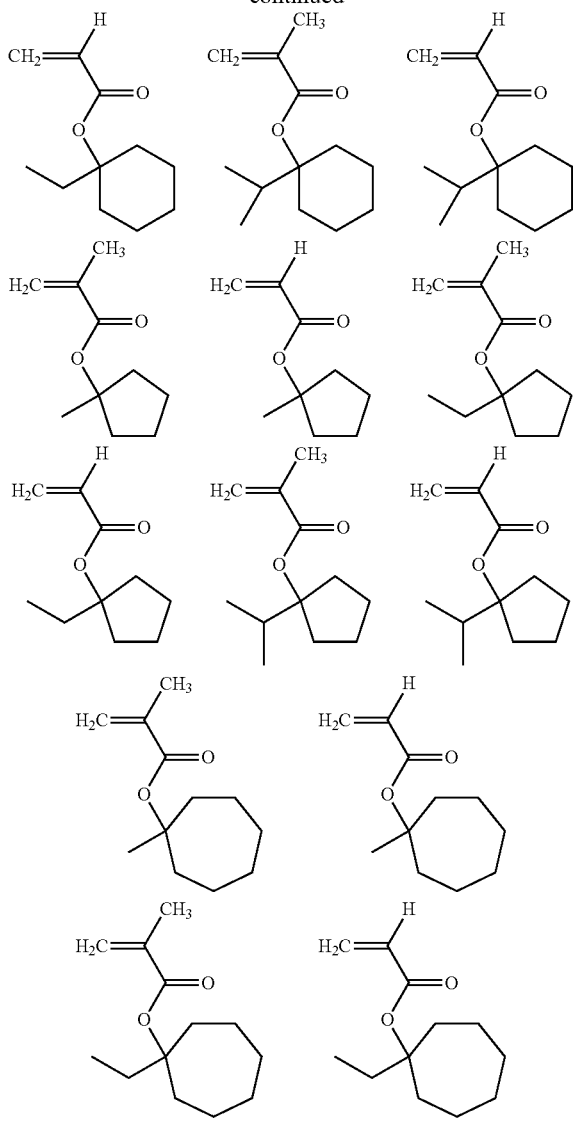

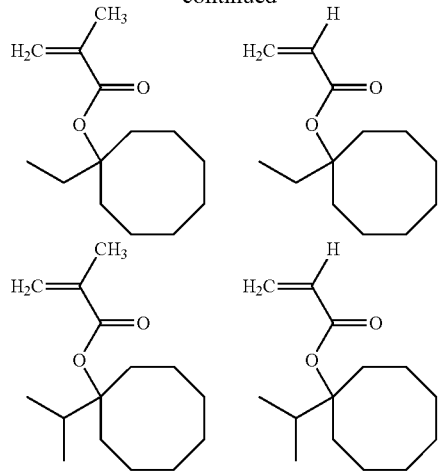

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a monomer having an acid-labile group in the resin is usually 10 to 95% by mole, preferably 15 to 90% by mole and more preferably 20 to 85% by mole based on 100% by mole of all the structural units of the resin.

Other examples of the monomer having an acid-labile group include a monomer represented by the formula (a1-3):

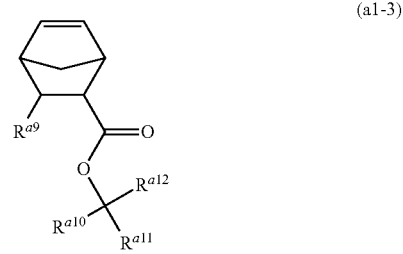

(a1-3)

wherein $R^{a9}$ represents a hydrogen atom, a C1-C3 aliphatic hydrocarbon group which can have one or more hydroxyl groups, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ each independently represent a C1-C12 aliphatic hydrocarbon group or a C3-C12 saturated cyclic hydrocarbon group, and $R^{a10}$ and $R^{a11}$ can be bonded each other to form a C3-C20 ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the C1-C3 aliphatic hydrocarbon group which can have one or more hydroxyl groups include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the C3-C20 ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

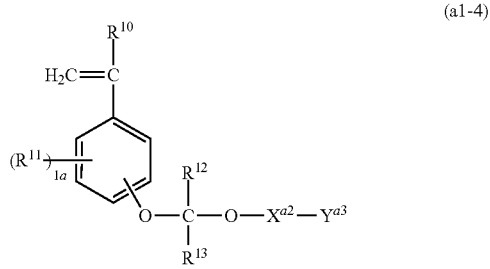

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C17 divalent saturated hydrocarbon group, the C1-C12 aliphatic hydrocarbon group, the C2-C18 saturated cyclic hydrocarbon group and the C6-C18 aromatic hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

Examples of the halogen atom include a fluorine atom, a chlorine atom, a bromine atom and an iodine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, a C3-C12 alicyclic hydrocarbon group such as a cyclohexyl group, an adamantyl group, a 2-alkyl-2-adamantyl group, a 1-(1-adamantyl)-1-alkyl group and an isobornyl group, an C6-C12 aromatic hydrocarbon group and a group formed by combining one or more above-mentioned groups. Among them, preferred are an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,1'-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

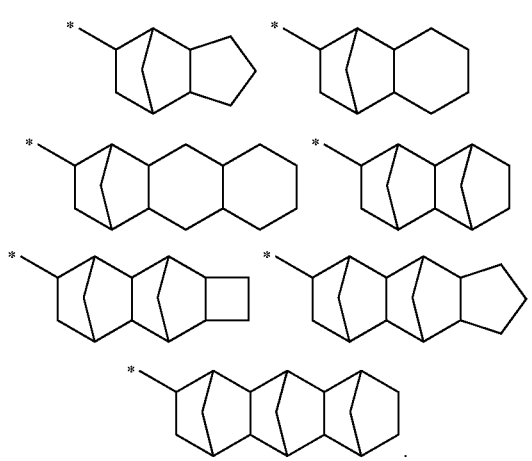
Examples the C6-C18 aromatic hydrocarbon group include a phenyl group, a naphthyl group, an anthryl group, a p-methylphenyl group, a p-tert-butylphenyl group and a p-adamantylphenyl group.
Preferred substituents of $X^{a2}$ and $Y^{a3}$ is a hydroxyl group.
Examples of the monomer represented by the formula (a1-4) include the followings.
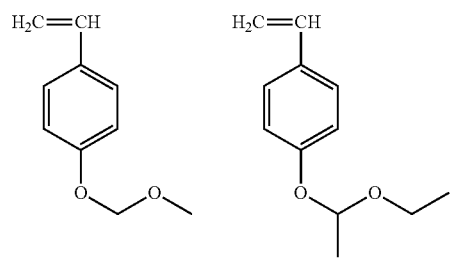
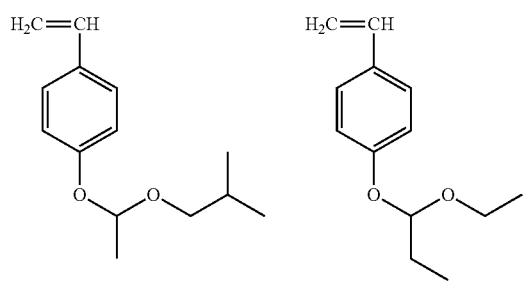
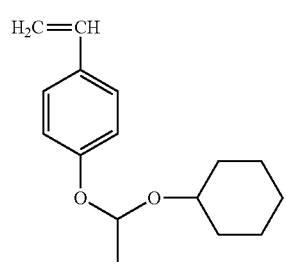
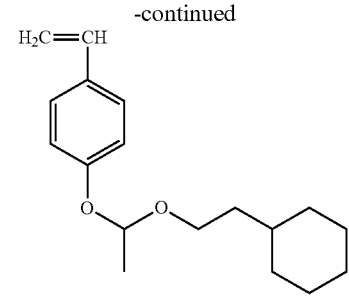
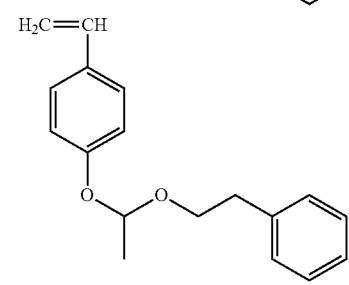
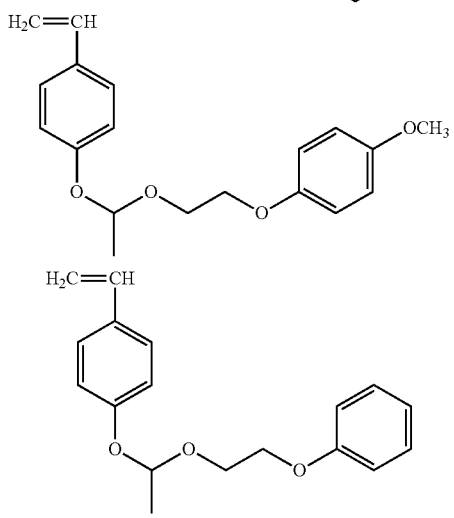
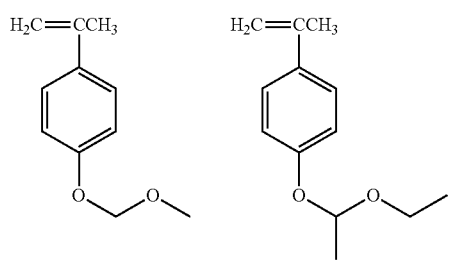
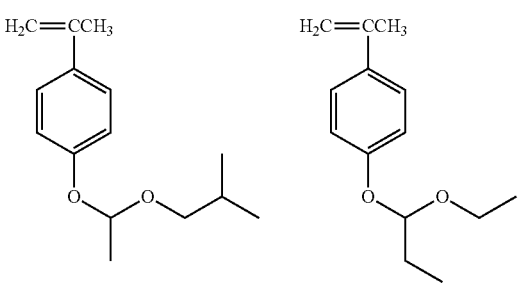

87
-continued
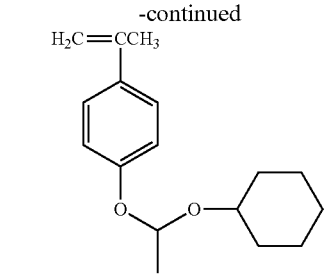
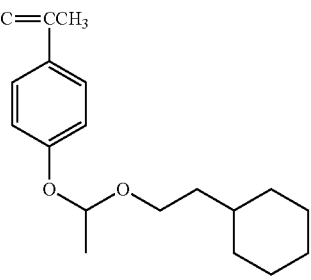
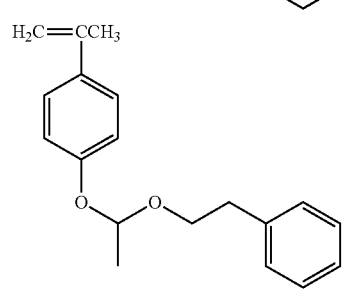
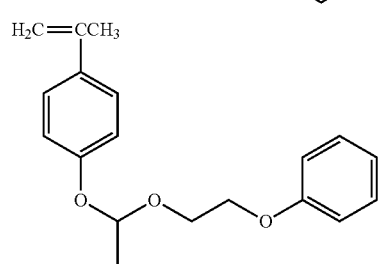
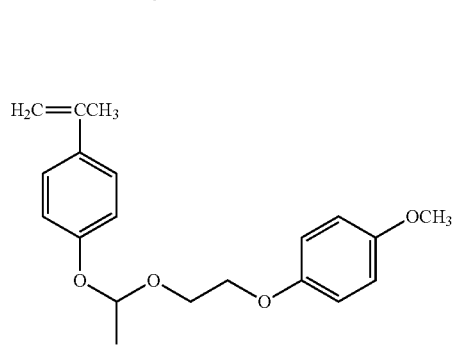
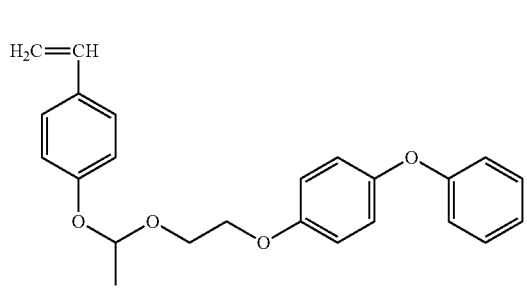
88
-continued
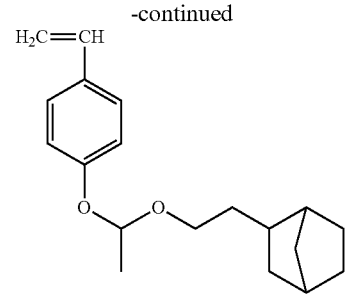
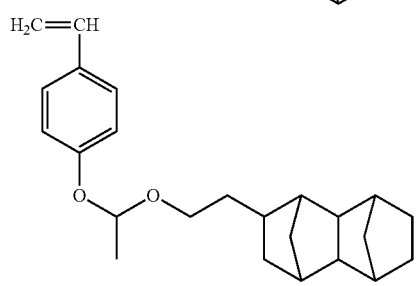
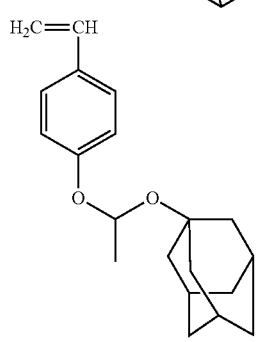
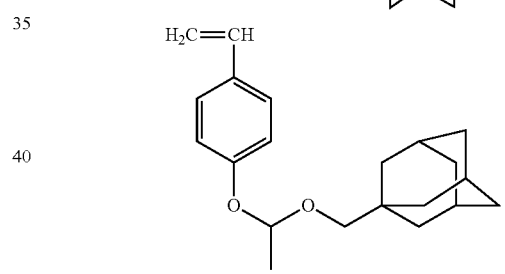
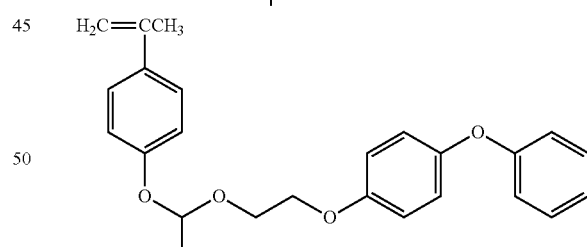
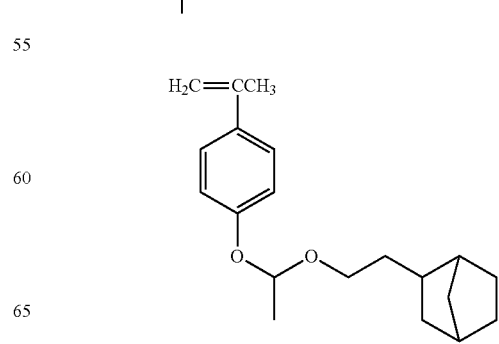

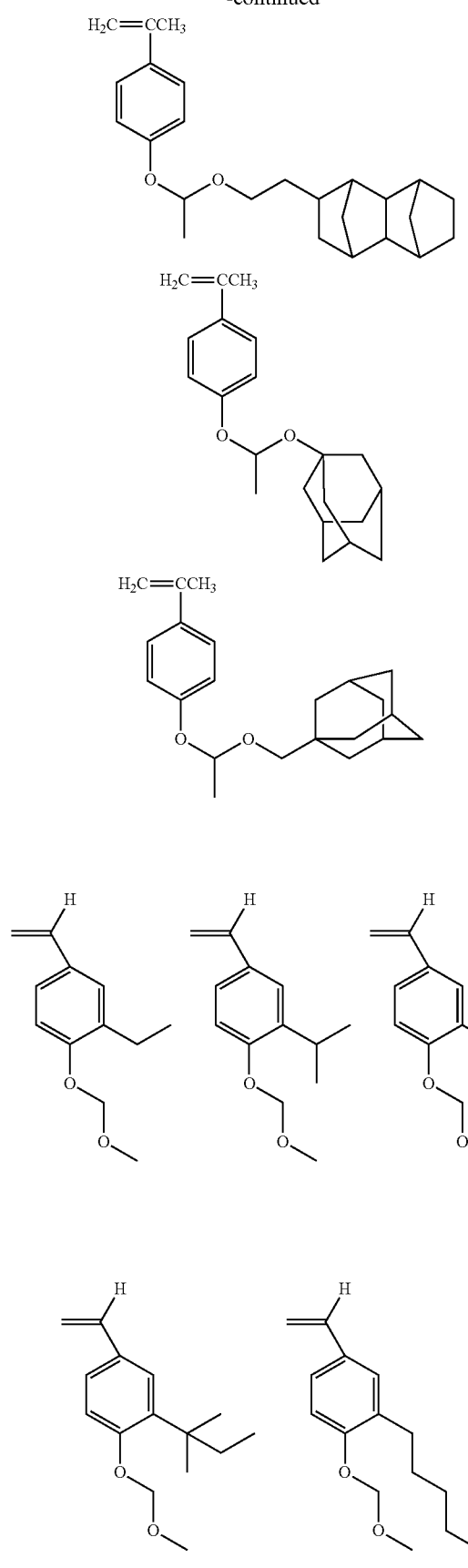
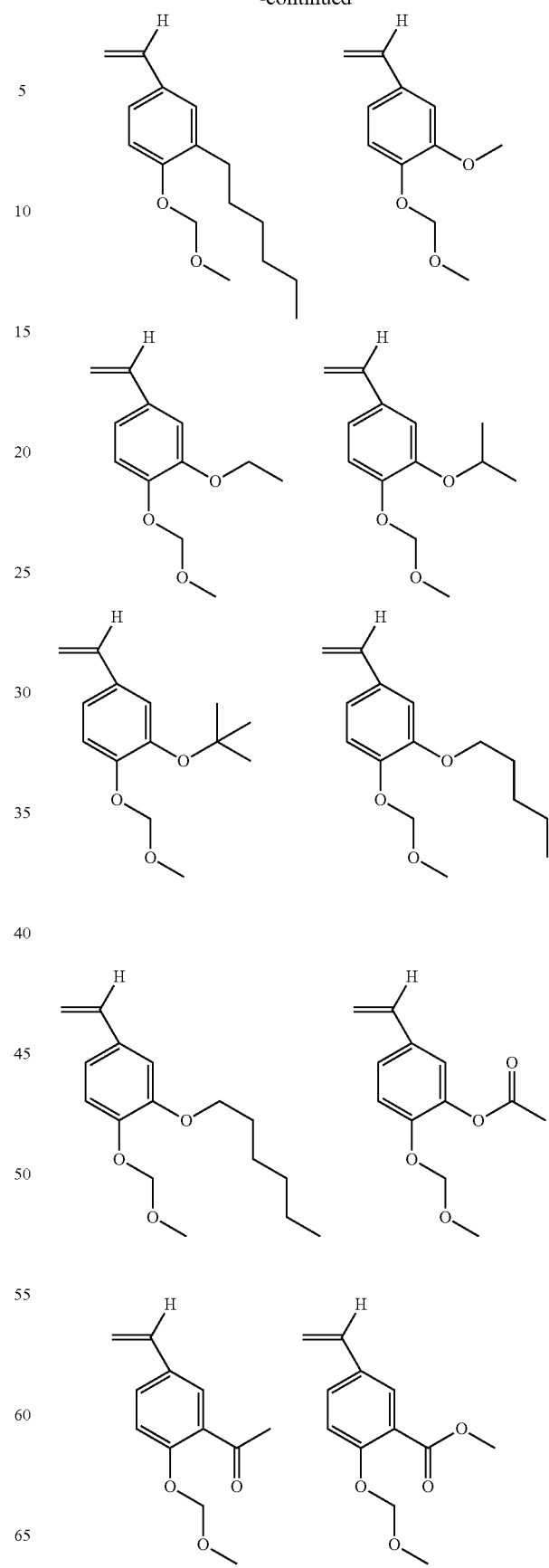

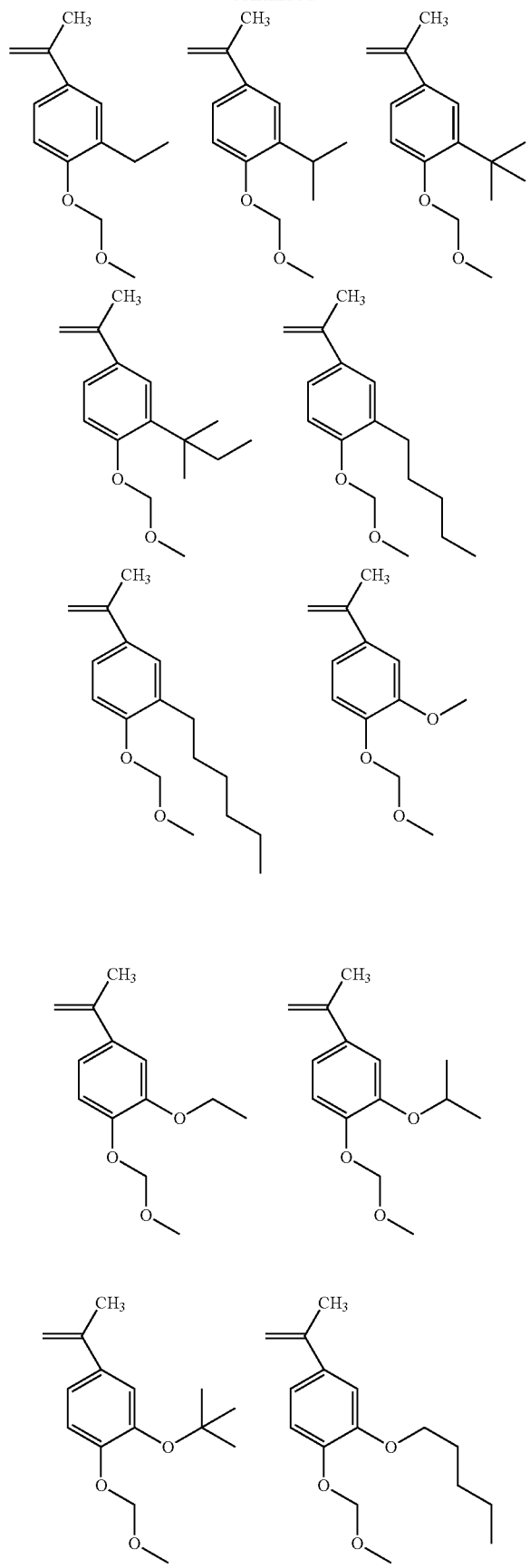
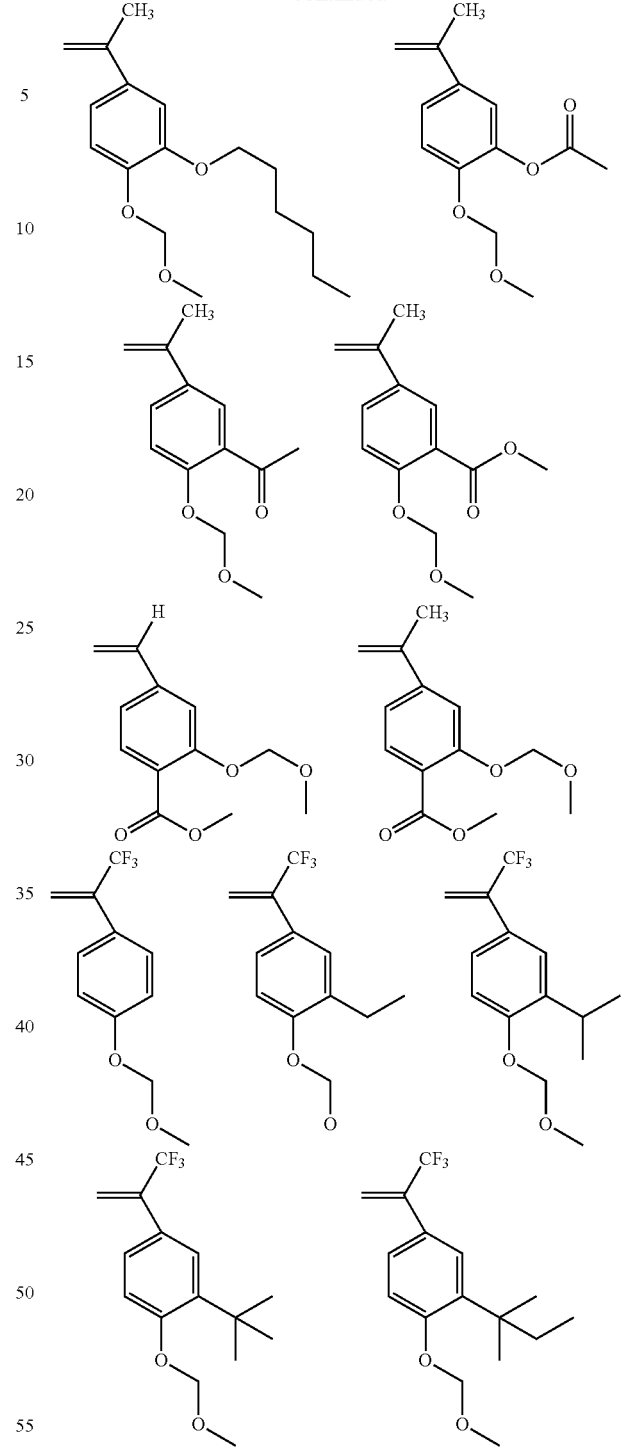

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-5):

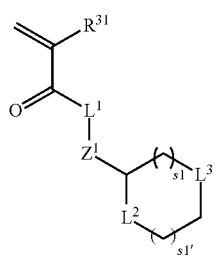
(a1-5)

wherein $R^{31}$ represents a hydrogen atom, a halogen atom, a C1-C4 alkyl group which may be substituted with a halogen atom, $L^1$ represents —O—, —S— or *—O—$(CH_2)_{k1}$—CO—O—, k1 represents an integer of 1 to 7, * represents a binding position to —CO—, $L^2$ and $L^3$ independently each represent —O— or —S—, $Z^1$ represents a single bond or a C1-C6 alkylene group in which one or more —$CH_2$— may be replaced by —O— or —CO—, s1 and s1' independently each represent an integer of 0 to 4.

$R^{31}$ is preferably a hydrogen atom or a methyl group.

$L^1$ is preferably —O—.

It is preferred that one of $L^2$ and $L^3$ is —O— and the other is —S—.

In the formula (a1-5), s1 is preferably 1 and s1 is preferably 0, 1 or 2.

$Z^1$ is preferably a single bond or —$CH_2$—CO—O—.

Examples of the monomer represented by the formula (a1-5) include the following.

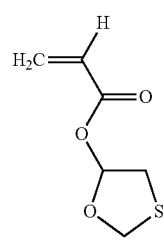 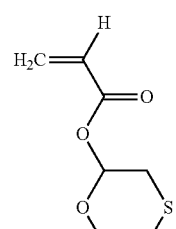 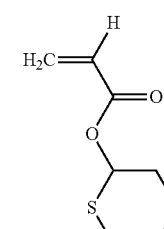

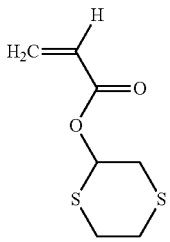 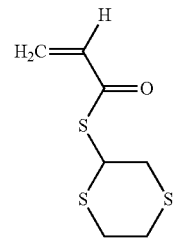 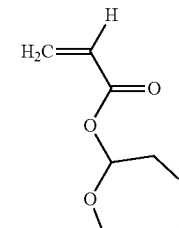

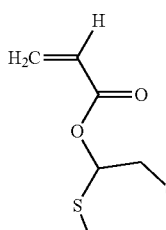 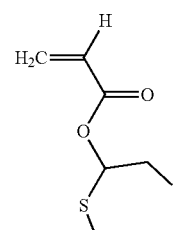 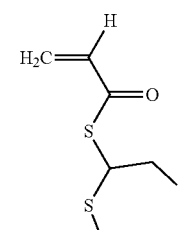

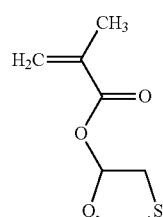 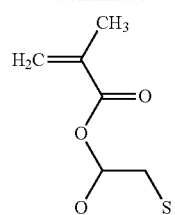 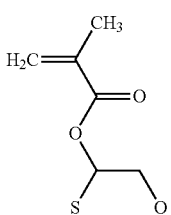

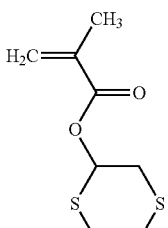 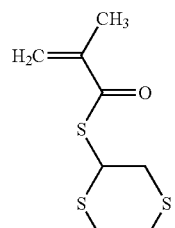 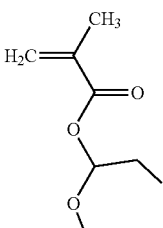

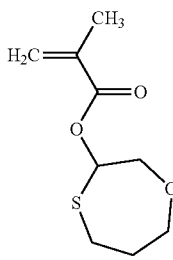 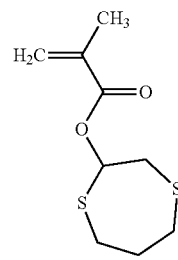 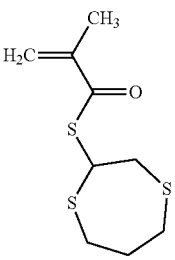

-continued

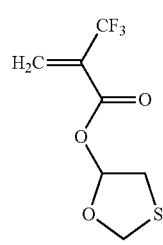 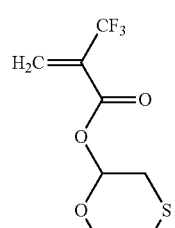 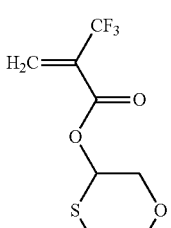

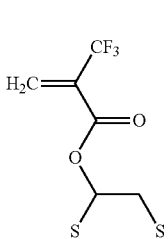 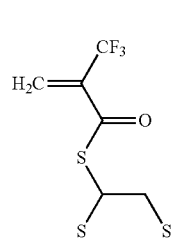 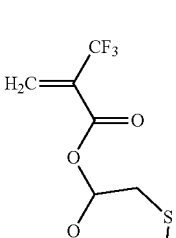

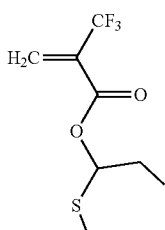 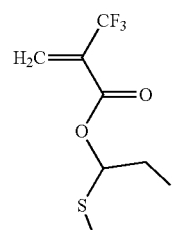 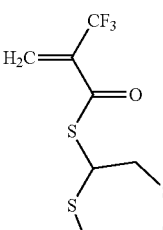

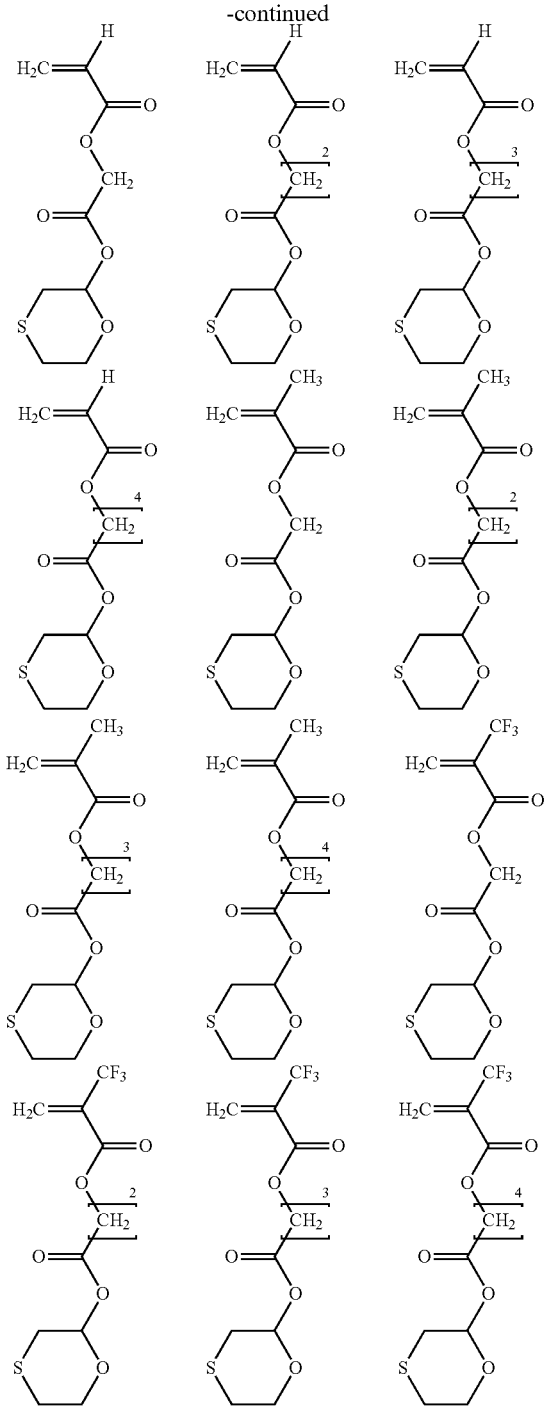

When the resin contains the structural unit derived form the monomer represented by the formula (a1-5), the content of the structural unit derived from the monomer represented by the formula (a1-5) is usually 10 to 95% by mole and preferably 15 to 90% by mole and more preferably 20 to 85% by mole based on total molar of all the structural units of the resin.

The resin can have two or more kinds of structural units derived from the monomers having an acid-labile group.

The resin preferably contains the structural unit derived from the monomer having an acid-labile group and a structural unit derived from the monomer having no acid-labile group. The resin can have two or more kinds of structural units derived from the monomers having no acid-labile group. When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

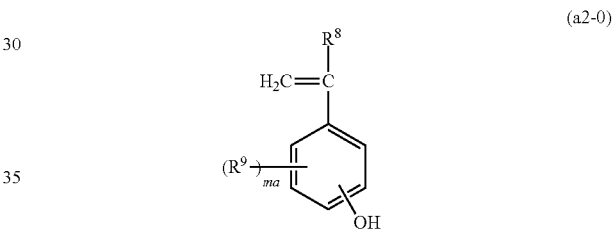

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

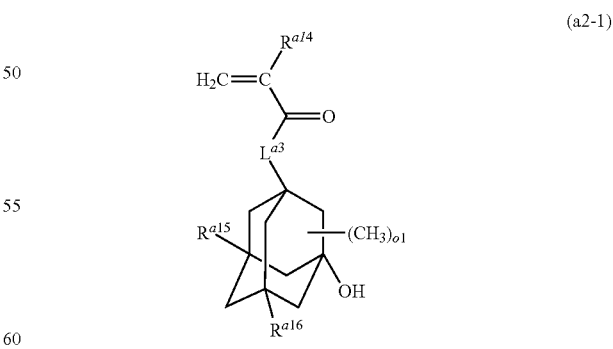

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

Examples of the monomer represented by the formula (a2-0) include the followings.

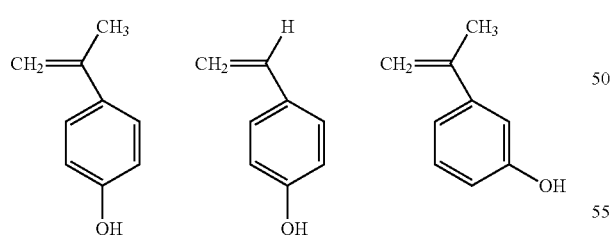

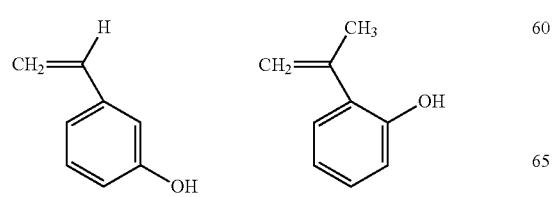

-continued

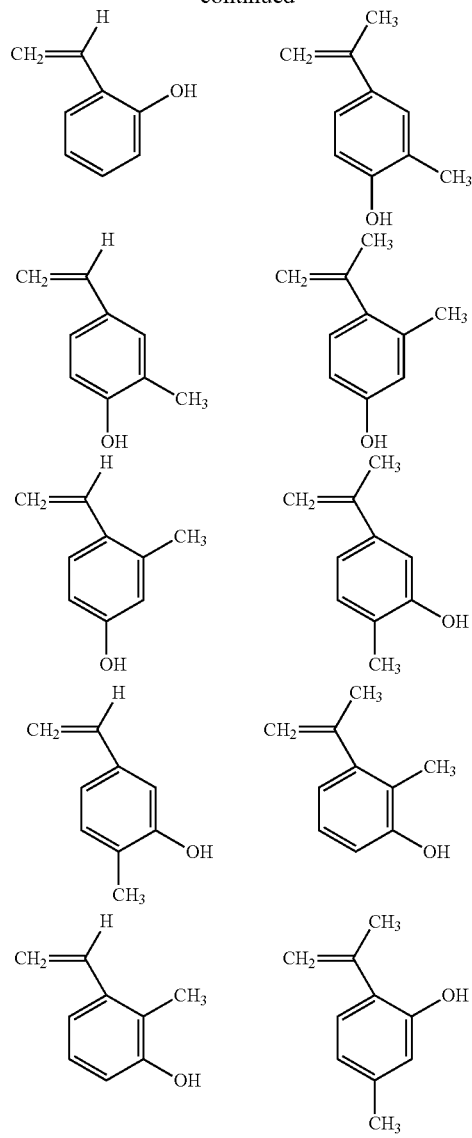

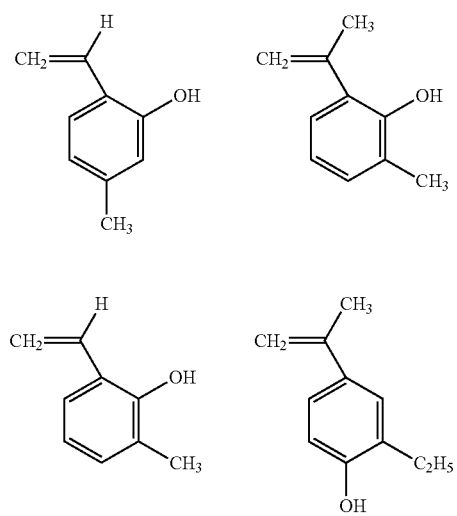

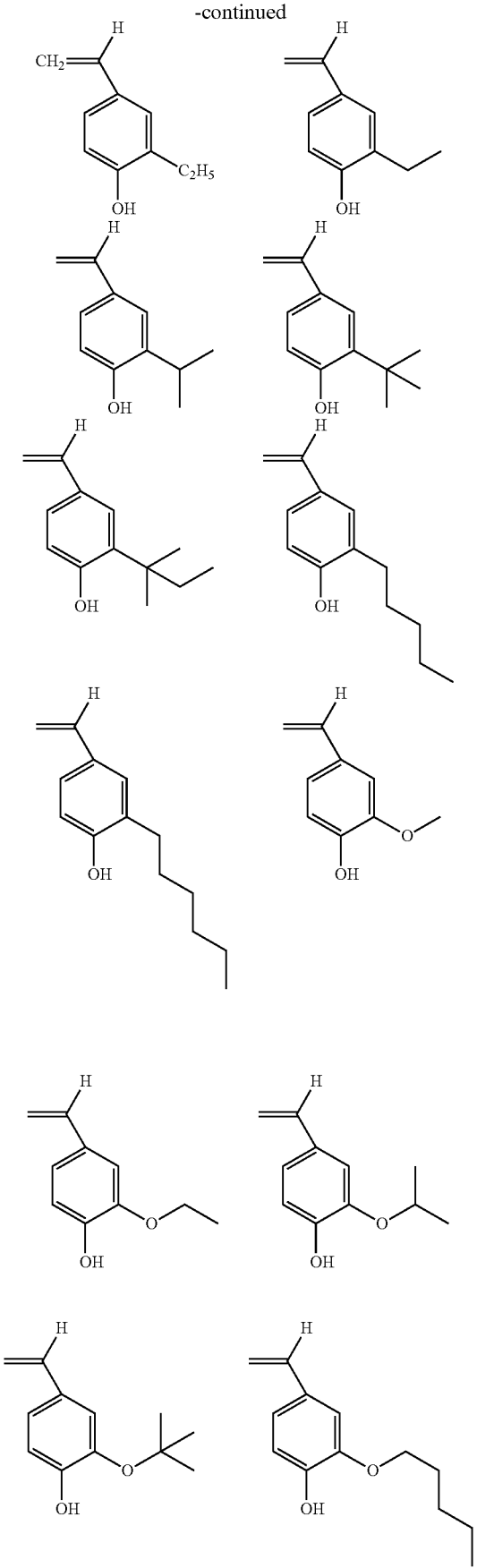
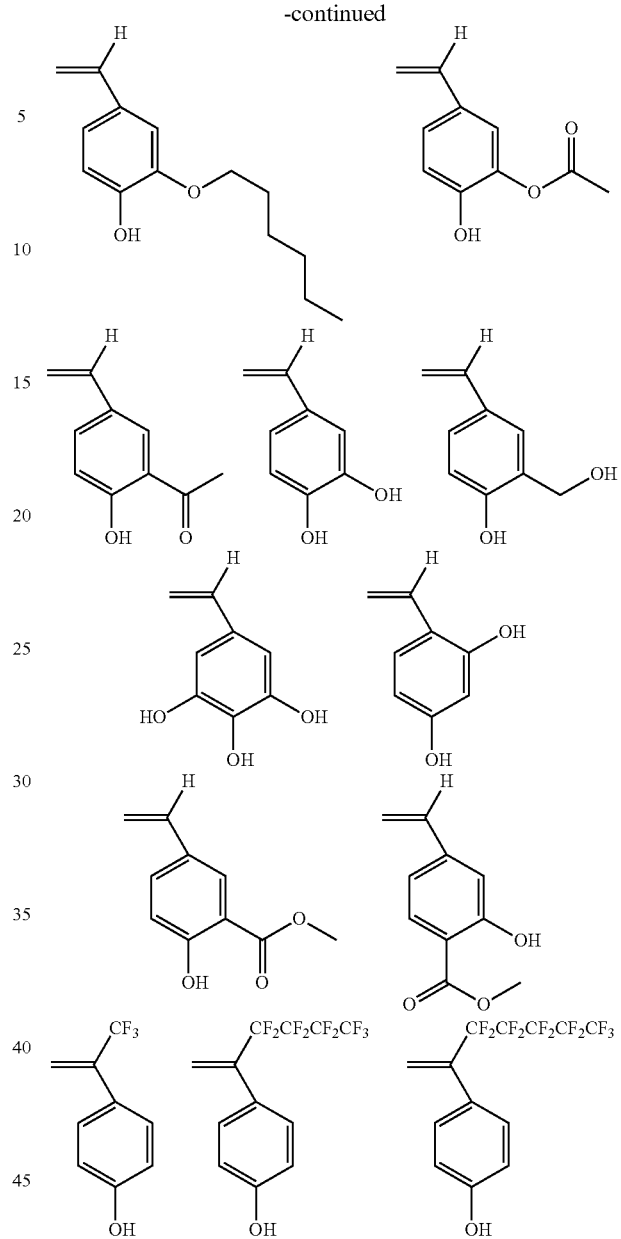

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 95% by mole and preferably 10 to 80% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and of is preferably 0, 1, 2 or 3 and is more preferably 0 or 1.

Examples of the monomer represented by the formula (a2-1) include the following.

101
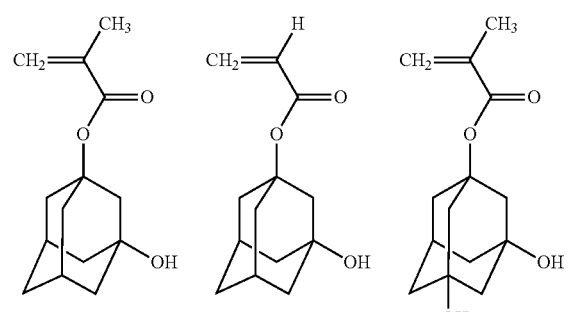
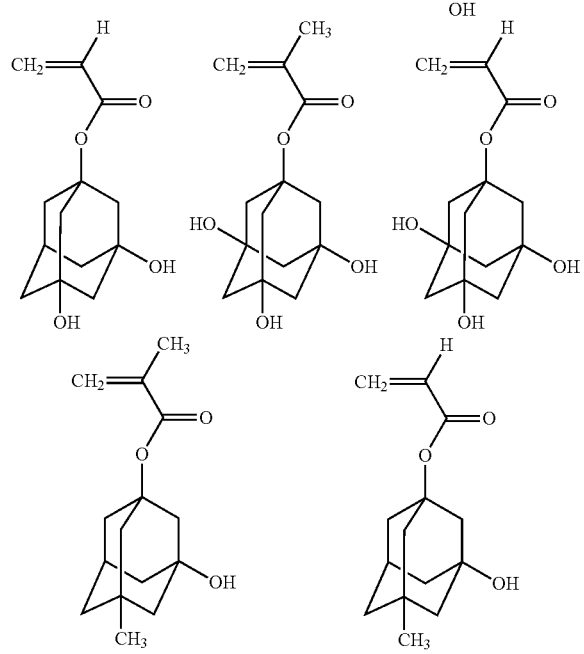
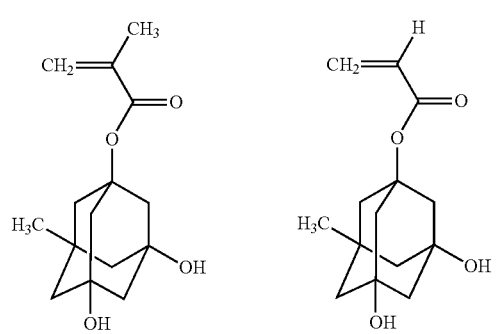
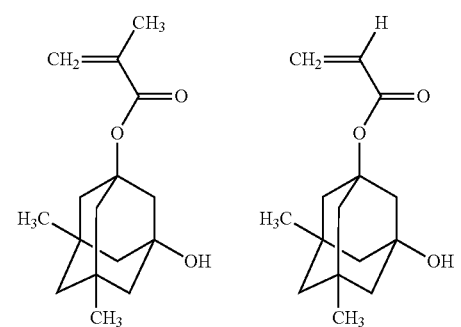
102
-continued
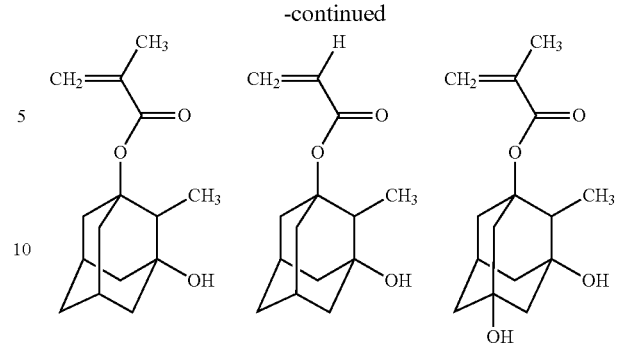
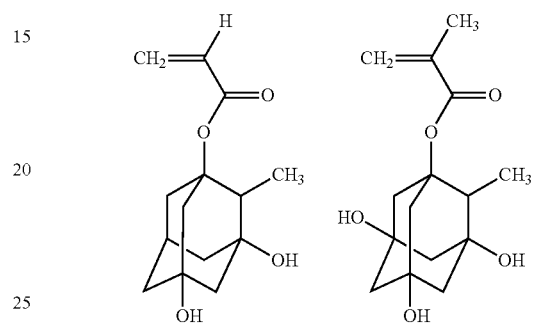
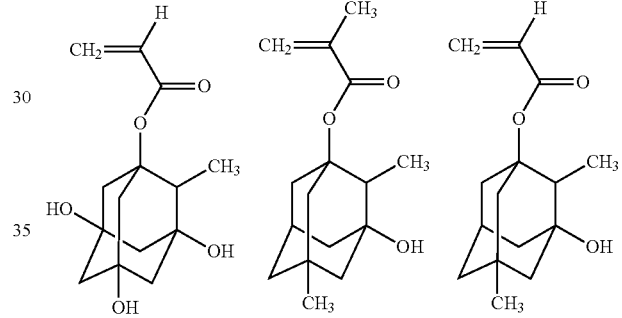
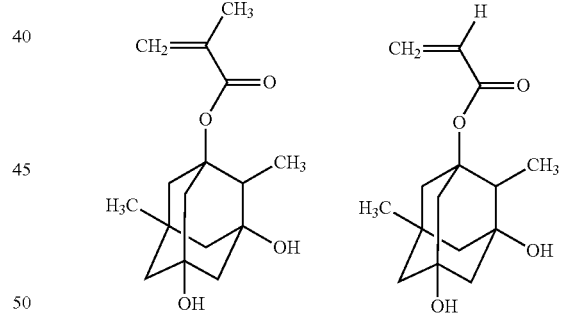
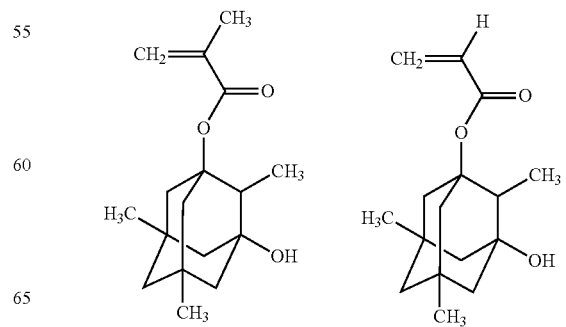

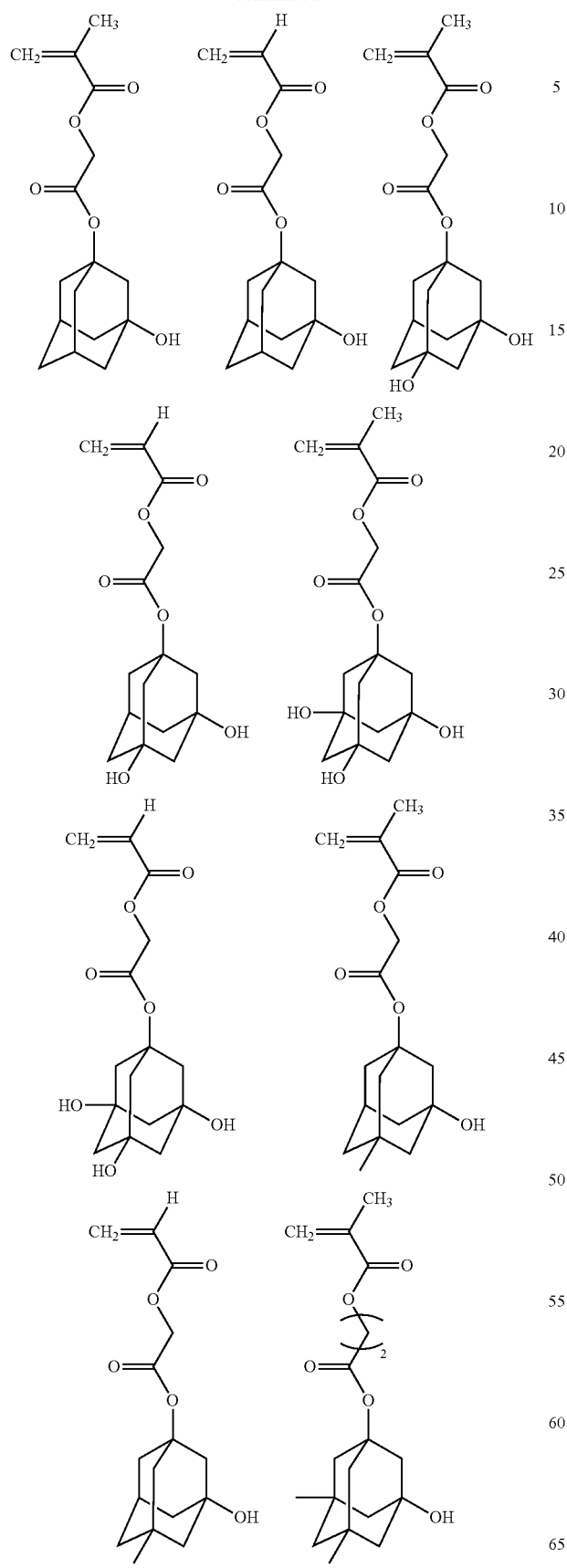
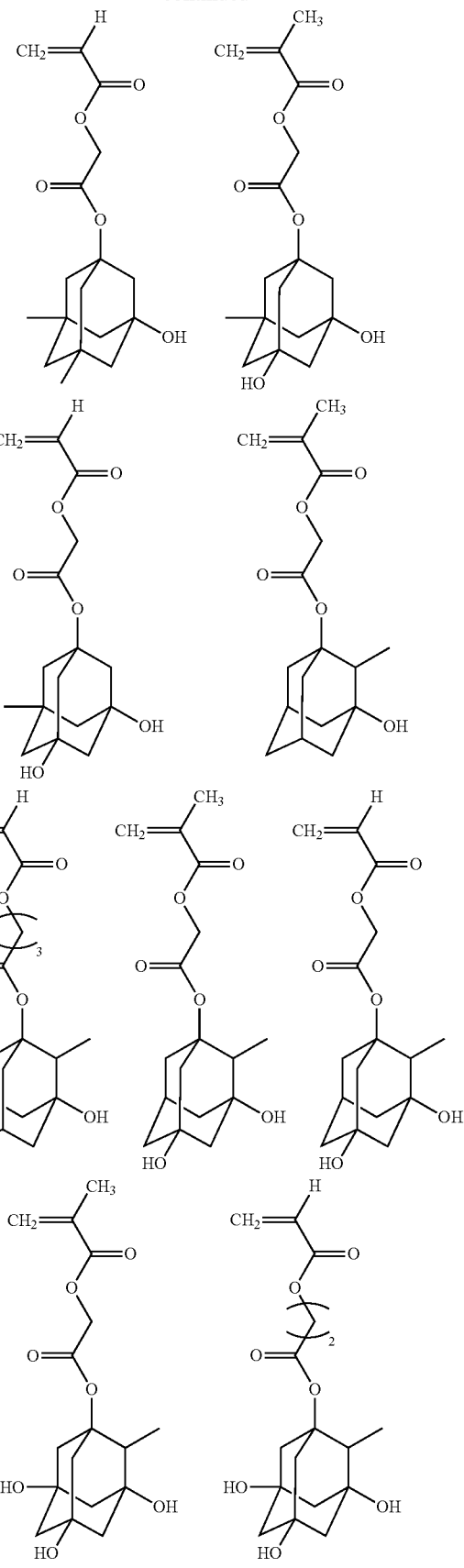

Among them, preferred are 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate, and more preferred are 3-hydroxy-1-adamantyl methacrylate and 3,5-dihydroxy-1-adamantyl methacrylate.

When the resin contains the structural unit derived from the monomer represented by the formula (a2-1), the content of the structural unit derived from the monomer represented by the formula (a2-1) is usually 3 to 40% by mole based on total molar of all the structural units of the resin, and preferably 5 to 35% by mole, and more preferably 5 to 30% by mole, and especially preferably 5 to 20% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

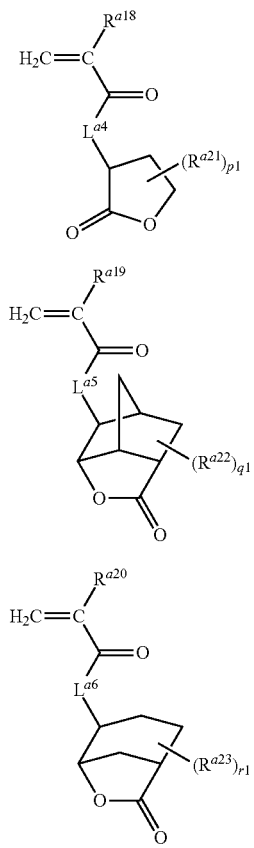

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$, and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the following.

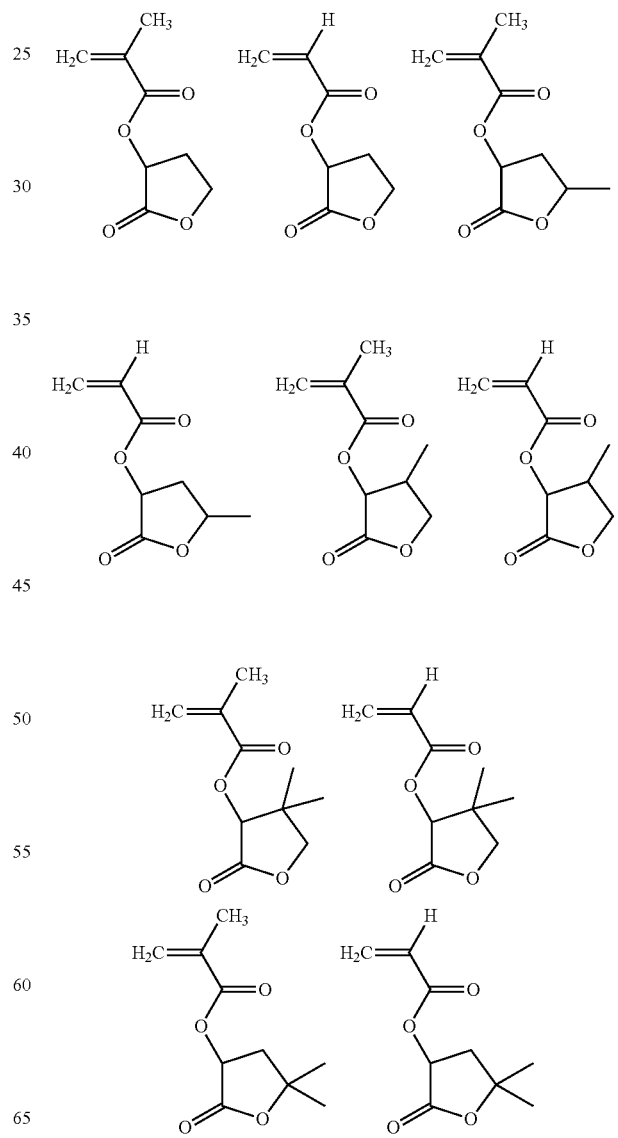

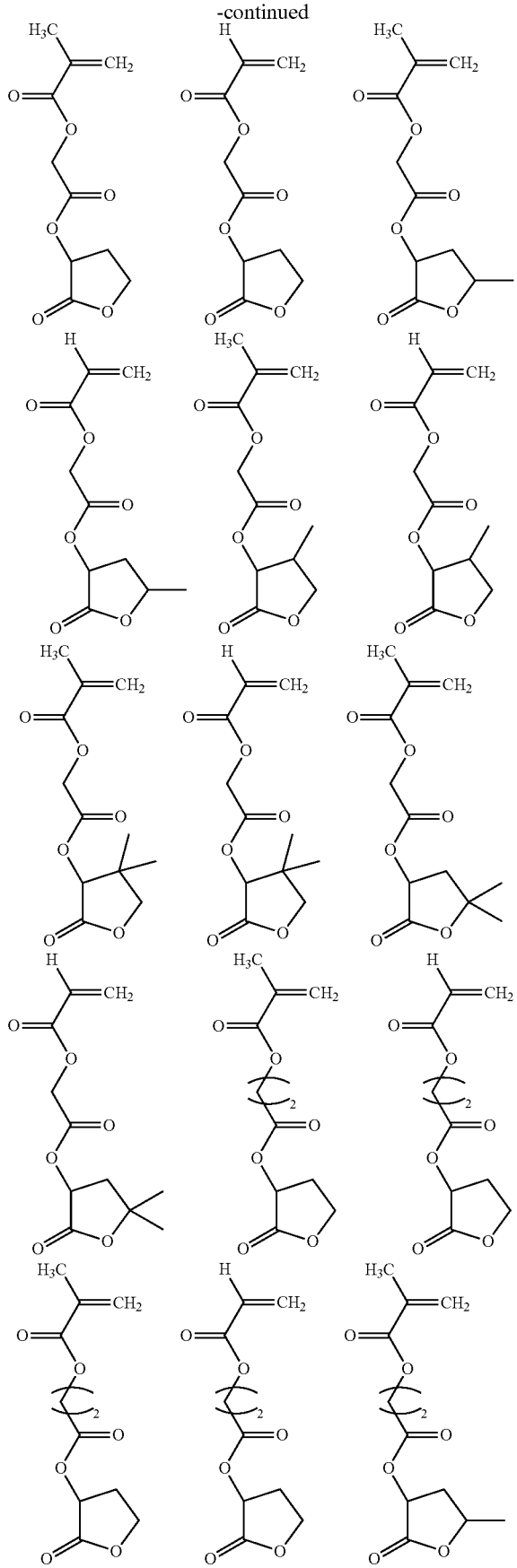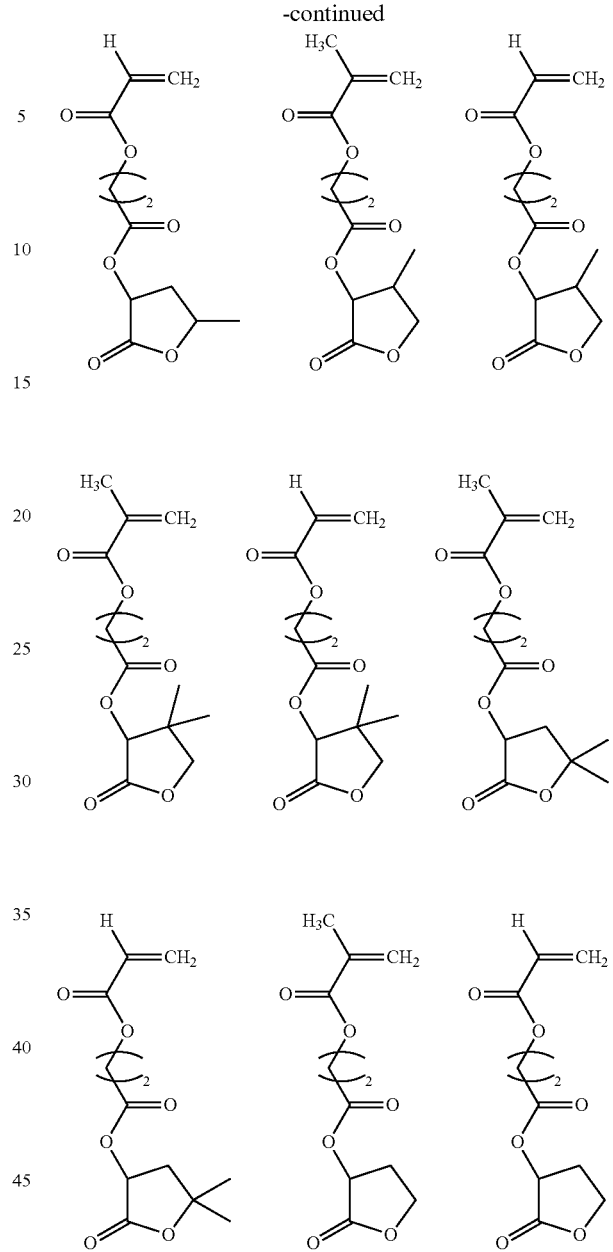
Examples of the monomer represented by the formula (a3-2) include the following.
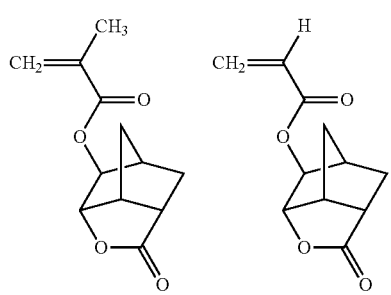

109
-continued
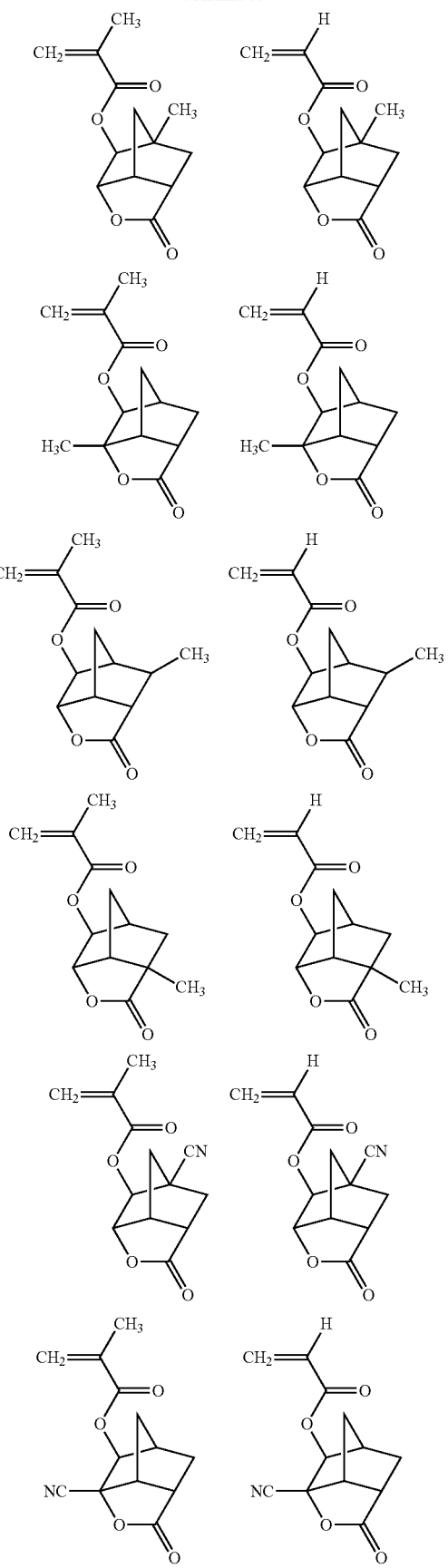
110
-continued
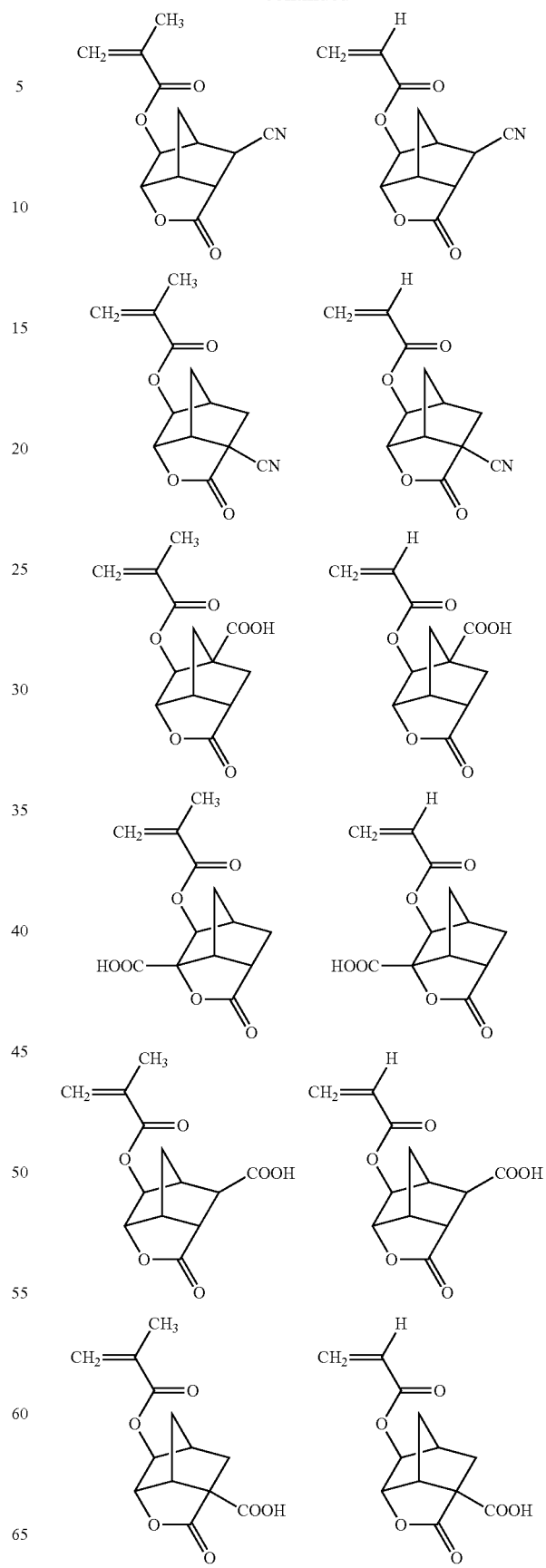

111
-continued
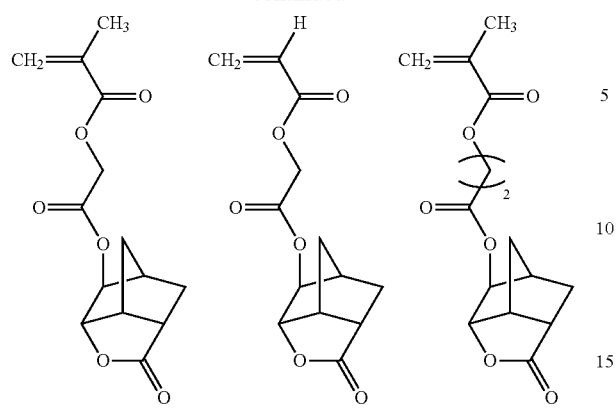
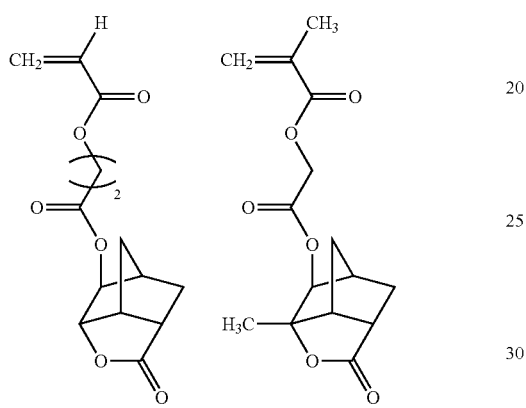
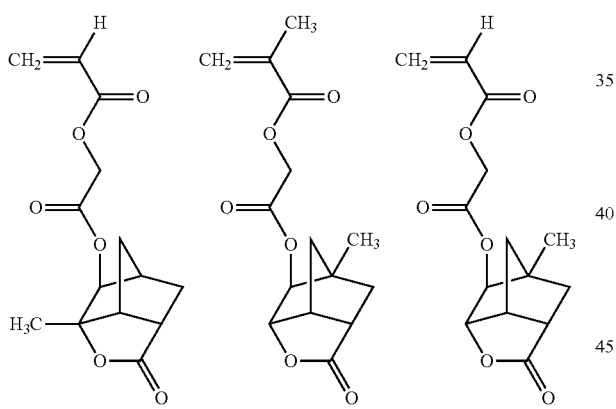
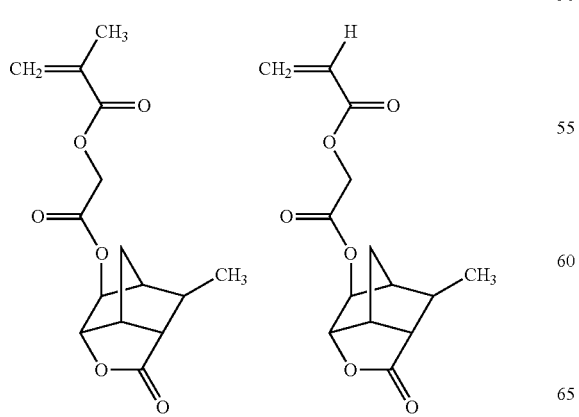
112
-continued
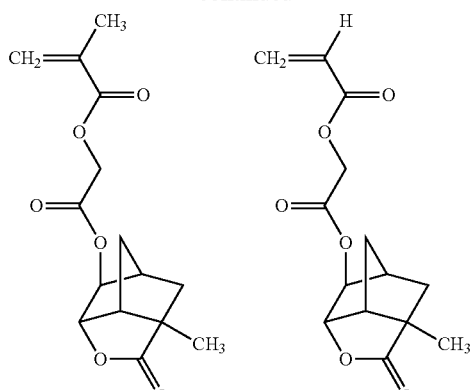
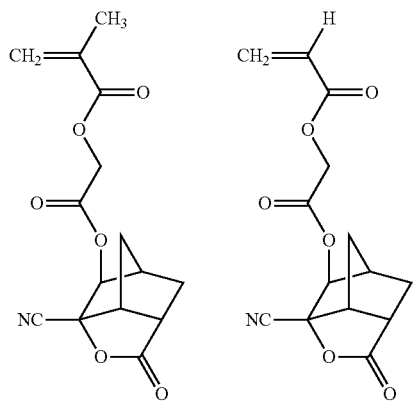
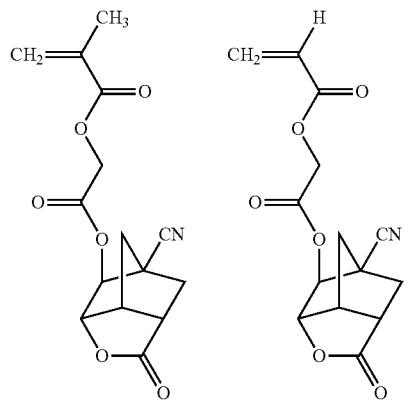
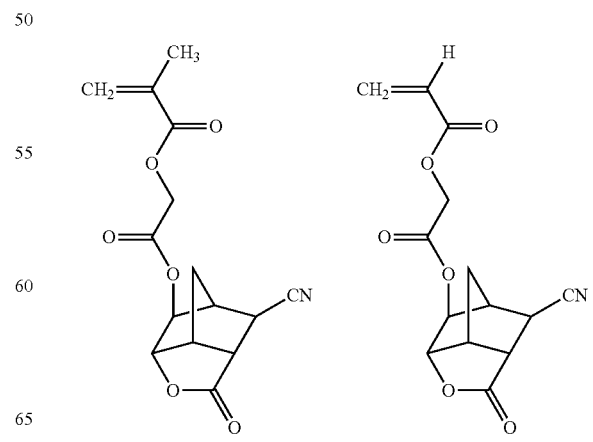

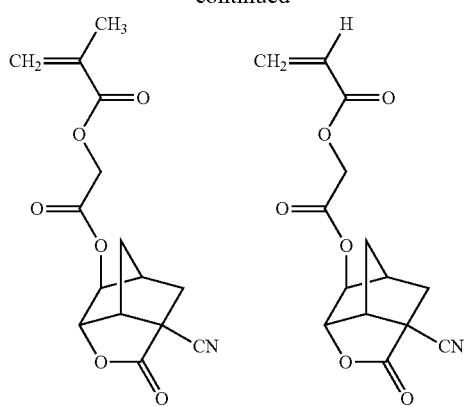
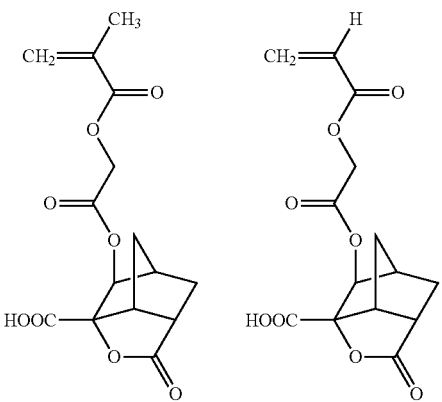
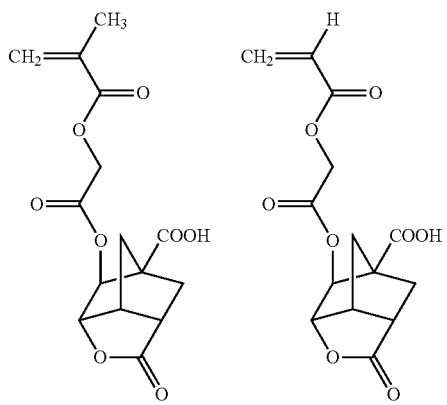
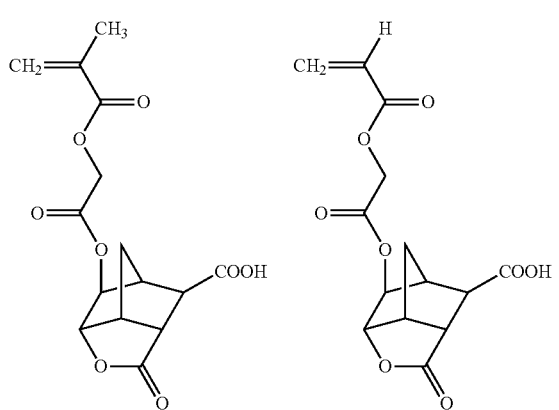
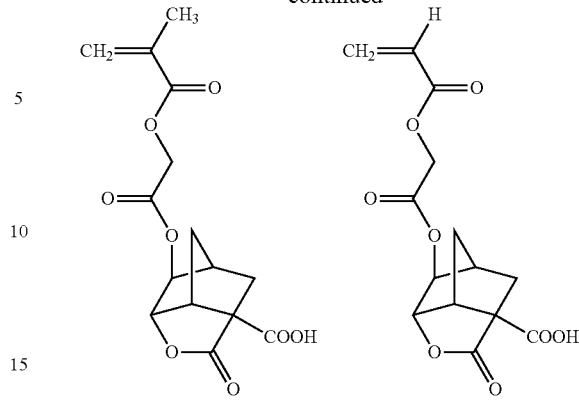
Examples of the monomer represented by the formula (a3-3) include the following.
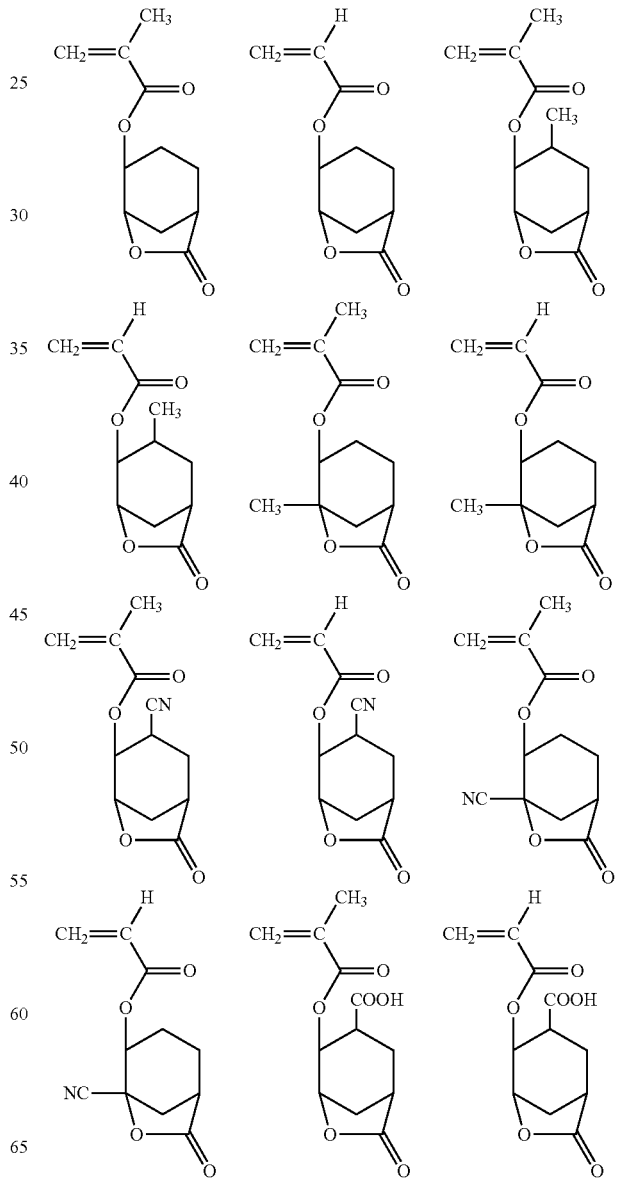

-continued
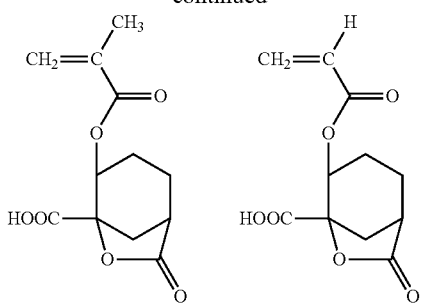
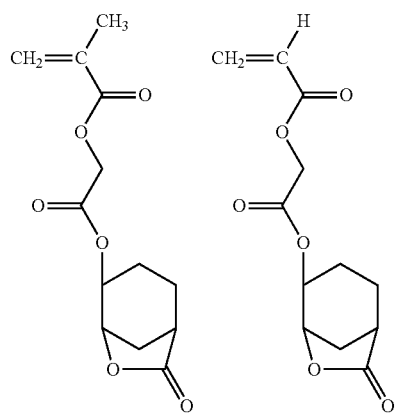
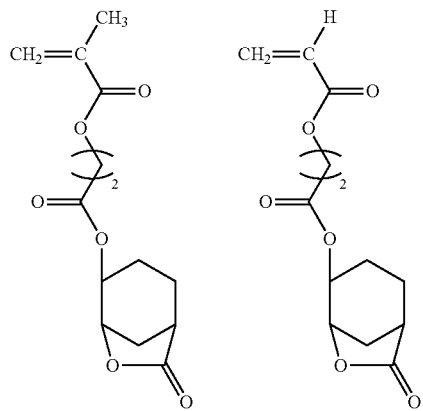
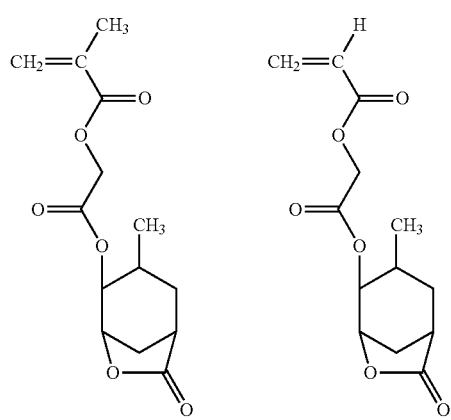
-continued
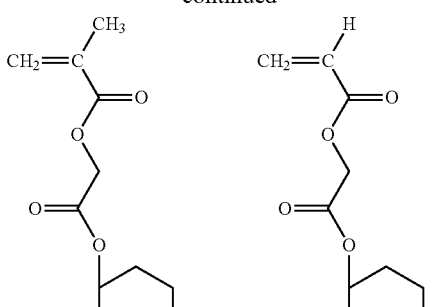
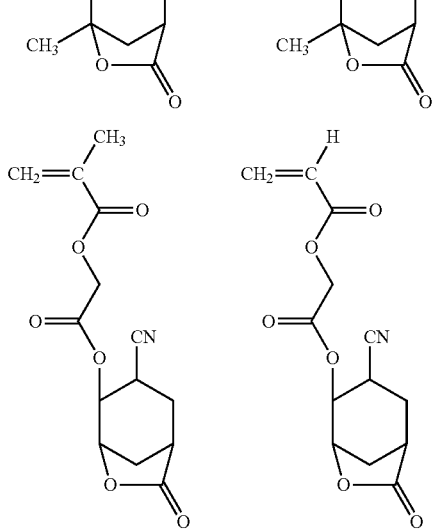
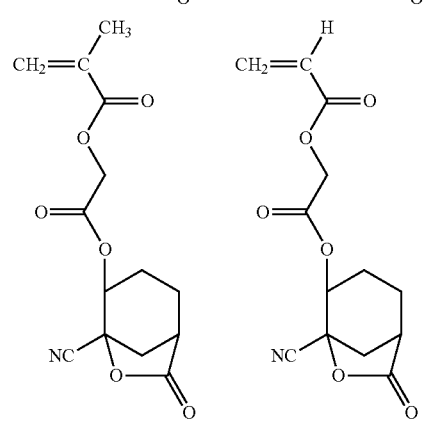
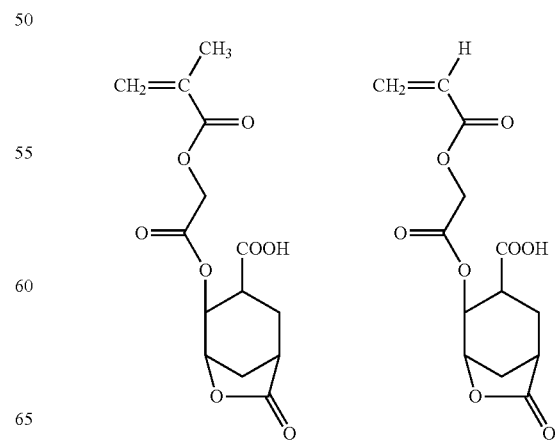

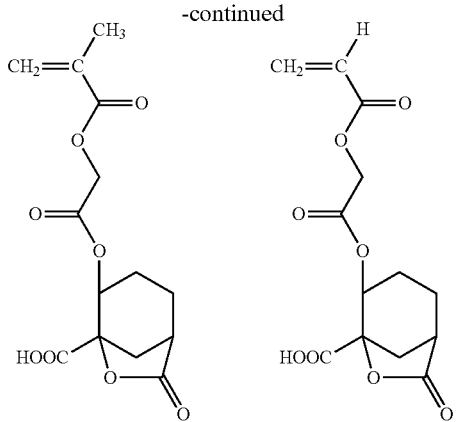

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When the resin contains the structural unit derived from the monomer having no acid-labile group and having a lactone ring, the content thereof is usually 5 to 60% by mole based on total molar of all the structural units of the resin, and preferably 5 to 50% by mole and more preferably 10 to 40% by mole and especially preferably 15 to 40% by mole.

When the resin contains the structural unit derived from the monomer represented by the formula (a3-1), (a3-2) or (a3-3), the content thereof is usually 5 to 60% by mole based on total molar of all the structural units of the resin, and preferably 10 to 55% by mole and more preferably 20 to 50% by mole.

Examples of the other monomer having no acid-labile group include the monomers represented by the formulae (a4-1), (a4-2) and (a4-3):

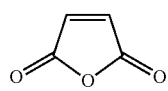

(a4-1)

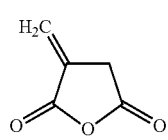

(a4-2)

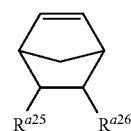

(a4-3)

wherein R$^{a25}$ and R$^{a26}$ each independently represents a hydrogen atom, a C1-C3 aliphatic hydrocarbon group which can have one or more hydroxyl groups, a carboxyl group, a cyano group or a —COOR$^{a27}$ group in which R$^{a27}$ represents a C1-C18 aliphatic hydrocarbon group or a C3-C18 alicyclic hydrocarbon group, and one or more —CH$_2$— in the C1-C18 aliphatic hydrocarbon group and the C3-C18 alicyclic hydrocarbon group can be replaced by —O— or —CO—, with the proviso that the carbon atom bonded to —O— of —COO— of R$^{a27}$ is not a tertiary carbon atom, or R$^{a25}$ and R$^{a26}$ are bonded together to form a carboxylic anhydride residue represented by —C(=O)—O—C(=O)—.

Examples of the substituent of the C1-C3 aliphatic hydrocarbon group include a hydroxyl group. Examples of the C1-C3 aliphatic hydrocarbon group which can have one or more hydroxyl groups include a C1-C3 alkyl group such as a methyl group, an ethyl group and a propyl group, and a C1-C3 hydroxyalkyl group such a hydroxymethyl group and a 2-hydroxyethyl group. The C1-C18 aliphatic hydrocarbon group represented by R$^{a27}$ is preferably a C1-C8 aliphatic hydrocarbon group and is more preferably a C1-C6 aliphatic hydrocarbon group. The C3-C18 alicyclic hydrocarbon group represented by R$^{a27}$ is preferably a C4-C18 alicyclic hydrocarbon group, and is more preferably C4-C12 alicyclic hydrocarbon group. Examples of R$^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Examples of the other monomer having no acid-labile group include a monomer represented by the formula (a4-4):

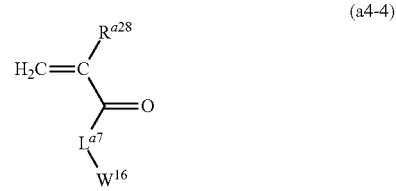

(a4-4)

wherein R$^{a28}$ represents a hydrogen atom or a methyl group, L$^{a7}$ represents —O— or *—O—(CH$_2$)$_{k2}$—CO—O— in which * represents a binding position to —CO— and k2 represents an integer of 1 to 7, and W$^{16}$ represents a group containing a sultone ring which may have one or more substituents.

Examples of the sultone ring include the following.

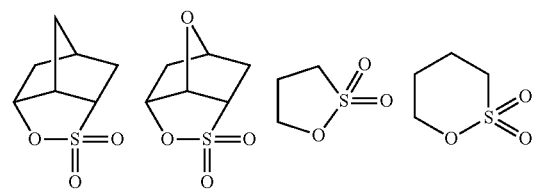

Examples of the group containing a sultone ring include groups formed by removing any one hydrogen atom from the above-mentioned sultone ring. Examples of the substituents include a hydroxyl group, a cyano group, a C1-C6 alkyl group, a C1-C6 fluorinated alkyl group, a C1-C6 hydroxyalkyl group, a C1-C6 alkoxy group, a C2-C7 alkoxycarbonyl group, a C2-C8 acyl group and a C2-C7 acyloxy group.

Examples of the fluorinated alkyl group include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl) methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl) ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2,3,3,4,4,5,5,6,6-dodecafluorohexyl group, a (perfluoropentyl) methyl group and a perfluorohexyl group. Among them preferred is a C1-C4 fluorinated alkyl group, and more preferred are a trifluoromethyl group, a perfluoroethyl group and a perfluoropropyl group, and especially preferred is a trifluoromethyl group.

Examples of the hydroxyalkyl group include a hydroxymethyl group and a 2-hydroxyethyl group.

Examples of the monomer represented by the formula (a4-4) include the following.

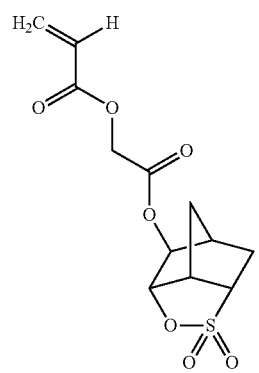

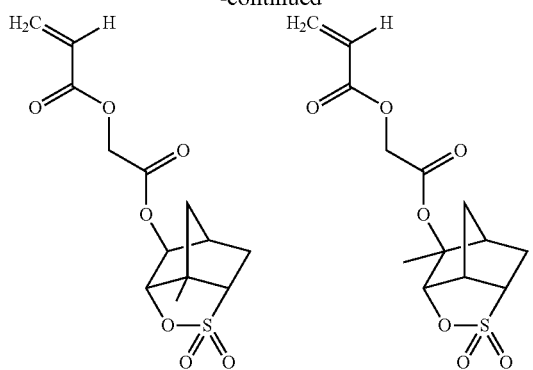

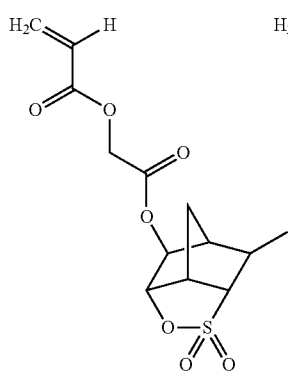

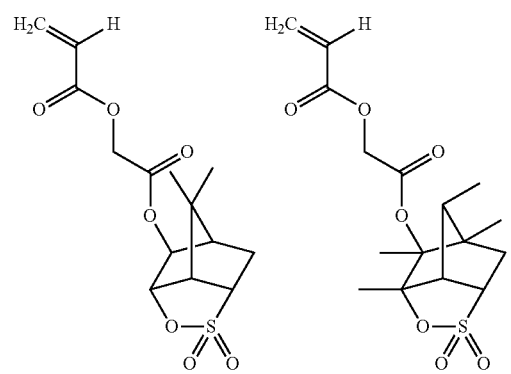

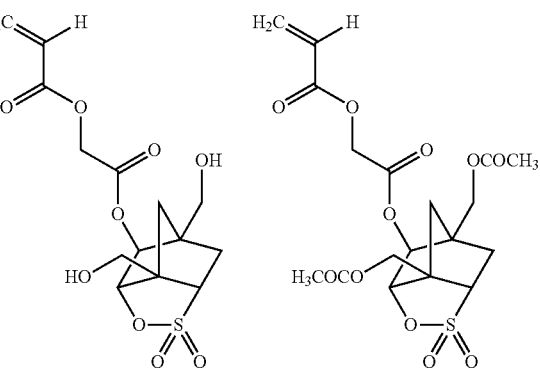

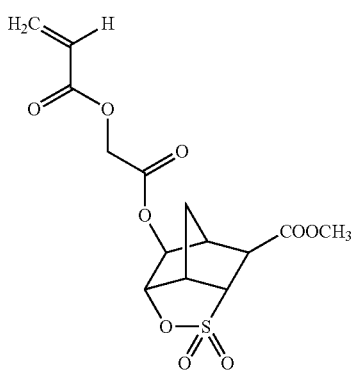

121
-continued
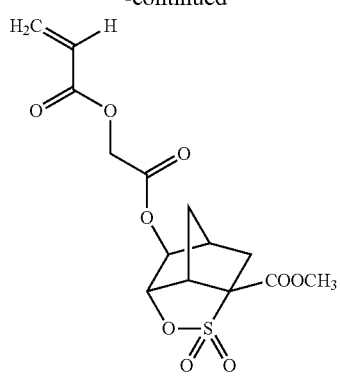
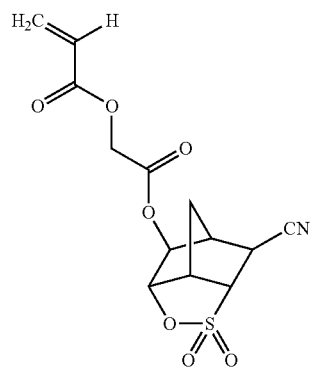
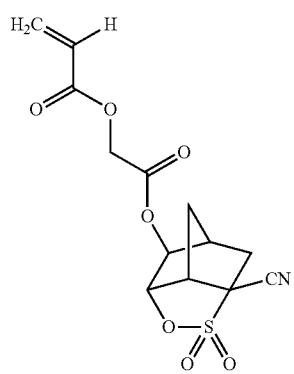
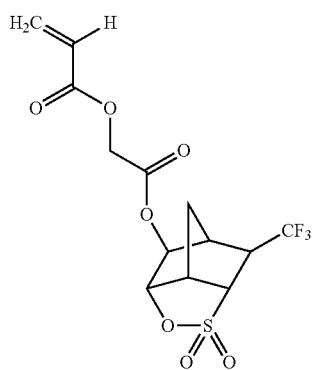
122
-continued
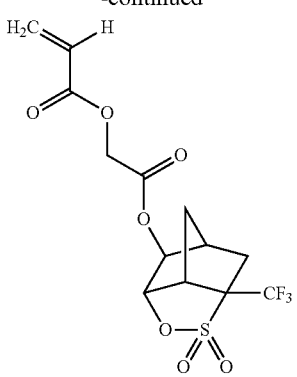
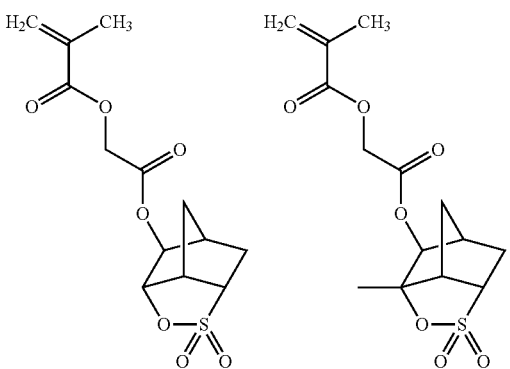
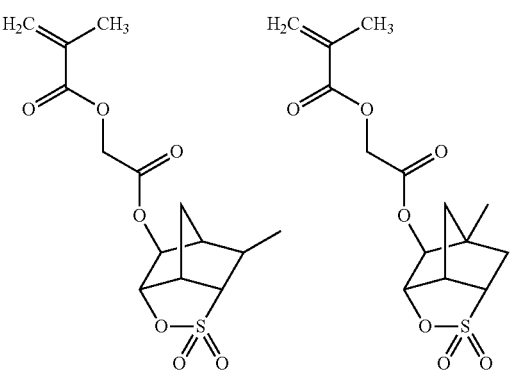
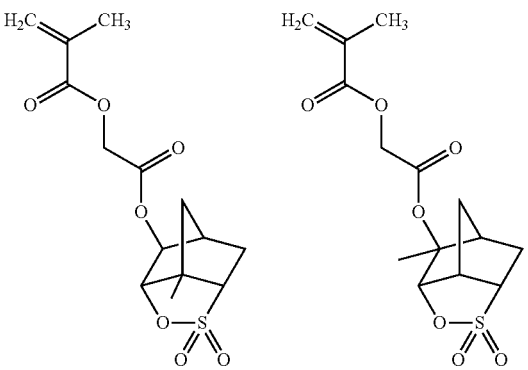

123
-continued
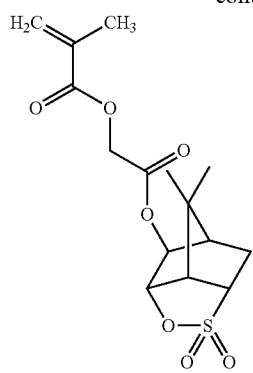
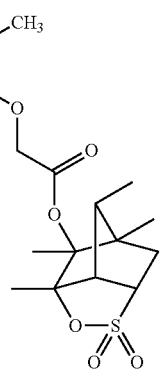
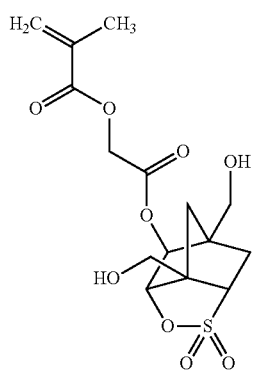
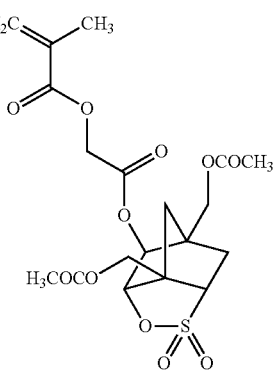
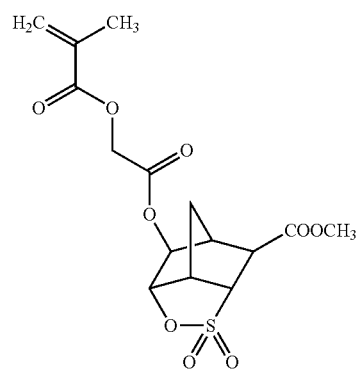
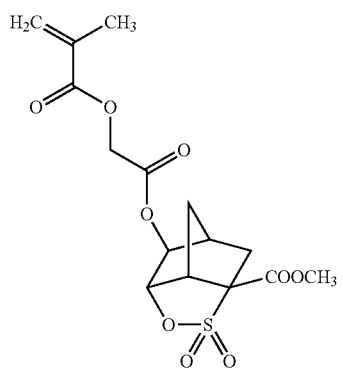
124
-continued
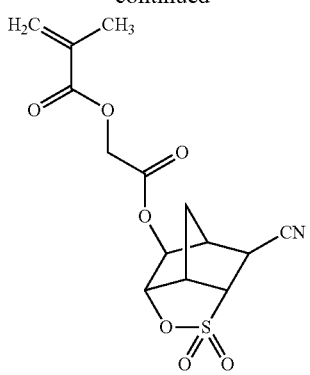
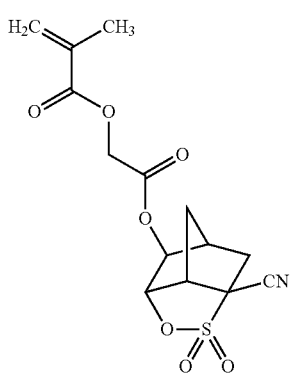
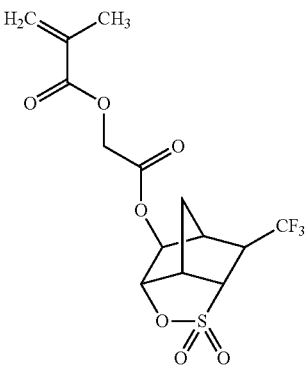
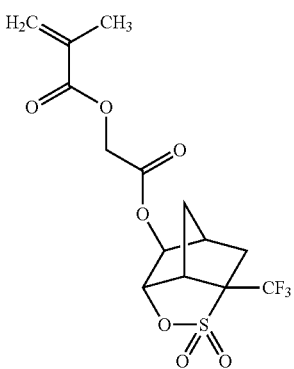

125
-continued
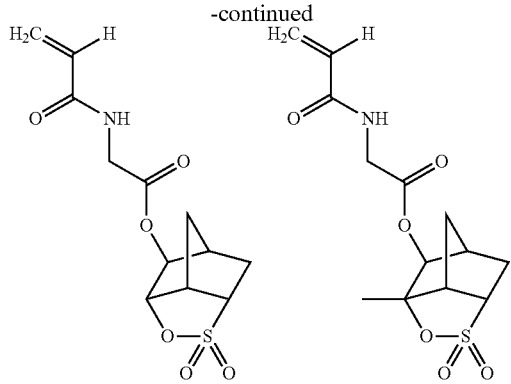
126
-continued
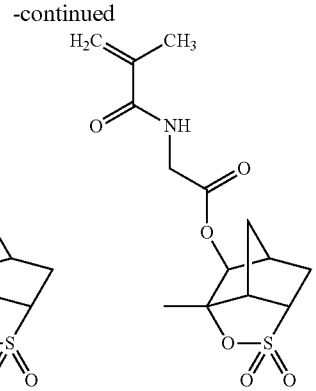

127
-continued
128
-continued
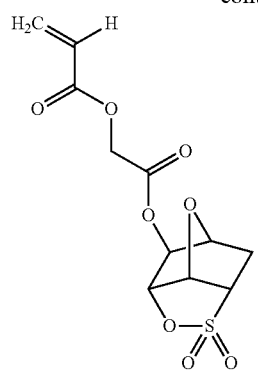
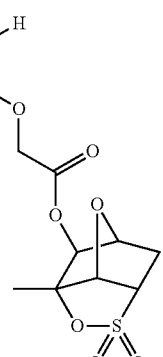
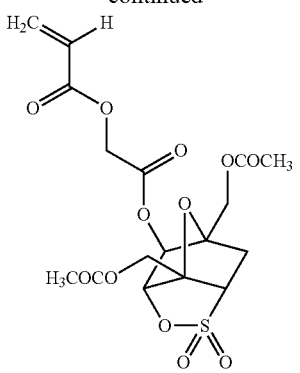
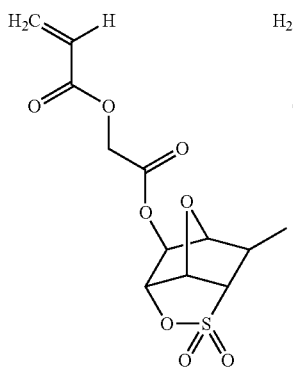
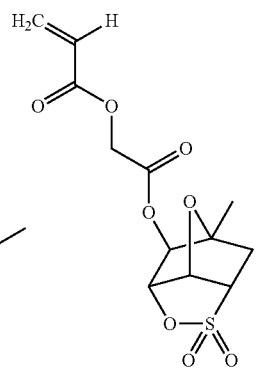
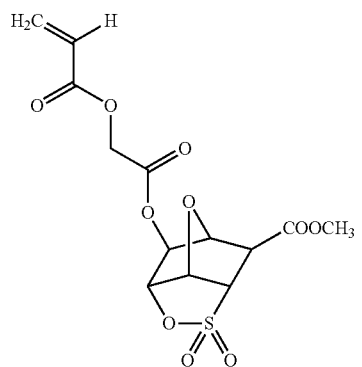
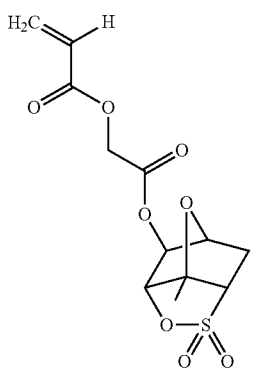
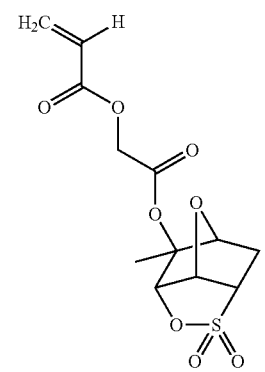
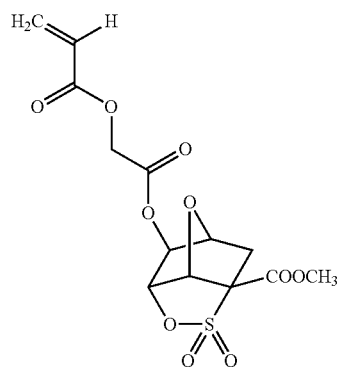
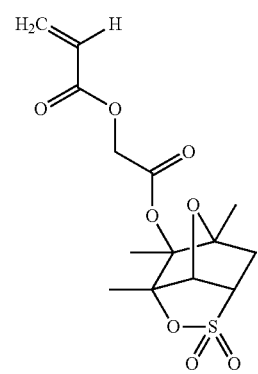
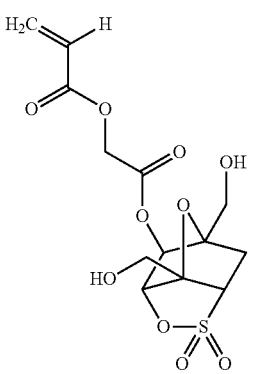
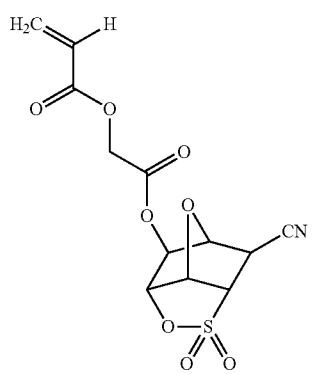

129
-continued
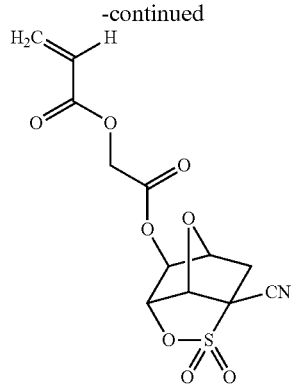
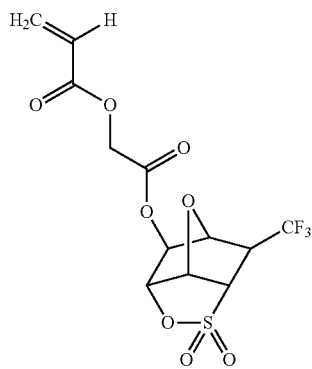
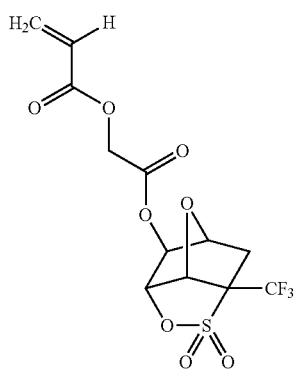
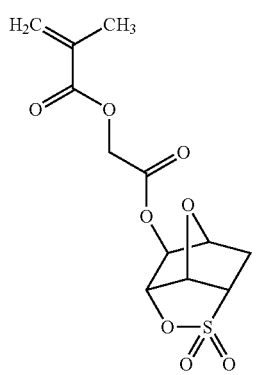 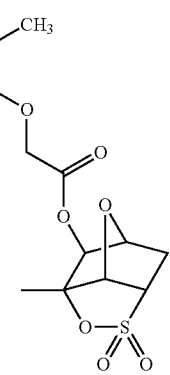
130
-continued
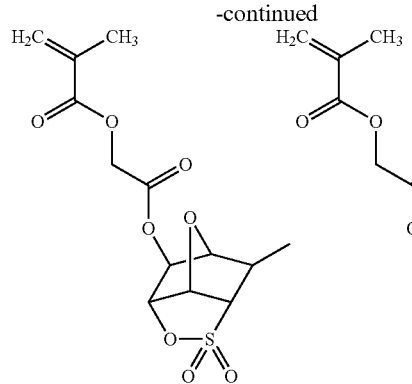
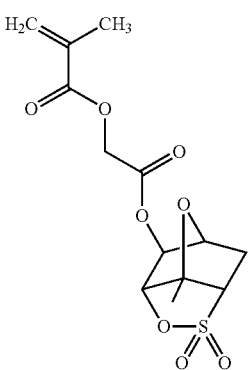 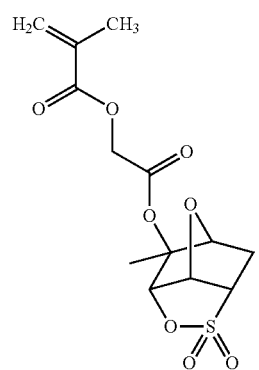
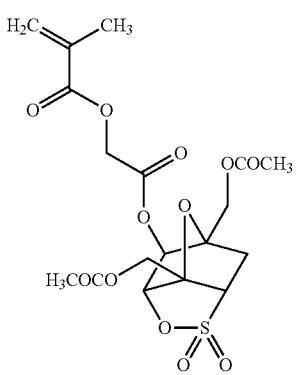

131
-continued
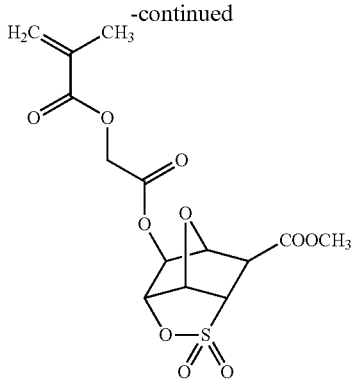
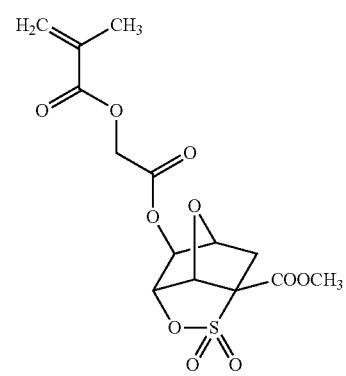
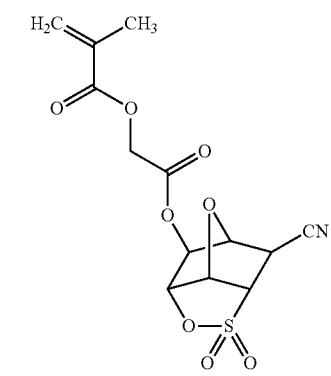
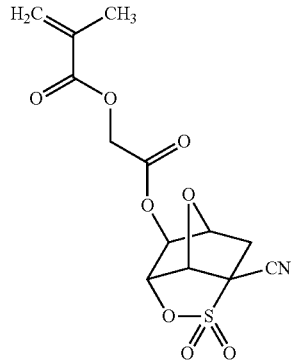
132
-continued
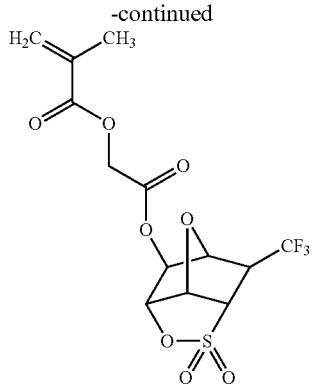
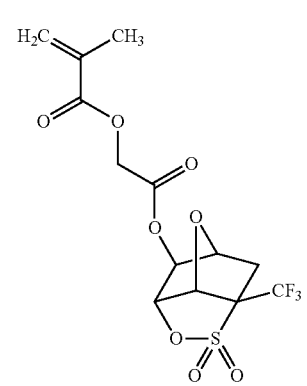
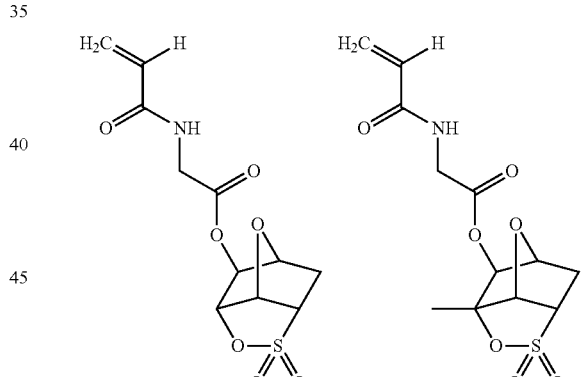
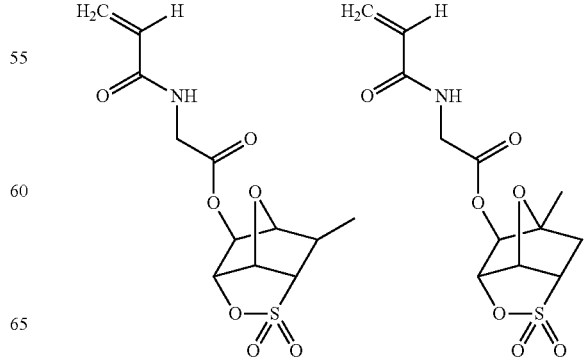

133
-continued
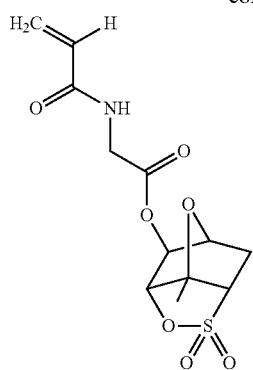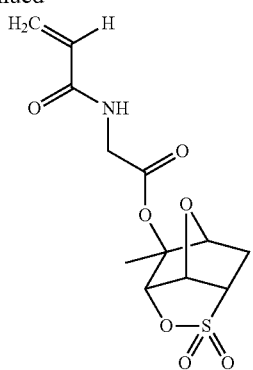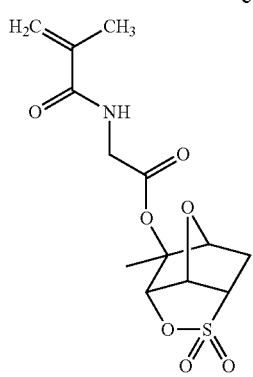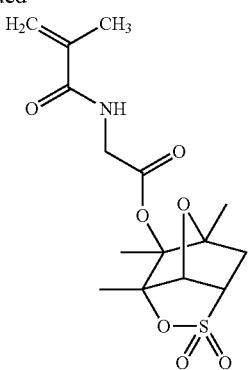
134
-continued
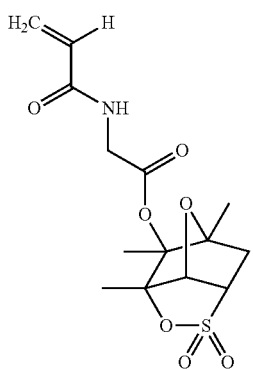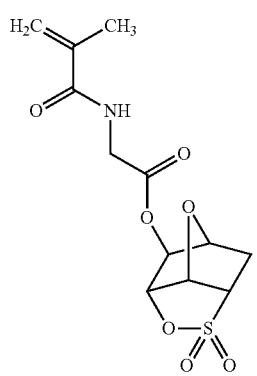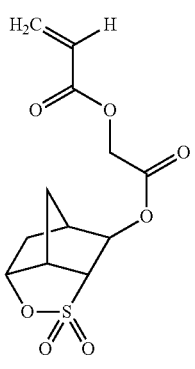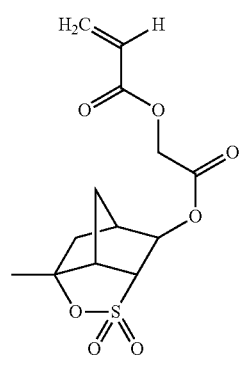
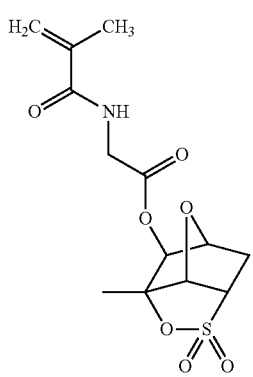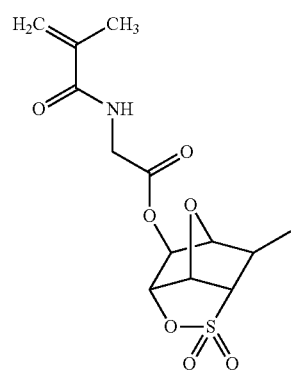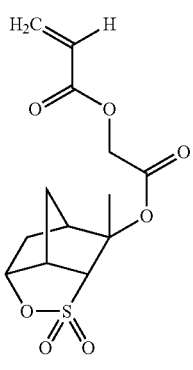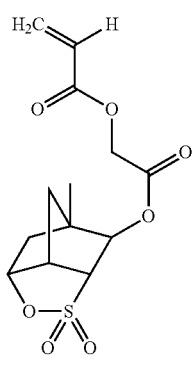
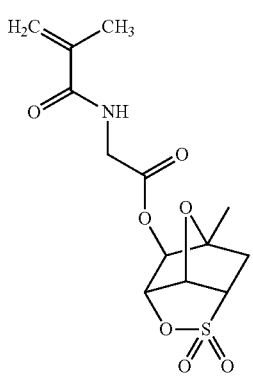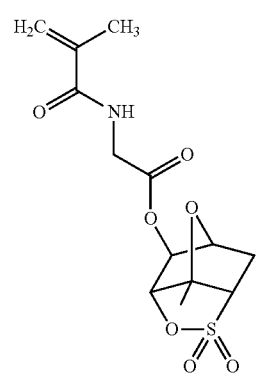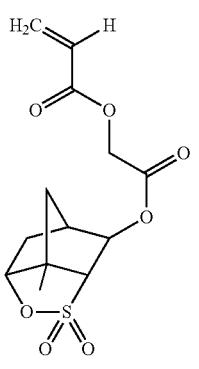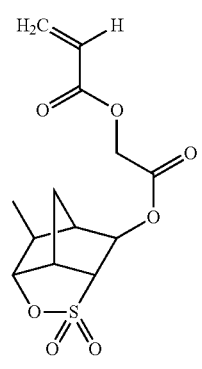

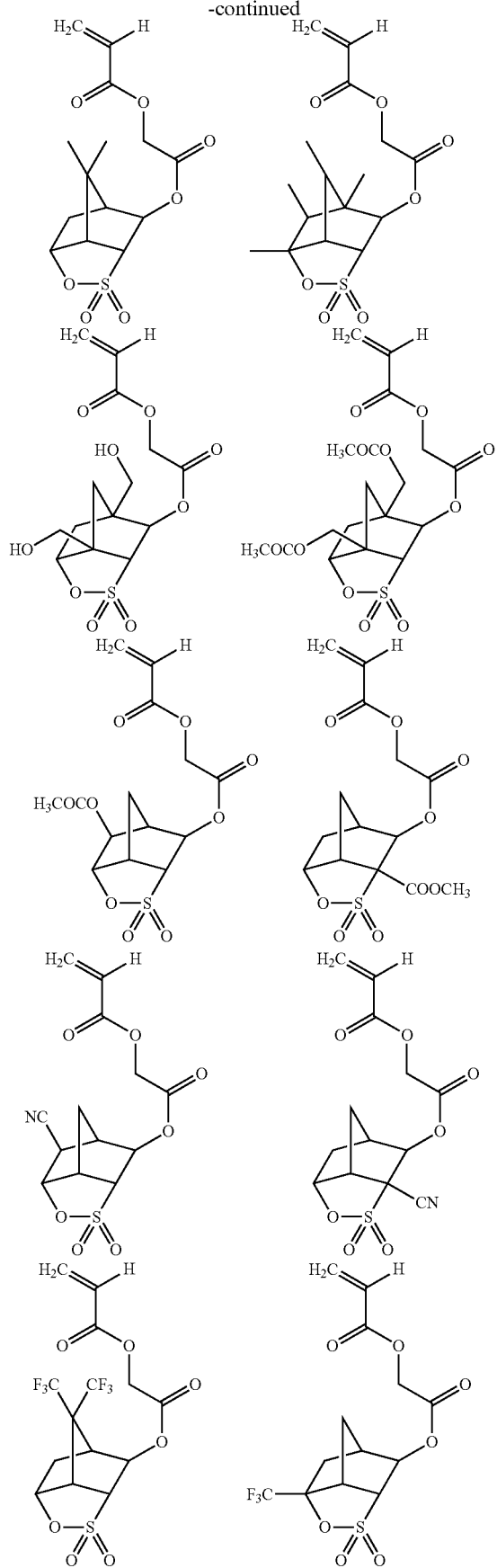
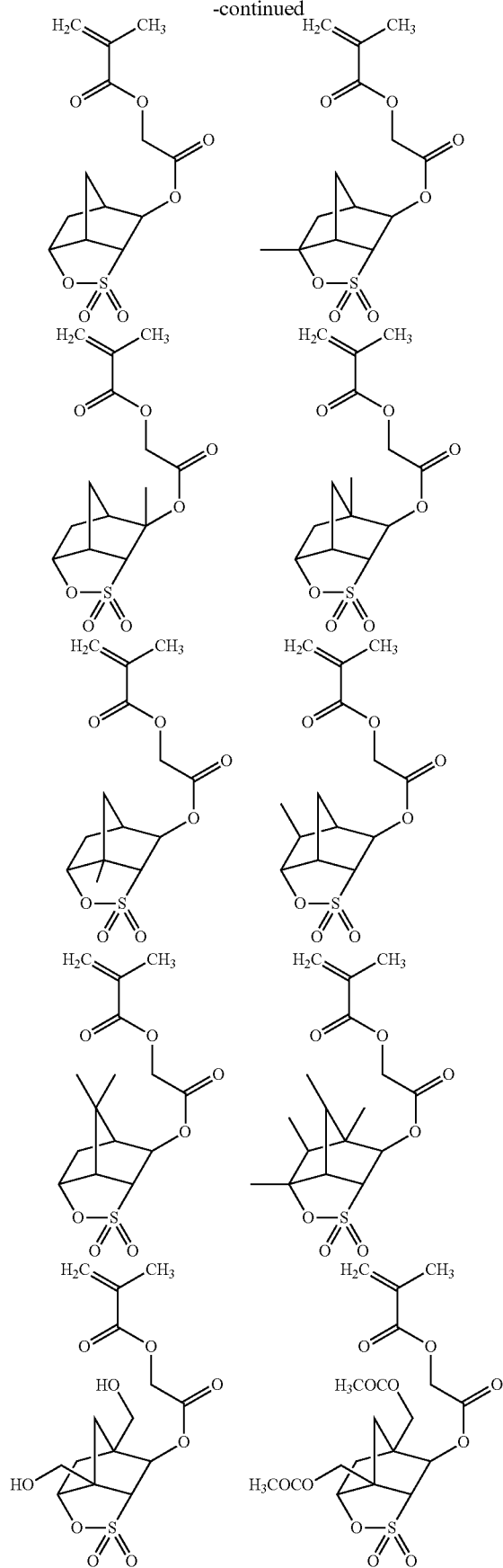

137
-continued
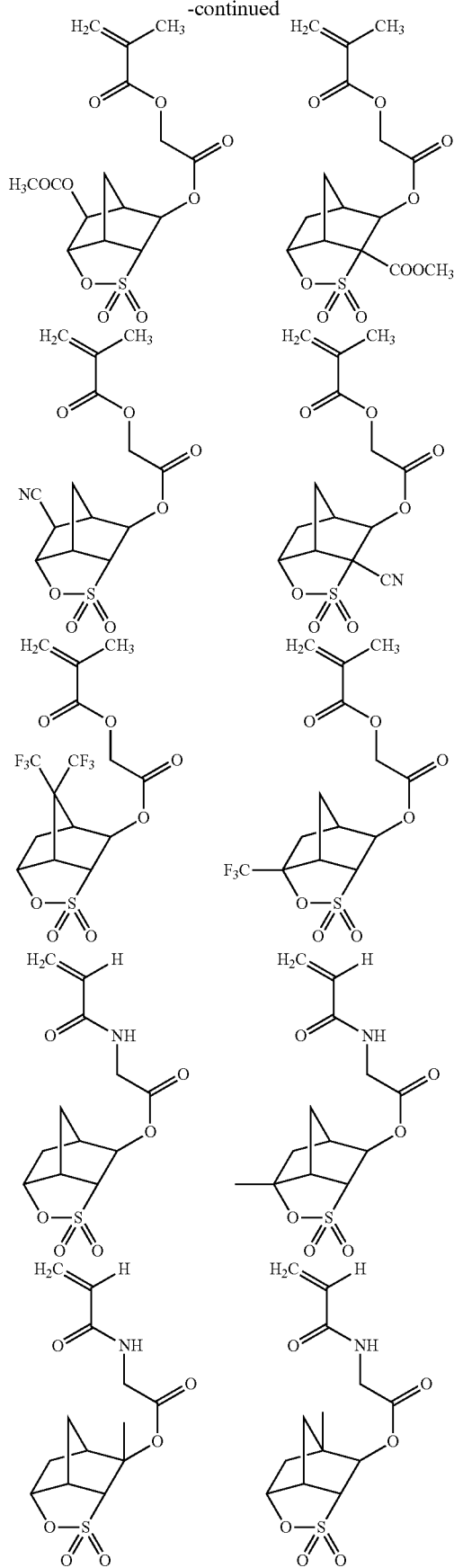
138
-continued
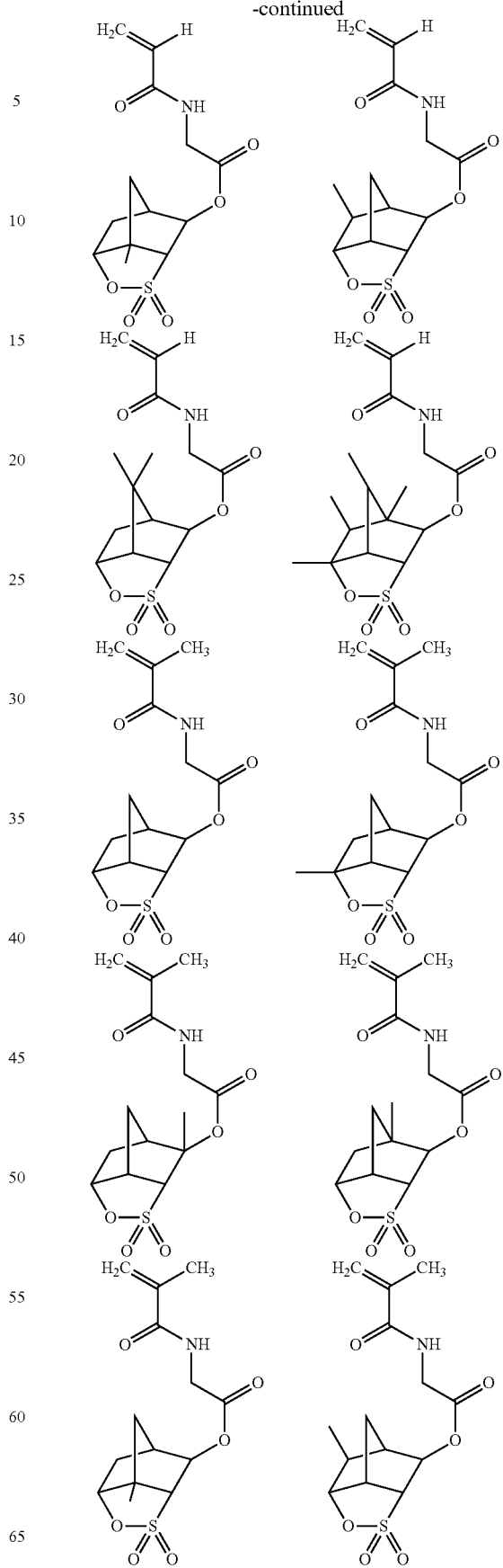

-continued
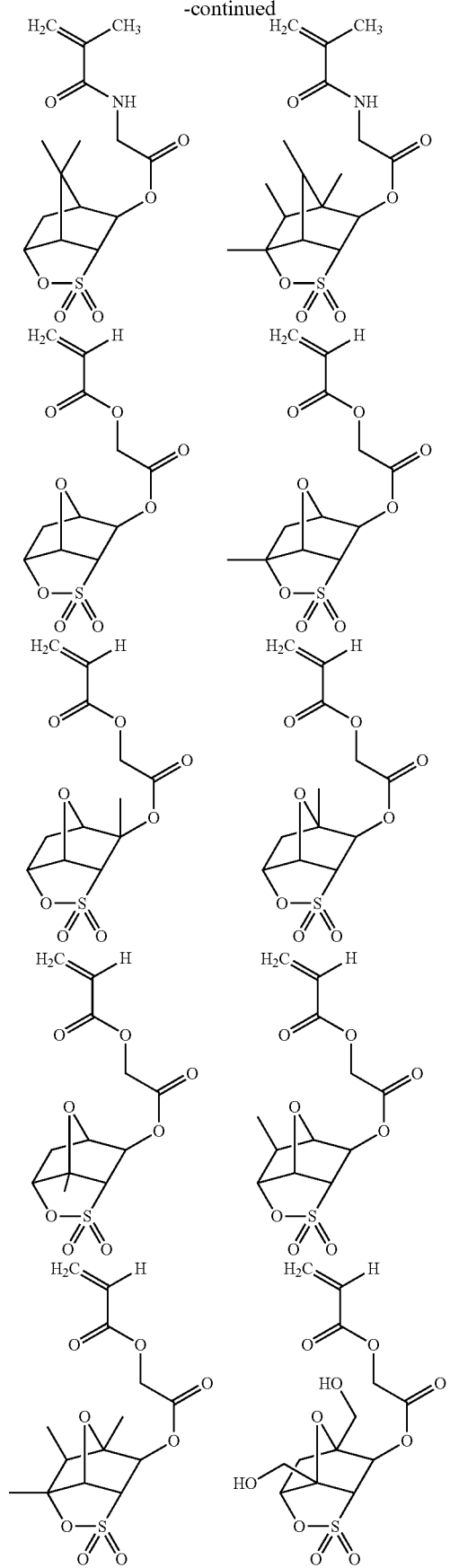
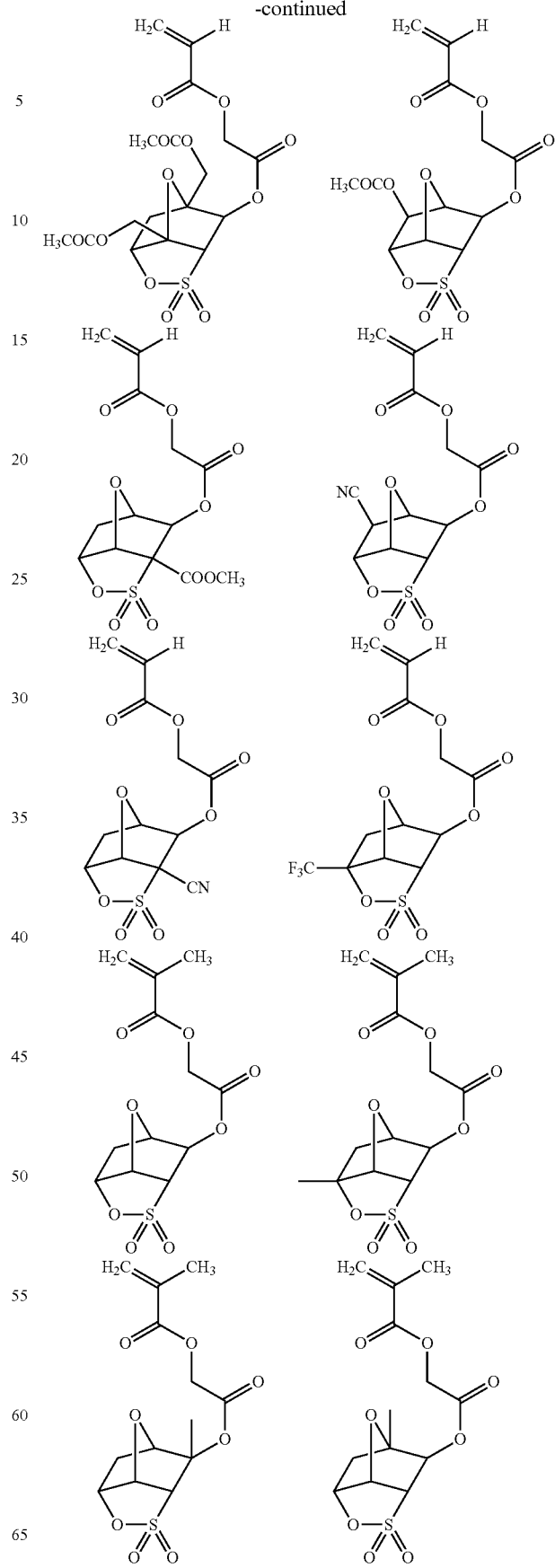

141
-continued
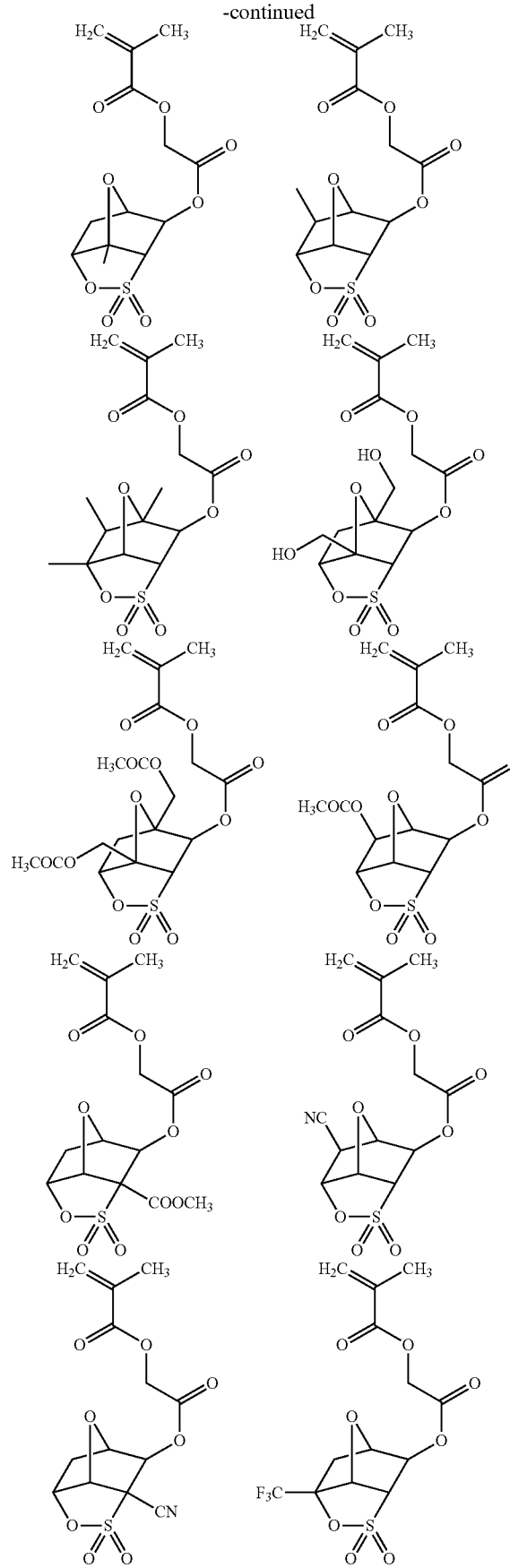
142
-continued
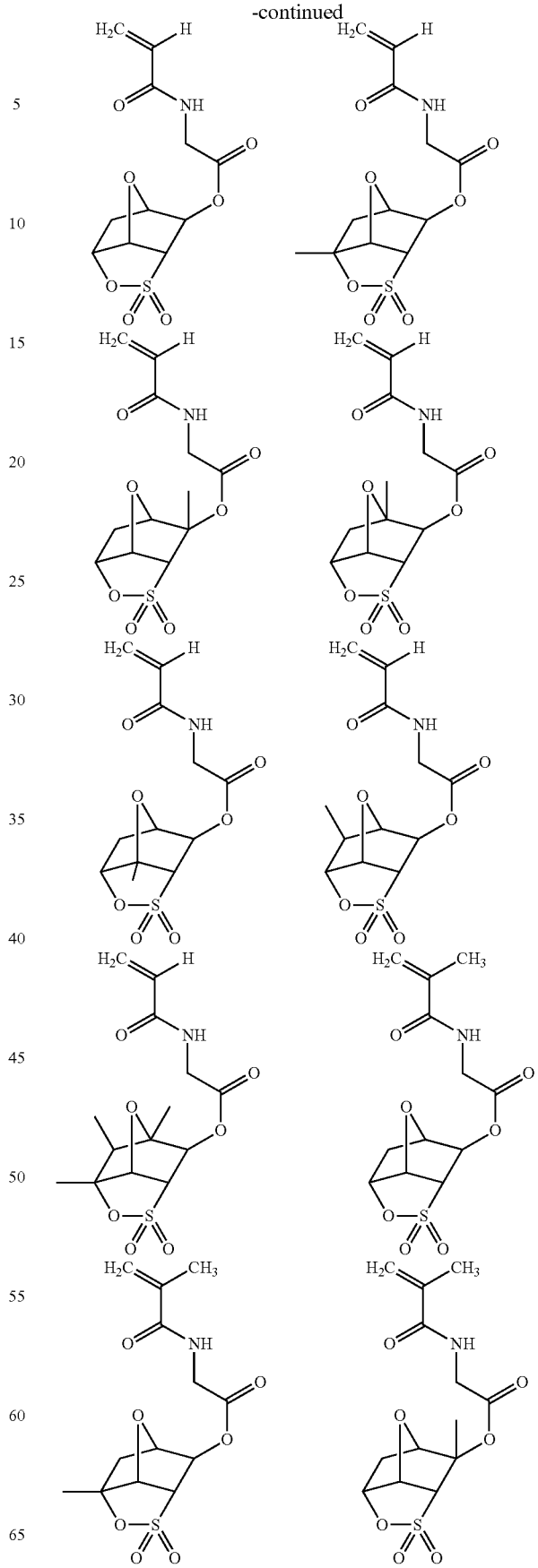

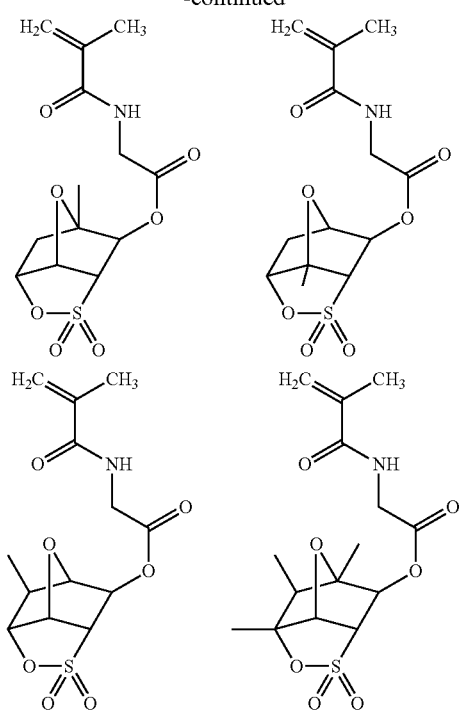
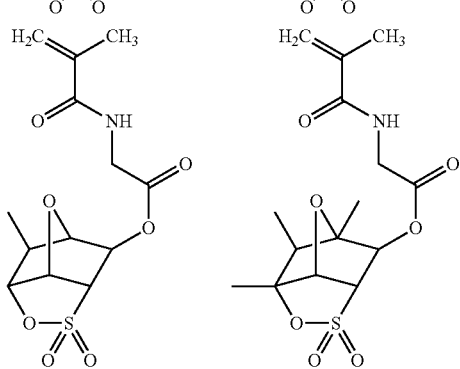

When the resin contains a structural unit derived from a monomer represented by the formula (a4-4), the content thereof is usually 2 to 40% by mole based on total molar of all the structural units of the resin, and preferably 3 to 35% by mole and more preferably 5 to 30% by mole.

Examples of the other monomer having no acid-labile group include the fluorine-containing monomers represented by the following formulae.

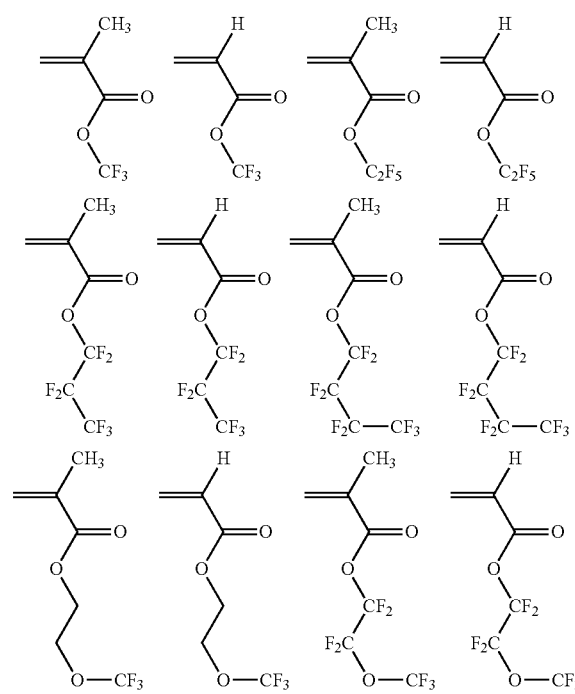

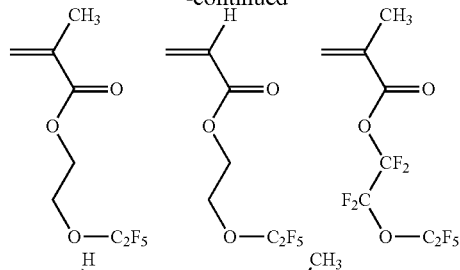
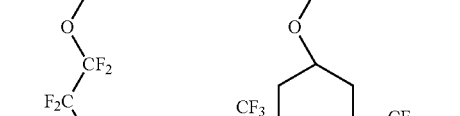
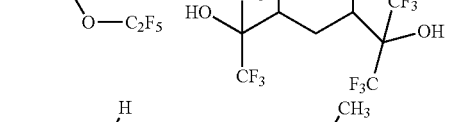
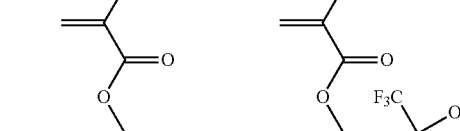
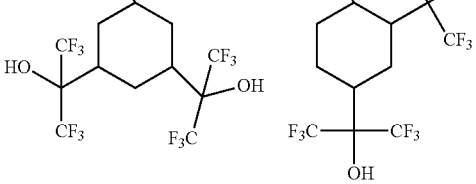
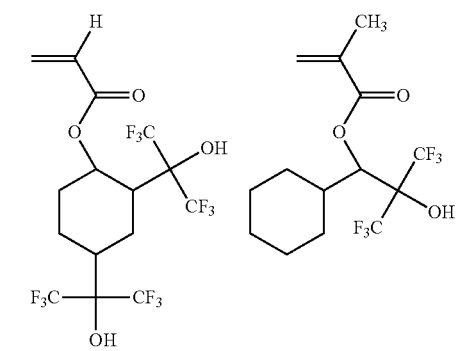
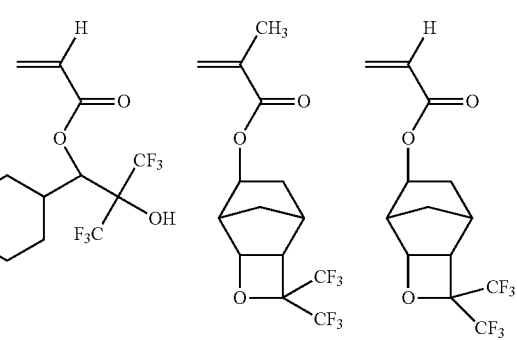

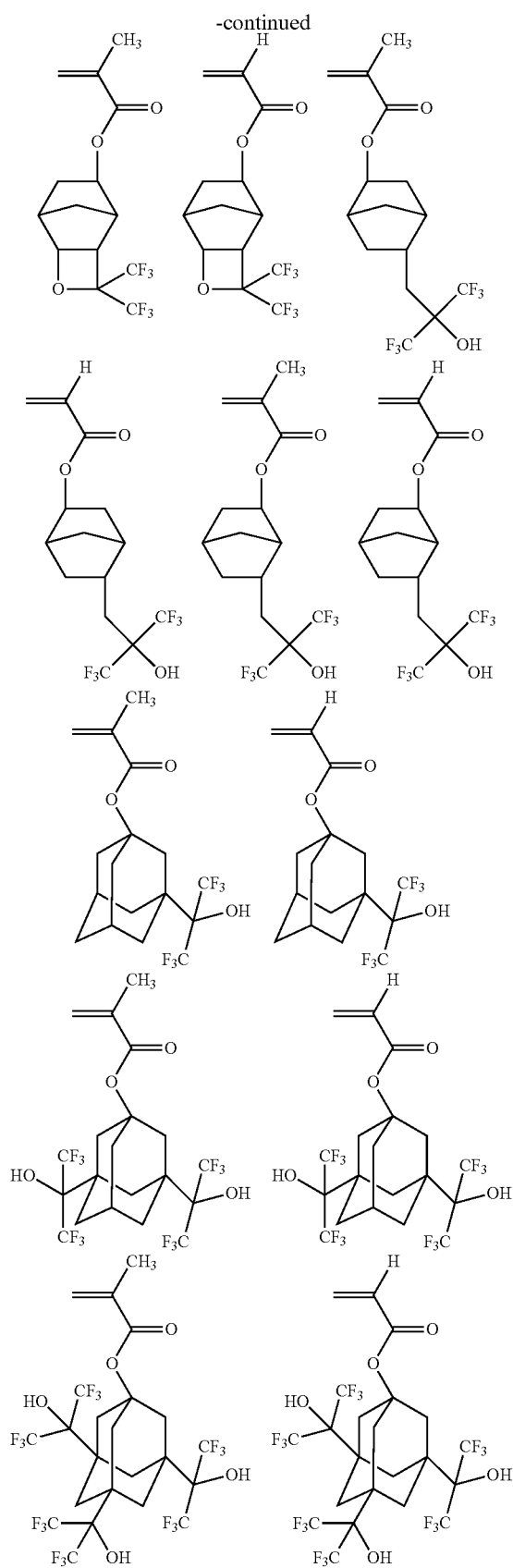

Among them, preferred are 5-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 6-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 4,4-bis(trifluoromethyl)-3-oxatricyclo[4.2.1.0$^{2,5}$]nonyl acrylate and 4,4-bis(trifluoromethyl)-3-oxatricyclo[4.2.1.0$^{2,5}$]nonyl methacrylate.

When the resin contains a structural unit derived from the above-mentioned fluorine-containing monomer, the content thereof is usually 1 to 20% by mole based on total molar of all the structural units of the resin, and preferably 2 to 15% by mole and more preferably 3 to 10% by mole.

Examples of the other monomer having no acid-labile group include the monomers having a group represented by the formula (3):

wherein R$^{10}$ represents a C1-C6 fluorinated alkyl group, in its side chain.

Examples of the C1-C6 fluorinated alkyl group include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl)methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl)ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2,3,3,4,4,5,5,6,6-dodecafluorohexyl group, a (perfluoropentyl)methyl group and a perfluorohexyl group. Among them preferred is a C1-C4 fluorinated alkyl group, and more preferred are a trifluoromethyl group, a perfluoroethyl group and a perfluoropropyl group, and especially preferred is a trifluoromethyl group.

Examples of the monomer having the group represented by the formula (3) in its side chain include the following.

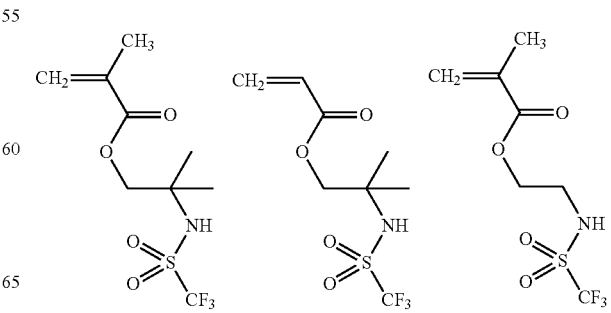

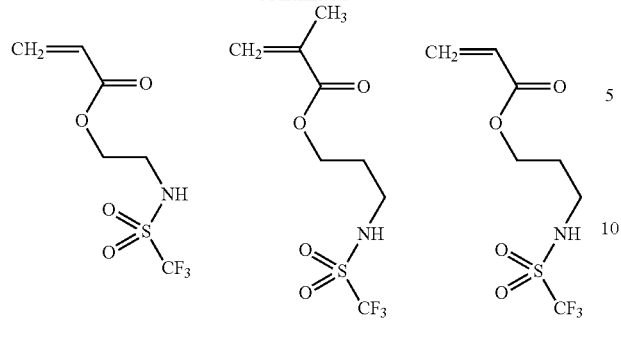
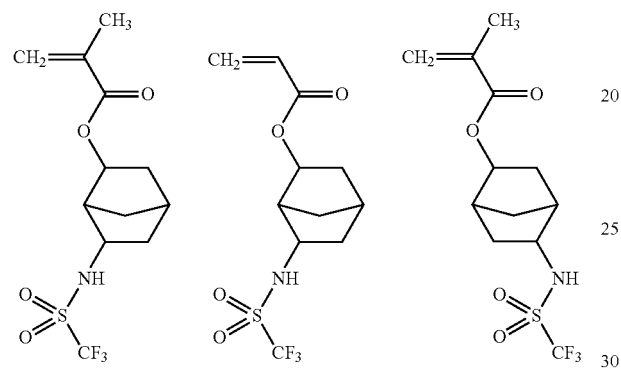
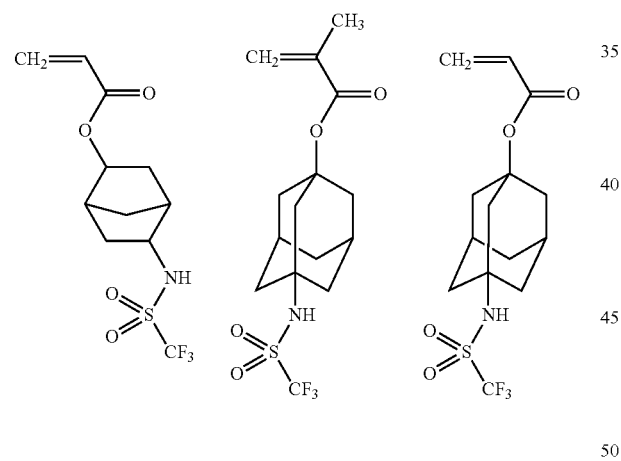
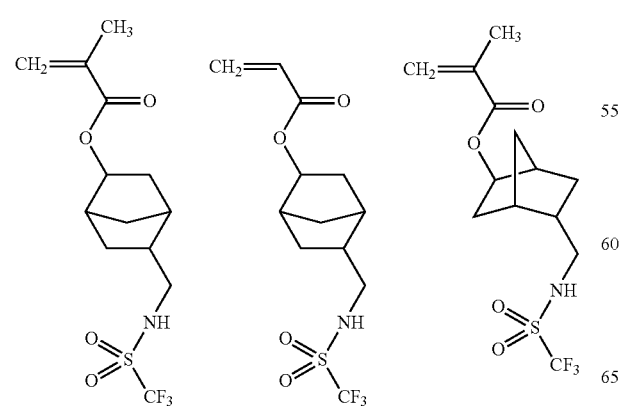
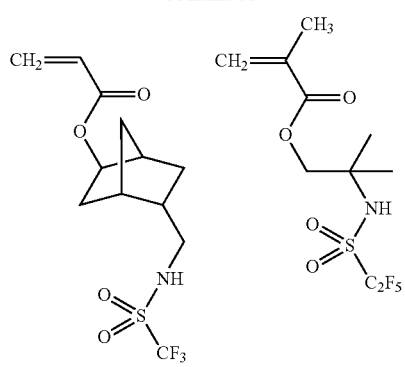
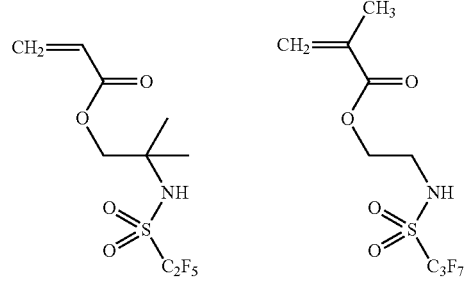
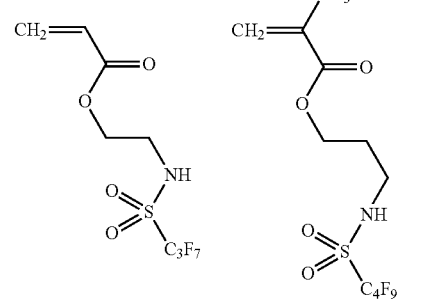
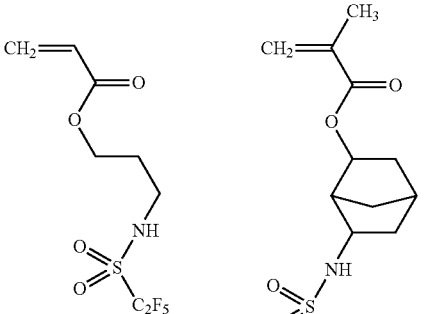
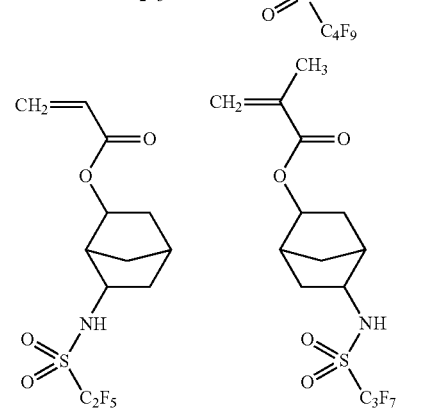

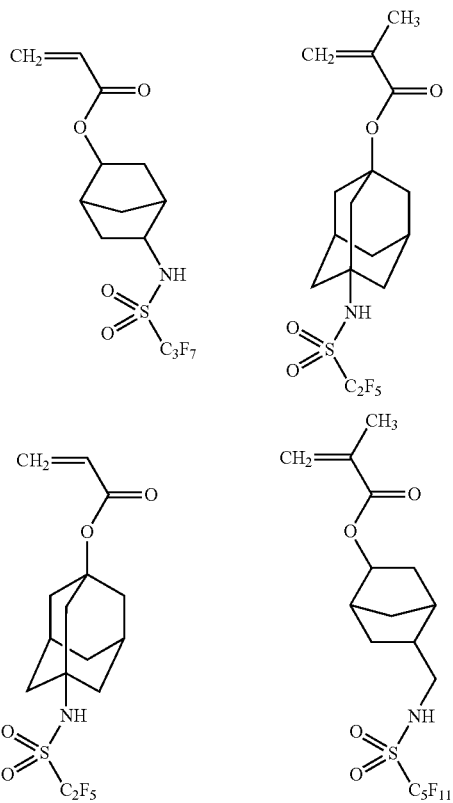
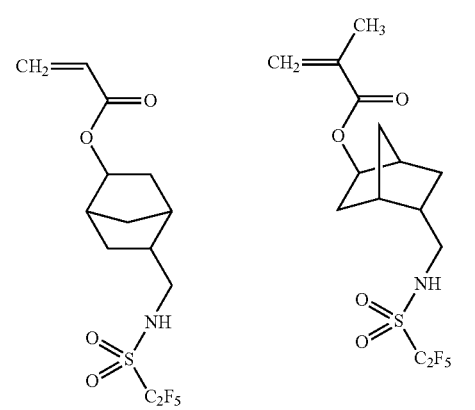
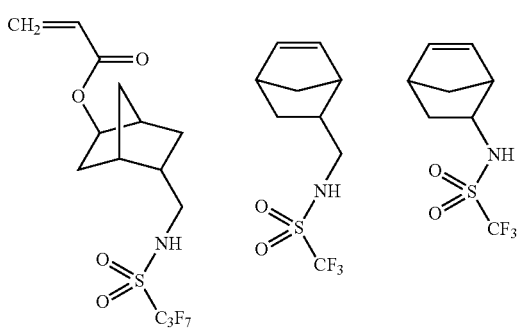

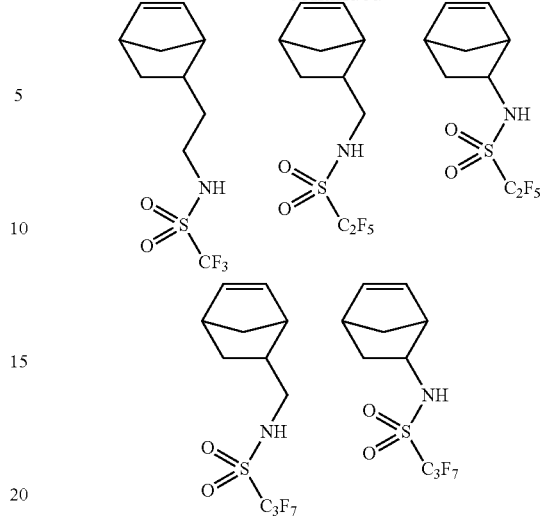

When the resin contains a structural unit derived from the above-mentioned monomer having the group represented by the formula (3) in its side chain, the content thereof is usually 5 to 90% by mole based on total molar of all the structural units of the resin, and preferably 10 to 80% by mole and more preferably 20 to 70% by mole.

Examples of the other monomer having no acid-labile group include the monomers having a group represented by the formula (4):

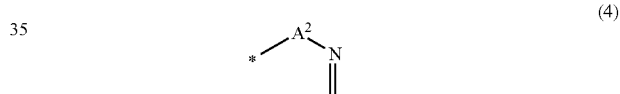

(4)

wherein $R^{11}$ represents a C6-C12 aromatic hydrocarbon group which may have one or more substituents, $R^{12}$ represents a C1-C12 hydrocarbon group which may have one or more substituents and which may contain one or more heteroatoms, and $A^2$ represents a single bond, —$(CH_2)_m$—$SO_2$—O—* or —$(CH_2)_m$—CO—O—* in which one or more —$CH_2$— may be replaced by —O—, —CO— or —$SO_2$— and in which one or more hydrogen atoms may be replaced by a fluorine atom, and m represents an integer of 1 to 12, in its side chain.

Examples of the substituents of the aromatic hydrocarbon group include a C1-C4 alkyl group such as a methyl group, an ethyl group, a propyl group, an isopropyl group, a butyl group, an isobutyl group and a tert-butyl group, a halogen atom such as a fluorine atom, a chlorine atom and a bromine atom, a phenyl group, a nitro group, a cyano group, a hydroxyl group, a phenoxy group and a tert-butylphenyl group.

Examples of $R^{11}$ include the following. In the following formulae, * represents a binding position to —$C(R^{12})$=N.

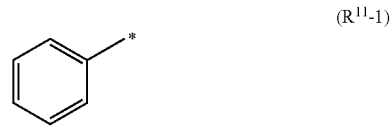

($R^{11}$-1)

(R¹¹-2) 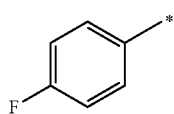

(R¹¹-3) 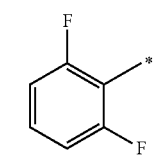

(R¹¹-4) 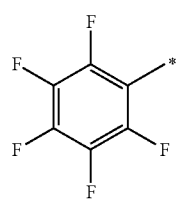

(R¹¹-5) 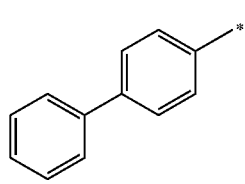

(R¹¹-6) 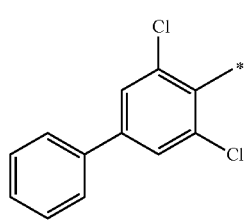

(R¹¹-7) 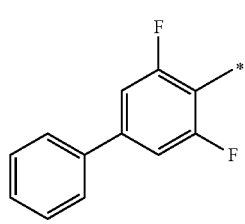

(R¹¹-8) 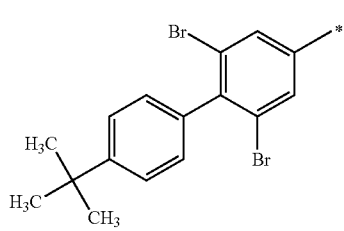

(R¹¹-9) 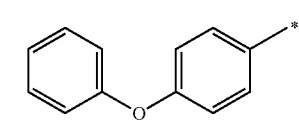

(R¹¹-10) 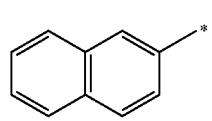

(R¹¹-11) 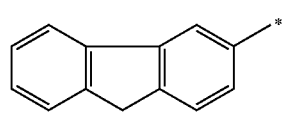

(R¹¹-12) 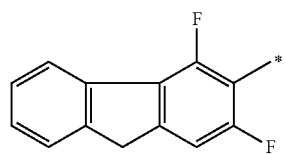

(R¹¹-13) 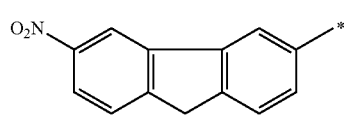

(R¹¹-14) 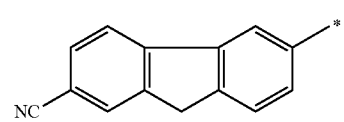

Examples of the C1-C12 hydrocarbon group include a C1-C12 aliphatic hydrocarbon group, a C3-C12 alicyclic hydrocarbon group and a C6-C12 aromatic hydrocarbon group. Examples of the C1-C12 aliphatic hydrocarbon group include a linear aliphatic hydrocarbon group such as a methyl group, an ethyl group, a propyl group, a butyl group, a pentyl group, a hexyl group, a heptyl group, an octyl group, a nonyl group, a decyl group, an undecyl group and a dodecyl group, and a branched chain aliphatic hydrocarbon group such as an isopropyl group, a sec-butyl group, a tert-butyl group, a methylpentyl group, an ethylpentyl group, a methylhexyl group, an ethylhexyl group, a propylhexyl group and a tert-octyl group. Preferred is a branched chain aliphatic hydrocarbon group, and more preferred are an isopropyl group, a sec-butyl group, a tert-butyl group and an ethylhexyl group.

Examples of the C3-C12 alicyclic hydrocarbon group include the following. In the following formulae, * represents a binding position to —C(R¹¹)=N.

(R¹²-19) 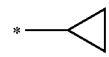

(R¹²-20) 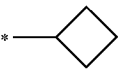

(R¹²-21) 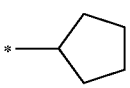

(R¹²-22) 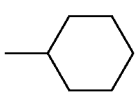

(R¹²-23) 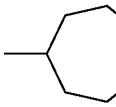

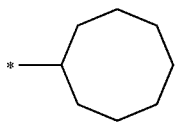 (R¹²-24)

 (R¹²-25)

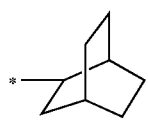 (R¹²-26)

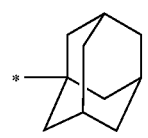 (R¹²-27)

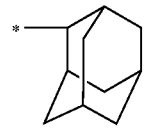 (R¹²-28)

The C1-C12 hydrocarbon group may contain one or more heteroatoms such as a halogen atom, a sulfur atom, an oxygen atom and a nitrogen atom, and it may also contain a group formed by combining two or more heteroatoms such as —SO$_2$— and —CO—. Examples of the C1-C12 hydrocarbon group containing one or more heteroatoms include the following.

\*—CF$_3$ (R¹²-1)

\*—CN (R¹²-2)

\*—CH$_3$ (R¹²-3)

\*—CF$_2$CH$_3$ (R¹²-4)

\*—CF$_2$CF$_3$ (R¹²-5)

\*—CF$_2$CF$_2$CF$_3$ (R¹²-6)

\*—CF$_2$C$_2$H$_5$ (R¹²-7)

\*—CF$_2$CF$_2$CF$_2$—CO$_2$—CH$_3$ (R¹²-8)

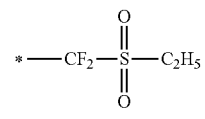 (R¹²-9)

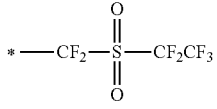 (R¹²-10)

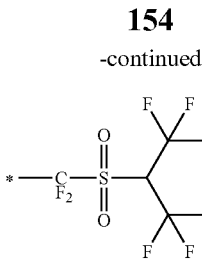 (R¹²-11)

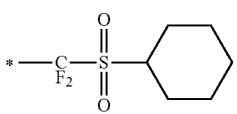 (R¹²-12)

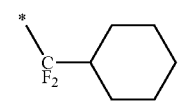 (R¹²-13)

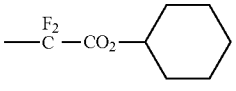 (R¹²-14)

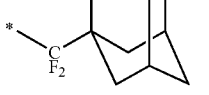 (R¹²-15)

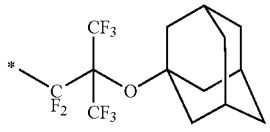 (R¹²-16)

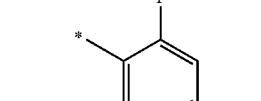 (R¹²-17)

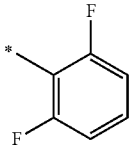 (R¹²-18)

Examples of the C6-C12 aromatic hydrocarbon group include the same as those of R¹¹.

Examples of A² include the following.

— (A²-1)

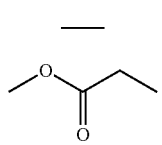 (A²-2)

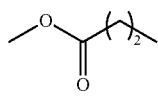 (A²-3)

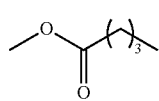
(A²-4)

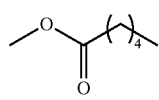
(A²-5)

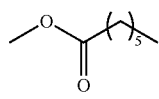
(A²-6)

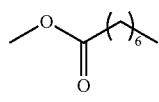
(A²-7)

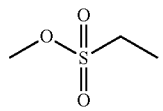
(A²-8)

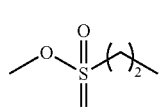
(A²-9)

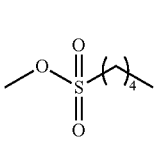
(A²-10)

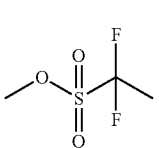
(A²-11)

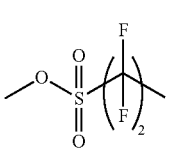
(A²-12)

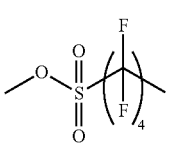
(A²-13)

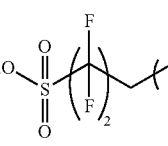
(A²-14)

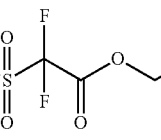
(A²-15)

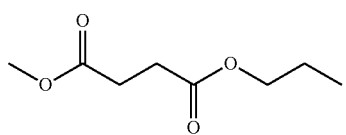
(A²-16)

In the formulae, the group represented by the formula (A²-1) represents a single bond.

Preferable examples of the monomer having the group represented by the formula (4) include a monomer represented by the formula (a6-1):

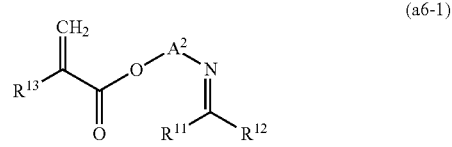
(a6-1)

wherein $A^2$, $R^{11}$ and $R^{12}$ are the same as defined above, and $R^{13}$ represents a hydrogen atom or a methyl group.

Examples of the monomer represented by the formula (a6-1) include the following.

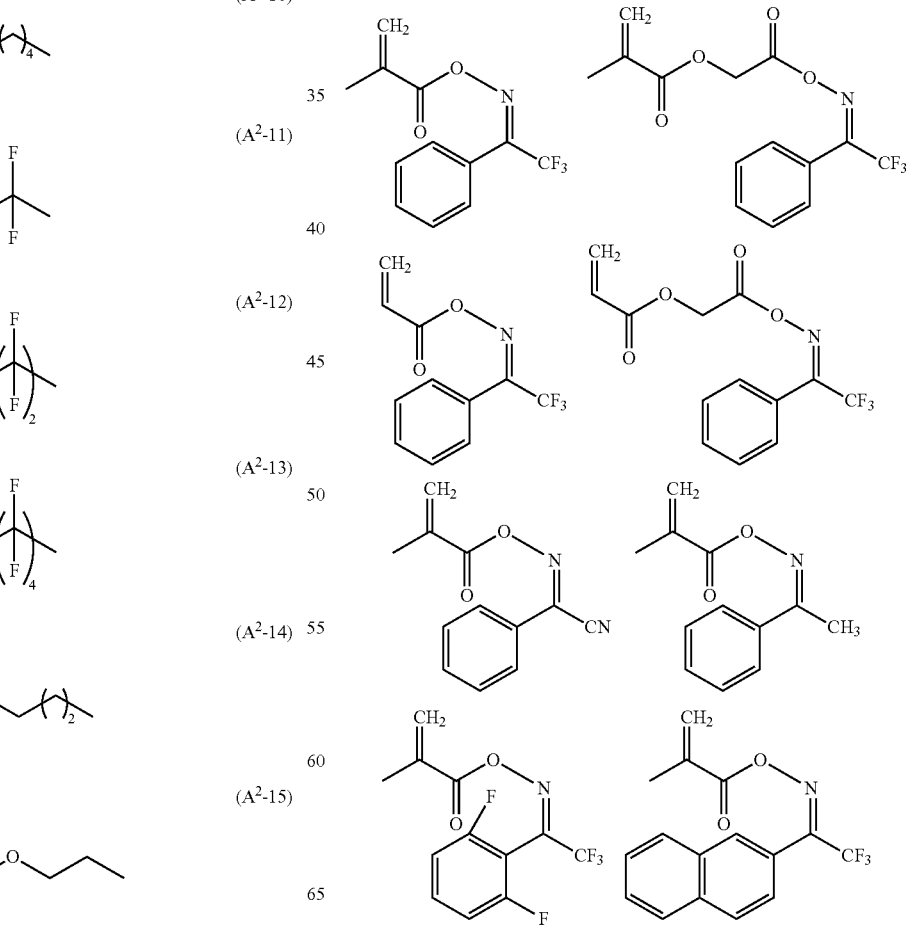

-continued

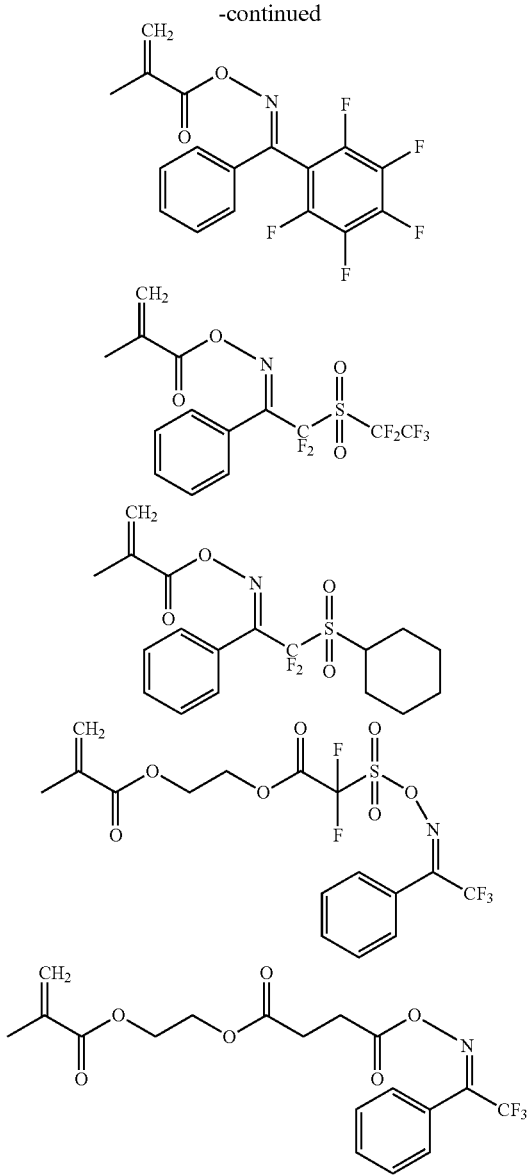

When the resin contains a structural unit derived from the above-mentioned monomer having the group represented by the formula (4) in its side chain, the content thereof is usually 5 to 90% by mole based on total molar of all the structural units of the resin, and preferably 10 to 80% by mole and more preferably 20 to 70% by mole.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with gel permeation chromatography.

The photoresist composition of the present invention usually includes 60% by weight or more of the resin based on sum of solid component and preferably include 80% by weight or more. The photoresist composition of the present invention usually includes 99% by mass or less of the resin based on sum of solid component. In this specification, "solid component" means components other than solvent in the photoresist composition.

The photoresist composition of the present invention usually includes 1% by weight or more of SALT (I) based on sum of solid component. The photoresist composition of the present invention usually includes 40% by weight or less of SALT (I) based on sum of solid component, preferably include 35% by weight or less of SALT (I) and more preferably include 30% by weight or less of SALT (I).

When the photoresist composition of the present invention contain the acid generator other than SALT (I), the content of the acid generator other than SALT (I) is usually 0.01 part by weight or more per 100 parts by weight of the resin, preferably 1 part by weight or more, and more preferably 3 parts by weight or more. The content of the acid generator other than SALT (I) is usually 30 parts by weight or less per 100 parts by weight of the resin, preferably 25 parts by weight or less, and more preferably 20 parts by weight or less.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

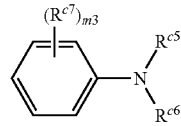

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

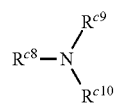

(C3)

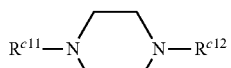

(C4)

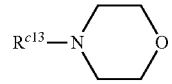

(C5)

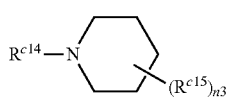

(C6)

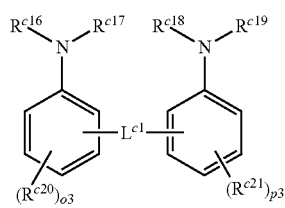

(C7)

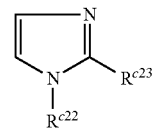

(C8)

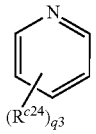

(C9)

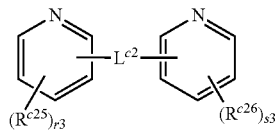

(C10)

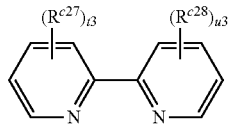

(C11)

wherein $R^{c8}$, $R^{c20}$, $R^{c21}$, and $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR$^{c3}$)—, —S—, —S—S— or a combination thereof and R$^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 1% by weight based on sum of solid component. The content of the basic compound is preferably smaller than total content of SALT (I) and the acid generator other than SALT (I).

The photoresist composition of the present invention can contain a compound represented by the formula (V):

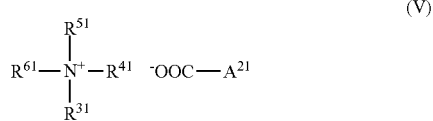

(V)

wherein $R^{31}$, $R^{41}$, $R^{51}$ and $R^{61}$ independently each represent a C1-C20 alkyl group which can have one or more substituents, a C3-C30 saturated cyclic hydrocarbon group which can have one or more substituents, or a C2-C20 alkenyl group which can have one or more substituents, and $A^{21}$ represents a C1-C36 hydrocarbon group which can contain one or more heteroatoms and which have one or more substituents. The compound represented by the formula (V) also acts as a quencher.

Examples of the C1-C20 alkyl group include a methyl group, an ethyl group, a propyl group, an isopropyl group, a butyl group, an isobutyl group, a sec-butyl group, a tert-butyl group, a pentyl group, an isopentyl group, a tert-pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and isocyl group, and a C1-C15 alkyl group is preferable, and C1-C10 alkyl group is more preferable.

Examples of the C3-C30 saturated cyclic hydrocarbon group include an adamantyl group, a norbornyl group, an isobornyl group, a tricyclodecyl group and a tetracyclodecyl group. The saturated cyclic hydrocarbon group preferably has 5 to 30 carbon atoms, more preferably 5 to 20 carbon atoms, much more preferably 6 to 15 carbon atoms and especially preferably 6 to 12 carbon atoms.

The alkenyl group preferably has 2 to 5 carbon atoms, and alkenyl group formed by combining the above-mentioned alkyl group with a vinyl group is more preferable.

Examples of the substituents include a halogen atom, a halogenated alkyl group such as a C1-C20 halogenated alkyl group, an alkyl group such as a C1-C20 alkyl group, an alkoxy group, a hydroxyalkoxy group, an alkoxyalkoxy group, an alkoxycarbonyloxy group, an alkoxycarbonylalkoxy group, an alkoxycarbonyl group, an aryl group, a heteroaryl group and an aralkyl group. Examples of the halogen atom include a fluorine atom, a chlorine atom, a bromine atom and an iodine atom, and a fluorine atom is preferable.

As the halogenated alkyl group, a fluorinated alkyl group is preferable. Examples of the alkyl group include the same as described in $R^{61}$, $R^{62}$, $R^{63}$ and $R^{64}$. Examples of aryl group include a phenyl group, a biphenyl group, a fluorenyl group, a naphthyl group, an anthryl group and a phenanthryl group. Examples of the heteroaryl group include the above-mentioned aryl groups in which one or more carbon atoms composed of the aromatic ring is replaced by a heteroatom such as an oxygen atom, a sulfur atom and a nitrogen atom. Examples of the aralkyl group include a benzyl group, a phenethyl group, a 1-naphthylmethyl group, a 2-naphthylmethyl group, a 1-naphthylethyl group and a 2-naphthylethyl group. As the aralkyl group, an aryl-substituted C1-C4 alkyl group is preferable, and an aryl-substituted C1-C2 alkyl group is more preferable, and an aryl-substituted methyl group is especially preferable. The aryl group, the heteroaryl group and the aralkyl group can have one or more substituents such as a C1-C10 alkyl group, a halogenated alkyl group (e.g. a C1-C8 halogenated alkyl group), an alkoxy group, a hydroxyl group and a halogen atom.

It is preferred that $R^{31}$, $R^{41}$, $R^{51}$ and $R^{61}$ independently each represent a linear alkyl group, a linear alkenyl group, or a saturated cyclic hydrocarbon group, and it is more preferred that $R^{31}$, $R^{41}$, $R^{51}$ and $R^{61}$ independently each represent a linear alkyl group. It is preferred that one of $R^{31}$, $R^{41}$, $R^{51}$ and $R^{61}$ represents an alkyl group having 1 to 4 carbon atoms.

Examples of the C1-C36 hydrocarbon group represented by $A^{21}$ include a saturated hydrocarbon group, an unsaturated hydrocarbon group, an aromatic hydrocarbon group and an aralkyl group. Examples of the saturated hydrocarbon group include a C1-C20 alkyl group and a C3-C20 saturated cyclic hydrocarbon group which are described in $R^{61}$, $R^{62}$, $R^{63}$ and R⁶⁴. The unsaturated hydrocarbon group preferably has 2 to 5 carbon atoms, more preferably 2 to 4 carbon atoms, and especially has 3 carbon atoms. Examples of the unsaturated hydrocarbon group include a vinyl group, a propenyl group, a butynyl group, a 1-methylpropenyl group, and a 2-methylpropenyl group, and a propenyl group is preferable. The aromatic hydrocarbon group preferably has 6 to 36 carbon atoms, more preferably 6 to 30 carbon atoms, much more preferably 6 to 20 carbon atoms, and especially preferably 6 to 15 carbon atoms. Examples of the aromatic hydrocarbon group include an aryl group such as a phenyl group, a biphenyl group, a fluorenyl group, a naphthyl group, an anthryl group and a phenanthryl group. Examples of the aralkyl group include a benzyl group, a phenethyl group, a 1-naphthylmethyl group, a 2-naphthylmethyl group, a 1-naphthylethyl group and a 2-naphthylethyl group. As the aralkyl group, an aryl-substituted C1-C4 alkyl group is preferable, and an aryl-substituted C1-C2 alkyl group is more preferable, and an aryl-substituted methyl group is especially preferable.

The C1-C36 hydrocarbon group can have one or more substituents, and examples of the substituents include an alkyl group, an aryl group, an alkoxy group, a halogen atom, a halogenated alkyl group, a hydroxyl group and an oxo group (═O), and a halogen atom and a hydroxyl group are preferable, and a hydroxyl group is more preferable. The C1-C36 hydrocarbon group can contain one or more heteroatoms such as an oxygen atom, a sulfur atom and a nitrogen atom. Examples of the alkyl group include a C1-C5 alkyl group such as a methyl group, an ethyl group, a propyl group, a butyl group and a tert-butyl group, and examples of the aryl group include the same as described above. Examples of the alkoxy group include a C1-C5 alkoxy group such as a methoxy group, an ethoxy group, a propoxy group, a butoxy group and a tert-butoxy group, and methoxy and ethoxy groups are preferable. Examples of the halogen atom include a fluorine atom, a chlorine atom, a bromine atom and an iodine atom, and a fluorine atom is preferable.

Preferable examples of the compound represented by the formula (V) include a compound represented by the formula (IV):

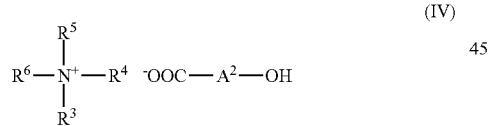

(IV)

wherein $R^3$, $R^4$, $R^5$ and $R^6$ independently each represent a C1-C6 alkyl group and $A^2$ represents a C3-C36 divalent saturated cyclic hydrocarbon group which can contain one or more heteroatoms and which have one or more substituents or a C6-C20 divalent aromatic hydrocarbon group which can contain one or more heteroatoms and which have one or more substituents.

Examples of the C1-C6 alkyl group include a methyl group, an ethyl group, a propyl group, an isopropyl group, a butyl group, an isobutyl group, a sec-butyl group, a tert-butyl group, a pentyl group, an isopentyl group, a tert-pentyl group, a neopentyl group, a 1-methylbutyl group, a 2-methylbutyl group, a 1,2-dimethylpropyl group, a 1-ethylpropyl group, a hexyl group, a 1-methylpentyl group and a heptyl group.

Examples of the C3-C36 divalent saturated cyclic hydrocarbon group include a C3-C8 cycloalkanediyl group such as a cyclopropanediyl group, a cyclobutanediyl group, a cyclopentanediyl group, a cyclohexanediyl group, a methylcyclohexanediyl group, a cycloheptanediyl group and a cyclooctanediyl group, a C5-C12 cycloalkylalkane-diyl group such as a cyclobutylmethane-diyl group, a cyclopentylmethane-diyl group, a cyclohexylmethane-diyl group, a cycloheptylmethane-diyl group and a cyclooctylmethane-diyl group, and an adamantanediyl group and a 1-asamantylmethane-diyl group.

Examples of the C6-C20 divalent aromatic hydrocarbon group include a phenylene group which can have one or more alkyl groups such as a phenylene group, a methylphenylene group, an ethylphenylene group, a tert-butylphenylene group and a dimethylphenylene group, and a naphthylene group which can have one or more alkyl groups such as a naphthylene group and a methylnaphthylene group.

Examples of the C3-C36 divalent saturated cyclic hydrocarbon group containing one or more heteroatoms include a pyrrolidinediyl group, a pyrazolidinediyl group, an imidazolidinediyl group, an isooxazolidinediyl group, an isothiazolidinediyl group, a piperidinediyl group, a piperazinediyl group, a morpholinediyl group, a thiomorpholinediyl group, a diazolediyl group, a triazolediyl group and a tetrazolediyl group. Examples of the C6-C20 divalent aromatic hydrocarbon group containing one or more heteroatoms include a pyridinediyl group and a bipyridinediyl group.

Examples of the substituents include a halogen atom, a hydroxyl group, an amino group, a mercapto group (—SH), a hydrocarbon group having 30 or less carbon atoms, a heterocyclic group and an oxo group (═O).

Examples of the cation parts of the compounds represented by the formulae (IV) and (V) include the cations represented by the formulae (IA-1) to (IA-8):

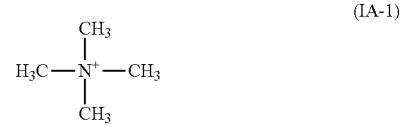

(IA-1)

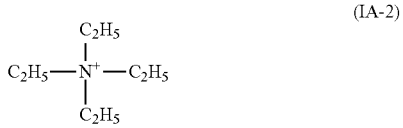

(IA-2)

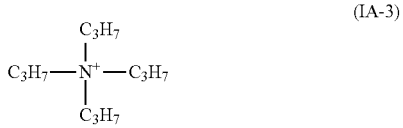

(IA-3)

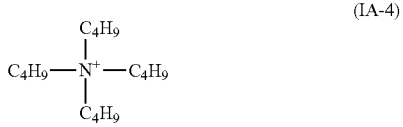

(IA-4)

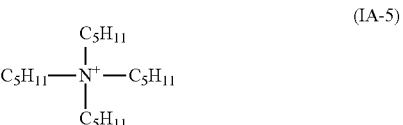

(IA-5)

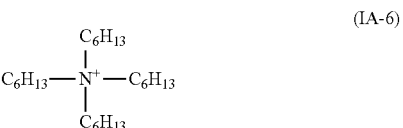

(IA-6)

-continued (IA-7)

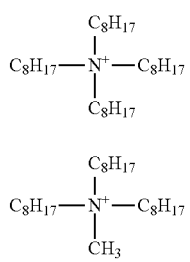

(IA-8)

C₈H₁₇—N⁺(C₈H₁₇)(C₈H₁₇)—CH₃

Examples of the anion parts of the compounds represented by the formulae (IV) and (V) include the anions represented by the formulae (IB-1) to (IB-11):

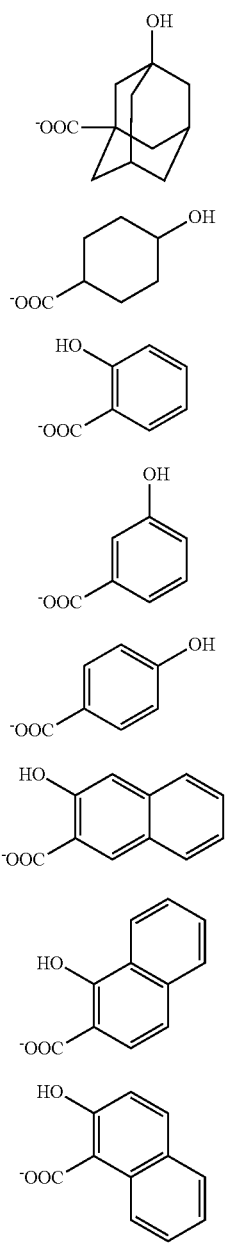

-continued

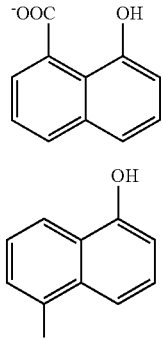

(IB-9)

(IB-10)

(IB-11)

$^-OOC—CF_3$

Examples of the compound represented by the formula (V) or (IV) include compounds Nos. (V-1) to (V-31) as shown in Table 1 and Table 2. Among them, preferred are compounds Nos. (V-1) to (V-5) and (V-12) to (V-20), and more preferred are compound Nos. (V-12) to (V-16).

TABLE 1

| Compound No. | Cation | Anion |
|---|---|---|
| (V-1) | (IA-1) | (IB-1) |
| (V-2) | (IA-1) | (IB-2) |
| (V-3) | (IA-1) | (IB-3) |
| (V-4) | (IA-1) | (IB-4) |
| (V-5) | (IA-1) | (IB-5) |
| (V-6) | (IA-2) | (IB-1) |
| (V-7) | (IA-2) | (IB-2) |
| (V-8) | (IA-2) | (IB-3) |
| (V-9) | (IA-3) | (IB-1) |
| (V-10) | (IA-3) | (IB-3) |
| (V-11) | (IA-3) | (IB-5) |
| (V-12) | (IA-4) | (IB-1) |
| (V-13) | (IA-4) | (IB-2) |
| (V-14) | (IA-4) | (IB-3) |
| (V-15) | (IA-4) | (IB-4) |
| (V-16) | (IA-4) | (IB-5) |
| (V-17) | (IA-5) | (IB-1) |
| (V-18) | (IA-5) | (IB-3) |
| (V-19) | (IA-6) | (IB-1) |
| (V-20) | (IA-6) | (IB-3) |

TABLE 2

| Compound No. | Cation | Anion |
|---|---|---|
| (V-21) | (IA-4) | (IB-6) |
| (V-22) | (IA-4) | (IB-7) |
| (V-23) | (IA-4) | (IB-8) |
| (V-24) | (IA-4) | (IB-9) |
| (V-25) | (IA-4) | (IB-10) |
| (V-26) | (IA-5) | (IB-8) |
| (V-27) | (IA-6) | (IB-8) |
| (V-28) | (IA-7) | (IB-1) |
| (V-29) | (IA-7) | (IB-3) |
| (V-30) | (IA-7) | (IB-8) |
| (V-31) | (IA-8) | (IB-11) |

The compounds represented by the formula (IV) and (V) can be produced, for example, by reacting tetraalkylammonium hydroxide such as tetramethylammonium hydroxide with hydroxyalkanecarboxlic acid such as hydroxyadamantanecarbozylic acid.

Two or more kinds of the compounds represented by the formula (IV) and (V) can be used in combination.

The content of the compound represented by the formula (IV) or (V) is usually 0.001 to 10% by weight, preferably 0.05 to 8% by weight and more preferably 0.01 to 5% by weight based on solid component.

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):

(1) a step of applying the first or second photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material. Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Example 1

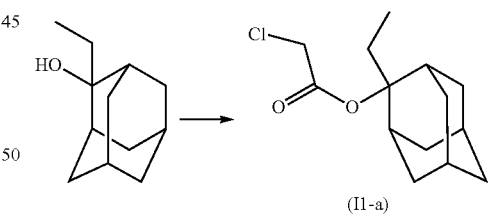

(I1-a)

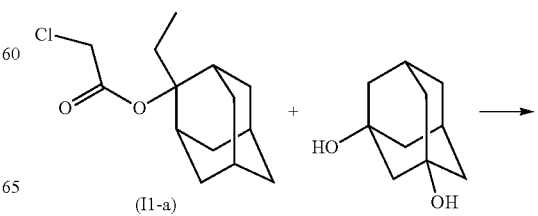

(I1-a)

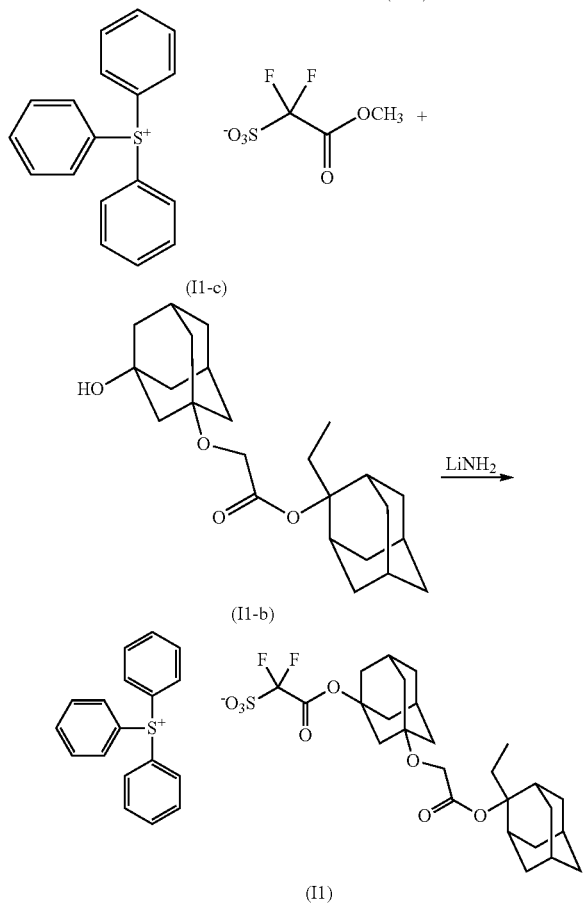

A mixture of 27.11 parts of 2-ethyl-2-adamantanol and 200 parts of tetrahydrofuran was stirred at room temperature to prepare a solution. To the solution, 14.27 parts of pyridine was added, and the resultant mixture was heated up to 40° C. To the mixture, a solution prepared by dissolving 25.47 parts of chloroacetyl chloride in 50 parts of tetrahydrofuran was added dropwise over 1 hour. The resultant mixture was stirred at 40° C. for 8 hours. The obtained mixture was cooled down to 5° C., and then, 100 parts of ion-exchanged water at 5° C. was added thereto followed by conducting separation. The obtained aqueous layer was extracted with 65 parts of ethyl acetate, and the organic layer obtained was washed with 65 parts of aqueous 10% potassium carbonate solution at 5° C. The organic layer obtained was washed three times with 65 parts of ion-exchanged water. The obtained organic layer was concentrated and the residue obtained was mixed with 50 parts of heptane. The resultant mixture was stirred and fil-trated to obtain solids. The obtained solids were dried to obtain 18.98 parts of a compound represented by the formula (I1-a).

A mixture of 5.12 parts of a compound represented by the formula (I1-a) and 25 parts of N,N-dimethylformamide was stirred at 23° C. for 30 minutes. To the mixture, 1.66 parts of potassium carbonate and 0.84 part of potassium iodide were added and the resultant mixture was stirred at 50° C. for 1 hour. The obtained mixture was cooled down to 40° C. To the mixture, a solution prepared by dissolving 3.31 parts of 1,3-adamantanediol in 25 parts of N,N-dimethylformamide was added dropwise over 1 hour. The resultant mixture was stirred at 75° C. for 5 hours. The obtained mixture was cooled down to 23° C., and 60 parts of chloroform and 60 parts of 1N hydrochloric acid were added thereto to conduct separation. The organic layer obtained was repeated to wash with 60 parts of ion-exchanged water until the aqueous layer was neutralized. The obtained organic layer was concentrated and the obtained residue was purified with silica gel column chromatography (silica gel: silica gel 60-200 mesh available from Merck KGaA, solvent: ethyl acetate) to obtain 2.69 parts of a compound represented by the formula (I1-b).

A salt represented by the formula (I 1-c) was prepared according to the method described in JP 2008-13551 A1. A mixture of 2.26 parts of the salt represented by the formula (I1-c), 15 parts of chloroform, 2.33 parts of a compound represented by the formula (I1-b), 2.5 parts of molecular sieves (Molecular Sieves 5 A available from Wako Pure Chemical Industries, Ltd.) and 0.07 part of lithium amide was refluxed at 80° C. for 24 hours. The reaction mixture obtained was filtrated. To the filtrate obtained, 0.14 part of oxalic acid and 5 parts of ion-exchanged water were added followed by conducting separation. The obtained organic layer was washed six times with ion-exchanged water. To the organic layer, 1 part of active carbon was added to stir at 23° C. for 30 minutes followed by filtration. The filtrate obtained was concentrated. To the residue obtained, 5 parts of acetonitrile was added to prepare a solution. The obtained solution was concentrated, and 10 parts of ethyl acetate was added to the obtained residue. The resultant mixture was stirred and then, the supernatant solution was removed from the mixture. To the obtained residue, 10 parts of tert-butyl methyl ether was added to the obtained residue. The resultant mixture was stirred and then, the supernatant solution was removed from the mixture. The obtained residue was dissolved in chloroform, and the obtained solution was concentrated and the obtained residue was purified with silica gel column chromatography (silica gel: silica gel 60-200 mesh available from Merck KGaA, solvent: chloroform/methanol=5/1) to obtain 0.11 part of a salt represented by the formula (I1). This is called as Salt I1.

MS (ESI(+) Spectrum): M⁺ 263.1
MS (ESI(−) Spectrum): M⁻ 545.2

Example 2

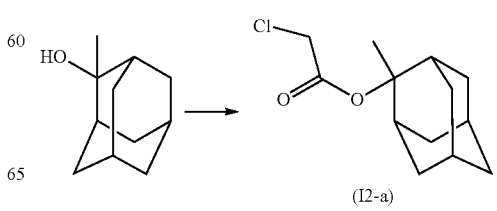

171

-continued

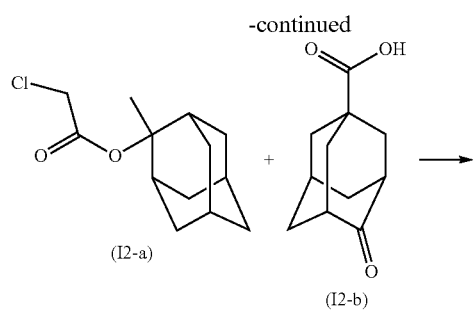

(I2-a)  (I2-b)

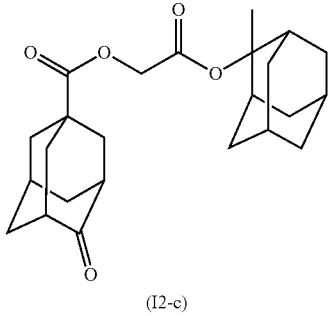

(I2-c)

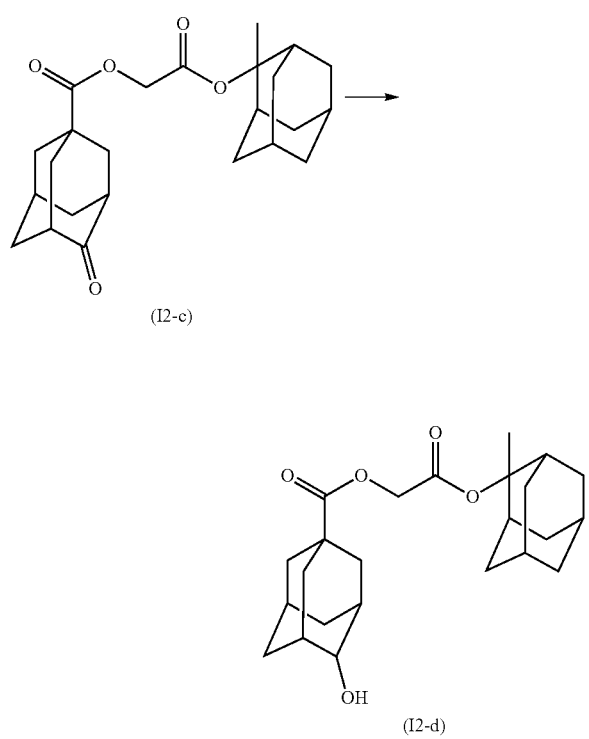

(I2-c)

(I2-d)

(I2-e)  (I2-f)

172

-continued

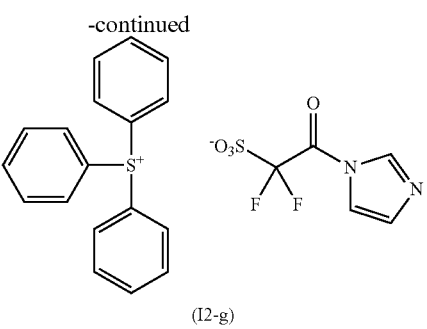

(I2-g)

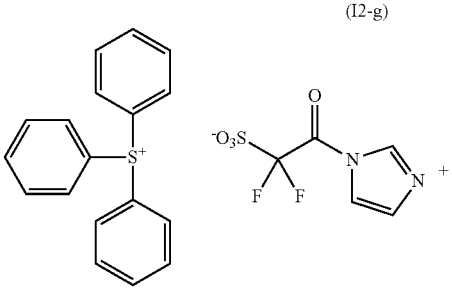

(I2-g)

(I2-d)

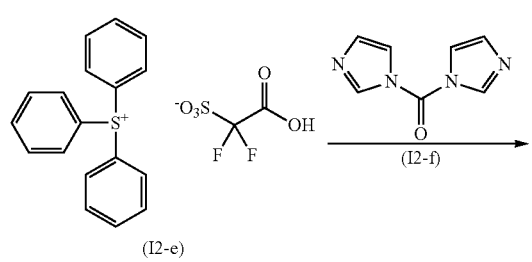

(I2)

A mixture of 25.00 parts of 2-methyl-2-adamantanol and 200 parts of tetrahydrofuran was stirred at room temperature to prepare a solution. To the solution, 14.27 parts of pyridine was added, and the resultant mixture was heated up to 40° C. To the mixture, a solution prepared by dissolving 25.47 parts of chloroacetyl chloride in 50 parts of tetrahydrofuran was added dropwise over 1 hour. The resultant mixture was stirred at 40° C. for 8 hours. The obtained mixture was cooled down to 5° C., and then, 100 parts of ion-exchanged water at 5° C. was added thereto followed by conducting separation. The obtained aqueous layer was extracted with 65 parts of ethyl acetate, and the organic layer obtained was washed with 65 parts of aqueous 10% potassium carbonate solution at 5° C. The organic layer obtained was washed three times with 65 parts of ion-exchanged water. The obtained organic layer was concentrated and the residue obtained was mixed with 40 parts of heptane. The resultant mixture was stirred and filtrated to obtain solids. The obtained solids were dried to obtain 17.62 parts of a compound represented by the formula (I2-a).

A mixture of 15 parts of a compound represented by the formula (I2-b) and 75 parts of N,N-dimethylformamide was stirred at 23° C. for 30 minutes. To the mixture, 6.4 parts of potassium carbonate and 1.92 parts of potassium iodide were added and the resultant mixture was stirred at 50° C. for 1 hour. To the mixture, a solution prepared by dissolving 16.87 parts of a compound represented by the formula (I2-a) in 33.74 parts of N,N-dimethylformamide was added dropwise over 1 hour. The resultant mixture was stirred at 50° C. for 5 hours. The obtained mixture was cooled down to 23° C., and 300 parts of ethyl acetate and 150 parts of ion-exchanged water were added thereto to conduct separation. The organic layer obtained was repeated to wash with 150 parts of ion-exchanged water until the aqueous layer was neutralized. The obtained organic layer was concentrated and the obtained residue was mixed with 150 parts of heptane. The resultant mixture was stirred and filtrated to obtain solids. The obtained solids were dried to obtain 22.67 parts of a compound represented by the formula (I2-c).

A mixture of 15 parts of a compound represented by the formula (I2-c) and 75 parts of acetonitrile was stirred at 23° C. for 30 minutes. The mixture was cooled down to 5° C. To the mixture, 0.71 part of sodium borohydride and 10.63 parts of ion-exchanged water were added, and then, the resultant mixture was stirred at 5° C. for 3 hours. To the mixture obtained, 50 parts of ion-exchanged water and 100 parts of ethyl acetate were added to conduct separation. The organic layer obtained was repeated to wash with 50 parts of ion-exchanged water until the aqueous layer was neutralized. The obtained organic layer was concentrated and the obtained residue was purified with silica gel column chromatography (silica gel: silica gel 60-200 mesh available from Merck KGaA, solvent: ethyl acetate) to obtain 12.43 parts of a compound represented by the formula (I2-d).

A salt represented by the formula (I2-e) was prepared according to the method described in JP 2008-127367 A1. A mixture of 10 parts of the salt represented by the formula (I2-e) and 60 parts of acetonitrile was stirred at 40° C. for 30 minutes. To the resultant mixture, 4.44 parts of a compound represented by the formula (I2-f) was added, and then, the mixture obtained was stirred at 50° C. for 1 hour to obtain a solution containing a compound represented by the formula (I2-g).

To the solution containing a compound represented by the formula (I2-g), 9.19 parts of a compound represented by the formula (I2-d) was added, and the resultant mixture was stirred at 23° C. for 1 hour. To the reaction mixture obtained, 100 parts of chloroform and 50 parts of ion-exchanged water were added to conduct separation.

The organic layer obtained was washed five times with ion-exchanged water. To the organic layer, 1 part of active carbon was added to stir at 23° C. for 30 minutes followed by filtration. The filtrate obtained was concentrated. To the residue obtained, 50 parts of acetonitrile was added to prepare a solution. The obtained solution was concentrated, and 50 parts of ethyl acetate was added to the obtained residue. The resultant mixture was stirred and then, the supernatant solution was removed from the mixture. To the obtained residue, 50 parts of tert-butyl methyl ether was added to the obtained residue. The resultant mixture was stirred and then, the supernatant solution was removed from the mixture. The obtained residue was dissolved in chloroform, and the obtained solution was concentrated. The residue obtained was purified with silica gel column chromatography (silica gel: silica gel 60-200 mesh available from Merck KGaA, solvent: chloroform/methanol=5/1) to obtain 16.84 parts of a salt represented by the formula (I2). This is called as Salt I2.

MS (ESI(+) Spectrum): M$^+$ 263.1

MS (ESI(−) Spectrum): M$^-$ 559.2

Example 3

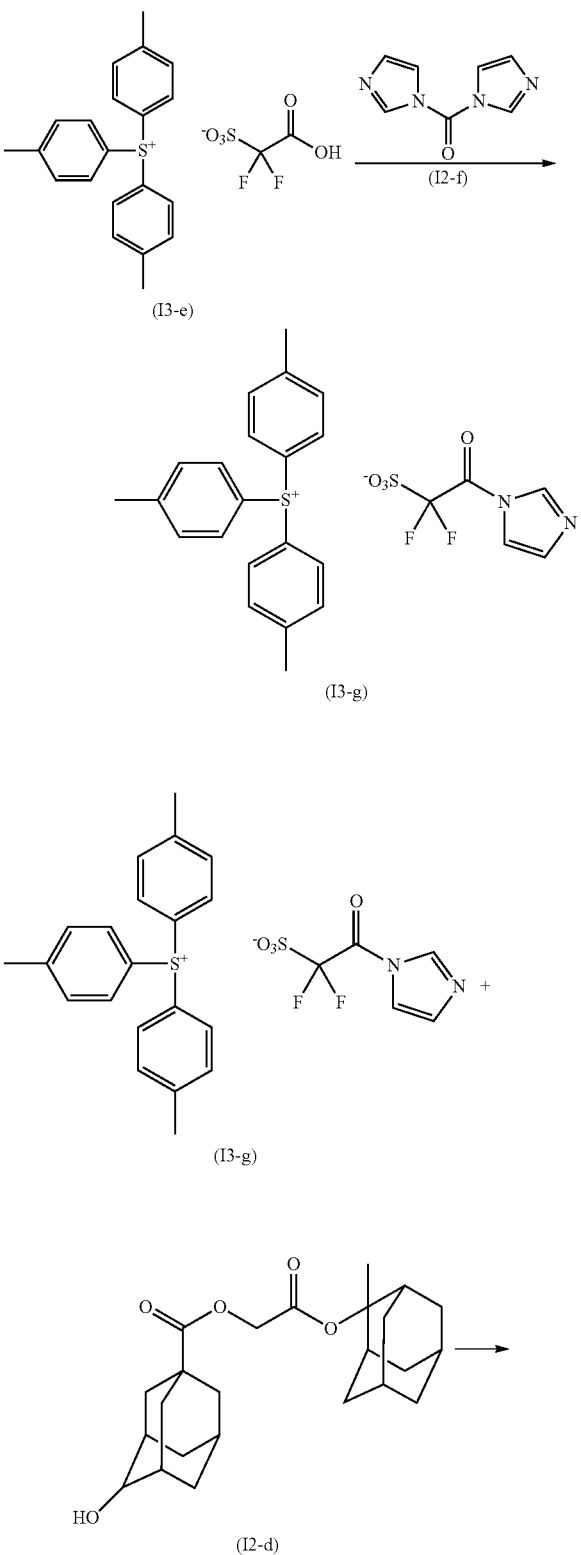

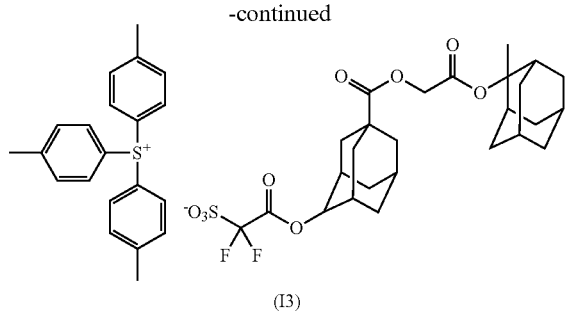

(I3)

A mixture of 10.96 parts of a salt represented by the formula (I2-e) and 65.76 parts of acetonitrile was stirred at 40° C. for 30 minutes. To the mixture obtained, 4.44 parts of a compound represented by the formula (I2-f) was added, and then, the mixture obtained was stirred at 50° C. for 1 hour to obtain a solution containing a compound represented by the formula (I3-g).

To the solution containing a compound represented by the formula (I3-g), 9.19 parts of a compound represented by the formula (I2-d) was added, and the resultant mixture was stirred at 23° C. for 1 hour. To the reaction mixture obtained, 100 parts of chloroform and 50 parts of ion-exchanged water were added to conduct separation. The organic layer obtained was washed five times with ion-exchanged water. To the organic layer, 1 part of active carbon was added to stir at 23° C. for 30 minutes followed by filtration. The filtrate obtained was concentrated. To the residue obtained, 50 parts of acetonitrile was added to prepare a solution. The obtained solution was concentrated, and 80 parts of ethyl acetate was added to the obtained residue. The resultant mixture was stirred and then, the supernatant solution was removed from the mixture. To the obtained residue, 60 parts of tert-butyl methyl ether was added to the obtained residue. The resultant mixture was stirred and then, the supernatant solution was removed from the mixture. The obtained residue was dissolved in chloroform, and the obtained solution was concentrated to obtain 17.09 parts of a salt represented by the formula (I3). This is called as Salt I3.

MS (ESI(+) Spectrum): M$^+$ 305.1

MS (ESI(−) Spectrum): M$^-$ 559.2

Example 4

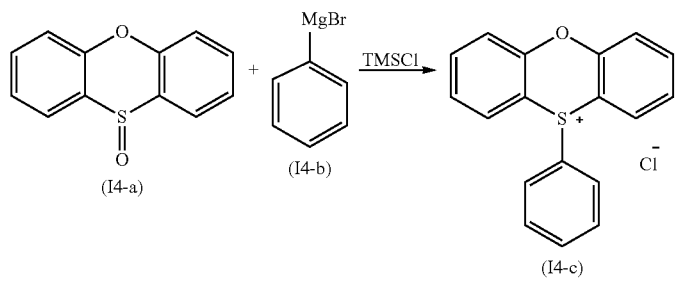

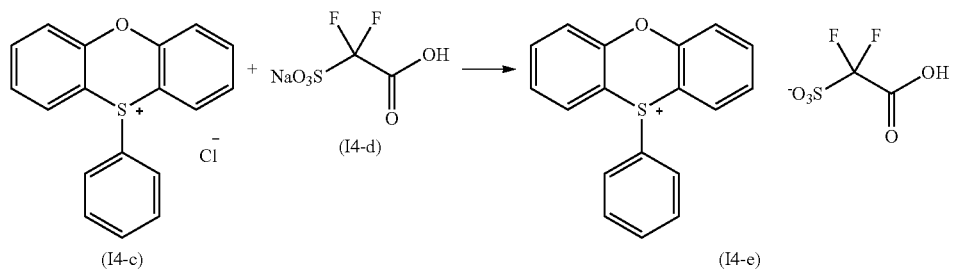

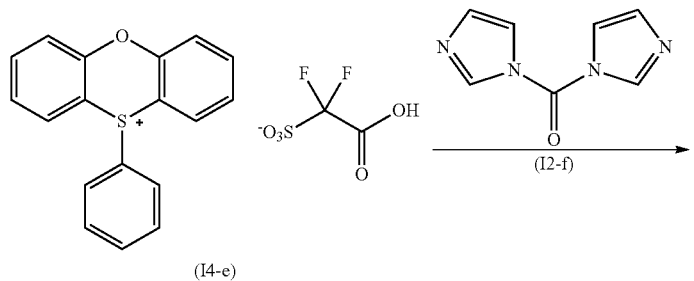

-continued

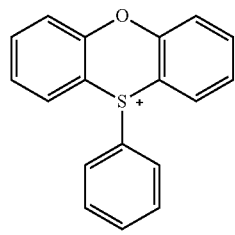

(I4-f)

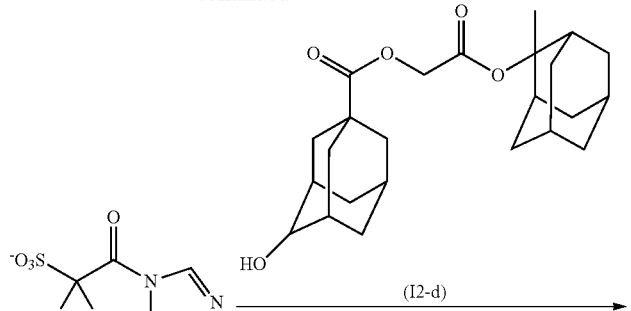

(I4)

A mixture of 50 parts of a compound represented by the formula (I4-a) and 250 parts of tetrahydrofuran was stirred at 30° C. for 30 minutes. To the mixture, 50.23 parts of trimethylsilyl chloride was added dropwise. The resultant mixture was cooled down to 0° C., and then, 157.2 parts of a compound represented by the formula (I4-b), which was available from Tokyo Chemical Industry Co., LTD, and of which purity was 32%, was added dropwise to the mixture over 30 minutes. The resultant mixture was heated up to 23° C., and then, stirred at 23° C. for 1 hour. To the reaction mixture obtained, 125 parts of 1N hydrochloric acid was added to conduct separation. The aqueous layer obtained was washed with 125 parts of tert-butyl methyl ether. The aqueous layer was extracted with 125 parts of chloroform, and the organic layer obtained was filtrated followed by concentration. To the residue obtained, 28.33 parts of acetonitrile and 354.15 parts of tert-butyl methyl ether were added, and the resultant mixture was stirred at 23° C. for 30 minutes followed by filtrating the precipitate to obtain 53 parts of a salt represented by the formula (I4-c).

A mixture of 13.12 parts of a compound represented by the formula (I4-d) and 73.86 parts of chloroform was stirred at 30° C. for 30 minutes. To the mixture, 20.71 parts of a salt represented by the formula (I4-c) and 62.27 parts of ion-exchanged water were added. To the resultant mixture, 6.9 parts of 35% hydrochloric acid was added dropwise, and the resultant mixture was stirred at 23° C. for 12 hours. To the reaction mixture obtained, 12 parts of 28% aqueous ammonia solution was added dropwise followed by conduct separation. The organic layer obtained was washed five times with 50 parts of ion-exchanged water. To the organic layer, 2 parts of active carbon was added to stir at 23° C. for 30 minutes followed by filtration. The filtrate obtained was concentrated. To the residue obtained, 30 parts of acetonitrile and 150 parts of tert-butyl methyl ether were added, and then, the resultant mixture was filtrated to obtain 14.28 parts of a salt represented by the formula (I4-e).

A mixture of 10.32 parts of a salt represented by the formula (I4-e) and 61.91 parts of acetonitrile was stirred at 40° C. for 30 minutes. To the mixture obtained, 4.44 parts of a compound represented by the formula (I2-f) was added, and then, the mixture obtained was stirred at 50° C. for 1 hour to obtain a solution containing a compound represented by the formula (I4-f).

To the solution containing a compound represented by the formula (I4-f), 9.2 parts of a compound represented by the formula (I2-d) was added, and the resultant mixture was stirred at 50° C. for 3 hours. To the reaction mixture obtained, 120 parts of chloroform and 50 parts of ion-exchanged water were added to conduct separation. The organic layer obtained was washed five times with ion-exchanged water. To the organic layer, 1 part of active carbon was added to stir at 23° C. for 30 minutes followed by filtration. The filtrate obtained was concentrated. To the residue obtained, 40 parts of acetonitrile was added to prepare a solution. The obtained solution was concentrated, and 70 parts of ethyl acetate was added to the obtained residue. The resultant mixture was stirred and then, the supernatant solution was removed from the mixture. To the obtained residue, 50 parts of tert-butyl methyl ether was added to the obtained residue. The resultant mixture was stirred and then, the supernatant solution was removed from the mixture. The obtained residue was dissolved in chloroform, and the obtained solution was concentrated to obtain 16.41 parts of a salt represented by the formula (I4). This is called as Salt I4.

MS (ESI(+) Spectrum): M$^+$ 277.1
MS (ESI(−) Spectrum): M$^−$ 559.2

Example 5
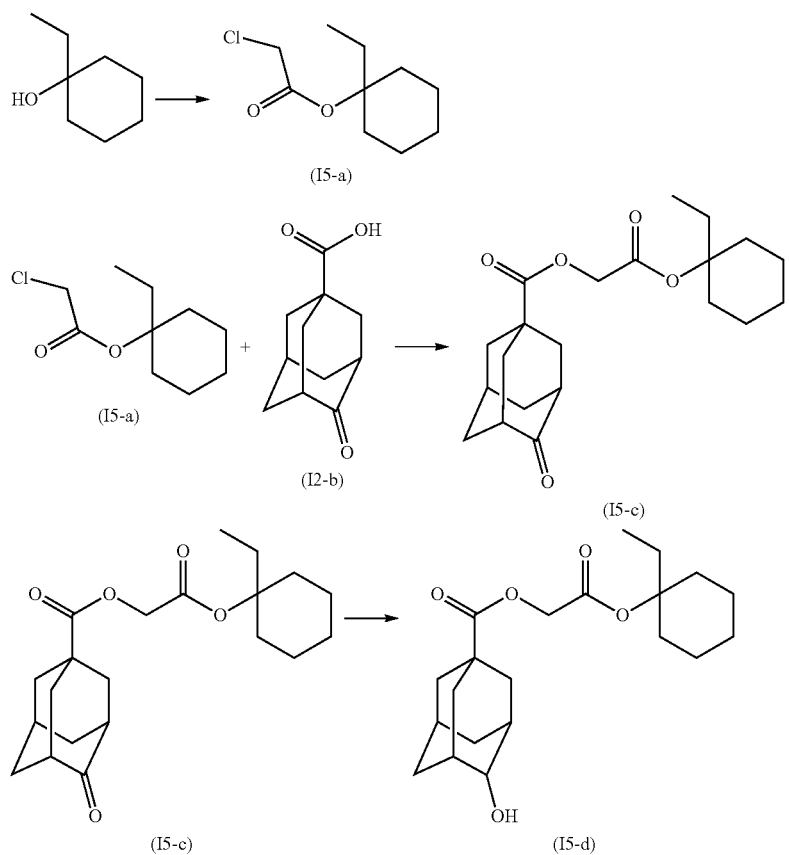
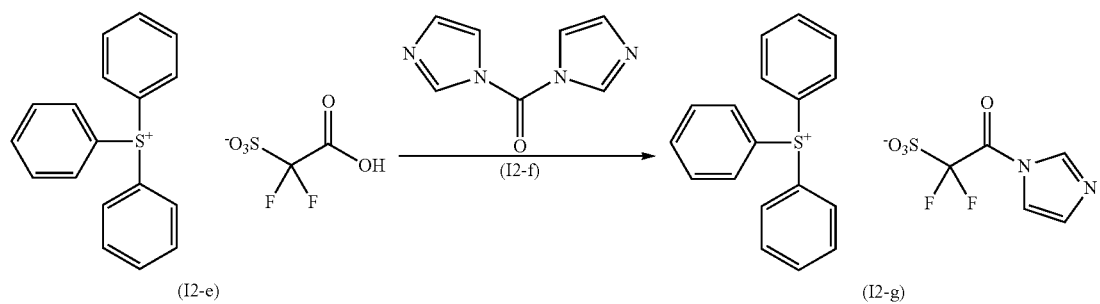
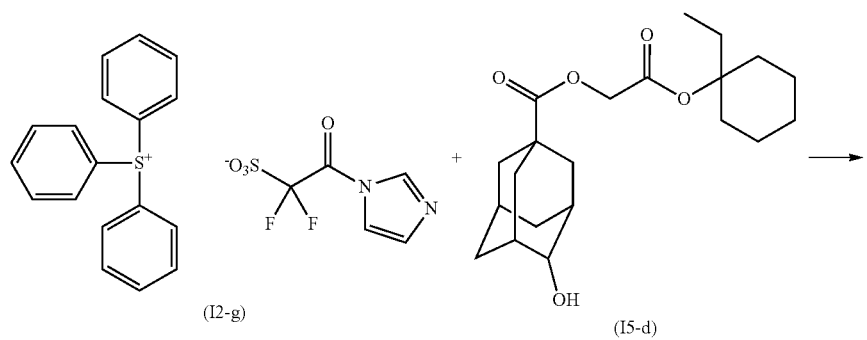

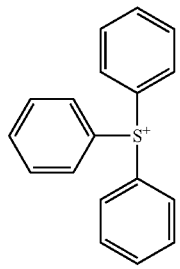 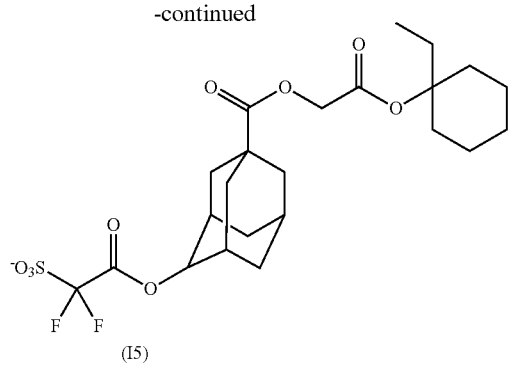

(I5)

A mixture of 19.28 parts of 1-ethylcyclohexanol and 150 parts of tetrahydrofuran was stirred at room temperature to prepare a solution. To the solution, 14.27 parts of pyridine was added, and the resultant mixture was heated up to 40° C. To the mixture, a solution prepared by dissolving 25.47 parts of chloroacetyl chloride in 50 parts of tetrahydrofuran was added dropwise over 1 hour. The resultant mixture was stirred at 40° C. for 8 hours. The obtained mixture was cooled down to 5° C., and then, 100 parts of ion-exchanged water at 5° C. was added thereto followed by conducting separation. The obtained aqueous layer was extracted with 80 parts of ethyl acetate, and the organic layer obtained was washed with 80 parts of aqueous 10% potassium carbonate solution at 5° C. The organic layer obtained was washed three times with 80 parts of ion-exchanged water. The obtained organic layer was concentrated and the residue obtained was purified with silica gel column chromatography (silica gel: silica gel 60-200 mesh available from Merck KGaA, solvent: heptane/ethyl acetate=1/3) to obtain 14.23 parts of a compound represented by the formula (I5-a).

A mixture of 15 parts of a compound represented by the formula (I2-b) and 75 parts of N,N-dimethylformamide was stirred at 23° C. for 30 minutes. To the mixture, 6.4 parts of potassium carbonate and 1.92 parts of potassium iodide were added and the resultant mixture was stirred at 50° C. for 1 hour. To the mixture, a solution prepared by dissolving 14.23 parts of a compound represented by the formula (I5-a) in 30 parts of N,N-dimethylformamide was added dropwise over 1 hour. The resultant mixture was stirred at 50° C. for 5 hours. The obtained mixture was cooled down to 23° C., and 300 parts of ethyl acetate and 150 parts of ion-exchanged water were added thereto to conduct separation. The organic layer obtained was repeated to wash with 150 parts of ion-exchanged water until the aqueous layer was neutralized. The obtained organic layer was concentrated and the obtained residue was mixed with 150 parts of heptane. The resultant mixture was stirred and filtrated to obtain solids. The obtained solids were dried to obtain 19.98 parts of a compound represented by the formula (I5-c).

A mixture of 13.57 parts of a compound represented by the formula (I5-c) and 70 parts of acetonitrile was stirred at 23° C. for 30 minutes. The mixture was cooled down to 5° C. To the mixture, 0.71 part of sodium borohydride and 10.63 parts of ion-exchanged water were added, and then, the resultant mixture was stirred at 5° C. for 3 hours. To the mixture obtained, 50 parts of ion-exchanged water and 100 parts of ethyl acetate were added to conduct separation. The organic layer obtained was repeated to wash with 50 parts of ion-exchanged water until the aqueous layer was neutralized. The obtained organic layer was concentrated and the obtained residue was purified with silica gel column chromatography (silica gel: silica gel 60-200 mesh available from Merck KGaA, solvent: ethyl acetate) to obtain 10.79 parts of a compound represented by the formula (I5-d).

A mixture of 10 parts of a salt represented by the formula (I2-e) and 60 parts of acetonitrile was stirred at 40° C. for 30 minutes. To the resultant mixture, 4.44 parts of a compound represented by the formula (I2-f) was added, and then, the mixture obtained was stirred at 50° C. for 1 hour to obtain a solution containing a compound represented by the formula (I2-g).

To the solution containing a compound represented by the formula (I2-g), 8.32 parts of a compound represented by the formula (I5-d) was added, and the resultant mixture was stirred at 23° C. for 1 hour. To the reaction mixture obtained, 100 parts of chloroform and 50 parts of ion-exchanged water were added to conduct separation. The organic layer obtained was washed five times with ion-exchanged water. To the organic layer, 1 part of active carbon was added to stir at 23° C. for 30 minutes followed by filtration. The filtrate obtained was concentrated. To the residue obtained, 50 parts of acetonitrile was added to prepare a solution. The obtained solution was concentrated, and 50 parts of ethyl acetate was added to the obtained residue. The resultant mixture was stirred and then, the supernatant solution was removed from the mixture. To the obtained residue, 50 parts of tert-butyl methyl ether was added to the obtained residue. The resultant mixture was stirred and then, the supernatant solution was removed from the mixture. The obtained residue was dissolved in chloroform, and the obtained solution was concentrated to obtain 14.88 parts of a salt represented by the formula (I5). This is called as Salt I5.

MS (ESI(+) Spectrum): M$^+$ 263.1

MS (ESI(−) Spectrum): M$^-$ 521.2

Monomers used in the following Resin Synthesis Examples 1 to 6 are following monomers (A), (B), (C), (D), (E) and (F).

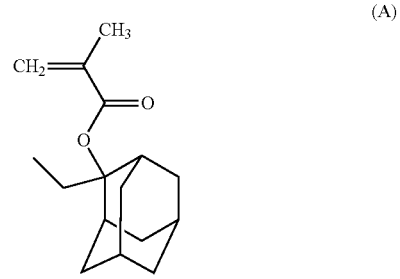

(A)

Resin Synthesis Example 1

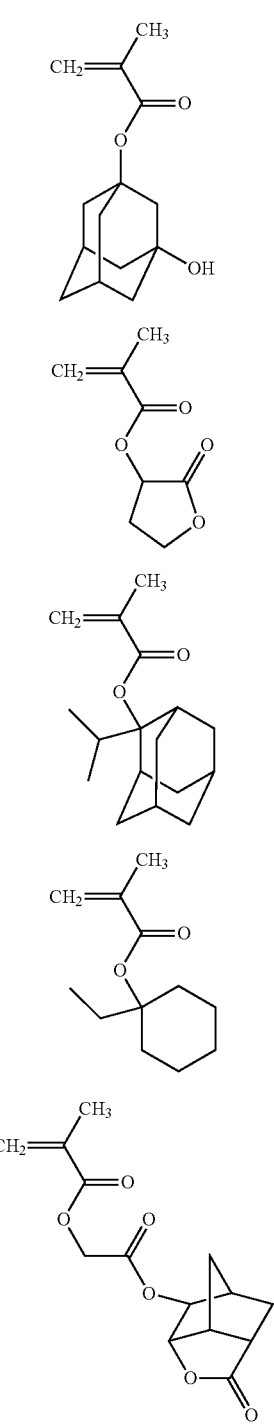

The monomers (D), (E), (B), (C) and (F) were mixed in a molar ratio of 30/14/6/20/30 (monomer (D)/monomer (E)/ monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated again for purification. As a result, a resin having a weight-average molecular weight of about $8.1 \times 10^3$ was obtained in a yield of 65%. This resin is called as resin A1. Resin A1 had the following structural units.

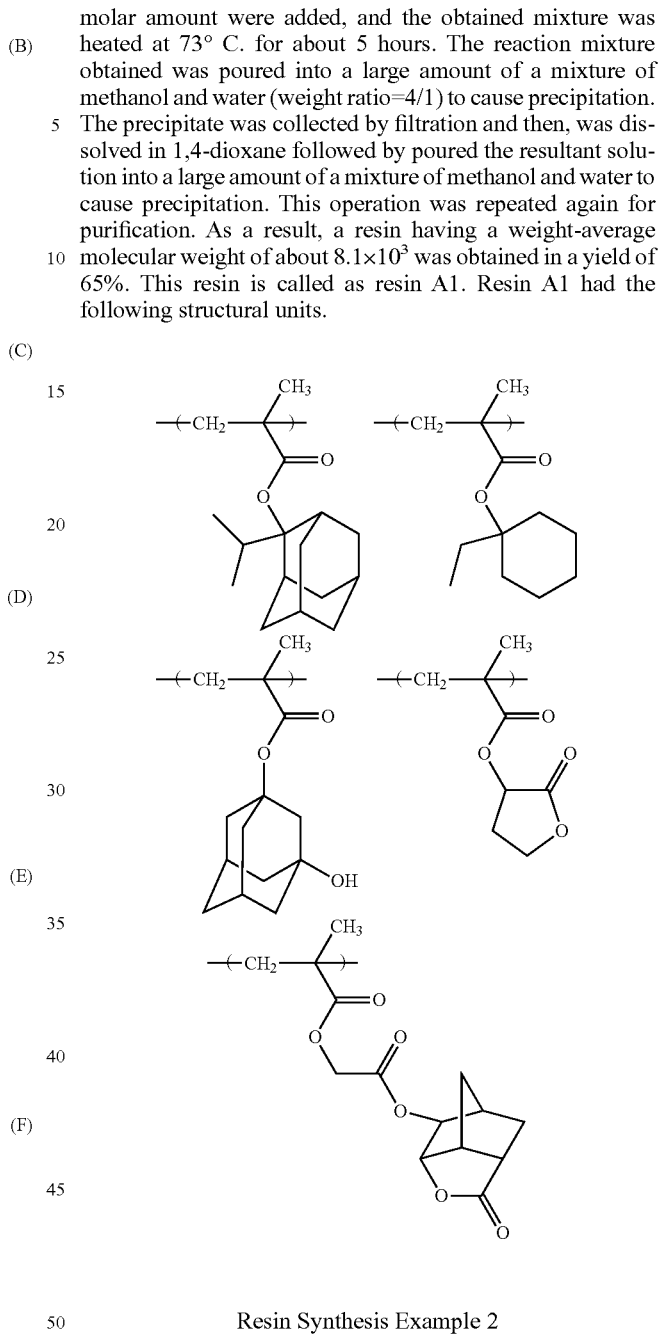

Resin Synthesis Example 2

The monomers (A), (E), (B), (C) and (F) were mixed in a molar ratio of 30/14/6/20/30 (monomer (A)/monomer (E)/ monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $7.8 \times 10^3$ was obtained in a yield of 68%. This resin is called as resin A2. Resin A2 had the following structural units.

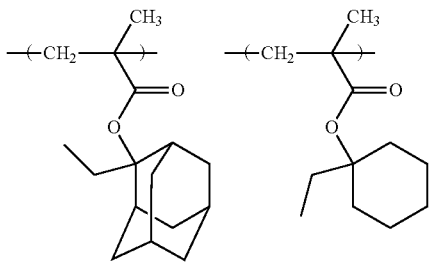

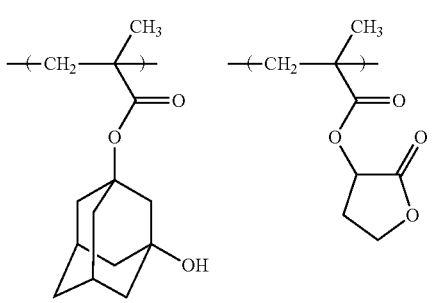

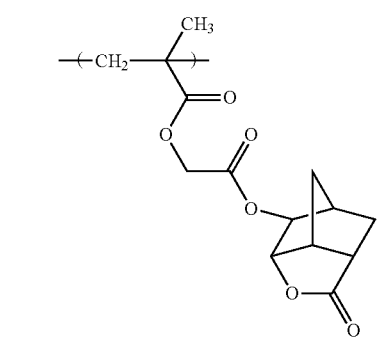

Resin Synthesis Example 3

The monomers (A), (B) and (C) were mixed in a molar ratio of 50/25/25 (monomer (A)/monomer (B)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 8 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $9.2 \times 10^3$ was obtained in a yield of 60%. This resin is called as resin A3. Resin A3 had the following structural units.

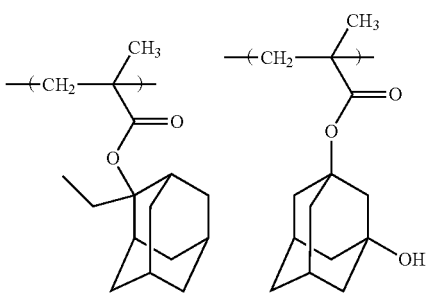

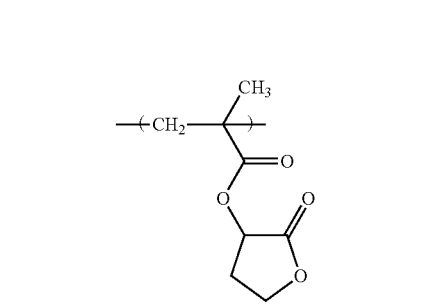

Resin Synthesis Example 4

A solution prepared by dissolving 11.18 parts of monomer (A), 14.60 parts of p-acetoxystyrene and 3.55 parts of monomer (B) in 28.82 parts of 1,4-dioxane was heated up to 87° C. To the solution, 2.96 parts of azobisisobutyronitrile was added. The resultant mixture was stirred at 87° C. for 6 hours. The reaction mixture obtained was cooled and then, was poured into a mixture of 291.41 parts of methanol and 124.89 parts of ion-exchanged water to cause precipitation. The precipitate was collected by filtration to obtain a polymer. The polymer obtained and 2.93 parts of 4-dimethylaminopyridine were mixed with methanol of which amount was same as the amount of the polymer obtained. The obtained mixture was refluxed for 15 hours and then, cooled. The obtained reaction mixture was neutralized with 2.16 parts of glacial acetic acid and the resultant mixture was poured into a large amount of water to cause precipitation. The precipitate was isolated by filtration and then, was dissolved in acetone. The obtained solution was poured into a large amount of water to cause precipitation. This operation was repeated three times for purification. As a result, 27.71 parts of a polymer having a weight-average molecular weight of about $3.4 \times 10^3$ was obtained. The polymer had the following structural units. This is called as resin A4.

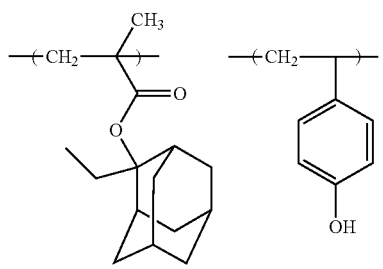

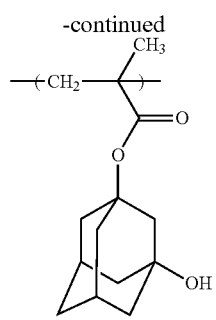

Resin Synthesis Example 5

A solution prepared by dissolving 10.54 parts of monomer (A), 14.60 parts of p-acetoxystyrene and 3.55 parts of monomer (B) in 47.09 parts of 1,4-dioxane was heated up to 87° C. To the solution, 2.96 parts of azobisisobutyronitrile was added. The resultant mixture was stirred at 87° C. for 6 hours. The reaction mixture obtained was cooled and then, was poured into a mixture of 285.67 parts of methanol and 122.43 parts of ion-exchanged water to cause precipitation. The precipitate was collected by filtration to obtain a polymer. The polymer obtained and 2.93 parts of 4-dimethylaminopyridine were mixed with methanol of which amount was same as the amount of the polymer obtained. The obtained mixture was refluxed for 15 hours and then, cooled. The obtained reaction mixture was neutralized with 2.16 parts of glacial acetic acid and the resultant mixture was poured into a large amount of water to cause precipitation. The precipitate was isolated by filtration and then, was dissolved in acetone. The obtained solution was poured into a large amount of water to cause precipitation. This operation was repeated three times for purification. As a result, 28.15 parts of a polymer having a weight-average molecular weight of about $3.7 \times 10^3$ was obtained. The polymer had the following structural units. This is called as resin A5.

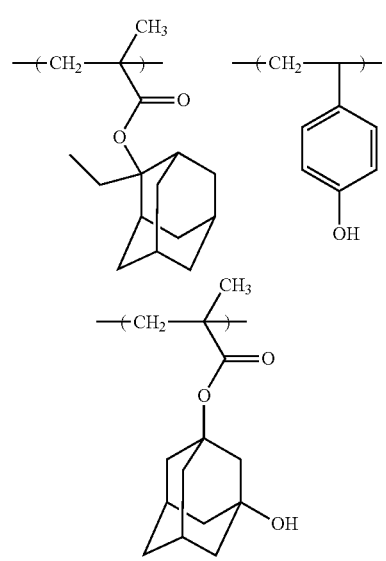

Resin Synthesis Example 6

A solution prepared by dissolving 11.18 parts of monomer (A), 15.09 parts of p-acetoxystyrene and 3.55 parts of monomer (B) in 28.82 parts of 1,4-dioxane was heated up to 82° C. To the solution, 0.86 parts of azobisisobutyronitrile was added. The resultant mixture was stirred at 82° C. for 6 hours. The reaction mixture obtained was cooled and then, was poured into a mixture of 291.41 parts of methanol and 124.89 parts of ion-exchanged water to cause precipitation. The precipitate was collected by filtration to obtain a polymer. The polymer obtained and 2.93 parts of 4-dimethylaminopyridine were mixed with methanol of which amount was same as the amount of the polymer obtained. The obtained mixture was refluxed for 15 hours and then, cooled. The obtained reaction mixture was neutralized with 2.16 parts of glacial acetic acid and the resultant mixture was poured into a large amount of water to cause precipitation. The precipitate was isolated by filtration and then, was dissolved in acetone. The obtained solution was poured into a large amount of water to cause precipitation. This operation was repeated three times for purification. As a result, 22.42 parts of a polymer having a weight-average molecular weight of about $8.5 \times 10^3$ was obtained. The polymer had the following structural units. This is called as resin A6.

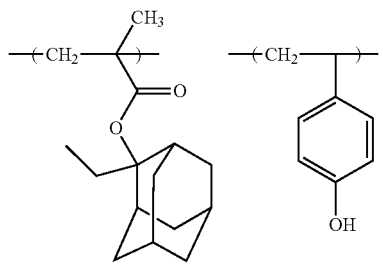

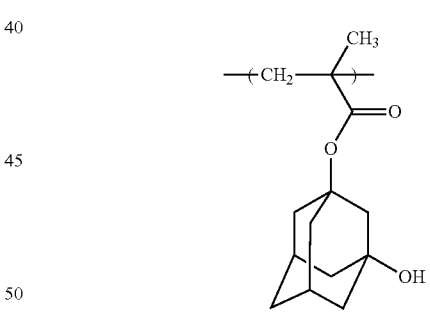

Examples 6 to 16 and Comparative Example 1

Resin

Resin A1, A2, A3

<Acid Generator>

I1: Salt I1

I2: Salt I2

I3: Salt I3

I4: Salt I4

I5: Salt I5

B1:

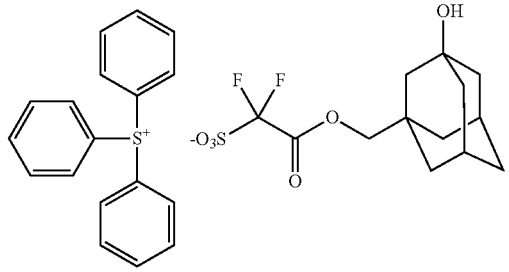

B2:

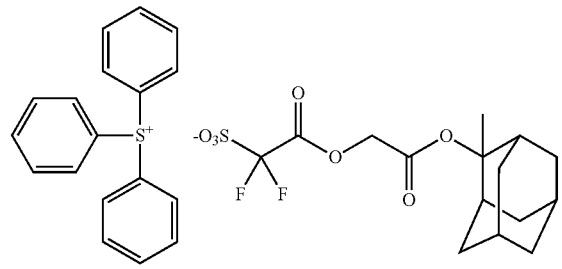

<Quencher>
C1: 2,6-diisopropylaniline
<Solvent>

| E1: | propylene glycol monomethyl ether acetate | 265 parts |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 3)
Acid generator (kind and amount are described in Table 3)
Quencher (kind and amount are described in Table 3)
Solvent E1

TABLE 3

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 6 | A2/10 | I1/1.00 | C1/0.07 | 105 | 105 |
| Ex. 7 | A1/10 | I2/1.00 | C1/0.07 | 95 | 95 |
| Ex. 8 | A2/10 | I2/1.00 | C1/0.07 | 105 | 105 |
| Ex. 9 | A2/10 | I2/0.7 B1/0.3 | C1/0.07 | 105 | 105 |
| Ex. 10 | A3/10 | I2/1.00 | C1/0.07 | 105 | 105 |
| Ex. 11 | A2/10 | I3/1.00 | C1/0.07 | 105 | 105 |
| Ex. 12 | A2/10 | I4/1.00 | C1/0.07 | 105 | 105 |
| Ex. 13 | A2/10 | I5/1.00 | C1/0.07 | 105 | 105 |
| Ex. 14 | A2/10 | I3/0.7 B1/0.3 | C1/0.07 | 105 | 105 |
| Ex. 15 | A2/10 | I4/0.7 B1/0.3 | C1/0.07 | 105 | 105 |
| Ex. 16 | A2/10 | I5/0.7 B1/0.3 | C1/0.07 | 105 | 105 |

TABLE 3-continued

| Ex. No. | Resin (kind/amount (part)) | Acid generator (kind/amount (part)) | Quencher (kind/amount (part)) | PB (° C.) | PEB (° C.) |
|---|---|---|---|---|---|
| Comp. Ex. 1 | A3/10 | B2/0.7 | C1/0.07 | 105 | 105 |

Silicon wafers (12 inches) were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 3 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern exposure with the exposure quantity being varied stepwise.

After the exposure, each wafer was subjected to post-exposure baking on a hotplate at a temperature shown in the column "PEB" in Table 3 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 4.

Effective Sensitivity (ES): It was expressed as the amount of exposure that the line width of the line and space pattern of 50 nm became 1:1 after exposure through line and space pattern mask and development.

Line Edge Roughness (LER): The photoresist pattern at ES was observed with a scanning electron microscope. The difference between the height of the highest point and height of the lowest point of the scabrous wall surface of the photoresist pattern was measured. When the difference is 3.5 nm or less, LER is excellent and its evaluation is marked by "⊚⊚", when the difference is more than 3.5 nm and 4 nm or less, LER is very good and its evaluation is marked by "⊚", when the difference is more than 4 nm and 4.5 nm or less, LER is good and its evaluation is marked by "○", and when the difference is more than 4.5 nm, LER is bad and its evaluation is marked by "X". Further, each of the differences is also shown in parentheses in a column of "LER". The smaller the difference is, the better the pattern is. The difference was shown in parentheses in Table 4.

TABLE 4

| Ex. No. | LER |
|---|---|
| Ex. 6 | ⊚ (3.78) |
| Ex. 7 | ⊚ (3.68) |
| Ex. 8 | ⊚⊚ (3.24) |
| Ex. 9 | ⊚ (3.52) |
| Ex. 10 | ○ (4.12) |
| Ex. 11 | ⊚⊚ (3.18) |
| Ex. 12 | ⊚⊚ (3.20) |
| Ex. 13 | ⊚⊚ (3.38) |
| Ex. 14 | ⊚⊚ (3.42) |
| Ex. 15 | ⊚⊚ (3.39) |
| Ex. 16 | ⊚ (3.59) |
| Comp. Ex. 1 | X (4.68) |

Examples 17 to 20 and Comparative Example 2

Resin

Resin A4, A5, A6
<Acid Generator>
I2: Salt I2
B2:

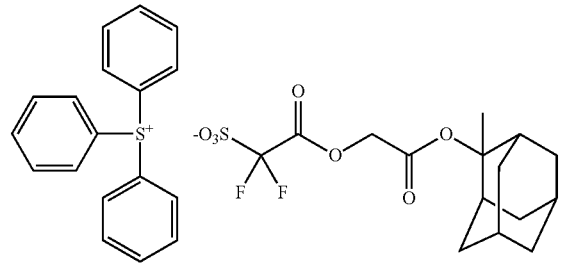

<Quencher>
C2: tetrabutylammonium hydroxide
C3:

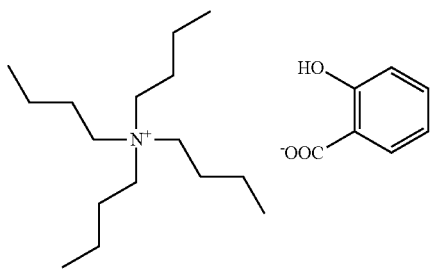

<Solvent>

| E2: | propylene glycol monomethyl ether acetate | 400 parts |
|---|---|---|
| | propylene glycol monomethyl ether | 100 parts |
| | γ-butyrolactone | 5 parts |

The following components were mixed and dissolved, further, filtrated through a fluorine resin filter having pore diameter of 0.2 μm, to prepare photoresist compositions.
Resin (kind and amount are described in Table 5)
Acid generator (kind and amount are described in Table 5)
Quencher (kind and amount are described in Table 5)
Solvent E2

TABLE 5

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 17 | A4/10 | I2/3 | C3/0.3 | 120 | 120 |
| Ex. 18 | A5/10 | I2/3 | C3/0.3 | 120 | 120 |
| Ex. 19 | A4/10 | I2/3 | C2/0.3 | 120 | 120 |
| Ex. 20 | A6/10 | I2/3 | C3/0.3 | 120 | 120 |
| Comp. Ex. 2 | A6/10 | B2/3 | C2/0.3 | 120 | 120 |

Silicon wafer was contacted with hexamethyldisilazane at 90° C. for 60 seconds on a direct hot plate and each of the photoresist compositions prepared as above was spin-coated over the silicon wafer to give a film thickness after drying of 0.06 μm. After application of the photoresist composition, the silicon wafer thus coated with the photoresist composition was prebaked on a direct hotplate at a temperature shown in column "PB" in Table 5 for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at the temperature shown in the column of "PEB" in Table 5 for 60 seconds and then to paddle development with an aqueous solution of 2.38% by weight tetramethylammonium hydroxide for 60 seconds.

Each of a pattern developed on the silicon substrate after the development was observed with a scanning electron microscope, and the results of which are shown in Table 6.

Line Edge Roughness (LER): The photoresist pattern at the amount of exposure that the line width of the photoresist pattern of 80 nm became 1:1 line and space pattern was as effective sensitivity was observed with a scanning electron microscope. The difference between the height of the highest point and height of the lowest point of the scabrous wall surface of the photoresist pattern was measured. When the difference is 5 nm or less, LER is good and its evaluation is marked by "⊚", and when the difference is more than 5 nm, LER is bad and its evaluation is marked by "X". Further, each of the differences is also shown in parentheses in a column of "LER". The smaller the difference is, the better the pattern is. The difference was shown in parentheses in Table 6.

TABLE 6

| Ex. No. | LER |
|---|---|
| Ex. 17 | ⊚ (3.82) |
| Ex. 18 | ⊚ (3.74) |
| Ex. 19 | ⊚ (4.01) |
| Ex. 20 | ⊚ (4.44) |
| Comp. Ex. 2 | X (5.16) |

Silicon wafer was contacted with hexamethyldisilazane at 90° C. for 60 seconds on a direct hot plate and the photoresist composition prepared in Example 17 was spin-coated over the silicon wafer to give a film thickness after drying of 0.05 μm. After application of the photoresist composition, the silicon wafer thus coated with the photoresist composition was prebaked on a direct hotplate at a temperature shown in column "PB" in Table 5 for 60 seconds. Using an EUV (extreme ultraviolet) exposure system, the wafer on which the resist film had been thus formed was exposed to a line and space pattern, while changing stepwise the exposure quantity.

After the exposure, the wafer was subjected to post-exposure baking on a hotplate at a temperature shown in column "PEB" in Table 5 for 60 seconds and then to paddle development with an aqueous solution of 2.38% by weight tetramethylammonium hydroxide for 60 seconds.

The pattern developed on the silicon substrate after the development was observed with a scanning electron microscope, and the result of which is shown in Table 7.

Line Edge Roughness (LER): The photoresist pattern at the amount of exposure that the line width of the photoresist pattern of 50 nm became 1:1 line and space pattern was as effective sensitivity was observed with a scanning electron microscope. The difference between the height of the highest point and height of the lowest point of the scabrous wall surface of the photoresist pattern was measured. When the difference is 5 nm or less, LER is good and its evaluation is marked by "⊚", and when the difference is more than 5 nm, LER is bad and its evaluation is marked by "X". Further, each of the differences is also shown in parentheses in a column of "LER". The smaller the difference is, the better the pattern is. The difference was shown in parentheses in Table 7.

TABLE 7

| Ex. No. | LER |
|---|---|
| Ex. 17 | ⊚ (3.31) |

The salt of the present invention is suitable for an acid generator and the photoresist composition comprising the salt of the present invention provides a good photoresist pattern having good line edge roughness.

What is claimed is:

1. A salt represented by the formula (I):

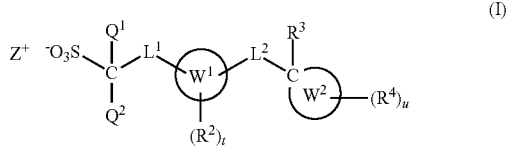

(I)

wherein $Q^1$ and $Q^2$ independently each represent a fluorine atom or a C1-C6 perfluoroalkyl group, $L^1$ and $L^2$ independently each represent a C1-C17 divalent saturated hydrocarbon group in which one or more —$CH_2$— can be replaced by —O— or —CO—, ring $W^1$ and ring $W^2$ independently each represent a C3-C36 aliphatic ring, $R^2$ is independently in each occurrence a C1-C6 alkyl group, $R^4$ is independently in each occurrence a C1-C6 alkyl group, $R^3$ represents a C1-C12 hydrocarbon group, t represents an integer of 0 to 2, u represents an integer of 0 to 2, and $Z^+$ represents an organic counter ion.

2. The salt according to claim 1, wherein $L^1$ is *—CO—O— in which * represents a binding position to —$C(Q^1)(Q^2)$-.

3. The salt according to claim 1, wherein $L^2$ is *—CO—O—$CH_2$—CO—O— or *—O—$CH_2$—CO—O— in which * represents a binding position to ring $W^1$.

4. The salt according to claim 1, wherein $Z^+$ is an arylsulfonium cation.

5. An acid generator comprising the salt according to claim 1.

6. A photoresist composition comprising the acid generator according to claim 5 and a resin having an acid-labile group, being insoluble or poorly soluble in an aqueous alkali solution but becoming soluble in an aqueous alkali solution by the action of an acid.

7. The photoresist composition according to claim 6, which further comprises a basic compound.

8. A process for producing a photoresist pattern comprising the following steps (1) to (5):
(1) a step of applying the photoresist composition according to claim 6 or 7 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *